US008580520B2

(12) United States Patent
Johansen et al.

(10) Patent No.: US 8,580,520 B2
(45) Date of Patent: Nov. 12, 2013

(54) YKL-40 AS A MARKER FOR GASTROINTESTINAL CANCERS

(75) Inventors: Julia Sidenius Johansen, Frederiksberg (DK); Nicolai Aagaard Schultz, Frederiksberg (DK); Benny Vittrup Jensen, Roskilde (DK); Stig Bojesen, København Ø (DK); Børge Grønne Nordestgaard, Genrofte (DK); Hans Jørgen Nielsen, Kongens Lyngby (DK); Ib Jarle Christensen, Hillerød (DK)

(73) Assignees: Herlev Hospital, Herlev (DK); Rigshospitalet, Kobenhavn O (DK); Hvidovre Hospital, Hvidovre (DK)

( * ) Notice: Subject to any disclaimer, the term of this patent is extended or adjusted under 35 U.S.C. 154(b) by 0 days.

(21) Appl. No.: 13/063,402

(22) PCT Filed: Sep. 14, 2009

(86) PCT No.: PCT/DK2009/050241
§ 371 (c)(1),
(2), (4) Date: Nov. 21, 2011

(87) PCT Pub. No.: WO2010/028658
PCT Pub. Date: Mar. 18, 2010

(65) Prior Publication Data
US 2012/0070853 A1   Mar. 22, 2012

(30) Foreign Application Priority Data

| Sep. 15, 2008 | (DK) | ................................. | 2008 01292 |
| Sep. 15, 2008 | (DK) | ................................. | 2008 01293 |
| Sep. 15, 2008 | (DK) | ................................. | 2008 01294 |
| Oct. 22, 2008 | (DK) | ................................. | 2008 01465 |
| Oct. 24, 2008 | (DK) | ................................. | 2008 01471 |
| Jan. 22, 2009 | (WO) | ................ | PCT/DK2009/050014 |
| Mar. 25, 2009 | (DK) | ................................. | 2009 00414 |
| Jul. 28, 2009 | (DK) | ................................. | 2009 00900 |

(51) Int. Cl.
*G01N 33/53* (2006.01)

(52) U.S. Cl.
USPC .......................... 435/7.1; 435/7.23

(58) Field of Classification Search
None
See application file for complete search history.

(56) References Cited

U.S. PATENT DOCUMENTS

| 5,726,061 A | 3/1998 | Robbins et al. |
| 5,811,535 A | 9/1998 | Adamou et al. |
| 6,060,590 A | 5/2000 | Bryant et al. |
| 7,229,770 B1 * | 6/2007 | Price et al. ........................ 435/7.1 |
| 2003/0215847 A1 | 11/2003 | Kirkpatrick |
| 2005/0209181 A1 | 9/2005 | Akil et al. |
| 2006/0210552 A1 | 9/2006 | Demopulos et al. |
| 2007/0161022 A1 | 7/2007 | Kim et al. |
| 2008/0171319 A1 | 7/2008 | Urdea et al. |
| 2009/0202989 A1 * | 8/2009 | Hillan ................................. 435/6 |

FOREIGN PATENT DOCUMENTS

| EP | 0 710 251 | 5/1996 |
| EP | 1804062 | 7/2007 |
| JP | 2005102601 | 4/2005 |
| WO | WO 95/01995 | 1/1995 |
| WO | WO 99/46390 | 9/1999 |
| WO | WO 00/19206 | 4/2000 |
| WO | WO 00/38786 | 7/2000 |
| WO | WO 00/62070 | 10/2000 |
| WO | WO 01/29081 | 4/2001 |
| WO | WO 02/065459 | 10/2002 |
| WO | WO 02/097125 | 12/2002 |
| WO | WO 03/009808 | 2/2003 |
| WO | WO 03/054166 | 7/2003 |
| WO | WO 03/073822 | 9/2003 |
| WO | WO 03/074654 | 9/2003 |
| WO | WO 03/087830 | 10/2003 |
| WO | WO 2004/053157 | 6/2004 |
| WO | WO 2005/039397 | 5/2005 |
| WO | WO 2005/039487 | 5/2005 |
| WO | WO 2005/081980 | 9/2005 |
| WO | WO 2005/116901 | 12/2005 |
| WO | WO 2006/009702 | 1/2006 |
| WO | WO 2006/050475 | 5/2006 |
| WO | WO 2006/054297 | 5/2006 |
| WO | WO 2006/062094 | 6/2006 |

(Continued)

OTHER PUBLICATIONS

Johansen et al, Expert Opin. Ther. Targets.11:220, 2007.*
Amado R.G. et al.; "Wild-Type KRAS Is Required for Panitumumab Efficacy in Patients With Metastatic Colorectal Cancer"; Journal of Clinical Oncology; vol. 26; No. 10; Apr. 1, 2008; pp. 1626-1634.
Andreassen M. et al. Concentrations of the acute phase reactants high-sensitive C-reactive protein and YKL-40 and of interleukin-6 before and after treatment in patients with acromegaly and growth hormone deficiency. Clinical Endocrinology 2007, 67, pp. 909-916.
Andreyev, H.J.N. et al.; "Kirsten ras Mutations in Patients With Colorectal Cancer: the Multicenter "Rascal" Study"; Journal of National Cancer Institute; vol. 90; No. 9; May 6, 1998; pp. 675-684.
Artale, S. et al.; "Mutations of KRAS and BRAF in Primary and Matched Metastatic Sites of Colorectal Cancer"; Journal of Clinical Oncology, 2008 by American Society of Clinical Oncology; vol. 26(25) pp. 4217-4218.

(Continued)

*Primary Examiner* — Lei Yao
(74) *Attorney, Agent, or Firm* — Clark & Elbing LLP; Kristina Bieker-Brady

(57) ABSTRACT

The present invention relates to gastrointestinal cancers and methods for selecting a treatment for said gastrointestinal cancer in a subject. The present invention further relates to a methods of diagnosing the presence of and/or classifying the severity of a gastrointestinal cancer; together with methods for determining the effect of a therapy administered and/or the prognosis for a subject suffering from a gastrointestinal cancer, before, during or after administering the treatment. For all the methods applies that a determined level of YKL-40 above one or more reference levels indicates the treatment, the severity of the disease, the effect of the treatment and/or the prognosis of the subject. The reference level is typically a level obtained from healthy individuals or a level previously obtained from the same subject. The subject may suffer from any one or more gastrointestinal cancers, such as upper gastrointestinal cancers, and metastatic colorectal cancer. The present invention further relates to a kit and a device that may be used in the method of the present invention.

14 Claims, 43 Drawing Sheets

(56) References Cited

FOREIGN PATENT DOCUMENTS

| WO | WO 2006/089549 | 8/2006 |
|---|---|---|
| WO | WO 2006/133923 | 12/2006 |
| WO | WO 2007/027748 | 3/2007 |
| WO | WO 2007/035651 | 3/2007 |
| WO | WO 2007/056523 | 5/2007 |
| WO | WO 2007/067813 | 6/2007 |
| WO | WO 2007/076439 | 7/2007 |
| WO | WO 2007/082352 | 7/2007 |
| WO | WO 2007/093819 | 8/2007 |
| WO | WO 2007/123976 | 11/2007 |
| WO | WO 2007/147011 | 12/2007 |
| WO | WO 2008/008284 | 1/2008 |
| WO | WO 2008/031056 | 3/2008 |
| WO | WO 2008/048508 | 4/2008 |
| WO | WO 2008/068428 | 6/2008 |
| WO | WO 2008/077165 | 7/2008 |
| WO | WO 2008/080195 | 7/2008 |

OTHER PUBLICATIONS

Baselga, J.; "Determinants of RASistance to Anti-Epidermal Growth Factor Receptor Agents"; Journal of Clinical Oncology, vol. 26, No. 10 (Apr. 1), 2008 pp. 1582-1584.

Benvenuti S, et al; oncogenic activation of the RAS/FAF signaling pathway impairs the response of metastatic colorectal caners to anti-epidermal growth factor receptor antibody therapies. Cancer Res, 67, pp. 2643-2648 (2007).

Bergmann OJ, et al; "High Serum Concentration of YKL-40 is Associated with Short Survival in Patient with Acute Myeloid Leukemia". Clin Cancer Res 11(24), pp. 8644-8652, Dec. 15, 2005.

Bigg HF, et al; "The mammalian chitinase-like lectin, YKL-40, binds specifically to type I collagen and modulates the rate of type I collagen fibril formation". J Biol Chem, 281, pp. 21082-21095 (2006).

Bojesen SE et al; "Integrin β3 leu33pro homozygosity and risk of cancer". J Natl Cancer Inst, 95 pp. 1150-1157 (2003).

Bokemeyer C. et al.; "Fluorouracil, Leucovorin, and Oxaliplatin With and Without Cetuximab in the First-Line Treatment of Metastatic Colorectal Cancer"; Journal of Clinical Oncology; vol. 27; No. 5, Feb. 10, 2009; pp. 663-671.

Bonneh-Barkay, et al. 2008. "YKL-40, a marker of simian immunodeficiency virus encephalitis, modulates the biological activity of basic fibroblast growth factor" The American Journal of Pathology, vol. 173, No. 1, July, 130-143.

Bonner J.A., et al.; "Radiotherapy plus Cetuximab for Squamous-Cell Carcinoma of the Head and Neck"; New England Journal of Medicine 354,6, Feb. 9, 2006; pp. 567-578

Boot RG et al; "Strong induction of members of the chitinase family of proteins in atherosclerosis Chitotriosidase and human cartilage gp-39 expressed in lesion macrophages". Arterioscler Thromb Vasc Biol, 19, pp. 687-694 (1999).

Brasso K. et. al. Prognostic value of PINP, bone alkaline phosphatase CTX-I, and YKL-40 in patients with metastatic prostate carcinoma. The Prostate 2006, 66, pp. 503-513.

Bray F, et al.; Estimates of Cancer incidence and mortality in Europe in 1995. Eur J. Cancer 2002; 38: 99-166.

Brune K., et al.; "Genetic and Epigenetic Alterations of Familial Pancreatic Cancers"; Cancer Epidemiol Biomarkers Prev 2008; 17(12). Dec. 2008; pp. 3536-3542.

Burris III H.A. et al.; "Improvements in Survival and Clinical Benefit With Gemcitabine as First-Line Therapy for Patients With Advanced Pacreas Cancer: A Randomized Trial"; Journal of Clinical Oncology; Vo. 15; No. 6; Jun. 1997; pp. 2403-2413.

Calonghi et al. 2007. "A new EGFR inhibitor induces apoptosis in colon cancer cells" Biochemical and Biophysical Research Communications, vol. 354, No. 2, Jan. 30, pp. 409-413.

Cascinu S., et al.; Cetuximab plus gemcitabine and cisplatin compared with gemcitabine and cisplatin alone in patients with advanced pancreatic cancer: a randomised, multicentre, phase II trial; Lancet Oncol 2008; 9; pp. 39-44.

Chung K.Y., et al.; "Cetuximab Shows Activity in Colorectal Cancer Patients With Tumors That Do Not Express the Epidermal Growth Factor Receptor by Immunohistochemistry"; Journal of Clinical Oncology; vol. 23; No. 9; Mar. 20, 2005; pp. 1803-1810.

Chupp, G.L. et al. 2007. "A chitinase-like protein in the lung and circulation of patients with severe asthma". The New England Journal of Medicine, 357, 20, Nov. 15, pp. 2016-2027.

Cintin C, et al. Serum YKL-40 and colorectal cancer. British Journal of Cancer, 1999, 79(9/10), pp. 1494-1499.

Cintin C, et.al. High serum YKL-40 level after surgery for colorectal carcinoma is related to short survival. American Cancer Society, Jul. 15, 2002, vol. 95, No. 2, pp. 267-274.

Cintin et al; "Postoperative elevation in serum YKL-40 in patients with colorectal cancer is related to short survival". Proceedings of the Annual Meeting of the American Association for Cancer Research, New York, NY, US. vol. 41, Abstract #4060, p. 639, Mar. 1, 2000.

Cunningham D., et al.; "Cetuximab Monotherapy and Cetuximab plus Irinotecan in Irinotecan-Refractory Metastatic Colorectal Cancer"; New England Journal of Medicine 2004; 351; pp. 337-345

De Ceuninck F. et al; "YKL-40 (Cartilage gp-39) induces proliferative events in cultured chondrocytes and synoviocytes and increases glycosaminoglycan synthesis in chondrocytes". Biochem Biophys Res Commun, 285, pp. 926-931 (2001).

de Reyniès A. et al.; "KRAS Mutation Signature in Colorectal Tumors Significantly Overlaps With the Cetuximab Response Signature"; Journal of Clinical Oncology 2008; May 1; 26 (13); pp. 2228-2232.

De Roock W., et al.; "KRAS wild-type state predicts survival and is associated to early radiological response in metastatic colorectal cancer treated with cetuximab"; Annals of Oncology vol. 19, No. 3, Mar. 2008; pp. 508-515.

Dehn H. et al. Plasma YKL-40, as a prognostic tumor marker in recurrent ovarian cancer. Acta Obstet Gynecol Scand 2003, 82, pp. 287-293.

Di Fiore F. et al.; "Clinical relevance of KRAS mutation detection in metastatic colorectal cancer treated By Cetuximab plus chemotherapy"; British Journal of Cancer (2007), 96(8) pp. 1166-1169.

Di Nicolantonio F. et al.; "Wild-Type BRAF Is Required for Response to Panitumumab or Cetuximab in Metastatic Colorectal Cancer"; Journal of Clinical Oncology, vol. 26, No. 35, Dec. 10, 2008; pp. 5705-5712.

Ferlay J. et al.; "Estimates of the cancer incidence and mortality in Europe in 2006"; Annals of Oncology 18; Feb. 7, 2007; pp. 581-592.

Fiore C.E. and Tamborino C. 2000. "YKL-40 and graft rejection" The American Journal of Medicine, vol. 108, Jun. 1, p. 688-689.

Frattini M., et al.; "PTEN loss of expression predicts cetuximab efficacy in metastatic colorectal cancer patients"; British Journal of Cancer (2007) 97; pp. 1139-1145.

Fredriksson S. et al. Multiplexed proximity ligation assays to profile putative biomarkers relevant to pancreatic and ovarian cancer. Clinical Chemistry 2008, 54:3, pp. 582-589.

Freeman D.J. et al.; "Association of K-ras mutational studies and clinical outcomes in patients with metastatic colorectal cancer receiving panitumumab alone"; Clin Colorectal Cancer 2008; 7; pp. 184-190.

Fukushima N. et al; "Gene expression alterations in the non-neoplastic parenchyma adjacent to infiltrating pancreatic ductal adenocarcinoma"; Modern Pathology (2005); 18; pp. 779-787

Hecht, J. R., et al; "A Randomized Phase IIIB Trial of Chemotherapy, Bevacizumab, and Panitumumab Compared With Chemotherapy and Bevacizumab Alone for Metastatic Colorectal Cancer"; Journal of Clinical Oncology; vol. 27; No. 5; Feb. 10, 2009; pp. 672-680.

Hormigo A., et al.; YKL-40 and Matrix Metalloproteinase-9 as Potential Serum Biomarkers for Patients with High-Grade Gliomas; Clin Cancer Res 2006, 12 (19) Oct. 1, 2006, pp. 5698-5704.

Jemal A. et al., "Cancer statistics" 2008. CA Cancer J Clin 2008; 58 pp. 71-96.

Jensen B.V. et al.; "High Levels of Serum HER-2/neu and YKL-40 Independently Reflect Aggressiveness of Metastatic Breast Cancer"; Clinical Cancer Research; vol. 9; pp. 4423-4434,2003.

Johansen J.S. et al.; "A New Biochemical Marker for Joint Injury, Analysis of YKL-40 in Serum and Synovial Fluid"; British Journal of Rheumatology 1993; vol. 32; pp. 949-955.

(56) References Cited

OTHER PUBLICATIONS

Johansen et al. 2007. "Changes of biochemical markers of bone turnover and YKL-following hormonal treatment for metastatic prostate cancer are related to survival" Clin. Cancer Research, vol. 13, No. 11, Jun. 1, pp. 3244-3249.
Johansen J.S. et al. 2007. "High serum YKL-40 level in a cohort of octogenarians is associated with increased risk of all-cause mortality" Clinical and Experimental Immunology, 151: 260-266.
Johansen J.S. et al. High serum YKL-40 levels in patients with primary breast cancer is related to short recurrence free survival. Breast Cancer Research and Treatment 2003, 80, pp. 15-21.
Johansen J.S. et al. YKL-40 in giant cells and macrophages from patients with giant cell arteritis Arthritis & Rheumatism, vol. 42, No. 12, Dec. 1999, pp. 2624-2630.
Johansen J.S. et al.; "Diurnal, Weekly, and Long-Time Variation in Serum Concentrations of YKL-40 in Healthy Subjects"; Cancer Epidemiol Biomarkers Prev. 2008; 17(10); Oct. 2008; pp. 2603-2608.
Johansen J.S. et al.; "Elevated Plasma YKL-40 Predicts Increased Risk of Gastrointestinal Cancer and Decreased Survival After Any Cancer Diagnosis in the General Population"; Journal of Clinical Oncology; vol. 27; No. 4; Feb. 1, 2008; pp. 572-578.
Johansen J.S. et al.; "Serum YKL-40 in Healthy Children and Adults. Comparison with Serum and Synovial Fluid Levels of YKL-40 Patients With Osteoarthritis or Trauma of the Knee Joint"; British Journal of Rheumatology 1996; vol. 35; pp. 553-559.
Johansen J.S. Studies on serum YKL-40 as a biomarker in diseases with inflammation, tissue remodelling, fibrosis and cancer. Danish Medical Bulletin, vol. 53, No. 2, May 2006, pp. 172-209.
Johansen J.S., et al; "Postoperative Elevation in Serum YKL-40 in Patients With Colorectal Cancer Is Related to Short Survival"; Proceedings for the American Association for Cancer Research; vol. 41; Mar. 2000; p. 639.
Johansen JS et al; "Identification of proteins secreted by human osteoblastic cells in culture". J Bone Miner Res, 7, pp. 501-512 (1992).
Johansen JS et al; "Serum YKL-40, a new prognostic biomarker in cancer patients?" Cancer Epidemiol Biomarkers Prev, 15, pp. 194-202 (2006).
Johansen, J.S. et al. 2008. "High-serum YKL-40 is associated with increased risk of and mortality from gastrointestinal cancer in the general population" Gastrointestinal cancer symposium No. 390, January. Abstract.
Johansen, J.S. et al. Serum YKL-40 concentrations in patients with rheumatoid arthritis: relation to disease activity. Rheumatology, 1999, 38, pp. 618-626.
Johansen, J.S. et al.; "Is YKL-40 a new therapeutic target in cancer?"; Expert Opinion. Ther. Targets (2007) 11(2); pp. 219-234.
Johansen, J.S., et al., "Serum YKL-40 is increased in patients with hepatic fibrosis"; J Hepatol 2000; 32; pp. 911-920.
Jonker et al. 2007. "Cetuximab for the treatment of colorectal cancer" The New England Journal of Medecine, vol. 357, No. 20, pp. 2040-2048.
Kamal S.M. et al. Progression of fibrosis in hepatitis C with and without schistosomiasis: correlation with serum markers of fibrosis. Hepatology, 2006, vol. 43, No. 4, pp. 771-779.
Karapetis C.S. et al.; "K-ras Mutations and Benefit from Cetuximab in Advanced Colorectal Cancer"; The New England Journal of Medicine; Oct. 23, 2008; vol. 359, No. 17; pp. 1757-1765.
Kaynar, et al. 2005. "YKL-40 levels in the cerebrospinal fluid and serum of patients with aneurysmal subarachnoid hemorrhage: preliminary results" Journal of Clinical Neuroscience, 12;7, 754-757.
Khambata-Ford S. et al.; "Expression of Epiregulin and Amphiregulin and K-ras Mutation Status Predict Disease Control in Metastatic Colorectal Cancer Patients Treated With Cetuximab"; Journal of Clinical Oncology; vol. 25; No. 22; Aug. 1, 2007; pp. 3230-3237.
Koutroubakis, I.E., et al.; Increased serum levels of YKL-40 in patients with inflammatory bowel disease; Int J Colorectal Dis (2003); 18: pp. 254-259.
Kushner I. et al; "What does minor elevation of C-reactive protein signify?" Am J Med, 119, pp. 166.e17-166.e28 (2006).
La Montagna, et al. 2003. "Cross-sectional evaluation of YKL-40 serum concentrations in patients with systemic sclerosis. Relationship with clinical and serological aspects of disease". J Rheumatol., 30;2147-51.
Li D. et al.; "Pancreatic cancer" Lancet 2004; 363-1049-59.
Lièvre A. et al.; "KRAS Mutations as an Independent Prognostic Factor in Patients with Advanced Colorectal Cancer Treated With Cetuximab"; Journal of Clinical Oncology; vol. 26; No. 3; Jan. 20, 2008; pp. 374-379.
Lièvre et al. 2006. "KRAS mutation status is predictive of response to cetuximab therapy in colorectal cancer" Cancer research, American Association for Cancer Research. vol. 66, No. 8, Apr. 15, pp. 3992-3995.
Lim J.E. et al.; Prognostic factors following curative resection for pancreatic adenocarcinoma; a population based, linked database analysis of 396 patients. Ann Surg 2003; 237:74-85.
Ling H. et al; "The chitinase 3-like protein human cartilage glycoprotein 39 inhibits cellular responses to the inflammatory cytokines interleukin-1 and tumour necrosis factor-alpha". Biochem J, 380, pp. 651-659 (2004).
Madazli, et al. 2008. "Chitotriosidase and YKL-40 in normal and pre-eclamptic pregnancies" International Journal of Gynecology and Obstetrics. 100, 239-243.
Malumbres M., et al.; "RAS oncogenes: the first 30 years"; Nature Reviews, vol. 3; Jun. 2003; pp. 7-13.
Messersmith W.A. et al.; "Targeting EGFR in Colorectal Cancer"; N.Engl. Journal of Medicine 359:17; Oct. 23, 2008; pp. 1834-1836.
Millis Ajt et al; "In vitro expression of a 38,000 dalton heparin-binding glycoprotein by morphologically differentiated smooth muscle cells". J Cell Physiol, 127, pp. 366-372 (1986).
Mylin, et al. 2008. "High serum YKL-40 concentration is associated with severe bone disease in newly diagnosed multiple myeloma patients" European Journal of Haematology, 310-317.
Nielsen, et al. 2008. "A BMI-independent marker of type 2 diabetes" Diabetes, vol. 57, November, 3078-3082.
Nishikawa KC et al; "gp38k (CHI3L1) is a novel adhesion and migration factor for vascular cells". Exp. Cell Res, 287, pp. 79-87 (2003).
Nordestgaard BG et al; "Nonfasting trigycerides and risk of myocardial infarction, ischemic heart disease, and death in men and women". JAMA, 298, pp. 299-308 (2007).
Nøjgaard, C et al. 2003. "Serum levels of YKL-40 and PIINP as prognostic markers in patients with alcoholic liver disease". Journal of Hepatology 39; 179-186.
Ockene Is et al; "Variability and classification accuracy of serial high-sensitivity C-reactive protein measurements in healthy adults". Clin Chem, 47, pp. 444-450 (2001).
Pfeiffer P. et al.; "Cetuximab and irinotecan as third line therapy in patients with advanced colorectal cancer after failure of irinotecan, oxaliplatin and 5-fluorouracil"; Acta Oncologica; 46:5; 2007; pp. 697-701.
Philip P.A. et al. Phase III study of gemcitabine (G) plus cetuximab (C) versus gemcitabinie in patients (pts) with locally advanced or metastatic pancreatic adenocarcinoma (PC): SWOG S0205 study; Proc AM Soc Clin Oncol; 25 (abstr 409).
Rathcke C.N. et al.; "YKL-40, a biomarker of inflammation, is elevated in patients with type 2 diabetes and is related to insulin resistance"; Inflamm. Res. 55 (2006); pp. 53-59.
Rathcke et al. 2010. "Plasma YKL-40 levels are elevated in patients with chronic heart failure" Scandinavian Cardiovascular Journal, 2010; 44: 92-99.
Rathcke, C.N. and Vestergaard, H. 2006. "YKL-40, a new inflammatory marker with relation to insulin resistance and with a role in endothelial dysfunction and atherosclerosis". Inflammation Research, 55, p. 221-227.
Recklies AD et al; "Inflammatory cytokines induce production of CHI3L1 by articular chondrocytes". J. Biol Chem., 280, pp. 41213-41221 (2005).
Recklies AD et al; "The chitinase 3-like protein human cartilage 39 (HC-gp39) stimulates proliferation of human connective-tissue cells

(56) References Cited

OTHER PUBLICATIONS and activates both extracellular signal-regulated kinase-and protein kinase B-mediated signalling pathways". Biochem J, 365, pp. 119-126 (2002).

Register TC et al; "Serum YKL-40 Is Associated with Osteoarthritis and Atherosclerosis in Nonhuman Primates". Clinical Chemistry 47, No. 12, 2001, Technical Briefs, pp. 2159-2161.

Renkema GH et al; "Chitotriosidase, a chitinase, and the 39-kDa human cartilage glycoprotein, a chitin-binding lectin, are homologues of family 18 glycosyl hydrolases secreted by human macrophages". Eur J Biochem, 251, pp. 504-509 (1998).

Roslind et al. 2008. "High serum levels of YKL-40 in patients with squamous cell carcinoma of the head and neck are associated with short survival" Int. J. Cancer, vol. 122, No. 4, February, pp. 857-863.

Royston, P. 1991. "Constructing time-specific reference ranges" Statistics in medicine, vol. 10, No. 5, pp. 675-690.

Saltz L.B. et al.; "Phase II Trial of Cetuximab in Patients With Refractory Colorectal Cancer That Express the Epidermal Growth Factor Receptor"; Journal of Clinical Oncology; vol. 22; No. 7; Apr. 1, 2004; pp. 1201-1208.

Schmidt, H. et al.; "Serum YKL-40 Predicts Relapse-Free and Overall Survival in Patients With American Joint Committee on Cancer Stage I and II Melanoma"; Journal of Clinical Oncology; vol. 24, No. 5, Feb. 10, 2006; pp. 798-804.

Schnohr P. et al; "Coronary heart disease risk factors ranked by importance for the individual and community. A 21 year follow-up of 12 000 men and women from The Copenhagen City Heart Study". Eur Heart J, 23, pp. 620-626 (2002).

Shackelton LM et al; "Identification of a 38-kDa heparin-binding glycoprotein (gp38k) in differentiating vascular smooth muscle cells as a member of a group of proteins associated with tissue remodelling". J Biol Chem, 270, pp. 13076-13083 (1995).

Tol J. et al.; "Chemotherapy, Bevacizumab, and Cetuximab in Metastatic Colorectal Cancer"; The New England Journal of Medicine; Feb. 5, 2009; vol. 360; No. 6; pp. 563-572.

Tsuji, et al. 2002. "Analysis of chondrex (YKL-40, HC gp-39) in the cerebrospinal fluid of patients with spine disease" SPINE, vol. 27, 7, 732-735.

van Cutsem, E., et al.; "Open-Label Phase III Trial of Panitumumab Plus Best Supportive Care Compared With Best Supportive Care Alone in Patients With Chemotherapy-Refractory Metastatic Colorectal Cancer"; Journal of Clinical Oncology; vol. 25; No. 13; May 1, 2007; pp. 1658-1664.

Vincenzi B. et al.; "Cetuximab and irinotecan as third-line therapy in advanced colorectal cancer patients: a single centre phase II trial"; British Journal of Cancer (2006) 94(6), pp. 792-797.

Vind, I et al. 2003. "Serum YKL-40, a Potential New Marker of Disease Activity in Patients with Inflammatory Bowel Disease" Scandinavian Journal of Gastroenterology 38:6, 599-605.

Wang et al. 2008. "YKL-40 a new biomarker in patients with acute coronary syndrome or stable coronary artery disease" Scandinavian Cardiovascular Journal, 42:5,295-302.

Winer E. et al.; "Clinical Cancer Advances 2008: Major Research Advances in Cancer Treatment, Prevention, and Screening—A Report From the American Society of Clinical Oncology"; Journal of Clinical Oncology; vol. 27; No. 5; Feb. 10, 2009; pp. 812-826.

Wong R. et al.; "Using Predictive Biomarkers to Select Patients With Advanced Colorectal Cancer for Treatment With Epidermal Growth Factor Receptor Antibodies"; Journal of Clinical Oncology; vol. 26; No. 35; Dec. 10, 2008; pp. 5668-5670.

Zheng, et al. 2005. "Determination of serum levels in YKL-40 and hyaluronic acid and in patients with hepatic fibrosis due to schistosomiasis japonica and appraisal of their clinical value" Acta Tropica 96, 148-152.

Østergaard, et al. 2002. "YKL-40 is elevated in cerebrospinal fluid from patients with purulent meningitis" Clinical and Diagnostic Laboratory Immunology, May, p. 598-604.

Bojesen et al., "Plasma YKL-40 levels in healthy subjects from the general population," Clin Chim Acta. 412:709-712 (2011).

Harutyunyan et al., "Serum YKL-40 predicts long-term mortality in patients with stable coronary disease: A prognostic study with the CLARICOR trial," Immunobiology. 1-7 (2012).

Harutyunyan et al., "The inflammatory biomarker YKL-40 as a new prognostic marker for all-cause mortality in patients with heart failures" Immunobiology. 217:652-656 (2012).

Messersmith et al., "Targeting EGFR in colorectal cancer," N Engl J Med. 359(17):1834-1836 (2008).

Mygind et al., "The inflammatory biomarker YKL-40 at admission is a strong predictor of overall mortality," J Intern Med. 273:205-216 (2013).

* cited by examiner

A

B

Individual changes in YKL-40 (ug/l) in patients with metastatic colorectal cancer during treatment with cetuximab and irinotecan Individual changes in YKL-40 (ratio) in patients with metastatic colorectal cancer during treatment with cetuximab and irinotecan

YKL-40 AS A MARKER FOR GASTROINTESTINAL CANCERS

CROSS-REFERENCE TO RELATED APPLICATIONS

This application is the U.S. National Stage of International Application PCT/DK2009/050241, filed Sep. 14, 2009, which in turn claims benefit of Denmark Application Nos. PA 2008 01292, filed Sep. 15, 2008; PA 2008 01293, filed Sep. 15, 2008; PA 2008 01294, filed Sep. 15, 2008; PA 2008 01465, filed Oct. 22, 2008; PA 2008 01471, filed Oct. 24, 2008; PCT/DK2009/050014, filed Jan. 22, 2009; PA 2009 00414, filed Mar. 25, 2009; and PA 2009 00900, filed Jul. 28, 2009; each of which is hereby incorporated by reference.

FIELD OF INVENTION

The present invention relates to the methods of classifying the severity, selecting a treatment for a gastrointestinal cancer in a subject and/or monitoring the progression of the disease before, during and after administering a treatment, wherein a predetermined level of YKL-40 above a reference level indicates the need for administering a treatment. The subject may suffer from any one or more gastrointestinal cancers. The present invention further relates to a kit and a device that may be used in the method of the present invention comprising means for measuring the level of YKL-40 in a sample; and means for comparing the measured level of YKL-40 with at least one reference level of YKL-40.

BACKGROUND OF INVENTION

Cancers of the gastrointestinal (GI) tract are some of the most common cancers in Europe and the US. Unfortunately, both upper and lower GI cancer remain relatively asymptomatic until late in the natural history of the disease. Upper GI cancer symptoms are often non-specific and by the time that 'alarm symptoms' such as dysphagia, abdominal pain, vomiting, weight loss, or anemia are present, the cancer is often at an advanced stage and the prognosis is poor. Therefore improving the survival diagnosis at an early stage is of utmost importance.

Treatment of patients with upper gastrointestinal (GI) cancers has not made the same positive progress as treatment of colorectal cancer during the last two decades. Pancreatic cancer is the $4^{th}$ most common cause of cancer death in men and women in US with approximately 34,000 estimated deaths in 2008. The incidence of gastic cancer is falling in US and Western Europe (1-3) and the estimated death in US in 2008 is 10,880 (1). The incidence of Gallbladder cancer and other extrahepatic biliary cancers are unchanged and there is 3,340 estimated death of this type of cancer in 2008 in US (1).

Operation is the only potentially curable treatment for upper GI cancers. A major problem is that 85% of patients with pancreatic cancer have already locally advanced or metastatic disease at time of diagnosis, and their median survival time is only 6 months and <10% are alive after 1 year. For patients with gastric cancer and biliary cancers there is an ongoing tendency towards better survival, because more patients have a lower stage at time of diagnosis with equivalent better chance of successful surgery, however <50% are alive after 1 year (and 24% after 5 years, US) (1-3). The treatment options for patients that can not be radically operated are palliative radio- or chemotherapy, with only poor response rates (4-6).

Administering a treatment for a given gastrointestinal cancer is typically based on the diagnosis of the disease, and occasionally on the severity of the disease disregarding the physiology of the individual suffering from the particular type of gastrointestinal cancer. Likewise, the continued treatment and monitoring of a gastrointestinal cancer is often according to a predetermined schedule, without paying too much attention to the individual patient.

Although, there might in the future be more effective chemotherapy regimes or new biological treatments, the best way to improve survival for patients with upper GI cancers is to diagnose the patients at an earlier stage. Identification of new biomarkers is a step in this direction.

A single marker or method that would facilitate selecting between treatments of varying efficacy and/or monitoring the progression or determining the stage of a gastrointestinal cancer prior to, during and following administration of a given treatment would greatly improve the ease with which these selection and monitoring processes occur today.

Carbohydrate (CA) 19-9 is the only routinely used biomarker in patients with pancreatic cancer, but has no value for screening or determining operability, and CA 19-9 is not useful in patients with gastric cancer or biliary cancer. Serum CA 19-9 is elevated in 70-80% of patients with pancreatic cancer, highest in metastatic disease, and high serum CA 19-9 is associated with short survival (7,8). However, 10-20% of patients with benign pancreatic diseases have also elevated serum CA 19-9. It is recommended to measure serum CA19-9 in patients with locally advanced metastatic pancreatic cancer at start of treatment and every 1-3 months during treatment. Elevations in serum CA 19-9 may reflect progression and should be confirmed with e.g. Computerized Tomography scanning (7,8).

The advantages associated with choosing the best possible treatment is not limited to be of benefit for the health of the individual suffering from the gastrointestinal cancer; it is also of benefit to the economy of the individual and the hospital/ the economy of the society at large.

Certain markers are known to be associated with specific cancer types; examples hereof include HER2 which is a marker of certain forms of breast cancer and EGFR which has been linked to e.g. colorectal cancer, pancreas cancer, head and neck cancer, lung cancer and glioblastoma multiforme.

Cetuximab (Erbitux®) is a chimeric mouse/human monoclonal antibody against the epidermal growth factor receptor (EGFR) and approved for use in patients with metastatic colorectal cancer and squamous cell carcinoma of the head and neck. Cetuximab is given as intravenous injection every week (400 mg/m² initial dose followed by 250 mg/m² every week) or every second week (400 mg/m² initial dose followed by 500 mg/m² every second week) as monotherapy or in combination with standard chemotherapy for metastatic colorectal cancer like irinotecan, oxaliplatin, and fluorouracil (5-FU) in combination with leucovorin or in combination with radiation therapy in patients with rectal cancer or squamous cell carcinoma of the head and neck (1-19).

Panitumumab (Vectibix®) is a fully human monoclonal antibody against the EGFR and approved for use in patients with metastatic colorectal cancer. Panitumumab is given as intravenous injection every second week (6 mg/kg) as monotherapy or in combination with standard chemotherapy for metastatic colorectal cancer (9, 20-23).

Recent data have demonstrated that patients with metastatic colorectal cancer and a mutation in the Kirsten ras (KRAS) gene, an oncogene downstream from the EGFR, have no effect of treatment with cetuximab and panitumumab. The KRAS encoded protein is a member of the small GTPAse superfamily, and a single amino acid substitution in the KRAS gene results in an activating mutation. Since summer 2008 only colorectal cancer patients with KRAS wild type are recommended to be treated with cetuximab and panitumumab. KRAS is mutated in approximately 30% to 45% of all colorectal tumors, resulting in a constitutively active EGF signalling pathway (6-9, 11, 12, 13, 14, 21, 24, 25, 26). The identification of KRAS as a predictive biomarker of response to anti-EGFR therapy has obvious benefits. First, close to half of patients with metastatic colorectal cancer will avoid unnecessary exposure to an ineffective therapy that has the potential to cause significant toxicities. Second, the potential cost savings to the health care system are profound, approximately $ 600 million each year in USA (8 weeks of treatment with cetuximab cost approximately $ 19,000).

However, KRAS mutations are not the only factor influencing response to anti-EGFR antibodies. Approximately 25% to 40% of patients with KRAS wild type do not respond to anti-EGFR antibody. Approximately 10% of these patients have mutations in the BRAF gene. This causes a change in the BRAF protein that can increase growth and spread of cancer cells. BRAF is an isoform of RAF. RAF proteins are intermediate to RAS and MAPK in the cellular proliferation pathway. RAF proteins are typically activated by RAS via phosphorylation, and activated RAF proteins in turn activate MAPK via phosphorylation. Furthermore some patients with KRAS wild type have a loss of protein expression of PTEN, a tumor supressor gene, and some have low expression of either amphiregulin (AREG) or epiregulin (EREG) and these patients have less response to cetuximab (9, 12, 26, 27, 28, 29). These recent studies need to be validated and it is not yet recommended to test for BRAF mutations or expression of PTEN, AREG or EREG before treatment with cetuximab or panitumumab. Even if both KRAS and e.g. BRAF was used in order to predict the responsiveness to such treatment about 40% KRAS wildtype patients remain that are unresponsive towards the treatment (26,29).

Thus identification of other predictive biomarkers is imperative to improve the selection of patients with GI cancers such as for example metastatic colorectal cancer for treatment with antibodies against EGFR or for the treatment with other biologic agents such as e.g. antibodies against VEGF.

An ideal biomarker for GI cancer should have the quality of being able to identify the patients at an early stage and help the surgeon select the right patients for operation. The biomarker could also be useful for monitoring the disease recurrence/progression after operation or chemotherapy and help the oncologist to evaluate the effect of chemotherapy in order to give a more individual treatment. There is no such biomarker for patients with GI cancer and especially upper GI cancer.

Administering the best possible treatment for each individual patient with gastrointestinal cancer would improve the efficacy of any treatment whether it involves administration of medicaments, surgery, or other and independent of whether the treatment given is prophylactic, curative or ameliorative. A classification of the individuals suffering from a gastrointestinal cancer according to survival prognosis and time to progression would be of assistance in determining the best possible treatment, improve the effect of an administered treatment, improve the survival rate, lower relapse risks, and heighten the quality of life following the outbreak of a gastrointestinal cancer.

Likewise, monitoring the treatment administered to any individual patient depending upon the progression and/or state of their disease would be of assistance in determining the most effective immediate and follow-up treatment, and be of guidance when counseling on e.g. lifestyle chances required subsequent to the occurrence of a gastrointestinal cancer.

SUMMARY OF INVENTION

The present invention relates to a method for diagnosing and/or classifying the severity and/or determining a therapy and/or monitoring a therapeutic treatment of a gastrointestinal cancer in a subject, said method comprising:
 i) determining the level of YKL-40 in a sample obtained from the subject; and
 ii) comparing said level of YKL-40 with a reference level of YKL-40;
wherein a level of YKL-40 in the sample above the reference level indicates the presence of a gastrointestinal cancer and/or the severity of said cancer is deduced from said comparison and/or deducing the progress and/or state of said cancer by said comparison, and/or based thereon determining a therapy to be initiated, continued, terminated or replaced.

The one or more reference levels of YKL-40 may for instance be one single reference level or a set of reference levels, e.g. one or more reference levels, of YKL-40 obtained by measuring the YKL-40 levels in samples from healthy individuals. Preferably the reference level is the $95^{th}$ percentile of YKL-40 in healthy individuals.

Thus it follows that a first aspect of the present invention relates to a method for diagnosing the presence of a gastrointestinal cancer in a subject, said method comprising
 i) determining the level of YKL-40 in a sample obtained from the subject; and
 ii) comparing said level of YKL-40 with one or more age-adjusted reference levels of YKL-40;
wherein a level of YKL-40 in the sample above the reference levels indicates the presence of a gastrointestinal cancer.

Additionally, a second aspect of the present invention relates to a method for classifying the severity of a gastrointestinal cancer in a subject, said method comprising
 i) determining the level of YKL-40 in a sample obtained from the subject; and
 ii) comparing said level of YKL-40 with one or more age-adjusted reference levels of YKL-40;
wherein a level of YKL-40 in the sample above the one or more reference levels indicates the severity of said gastrointestinal cancer.

Additionally, a third aspect of the present invention relates to a method for determining a therapy for a gastrointestinal cancer in a subject, said method comprising:
 i) determining the level of YKL-40 in a sample obtained from the subject; and
 ii) comparing said level of YKL-40 with one or more reference levels of YKL-40;
based thereon determining a therapy to be initiated, continued, terminated or replaced.

Additionally, a fourth aspect of the present invention relates to a method for monitoring therapeutic treatment, preferably selected from the group consisting of chemotherapeutic agents, biological agents, radiotherapy and combinations thereof, of a gastrointestinal cancer, preferably an upper gastrointestinal cancer, in a subject, said subject being treated for a specific disease, said method comprising
 i) determining the level of YKL-40 in a sample obtained from the subject;
 ii) comparing said level of YKL-40 with one or more reference levels of YKL-40; wherein the level of YKL-40 with respect to the one or more reference levels indicates the progress and/or state of said gastrointestinal cancer, and therefore the degree of efficacy of the ongoing therapeutic treatment; and iii) based thereon determining whether the therapeutic treatment of the gastrointestinal cancer is to be continued, terminated or replaced.

A further aspect of the present invention relates to a method for determining a prognosis for a subject suffering from an upper gastrointestinal cancer and being treated with a therapeutic treatment selected from the group consisting of chemotherapeutic agents, biological agents, radiotherapy, and combinations thereof, said method comprising i) determining the level of YKL-40 in a sample obtained from the subject;

ii) comparing said level of YKL-40 with one or more reference levels of YKL-40;

wherein the level of YKL-40 with respect to the reference levels indicates the development or progression of said gastrointestinal cancer during or after the specific treatment regime and therefore the prognosis.

Yet another aspect of the present invention relates to a method for determining the effect of a therapy for a gastrointestinal cancer in a subject, said method comprising:

i) determining the level of YKL-40 in a sample obtained from said subject after a period of treatment; and ii) comparing said YKL-40 level with one or more previously determined levels of YKL-40 from the same subject, where an YKL-40 level from step i) below or equal to the one or more previous levels in step ii) indicates a response to said treatment, or an YKL-40 level from step i) above the one or more previous levels in step ii) indicates that the subject may be non-responsive to said treatment.

The reference level(s) is in one embodiment of the above-mentioned four aspects of the present invention a reference level obtained from the same subject and thus a set of embodiments relate to the following:

A method for diagnosing and/or classifying the severity and/or determining a therapy and/or monitoring a therapeutic treatment of a gastrointestinal cancer in a subject, said method comprising:

i) determining the level of YKL-40 in a sample obtained from the subject; and ii) comparing said level of YKL-40 with a reference level of YKL-40, said reference level being a previously determined level of YKL-40 from the same subject;

wherein a level of YKL-40 in the sample above the reference level indicates the presence of a gastrointestinal cancer and/or the severity of said cancer is deduced from said comparison and/or deducing the progress and/or state of said cancer by said comparison, and/or based thereon determining a therapy to be initiated, continued, terminated or replaced.

The methods described above optionally relates to embodiments where the gastrointestinal cancer is an upper GI cancer such as: esophageal cancer, gastric/stomach cancer, pancreatic cancer and/or biliary cancer; most preferably the upper GI cancer is pancreatic cancer.

Alternatively, the methods describe above relates to embodiments where the gastrointestinal cancer is a lower GI cancer such as: small intestine cancer, duodenum cancer, appendix cancer, colon cancer, rectal cancer, colorectal cancer and/or anal cancer; most preferably the lower GI cancer is colorectal cancer.

Specific embodiments of the third and fourth aspect of the present invention relates to monitoration of the gastrointestinal cancer after operation or during treatment with a chemotherapeutic agent, radiotherapy or biologics, i.e. biologic agents. More specific embodiments relastes to the monitoration of the gastrointestinal cancer during treatment with a chemotherapeutic agent.

The present invention further encompass a fifth aspect relating to a device for determining a therapy for and/or monitoring a therapeutic treatment of a gastrointestinal cancer in a subject, wherein the device comprises means for measuring the level of YKL-40 in a sample; and means for comparing the measured level of YKL-40 with one or more reference levels of YKL-40.

Furthermore, the present invention encompass a sixth aspect relating to a kit of parts comprising i) means for measuring the level of YKL-40 in a sample; ii) means for comparing the measured level of YKL-40 with one or more reference level of YKL-40; and iii) instructions on how to age adjust the reference level of YKL-40, according to the age of the subject providing the sample.

DESCRIPTION OF DRAWINGS

in FIG. 17A) or multiple control or standard fields (4a. to 4.e. in FIG. 17B). Standards of a single (for 3.) or various (one concentration for each field in increasing or decreasing order, e.g.) YKL-40 concentrations may be applied to the control or standard fields to enable reading a positive/negative result with the stick portrayed in FIG. 17A or assessing an approximate concentration of YKL-40 in the biological sample compared to which of the control fields in FIG. 17B the sample/assay field resembles the most, post testing.

Figure 19A:
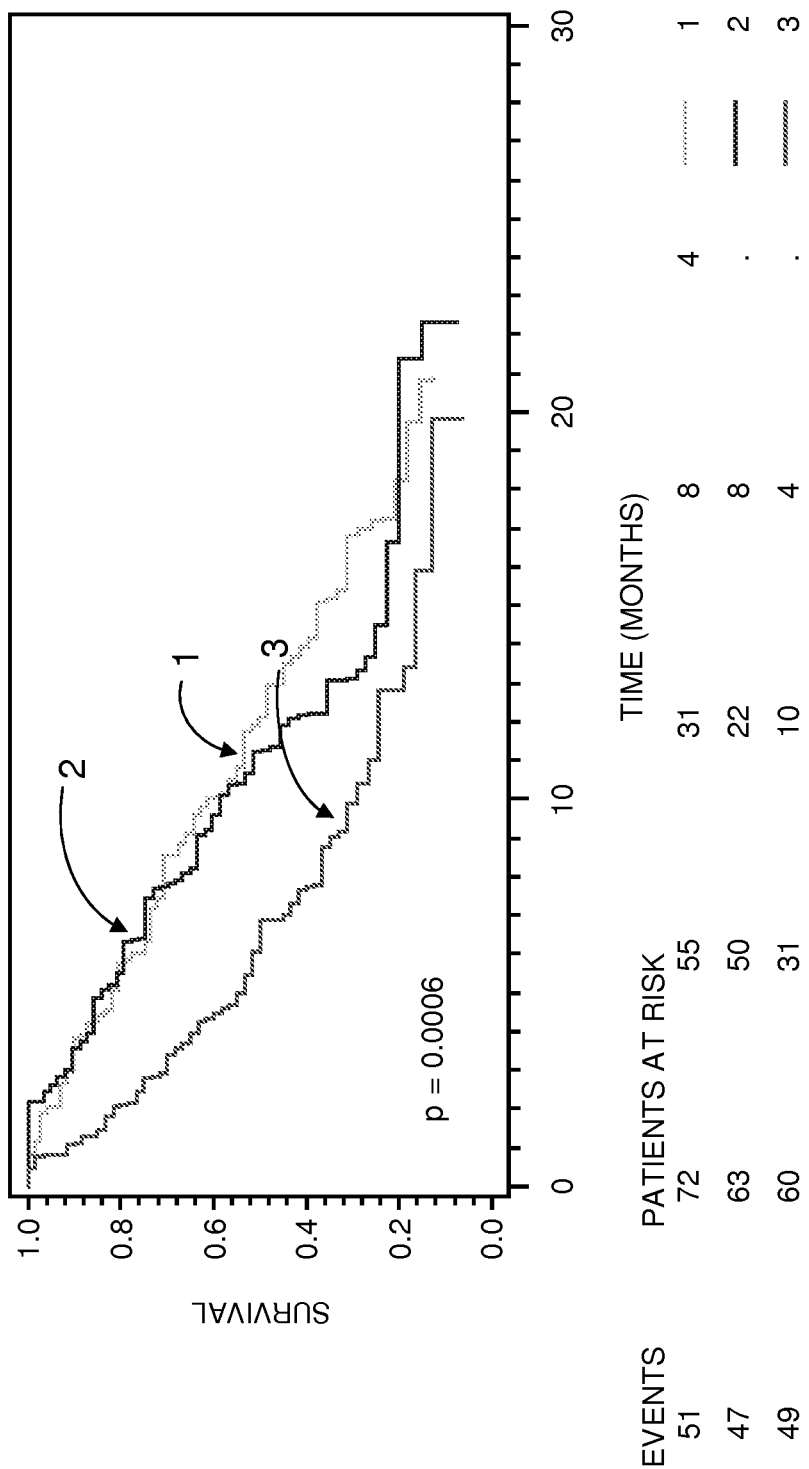
FIG. 19. Study 1. Kaplan-Meier curves showing the association between the pretreatment plasma YKL-40 levels and overall survival in patients with metastatic colorectal cancer treated with irinotecan and cetuximab (FIG. 19A). The P-value refers to the log-rank test for equality of strata. Patients are divided into tertiles according to their pretreatment plasma YKL-40 levels. Patients in Group 3 have the highest plasma YKL-40 levels. Plasma YKL-40: Group 1: <84 µg/l; Group 2: ≥84 and ≤218 µg/l; and Group 3: >218 µg/l.
Figure 19B:
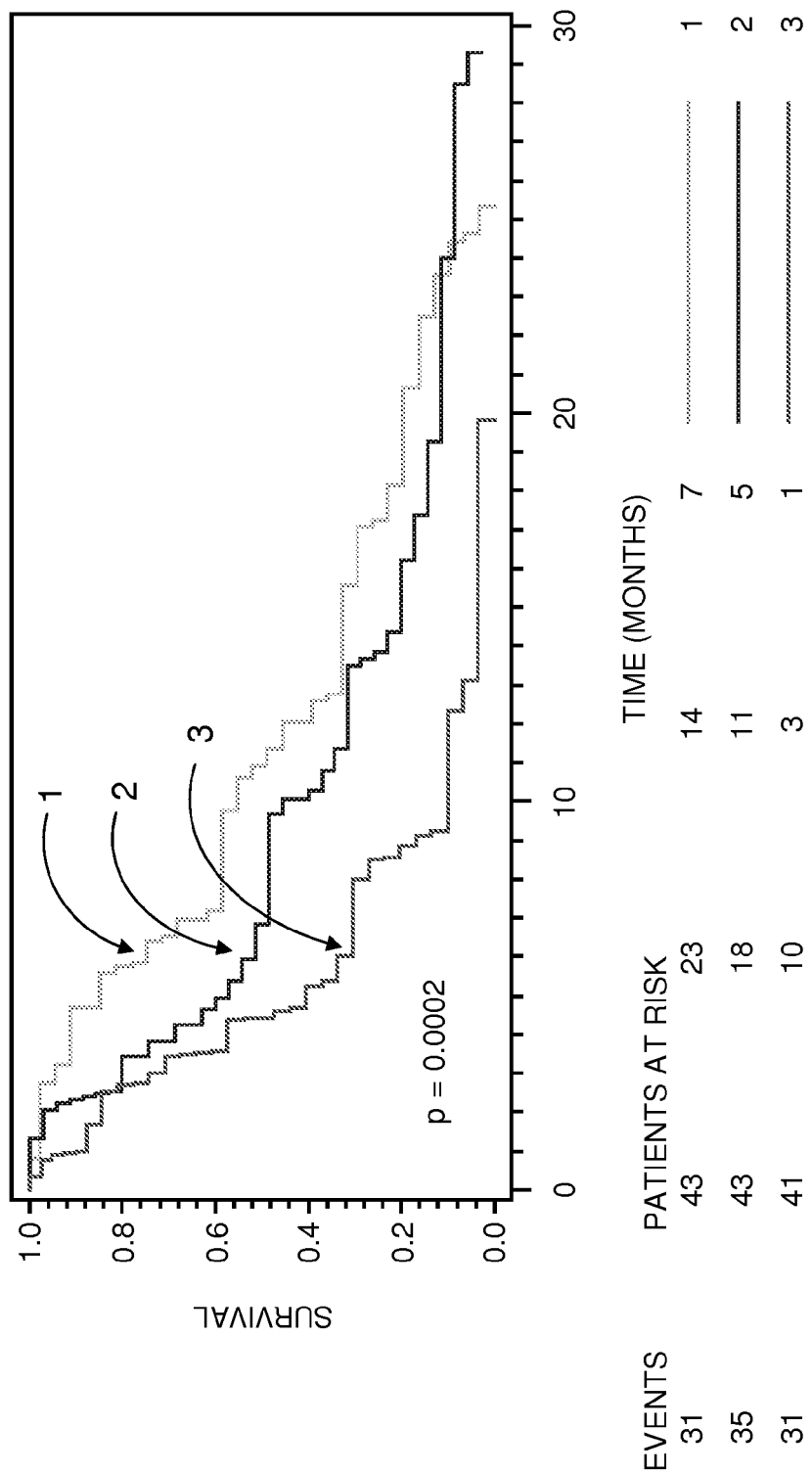

Study 2. Kaplan-Meier curves showing the association between the pretreatment serum YKL-40 levels and overall survival in patients with metastatic colorectal cancer treated with irinotecan and cetuximab (FIG. 19B). The P-value refers to the log-rank test for equality of strata. Patients are divided into tertiles according to their pretreatment serum YKL-40 levels. Patients in Group 3 have the highest serum YKL-40 levels. Serum YKL-40: Group 1: <94 µg/l; Group 2: ≥94 and ≤253 µg/l; and Group 3: >253 µg/l.

FIG. 20. Study 1. Kaplan-Meier curves showing the association between the pretreatment plasma YKL-40 levels and overall survival in patients with metastatic colorectal cancer treated with irinotecan and cetuximab according to KRAS status (FIG. 20A: wild type; FIG. 20B: mutations). The P-value refers to the log-rank test for equality of strata. Patients are divided into tertiles according to their pretreatment plasma YKL-40 levels. Patients in Group 3 have the highest plasma YKL-40 levels. Plasma YKL-40: Group 1: <84 μg/l; Group 2: ≥84 and ≤218 μg/l; and Group 3: >218 μg/l.

Study 2. Kaplan-Meier curves showing the association between the pretreatment serum YKL-40 levels and overall survival in patients with metastatic colorectal cancer treated with irinotecan and cetuximab according to KRAS status (FIG. 20C: wild type; FIG. 20D: mutations). The P-value refers to the log-rank test for equality of strata. Patients are divided into tertiles according to their pretreatment serum YKL-40 levels. Patients in Group 3 have the highest serum YKL-40 levels. Serum YKL-40: Group 1: <94 μg/l; Group 2: ≥94 and ≤253 μg/l; and Group 3: >253 μg/l.

FIG. 21. Study 1. Kaplan-Meier curves showing the association between the pretreatment plasma YKL-40 levels and overall survival in patients with metastatic colorectal cancer treated with irinotecan and cetuximab according to increasing cut-off levels of plasma YKL-40 in healthy subjects (age-corrected). FIG. 21A: 90 percentile; FIG. 21B: 95 percentile; FIG. 21C: 97.5 percentile; FIG. 21D: 99 percentile; FIG. 21E: 99.5 percentile; and FIG. 21F: 99.9 percentile. The P-value refers to the log-rank test for equality of strata.

FIG. 22. Study 2. Kaplan-Meier curves showing the association between the pretreatment serum YKL-40 levels and overall survival in patients with metastatic colorectal cancer treated with irinotecan and cetuximab according to increasing cut-off levels of serum YKL-40 in healthy subjects (age-corrected). FIG. 22A: 90 percentile; FIG. 22B: 95 percentile; FIG. 22C: 97.5 percentile; FIG. 22D: 99 percentile; FIG. 22E: 99.5 percentile; and FIG. 22F: 99.9 percentile. The P-value refers to the log-rank test for equality of strata.

Figure 23A:
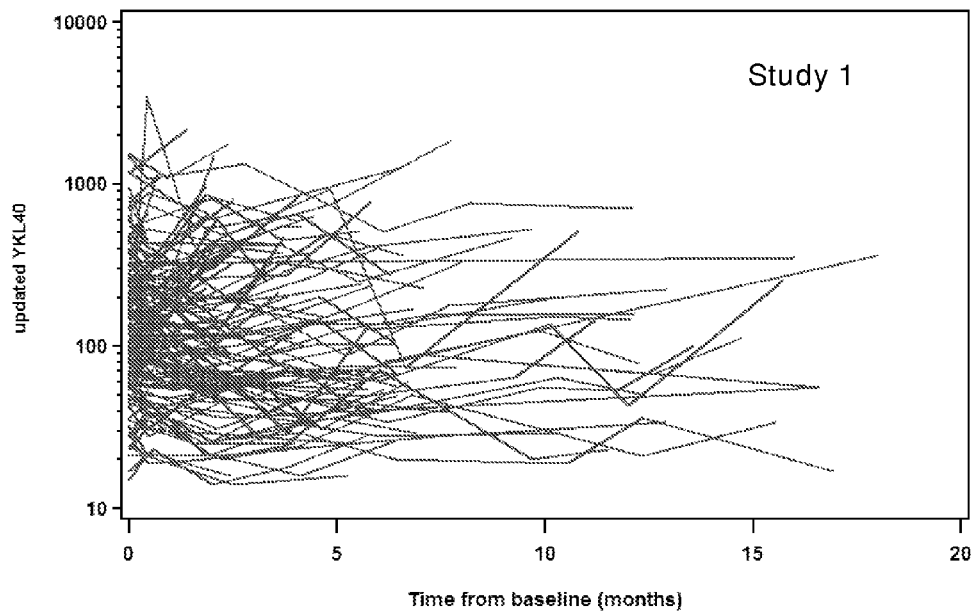
Figure 23B:
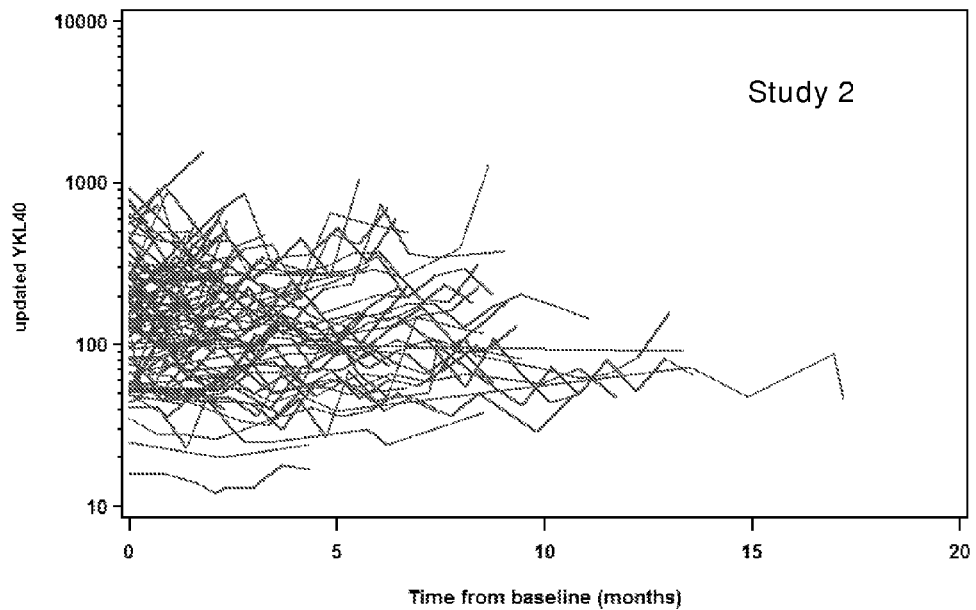

FIG. 23A-B. Individual changes in YKL-40 (μg/l) in patients with metastatic colorectal cancer during treatment with cetuximab and irinotecan. The results from Study 1 are shown in A, and from Study 2 in B.

Figure 24A:
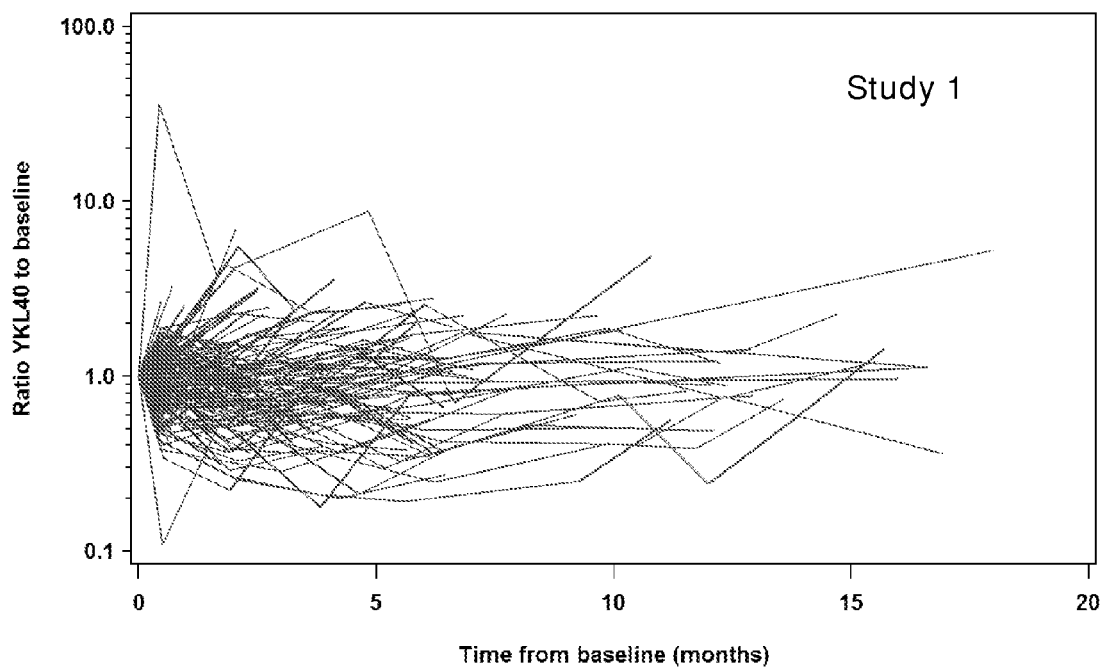
Figure 24B:
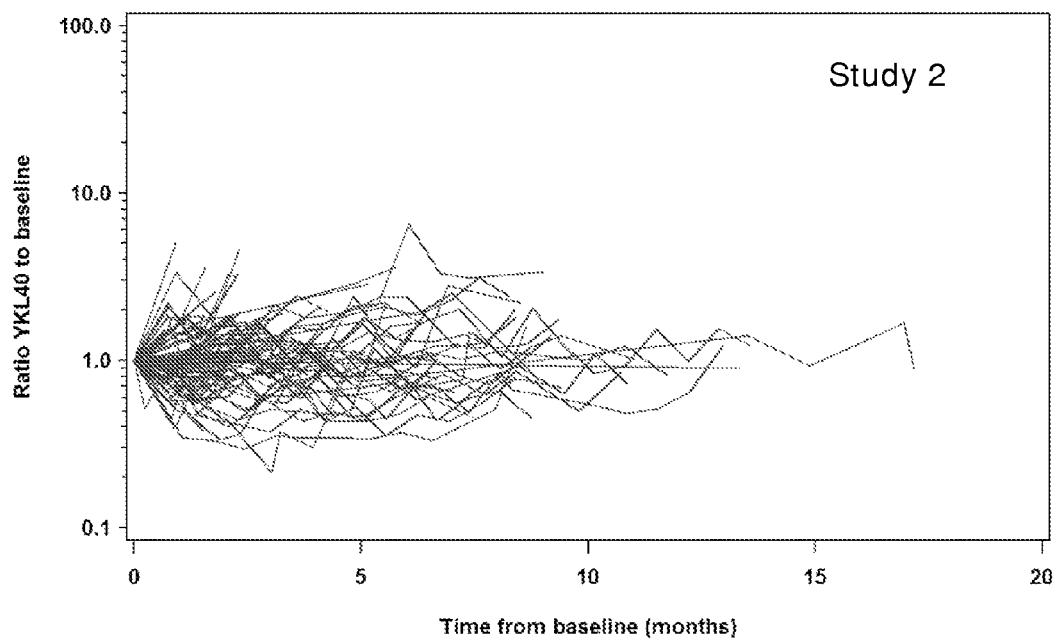

FIG. 24A-B. Individual changes in YKL-40 (ratio) (calculated/defined as the level at the different timepoints during treatment divided by the baseline level=pre-treatment level) in patients with metastatic colorectal cancer during treatment with cetuximab and irinotecan. The results from Study 1 are shown in A, and from Study 2 in B.

Figure 25A:
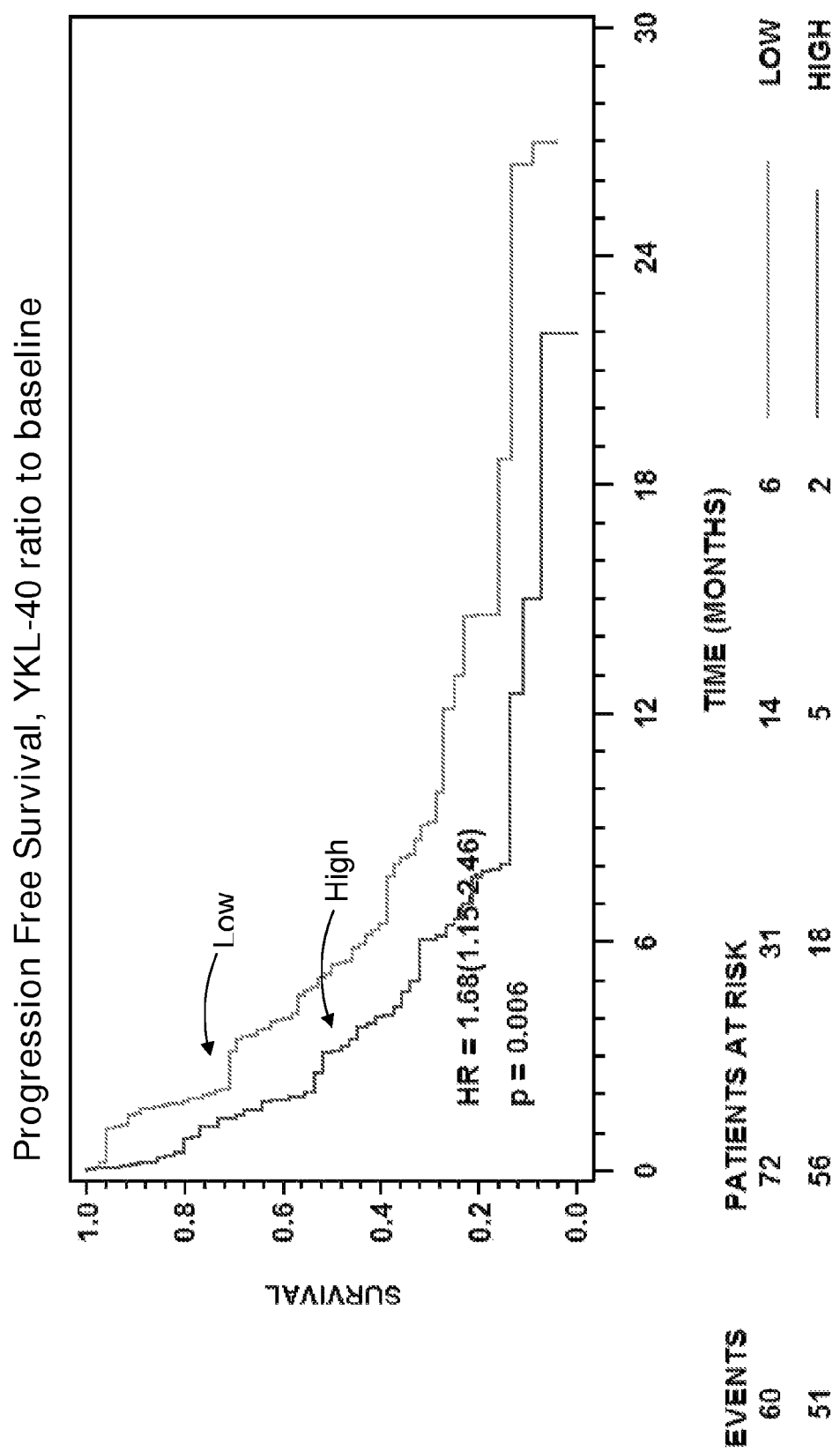
Figure 25B:
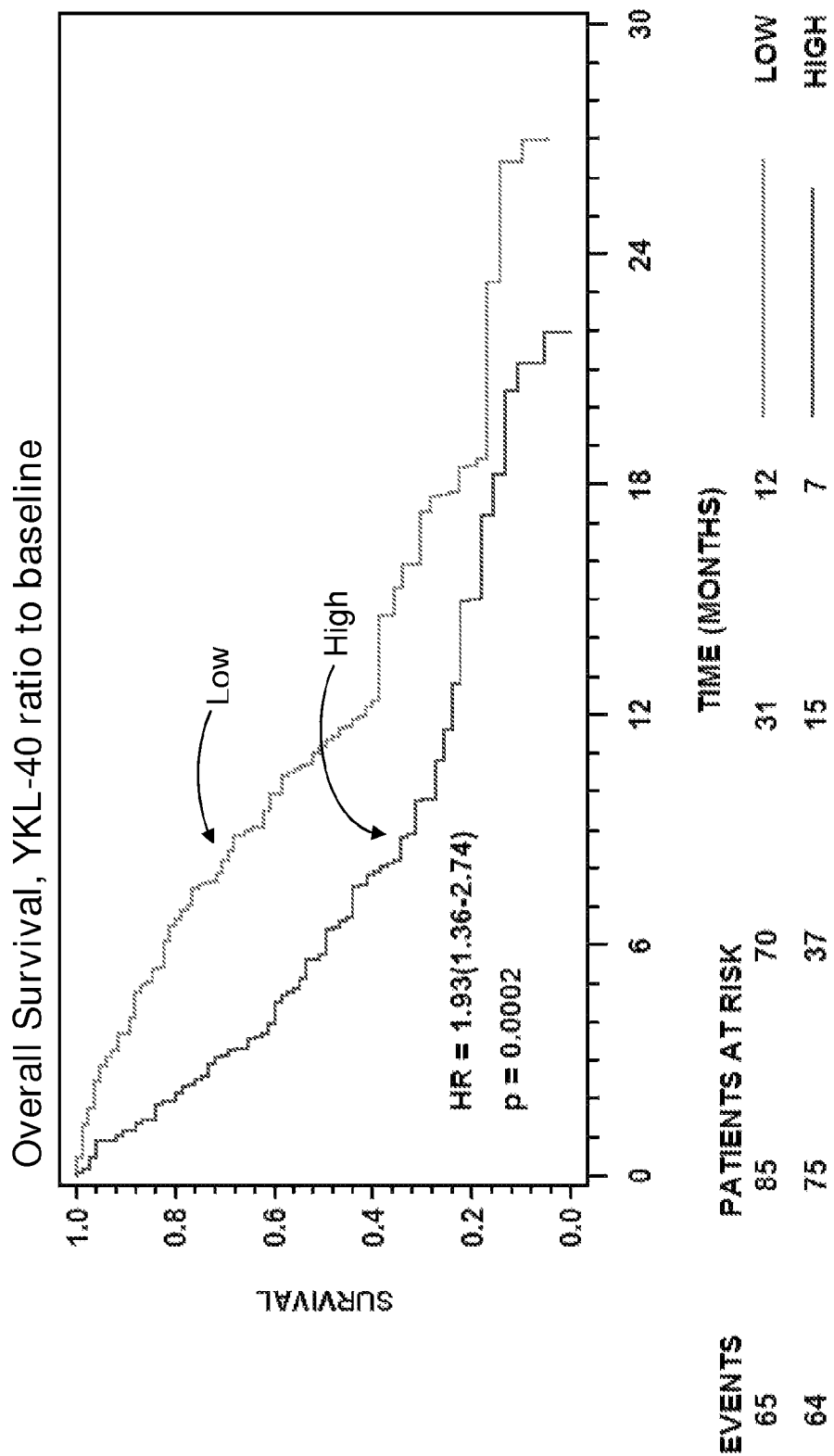

FIG. 25A-B. Kaplan-Meier survival curves of progression free survival (A) and overall survival (B) showing the association between the ratios of YKL-40 in blood samples collected 2-3 months after start of cetuximab treatment and compared to baseline YKL-40 levels in patients with metastatic colorectal cancer (the ratio is calculated/defined as the level of YKL-40 after 2-3 months of treatment divided by the baseline level=pre-treatment level). Low ratio (≤1) reflects a decrease in YKL-40 at 2-3 months compared to pre-treatment. High ratio (>1) reflects an increase in YKL-40 at 2-3 months compared to pre-treatment. The P-value refers to the log-rank test for equality of strata. The patients are dichotomized in two groups with high or low ratio.

DETAILED DESCRIPTION OF THE INVENTION

The present inventors have surprisingly found that the YKL-40 level can be used as a biomarker for determining a therapy for and/or monitoring a therapeutic treatment of a gastrointestinal cancer in a subject, based on a comparison of a measured YKL-40 level with one or more reference levels of YKL-40.

The present inventors have furthermore found that the YKL-40 level can be used as a marker for keeping track of the development of a gastrointestinal cancer and accordingly the prognosis of the patient, i.e. whether the gastrointestinal cancer e.g. evolves towards a more or a less severe stage of the disease, hereby repeatedly and/or continuously classifying the severity of a gastrointestinal cancer over time and thus allowing for the determination of whether to continue the ongoing treatment, replace the treatment with one of higher or lower efficacy or simply alter the administration of the ongoing treatment as well as whether it is prudent to terminate the ongoing treatment. In one embodiment of the invention this is especially interesting and feasible when an YKL-40 measurement in a subject is compared to one or more reference levels which are previously obtained measurement from the same subject. Accordingly, by the methods according to the present invention the YKL-40 level can be used not only to determine which treatment to administer based on a determination of the YKL-40 level in a subject, but also to determine which treatment to continue with as determined by monitoration of the YKL-40 level or the development in the YKL-40 level in a subject.

Furthermore, the present invention discloses that the YKL-40 level can be used as a biomarker giving an indication of the presence of a gastrointestinal cancer. Accordingly, by the method according to the present invention the YKL-40 level can be used to diagnose the presence of a gastrointestinal cancer.

The methods according to the present invention provides a new general biomarker in the form of the YKL-40 level in relation to gastrointestinal cancers and/or the treatment thereof. Accordingly, it is further envisaged that the method according to the present invention, may be used as a diagnostic tool in connection with a companion diagnostic test in personalized medicine. This could for instance be in relation to YKL-40 ligands, or any other type of active compounds used to treat a gastrointestinal cancer, or especially in relation to biologic agents such as EGFR ligands as described further herein below.

The following definitions are provided to simplify discussion of the invention. They should not, therefore, be construed as limiting the invention, which is defined in scope by the appended claims and the specification in its entirety.

The terms "gastrointestinal cancer", "GI cancer", "diseases" and "disorders" as used herein, are intended to mean any gastrointestinal cancer, such as, but not limited to, upper GI cancers, such as, but not limited to, esophageal cancer, gastric/stomach cancer, pancreatic cancer and/or biliary cancer; lower GI cancers, such as, but not limited to, small intestine cancer, duodenum cancer, appendix cancer, colon cancer, rectal cancer, colorectal cancer and/or anal cancer; and other GI cancers, such as, but not limited to, GIST, peritoneal and/or hepatic cancer. The gastrointestinal cancer may be either local or metastatic variants thereof, unless otherwise specified.

Patients with the same disease can have marked differences in the disease severity (i.e. different grades of how serious the disease is). The terms "severe stage", "severity", "less severe" and "more severe", as used herein, are intended to mean a graduation of severity according to for example prognosis for being cured, prognosis for survival, or according to different predetermined stages of diseases. Such stages may be according to various symptoms, and/or traditionally measureable levels of biomarkers, physical functions etc. When focusing on the development of a disease in one and same subject, then a more severe stage refers to a worsening of the disease, whereas a less severe stage than previously determined refers to a bettering of the disease, e.g. due to a satisfactory treatment regime. The stages may furthermore be in relation to for example local versus metastatic gastrointestinal cancers. As the prognosis of a patient may be independent of a classical staging of the disease in question, the terms "a more severe stage" and "a less severe stage", as used herein, is also intended to mean a worsening or a bettering of the prognosis of the patient, respectively. For patients suffering from a gastrointestinal cancer disease the prognosis is typically a prognosis relating to expected time before progression, or time before death. Accordingly, a worsening of the prognosis typically corresponds to a shorter survival period.

The terms "determining a therapy and/or therapeutic treatment", "determining a therapy" and "determining a therapeutic treatment" cover in principle the determination of any treatment that a person skilled in the art would administer to a subject for which the YKL-40 level has been determined and compared to that of one or more reference levels. Preferably, the terms cover the determination of the most optimal therapy and/or treatment. Hereby is meant the treatment that is best suited for the individual patient in terms of any of the following: ameliorating discomfort, alleviating symptoms, curing the disease, providing the best possible quality of life and so forth for the subject. The terms "therapy", "therapies", "therapeutic treatment", and "treatment" are used interchangeable herein. The terms "best possible", "most optimal", and so forth in regards to a therapy and/or therapeutic treatment are used interchangeably herein.

The therapies and or therapeutic treatments to be initiated, continued, terminated, altered or replaced may be any kind of therapy such as, but not limited to the administration of medicaments and/or surgery, and may be prophylactic, curative or ameliorative.

A therapy and/or therapeutic treatment may be initiated if none is ongoing, or may be continued if it is already taking place. A therapy and/or therapeutic treatment may be terminated if it is found unsuitable or if it requires replacing by an alternative method of therapy and/or therapeutic treatment. By altering a treatment is understood that the treatment is changed for example the dosage is increased or decreased, the concentrations of the drugs are increased or decreased, the administration/dosage regimen is increased or decreased and so on.

The term "ameliorate", as used herein, is intended to mean to improve or make better; in association with a disease state a lessening in the severity or progression of a disease state, including remission or cure thereof, alternatively the perceived lessening of severity such as lessening of associated pain.

The term "antibody", as used herein, is intended to mean Immunoglobulin molecules and active portions or fragments of immunoglobulin molecules such as Fab and F(ab').sub.2 which are capable of binding an epitopic determinant of the YKL-40 protein. Antibodies are for example intact immunoglobulin molecules or fragments thereof retaining the immunologic activity. An example of an antibody is Cetuximab, which is a monoclonal antibody directed against the epidermal growth factor receptor (EGFR). The term "antigen", as used herein, is intended to mean an immunogenic full-length or fragment of an YKL-40 molecule.

The term "biological sample", as used herein, is intended to mean a sample obtained from a subject or individual.

The term "biomarker", as used herein, is intended to mean a molecular indicator of a specific biological property, such as a pathological or physiological state.

The terms "subject" and/or "individual", as used herein, is intended to mean a single member of a species, herein preferably a mammalian species. The term "mammal", as used herein, is intended to include both humans and non-humans. The term "patient" as used herein, is intended to mean any individual suffering from a gastrointestinal cancer.

The term "hnRNA", as used herein, means heteronuclear RNA. The term "mAb", as used herein, means monoclonal antibody. The term "mRNA", as used herein, means messenger RNA. The term "RNA", as used herein, means any type of RNA originating alternatively isolated from nature or synthesized. The term "substantially pure", as used herein to describe YKL-40, refers to the substantially intact molecule which is essentially free of other molecules with which YKL-40 may be found in nature.

The term "chemonaive", as used herein in relation to subjects, is intended to refer to subjects that not previously have been treated with one or more chemotherapeutics in relation to their present gastrointestinal cancer disease.

The term "pre-treatment level", as used herein e.g. in relation to YKL-40 levels, is intended to mean the level of e.g. YKL-40 as measured in a subject prior to the initiation of a treatment, such as for example, but not limited to, an initiation of a specific treatment, a change in a specific treatment to another treatment regime, or an addition of a new treatment to an existing treatment regime. The subject may for example have been treated with a chemotherapeutic agent previously, and the pre-treatment level is then the level prior to the initiation of a new chemotherapeutic agent and/or a biologic agent. A pre-treatment level may furthermore, e.g. in the examples be termed a "baseline" level.

The terms "pre-treated", "previously treated", "first-line", "second-line", and "third-line", etc., as used herein in relation to chemotherapeutics or biologics, are intended to refer to subjects previously or at present being treated with chemotherapeutics or biologics in relation to the specific gastrointestinal cancer in question. For example, subjects being previously treated with first-line chemotherapeutics refers to subjects being treated for the first time with chemotherapeutics for locally advanced or metastatic cancer. Likewise, subjects being treated with second-line chemotherapeutics refers to subjects being treated previously with one other different chemotherapeutic regimen and optionally biologics for locally advanced or metastatic cancer. Likewise, subjects being treated with third-line chemotherapeutics refers to subjects being treated previously with two other different chemotherapeutic regimens and optionally biologics for locally advanced or metastatic cancer. Accordingly, subjects have during treatment of their present cancer disease received, or are still receiving, treatment with chemotherapeutic agents. The terms "pre-treated and "previously treated" are used interchangeably herein.

The present invention relates to a method for diagnosing and/or classifying the severity and/or determining a therapy and/or monitoring a therapeutic treatment of a gastrointestinal cancer in a subject, said method comprising:

i) determining the level of YKL-40 in a sample obtained from the subject; and
ii) comparing said level of YKL-40 with a reference level of YKL-40;

wherein a level of YKL-40 in the sample above the reference level indicates the presence of a gastrointestinal cancer and/or the severity of said cancer is deduced from said comparison and/or deducing the progress and/or state of said cancer by said comparison, and/or based thereon determining a therapy to be initiated, continued, terminated or replaced. Further, more specific aspects of the method(s) according to the present invention will be described in detail in the following, and especially in the sections relating to the different aspects.

One embodiment of the method according to the present invention relates to a method for determining a therapy for and/or monitoring a therapeutic treatment of a gastrointestinal cancer in a subject, said method comprising:
i) determining the level of YKL-40 in a sample obtained from the subject;
ii) comparing said level of YKL-40 with one or more reference levels of YKL-40, wherein the level of YKL-40 with respect to the reference levels indicates the progress and/or state of said gastrointestinal cancer; and
iii) deducing the progress and/or state of said gastrointestinal cancer by said comparison, and based thereon determining a therapy to be initiated, continued, terminated or replaced.

In some embodiments of the method(s) according to the invention said one or more YKL-40 reference levels is one or more previously determined levels of YKL-40 from the same subject.

Hence, a more specific embodiment of the above mentioned method of the present invention relates to a method for determining a therapy for and/or monitoring a therapeutic treatment of a gastrointestinal cancer in a subject, said method comprising
i) determining the level of YKL-40 in a sample obtained from the subject;
ii) comparing the level of YKL-40 with one or more reference levels of YKL-40, said reference levels being one or more previously determined levels of YKL-40 from the same subject wherein the level of YKL-40 with respect to the reference levels indicates the progress and/or state of said gastrointestinal cancer; and
iii) deducing the progress and/or state of said gastrointestinal cancer by said comparison, and based thereon determining a therapy to be initiated, continued, terminated or replaced,
wherein a level of YKL-40 in the sample being increased to at least a factor 1.10 compared to the reference level of YKL-40 indicates that the gastrointestinal cancer has evolved to a more severe stage of the gastrointestinal cancer, and e.g. thus requires a therapy of high efficacy to be initiated and/or requires a therapy with higher efficacy than the ongoing therapy to be initiated, e.g. the increase in YKL-40 may indicate that the subject do not respond to the present therapeutic regime, which may then be terminated and/or replaced by another therapeutic regime; and wherein a level of YKL-40 in the sample being decreased to at least a factor 0.90 compared to the reference level of YKL-40 indicates that the gastrointestinal cancer has evolved to a less severe stage of the gastrointestinal cancer, and e.g. that the subject has responded to the treatment and that the therapy therefore may be continued.

The methods according to the present invention are relevant for classifying the severity of any gastrointestinal cancer, such as e.g. any one or more diseases or disorders, for determining the best possible treatment hereof. Said diseases or disorders may for instance be any disease or disorder for which the YKL-40 level is increased. In relation to methods according to the invention where the one or more reference levels of YKL-40 is one or more previously determined YKL-40 levels from the same subject, the gastrointestinal cancer may have been diagnosed prior to, during or after the measurement of the previously determined YKL-40 levels; in a preferred embodiment, the gastrointestinal cancer is a previously diagnosed gastrointestinal cancer.

It is further an object of the present invention to provide a method for monitoring the health state of an individual suffering from any one or more diseases or disorders for determining the best possible treatment hereof in relation to a prognosis of their survival, said method comprising: measuring the level of YKL-40 in a biological sample from said individual; and comparing the measured level to a reference level of YKL-40.

It has been found that the serum or plasma YKL-40 level in an individual is stable over long time, and independent of diurnal and weekly changes; it has furthermore been found that the level is independent of at least 20 minutes of exercise. Accordingly, one measurement of the serum or plasma YKL-40 level in an individual can be used in the methods according to the invention. Preferably, the sample may be obtained from a subject that for example have abstained from heavy alcohol consumption the previous day and that for example do not have evident symptoms of e.g. bacterial infections. If necessary a second or further sample may be obtained at a later time point (e.g. after 2 weeks) to confirm the results of the first determined level of YKL-40.

The methods according to the present invention can be used to classify the severity of diseases that also may be identified and/or classified by CRP, but can furthermore be used to classify diseases that will not give a response in the CRP level. Accordingly, in one embodiment of the present invention, the gastrointestinal cancer is one or more diseases or disorders or a group of diseases or disorders that do not always provide an elevated C-reactive protein level.

The methods described herein above optionally relates to embodiments where the gastrointestinal cancer is an upper GI cancer such as: esophageal cancer, gastric/stomach cancer, pancreatic cancer and/or biliary cancer; most preferably the upper GI cancer is pancreatic cancer.

Alternatively, the methods described herein relates to embodiments where the gastrointestinal cancer is a lower GI cancer such as: small intestine cancer, duodenum cancer, appendix cancer, colon cancer, rectal cancer, colorectal cancer and/or anal cancer; more preferably the lower GI cancer is colorectal cancer.

First Aspect of the Invention—a Method for Diagnosing

At time of diagnosis many patients with pancreatic cancer, gastric cancer and biliary cancer (both patients with locally advanced disease and patients with metastatic disease) have elevated plasma YKL-40 levels compared to healthy age-matched subjects.

The first aspect of the present invention relates to a method for diagnosing the presence of a gastrointestinal cancer in a subject, said method comprising
i) determining the level of YKL-40 in a sample obtained from the subject; and
ii) comparing said level of YKL-40 with one or more reference levels of YKL-40 from the following age dependent cut-off values defined as:
the $70^{th}$ percentile: $\ln(\text{plasma YKL-40 µg/l}) = 3.1 + 0.02 \times$ age (years),
the $75^{th}$ percentile: $\ln(\text{plasma YKL-40 µg/l}) = 3.2 + 0.02 \times$ age (years),
the $85^{th}$ percentile: $\ln(\text{plasma YKL-40 µg/l}) = 3.4 + 0.02 \times$ age (years),
the $90^{th}$ percentile: $\ln(\text{plasma YKL-40 µg/l}) = 3.5 + 0.02 \times$ age (years),
the $95^{th}$ percentile: $\ln(\text{plasma YKL-40 µg/l}) = 3.6 + 0.02 \times$ age (years), and
the $97.5^{th}$ percentile: $\ln(\text{plasma YKL-40 µg/l}) = 3.9 + 0.02 \times \text{age (years)}$;
wherein a level of YKL-40 in the sample above the reference levels indicates the presence of a gastrointestinal cancer.

For this aspect of the invention, the reference level may be one or more reference levels of YKL-40 obtained by measuring the YKL-40 levels in samples from healthy individuals. More detail in relation to these YKL-40 reference levels and the preferred reference levels, can be found herein in the section termed "reference levels". Preferably one of the one or more reference levels may be an age adjusted cut-off values corresponding to the $95^{th}$ percentile of serum or plasma YKL-40 levels in healthy individuals. More preferably one of the one or more reference levels is an age adjusted cut-off value that is the $95^{th}$ percentile defined as: ln(plasma YKL-40)= 3.6+0.02×age (years). Alternatively, or additionally preferably one of the one or more reference levels may be an age adjusted cut-off values corresponding to the $90^{th}$ percentile of serum or plasma YKL-40 levels in healthy individuals. More preferably one of the one or more reference levels is an age adjusted cut-off value that is the $90^{th}$ percentile defined as ln(plasma YKL-40)=3.5+0.02×age (years)). Accordingly, in a even more preferred embodiment of this aspect of the invention, the one or more reference levels of YKL-40 is one or more from the following age dependent cut-off values defined as:

the $90^{th}$ percentile: ln(plasma YKL-40 µg/l)=3.5+0.02×age (years), and the $95^{th}$ percentile: ln(plasma YKL-40 µg/l)=3.6+0.02×age (years).

For this aspect of the invention the gastrointestinal (GI) cancer may be any GI cancer or group of GI cancer as described herein. Preferably, the GI cancer may be selected from a metastatic GI cancer, such as a metastatic pancreatic cancer and/or a metastatic colorectal cancer. More preferably, the GI cancer may be selected from metastatic upper GI cancer, such as metastatic pancreatic cancer.

Second Aspect of the Invention—a Method for Classifying the Severity

At time of diagnosis many patients with pancreatic cancer, gastric cancer and biliary cancer (both patients with locally advanced disease and patients with metastatic disease) have elevated plasma YKL-40 levels compared to healthy age-matched subjects. Furthermore it has been found that patients with e.g. metastatic upper GI cancers, such as e.g. pancreatic cancer, gastric cancer or biliary cancer, have higher levels of YKL-40 compared to patients with locally advanced upper GI cancers, such as pancreatic cancer, gastric cancer or biliary cancer. Furthermore patients with upper GI cancers and the highest levels of YKL-40 have the shortest survival, see example 3 herein.

The second aspect of the present invention relates to a method for classifying the severity of a gastrointestinal cancer, preferably an upper gastrointestinal cancer, in a subject, said method comprising i) determining the level of YKL-40 in a sample obtained from the subject; and ii) comparing said level of YKL-40 with one or more age-adjusted reference levels of YKL-40;

wherein a level of YKL-40 in the sample above the one or more reference levels indicates the severity of said gastrointestinal cancer.

Accordingly, the classification of the gastrointestinal cancer is provided by comparing the determined YKL-40 level from the sample with the one or more reference levels of YKL-40, wherein the higher the level of YKL-40 the more severe the specific gastrointestinal cancer is classified as and optionally the higher the efficacy of a therapy to be initiated, continued, or replaced should be. Likewise, the lower the level of YKL-40 the less severe the gastrointestinal cancer is classified as and optionally the lower the efficacy of a therapy to be initiated, continued, terminated or replaced should be.

For this aspect of the invention, the reference level may be one or more reference levels of YKL-40 obtained by measuring the YKL-40 levels in samples from healthy individuals. More detail in relation to these YKL-40 reference levels and the preferred reference levels, can be found herein in the section termed "reference levels". Preferably the one or more reference levels of YKL-40 are a set of YKL-40 age dependent cut-off values, such as e.g. defined in the following table:

| Age intervals (years) | Age dependent cut-off values for healthy subjects | | | | |
|---|---|---|---|---|---|
| | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 40 | 44 | 54 | 59 | 65 |
| 30-39 | 48 | 54 | 65 | 72 | 80 |
| 40-49 | 59 | 65 | 80 | 88 | 98 |
| 50-59 | 72 | 80 | 98 | 108 | 119 |
| 60-69 | 88 | 98 | 119 | 132 | 145 |
| 70-79 | 108 | 119 | 154 | 161 | 178 |
| 80-89 | 132 | 145 | 178 | 196 | 217 |

Alternatively the one or more reference levels of YKL-40 are a set of YKL-40 age dependent reference levels to be used in the methods according to the present invention are as follows:

| Age intervals (years) | Age dependent reference levels for healthy subjects | | | | |
|---|---|---|---|---|---|
| | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 33-40 | 37-44 | 45-54 | 49-59 | 55-65 |
| 30-39 | 40-48 | 45-54 | 55-65 | 60-72 | 67-80 |
| 40-49 | 49-59 | 55-65 | 67-80 | 74-88 | 81-98 |
| 50-59 | 60-72 | 67-80 | 81-98 | 90-108 | 99-119 |
| 60-69 | 74-88 | 81-98 | 99-119 | 110-132 | 122-145 |
| 70-79 | 90-108 | 99-119 | 122-154 | 134-161 | 148-178 |
| 80-89 | 110-132 | 122-145 | 148-178 | 164-196 | 181-217 |

For this aspect of the invention the gastrointestinal (GI) cancer may be any GI cancer or group of GI cancer as described herein. The GI cancer may be selected from the group consisting of pancreatic cancer and colorectal cancer. In one embodiment of this aspect of the invention, the GI cancer is an upper GI cancer, more preferably the upper GI cancer is pancreatic cancer.

The determined level of YKL-40 in the sample above one or more of the reference levels provides the classification of the gastrointestinal cancer and optionally evidence of therapy to be initiated, continued, terminated or replaced.

Reference levels in relation to the second aspect of the invention regarding classification of the severity of the disease may be any of the herein described reference levels or may be as described below: a specific embodiment of said method comprises i) determining the level of YKL-40 in a sample obtained from the subject; and ii) comparing the level of YKL-40 with one or more reference levels of YKL-40, said reference levels being one or more previously determined levels of YKL-40 from the same subject;

wherein a level of YKL-40 in the sample being increased to at least a factor 1.10 compared to the reference level of YKL-40 indicates that the disease or disorder has evolved to a more severe stage of the disease or disorder; and
wherein a level of YKL-40 in the sample being decreased to at least a factor 0.90 compared to the reference level of YKL-40 indicates that the disease or disorder has evolved to a less severe stage of the disease or disorder.

In a preferred embodiment of the second aspect of the invention, the one or more reference levels of YKL-40 are age adjusted. Preferably as described herein above, i.e. the one or more previously determined levels of YKL-40 from the same subject may be age adjusted by adding 0.5 µg/l per year for women, and 0.8 µg/l per year for men. This may for instance be relevant when the previously obtained reference level is more than 3 years old, such as e.g. more than 5 years old, more than 8 years old, or more than 10 years old. For example when the previously obtained reference level is more than 10 years old.

In one embodiment the one or more reference levels of YKL-40, i.e. the one or more previously determined levels of YKL-40 from the same subject, has been determined after diagnosis of the disease or disorder. In this case the method can be used to monitor the severity of the disease, i.e. whether the disease severity increases or decreases.

By determining the increase in the YKL-40 level of the sample compared to the one or more reference levels it can be determined whether a change in severity has taken place. Accordingly, in one embodiment of the method of the second aspect of the invention wherein a level of YKL-40 in the sample being increased to at least a factor of 1.20 or more compared to the YKL-40 reference level indicates that a disease or disorder has evolved to a more severe stage of the disease or disorder, more preferably increased to at least a factor of 1.25, such as e.g. a factor of 1.30, or a factor of 1.40; even more preferably increased to at least a factor of 1.50, such as e.g. a factor of 1.60, a factor of 1.70, or a factor of 1.75; yet even more preferably increased to at least a factor of 1.75, such as e.g. a factor of 1.80, or a factor of 1.90, or a factor of 2; most preferably increased to at least a factor of 2, such as e.g. a factor of 2.10, a factor of 2.20, a factor of 2.25, or a factor of 2.50 compared to the YKL-40 reference level indicates that a disease or disorder has evolved to a more severe stage of the disease or disorder. For calculation examples, see herein above. In a more preferred embodiment of the second aspect of the invention a level of YKL-40 in the sample being increased by 109% or more compared to the YKL-40 reference level significantly indicates that a disease or disorder has evolved to a more severe stage of the disease or disorder.

Likewise the classification of the severity of a disease or disorder according to the second aspect of the present invention may be performed by determining a decrease in the YKL-40 level of the sample compared to the one or more reference levels. Accordingly, in one embodiment wherein a level of YKL-40 in the sample being decreased at least to a factor of 0.80 compared to the YKL-40 reference level indicates that a disease or disorder has evolved to a less severe stage of the disease or disorder, more preferably decreased at least to a factor of 0.70; even more preferably decreased at least to a factor of 0.60; yet even more preferably decreased to least by a factor of 0.50; most preferably decreased to least by a factor of 0.48, such as e.g. a factor of 0.45, a factor of 0.43, a factor of 0.40, or a factor of 0.38, compared to the YKL-40 reference level indicates that a disease or disorder has evolved to a less severe stage of the disease or disorder. For calculation examples, see the section "reference levels". In a more preferred embodiment of the second aspect of the invention a level of YKL-40 in the sample being decreased by 52% or more compared to the YKL-40 reference level significantly indicates that a disease or disorder has evolved to a less severe stage of the disease or disorder.

Third Aspect of the Invention—a Method for Determining a Therapy

As is described herein in the section "background of invention" it has previously been found that by determining the mutation status of KRAS some of the EGFR inhibitor non-responsive subjects may be singled out, as it has been found that KRAS mutated subjects are non-responsive to EGFR inhibitor treatments. Likewise has the BRAF mutation status been found to be predictive of EGFR inhibitor responsiveness. However, these findings do not account for the remaining group of about 40% subjects being neither BRAF nor KRAS mutated but still being non-responsive to treatment with EGFR inhibitors. Accordingly, due to both medical and economical benefits of choosing the correct group of subjects to be treated with these biological agents there is an unmet need for discovering further biomarkers for determining which group of subjects will benefit from, i.e. be responsive to, such treatment.

It is an object of the present invention to use the YKL-40 pre-treatment level to evaluate whether subjects suffering from a GI cancer will benefit from a specific treatment. In one embodiment of this aspect of the invention the determination in step i) is performed prior to initiation of the treatment in question, i.e. a pre-treatment level. A low YKL-40 level as a pre-treatment level, i.e. an YKL-40 level below one or more reference levels, is indicative of responsiveness towards different types of chemotherapy and biologics and accordingly, whether the subject will benefit from treatment with biological agents, preferably EGFR inhibitors, and more preferably Cetuximab. The GI cancer may be any GI cancer, or preferably a metastatic colorectal cancer. Said use of the pre-treatment YKL-40 level is relevant for subjects being chemonaive or previously treated with chemotherapeutics, and is furthermore independent of KRAS status, age, sex, performance status and serum CEA.

Furthermore, for chemonaive subjects both the pre-treatment YKL-40 level and the YKL-40 level after a period of treatment, such as e.g. after about 4 weeks of treatment, are relevant for determining whether a subject will respond to treatment with chemotherapy or a biologic treatment, such as preferably a biologic treatment, and more preferably a EGFR inhibitor treatment, and even more preferably a Cetuximab treatment. In relation to subjects previously treated with chemotherapeutics it is the pre-treatment level of YKL-40, i.e. the level before treatment with a new therapeutic, that is especially relevant for the determination of whether the subject will be responsive to treatment with a new chemotherapy or a biological agent, as mentioned herein above, i.e. the YKL-40 level determined prior to the initiation of the treatment with e.g. biological agents.

The third aspect of the present invention relates to a method for determining a therapy for a gastrointestinal cancer in a subject, said method comprising:
  i) determining the level of YKL-40 in a sample obtained from the subject; and
  ii) comparing said level of YKL-40 with one or more age-adjusted reference levels of YKL-40;
based thereon determining a therapy to be initiated, continued, terminated or replaced. The one or more reference levels of YKL-40 may be as described herein elsewhere and especially as described in the section termed "reference levels".

In a preferred embodiment of this aspect of the invention the one or more reference levels of YKL-40 is one or more of the following age dependent cut-off values defined as:

the 70$^{th}$ percentile: ln(plasma YKL-40 µg/l)=3.1+0.02×age (years), the 75$^{th}$ percentile: ln(plasma YKL-40 µg/l)=3.2+0.02×age (years), the 85$^{th}$ percentile: ln(plasma YKL-40 µg/l)=3.4+0.02×age (years), the 90$^{th}$ percentile: ln(plasma YKL-40 µg/l)=3.5+0.02×age (years), the 95$^{th}$ percentile: ln(plasma YKL-40 µg/l)=3.6+0.02×age (years), and the 97.5$^{th}$ percentile: ln(plasma YKL-40 µg/l)=3.9+0.02× age (years).

In a more preferred embodiment of this aspect of the invention the one or more reference levels of YKL-40 is one or more of the following age dependent cut-off values defined as:

the 90$^{th}$ percentile: ln(plasma YKL-40 µg/l)=3.5+0.02×age (years), and the 95$^{th}$ percentile: ln(plasma YKL-40 µg/l)=3.6+0.02×age (years).

Specifically said method may be used to determine whether a therapy, such as e.g., a therapy including chemotherapeutics, radiotherapy and/or a biologic agent; preferably including chemotherapeutics and/or biologic agent, for example, but not limited to, an anti-epidermal growth factor receptor (EGFR) inhibitor or an anti-vascular endothelial growth factor (VEGF) inhibitor; is to be initiated, continued, terminated or replaced.

One embodiment of the third aspect of the present invention relates to a method for determining a therapy for a gastrointestinal cancer in a subject, said method comprising:
  i) determining the level of YKL-40 in a sample obtained from the subject; and
  ii) comparing said level of YKL-40 with one or more reference levels of YKL-40;
wherein a determined level of YKL-40 below the one or more reference levels determines that the subject is prone to respond to a treatment with a biological agent, such as e.g. an EGFR inhibitor or a VEGF inhibitor, and based thereon determining whether the therapy is to be initiated. The biological agent may be as described herein elsewhere, and may preferably be Cetuximab. The one or more reference levels of YKL-40 may be as described herein elsewhere and especially as described in the section termed "reference levels". The one or more reference levels of YKL-40 may preferably be the age corrected 90$^{th}$ percentile of YKL-40 in healthy subjects, and more preferably the 95$^{th}$ percentile. It can for instance be seen from Example 5 herein, e.g. tables 7 and 8, that the YKL-40 level can be used to identify true responders for a treatment with Cetuximab.

More specifically, said method may for example be used in chemonaive subjects suffering from a gastrointestinal cancer to determine whether a specific treatment, such as a treatment with a biological agent, is to be initiated. By measuring the pre-treatment level of YKL-40 in a chemonaive subject and comparing the level with one or more reference levels it may be determined whether the measured level is above or below the one or more reference levels. If the measured level is below the one or more reference levels then the subject may be prone to respond to the specific treatment with a biological agent, and the treatment can therefore be initiated. However, if the measured level is above the one or more reference levels the probability that the subject will respond to said specific biological treatment is so low that the benefit-risk ratio is against initiating the treatment with biological agent only or against initiating the treatment with biological agent at all. Accordingly, when the measured YKL-40 level is above the one or more reference levels then the biological agent may preferably be given in combination with one or more chemotherapeutics and this treatment may be initiated instead of a treatment consisting of a biological agent only. Alternatively, when the measured YKL-40 level is above the one or more reference levels then said specific treatment with biological agent is not to be initiated at all.

Hence, one embodiment of the third aspect of the invention relates to a method for determining a therapy for a gastrointestinal cancer in a chemonaive subject, said method comprising:
  i) determining the level of YKL-40 in a sample obtained from the subject; and
  ii) comparing said level of YKL-40 with one or more reference levels of YKL-40;
    based thereon determining a therapy to be initiated. Preferably the therapy is a therapy comprising biologic agents; more preferably the therapy is a therapy comprising EGFR inhibitors or VEGF inhibitors; even more preferably the therapy is a therapy comprising EGFR inhibitors, such as e.g. Cetuximab, Panitumumab, Zalutumumab, or Erlotinib. More specifically, when the determined level of YKL-40 is below one or more reference levels the therapy comprising biologic agents is to be initiated, and when the determined level of YKL-40 is above one or more reference levels the therapy comprising biologic agents is to be initiated in combination with one or more additional therapies, such as e.g. chemotherapeutics, or is not to be initiated at all. The one or more reference levels may preferably be the age corrected 90$^{th}$ percentile of YKL-40 in healthy subjects, and more preferably the 95$^{th}$ percentile.

Alternatively, said method according to the third aspect of the invention may for example be used in pre-treated subjects, such as preferably subjects pre-treated with chemotherapeutics and more preferably subjects pre-treated with first-line, second-line or third-line chemotherapeutics, to determine whether a specific treatment with a biological agent is to be initiated. By measuring the YKL-40 level in these pre-treated subjects and comparing the level with one or more reference levels it may be determined whether the measured level is above or below the one or more reference level. If the measured level is below the one or more reference levels then the subject may be prone to respond to the specific treatment with a biological agent optionally in combination with one or more chemotherapeutics, such as e.g. a biological agent selected from the group consisting of anti-epidermal growth factor receptor (EGFR) inhibitors and anti-vascular endothelial growth factor (VEGF) inhibitors, preferably an EGFR inhibitor, such as e.g. Cetuximab, Panitumumab, Zalutumumab, or Erlotinib. and the treatment can therefore be initiated. However, if the measured level is above the one or more reference levels the probability that the subject will respond to said specific biological treatment is lower and the benefit-risk ratio is against initiating the biological treatment. This scenario is illustrated in Example 4 herein, where the biological agent is Cetuximab and the subjects are heavily pre-treated with chemotherapeutics and suffers from metastatic colorectal cancer (mCRC).

Hence, an alternative embodiment of the third aspect of the invention relates to a method for determining a therapy for a gastrointestinal cancer in a subject pre-treated with chemotherapeutics, said method comprising:
  i) determining the level of YKL-40 in a sample obtained from the subject; and ii) comparing said level of YKL-40 with one or more reference levels of YKL-40;

wherein a determined level of YKL-40 below the one or more reference levels determines that the subject is prone to respond to a treatment with a biological agent, such as e.g. an EGFR inhibitor or a VEGF inhibitor, and based thereon determining whether the therapy is to be initiated. Preferably the therapy is a therapy comprising EGFR inhibitors or VEGF inhibitors; even more preferably the therapy is a therapy comprising EGFR inhibitors, such as e.g. Cetuximab, Panitumumab, Zalutumumab, or Erlotinib, yet even more preferably Cetuximab. More specifically, when the determined level of YKL-40 is above one or more reference levels the therapy comprising biologic agents is not to be initiated.

Accordingly, the YKL-40 level may advantageously be used to determine whether a subject will benefit i.e. responds to a certain treatment regime, more preferably whether a subject will be prone to respond to a treatment comprising EGFR inhibitors. With respect to EGFR inhibitors the selection of treatment regime depends on whether the subject in question is chemonaive or pre-treated with chemotherapeutics, and whether the YKL-40 level is above or below one or more YKL-40 reference levels, as further described herein above.

In relation to the third aspect of the invention, and the embodiments thereof as described herein, the one or more reference levels of YKL-40 may be as described herein elsewhere and especially as described in the section termed "reference levels". Preferably the one or more reference levels of YKL-40 is one or more age adjusted cut-off values corresponding to YKL-40 levels determined in healthy individuals. More preferably one of the one or more reference levels of YKL-40 is an age adjusted cut-off value corresponding to the $90^{th}$ percentile of YKL-40 as determined in healthy individuals. When determining the appropriate cut-off value it is necessary to consider the risk of including or excluding subjects wrongfully. Accordingly, in order to include the majority of subjects prone to be responsive to a treatment with a specific biological agent one of the one or more preferred cut-off values is the $90^{th}$ percentile as determined in healthy individuals, however at slightly more restrictive cut-off values is the $95^{th}$ percentile as determined in healthy individuals.

Preferably the one or more reference levels of YKL-40 is a set of YKL-40 age dependent cut-off values, such as e.g. defined in the following table:

| Age intervals (years) | Age dependent cut-off values for healthy subjects | | | | |
|---|---|---|---|---|---|
| | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 40 | 44 | 54 | 59 | 65 |
| 30-39 | 48 | 54 | 65 | 72 | 80 |
| 40-49 | 59 | 65 | 80 | 88 | 98 |
| 50-59 | 72 | 80 | 98 | 108 | 119 |
| 60-69 | 88 | 98 | 119 | 132 | 145 |
| 70-79 | 108 | 119 | 154 | 161 | 178 |
| 80-89 | 132 | 145 | 178 | 196 | 217 |

Alternatively the one or more reference levels of YKL-40 are a set of YKL-40 age dependent reference levels to be used in the methods according to the present invention are as follows:

| Age intervals (years) | Age dependent reference levels for healthy subjects | | | | |
|---|---|---|---|---|---|
| | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 33-40 | 37-44 | 45-54 | 49-59 | 55-65 |
| 30-39 | 40-48 | 45-54 | 55-65 | 60-72 | 67-80 |
| 40-49 | 49-59 | 55-65 | 67-80 | 74-88 | 81-98 |
| 50-59 | 60-72 | 67-80 | 81-98 | 90-108 | 99-119 |
| 60-69 | 74-88 | 81-98 | 99-119 | 110-132 | 122-145 |
| 70-79 | 90-108 | 99-119 | 122-154 | 134-161 | 148-178 |
| 80-89 | 110-132 | 122-145 | 148-178 | 164-196 | 181-217 |

For this aspect of the invention the gastrointestinal (GI) cancer may be any GI cancer or group of GI cancer as described herein. Preferably, the GI cancer may be selected from the group consisting of metastatic colorectal cancer and pancreatic cancer; more preferably metastatic colorectal cancer.

In addition to the above-mentioned determination of an YKL-40 level prior to selection of a therapeutic regime, which e.g. for chemonaive patients herein above is referred to as a pre-treatment level, the YKL-40 level may furthermore advantageously be determined after a period of treatment. This period may depend on the treatment in question and hence factors like expected response time etc. Preferably the YKL-40 level may be determined after 2 or more weeks of treatment, such as e.g. 3 or more weeks of treatment, 4 or more weeks of treatment, or 5 or more weeks of treatment. More preferably the YKL-40 level may be determined after about 4 weeks treatment. This is for example preferred when the subjects are treated with biological agents and/or chemotherapeutics.

Accordingly, the method according to the third aspect of the invention may further comprise the following steps:
   iii) determining the level of YKL-40 in a sample obtained from said subject after a period of treatment; and
   iv) comparing said YKL-40 level with the YKL-40 level obtained in step i),
where an YKL-40 level from step iii) below or equal to the level obtained in step i) indicates a response to said treatment, or an YKL-40 level from step iii) above the level obtained in step i) indicates that the subject may be non-responsive to said treatment.

If for instance a treatment of a chemonaive subject or a previously chemotreated subject suffering from a gastrointestinal cancer is initiated when the determined level of YKL-40 is above one or more reference levels, then the treatment may be further evaluated after a period of treatment, such as e.g. about 1 week, about 2 weeks, about 3 weeks, about 4 weeks, or about 5 weeks, or every $4^{th}$ to $8^{th}$ weeks during the treatment period. If the YKL-40 level at that time is lower or the same than the previously determined level it can be established that the subject responds to the initiated treatment or has stable disease and the treatment may advantageously be continued. However, if the YKL-40 level is further increased compared to the previously determined level then the subject may be said to be non-responsive to the initiated treatment, and the treatment may be terminated or replaced by another treatment.

It can be seen from the above that the YKL-40 level can be used to identify whether patients are responsive to a given treatment, accordingly, in a further aspect the present invention relates to a method for determining the effect of a therapy for a gastrointestinal cancer in a subject, said method comprising:
  i) determining the level of YKL-40 in a sample obtained from said subject after a period of treatment; and
  ii) comparing said YKL-40 level with one or more previously determined levels of YKL-40 from the same subject,
where an YKL-40 level from step i) below or equal to the one or more previous levels in step ii) indicates a response to said treatment, or an YKL-40 level from step i) above the one or more previous levels in step ii) indicates that the subject may be non-responsive to said treatment. For this aspect of the invention applies the same reference levels as described herein for the third aspect of the invention in the section "reference levels". Details described for the third aspect of the invention applies mutatis mutandis for this aspect as well.

Preferably, the determination in step i) is performed after initiation of the treatment in question, such as after at least 2 weeks of treatment, preferably after at least 4 weeks of treatment, such as e.g. after at least 6 weeks, more preferably after at least 2 months of treatment, such e.g. after at least 3 months, at least 4 months, at least 5 months, or at least 6 months of treatment. The YKL-40 level may be determined continuously through the treatment period, such as e.g. every 2 weeks or every 1 months, as appropriate for the treatment regime in question. The determination in step i) may furthermore be performed after end of treatment, and for example regularly thereafter in a follow-up period. Follow-up measurements could for example be made every 1 months, every 2 months or every 3 months.

A response to the treatment is preferably indicated by a ratio of 1, i.e. that the measured YKL-40 level is below or equal to the one or more previous levels, a ratio of ≤1 also corresponds to a factor of 1, e.g. a decrease to a factor of 0.90, see herein under "reference levels" for the concept of factor. The lower ratio or factor the greater the indication that the subject responds to the treatment, and the better the prognosis. Likewise, that the subject is non-responsive is indicated by a ratio of >1, i.e. that the measured YKL-40 level is above the one or more previous levels, a ratio of >1 corresponds to a factor of >1, e.g. an increase to a factor of 1.10, see herein under "reference levels". The higher the ratio or factor the greater the indication that the subject is non-responsive to the treatment. The increase or decrease to a higher or lower factor respectively, as described in the section "reference levels", applies mutatis mutandis for this aspect of the invention as well.

Details described herein for the third aspect of the invention applies mutatis mutandis for this aspect as well. The reference levels are further described in the section termed "reference levels".

Furthermore, the YKL-40 level may conveniently be measured in connection with traditionally performed monitoration and/or follow-up procedures, such as e.g. CT scan, PET/CT scan, MRI scan or Ultra Sound, hereby contributing as a monitoration marker. The period of treatment in step iii) of the third aspect of the invention or step i) of the aspect immediately above here, could in this case be after end of treatment.

Another manner of monitoring a subject is by determining the prognosis during or after the specific treatment given. The present invention therefore in a further aspect relates to a method for determining a prognosis for a subject suffering from a gastrointestinal cancer and being treated with therapeutic treatments selected from the group consisting of chemotherapeutic agents, biological agents, radiotherapy and combinations thereof, said method comprising i) determining the level of YKL-40 in a sample obtained from the subject after a period of treatment;
  ii) comparing said level of YKL-40 with one or more reference levels of YKL-40;
wherein the level of YKL-40 with respect to the reference levels indicates the development or progression of said gastrointestinal cancer during or after the specific treatment regime and therefore the prognosis. More specifically the prognosis of survival, such as e.g. the prognosis of survival expressed in months (e.g. more than 3 months, more than 6 months, more than 8 months, more than 10 months, more than 12 months, more than 14 months, or more than 16 months etc.).

Preferably, the determination in step i) may be performed after at least 2 weeks of treatment, more preferably after at least 4 weeks of treatment, such as at least 6 weeks of treatment. The determination in step i) may furthermore be performed continuously during the treatment period, such as e.g. every 2 weeks, every 3 weeks, every 1 month, every 2 months etc. Alternatively or additionally, the determination in step i) is performed after end of treatment, such as at least 2 weeks after end treatment, preferably at least 4 weeks after end treatment, such as at least 6 weeks after end treatment.

The methods of the present invention may furthermore be used to monitor a subject after end of treatment. Depending on the specific gastrointestinal cancer, it may be relevant to continuously monitor the subject in a follow-up period, which may be e.g. 1 year or as long as 5 to 10 years after end of treatment. By determining the YKL-40 level in the follow-up period it is possible to diagnose a re-lapse, determine the prognosis, or initiate a new or repeat a treatment. Hereby enabling the best possible treatment of the subject.

An even more specific preferred embodiment of this method of the present invention relates to a method, wherein the one or more reference levels is one or more previously determined levels of YKL-40 from the same subject;
wherein the level of YKL-40 with respect to the one or more reference levels indicates the development or progression of said gastrointestinal cancer during or after the specific treatment regime and therefore the prognosis,
where a level of YKL-40 in the sample being increased to at least a factor 1.10 compared to the reference level of YKL-40 indicates that the gastrointestinal cancer has evolved to a more severe stage of the gastrointestinal cancer; and
where a level of YKL-40 in the sample being decreased to at least a factor 0.90 compared to the reference level of YKL-40 indicates that the gastrointestinal cancer has evolved to a less severe stage of the gastrointestinal cancer.

Details described herein for the third aspect of the invention applies mutatis mutandis for this aspect as well. The reference levels are further described in the section termed "reference levels".

The third aspect of the present invention may further be phrased as follows: A method for determining a therapy for a gastrointestinal cancer in a subject, said method comprising:
  i) determining the level of YKL-40 in a sample obtained from the subject;
  ii) comparing the level of YKL-40 with one or more reference levels of YKL-40; and
  iii) deducing the progress of the gastrointestinal cancer toward one or more predetermined stages;
wherein the level of YKL-40 with respect to the reference levels indicates the progress of said gastrointestinal cancer, and therefore the therapy to be initiated, continued, or replaced.

A more specific embodiment of this method relates to a method for determining a therapy for a gastrointestinal cancer in a subject, said method comprising:
  i) determining the level of YKL-40 in a sample obtained from the subject;
  ii) comparing the level of YKL-40 with one or more reference levels of YKL-40, said reference levels being one or more previously determined levels of YKL-40 from the same subject; and
  iii) deducing the progress of the gastrointestinal cancer toward one of these predetermined stages;
wherein the level of YKL-40 with respect to the reference levels indicates the progress of said gastrointestinal cancer, and therefore the therapy to be initiated, continued, or replaced;
where a level of YKL-40 in the sample being increased to at least a factor 1.10 compared to the reference level of YKL-40 indicates that the gastrointestinal cancer has evolved to a more severe stage of the gastrointestinal cancer, and thus e.g. requires a therapy of high efficacy to be initiated; and
where a level of YKL-40 in the sample being decreased to at least a factor 0.90 compared to the reference level of YKL-40 indicates that the gastrointestinal cancer has evolved to a less severe stage of the gastrointestinal cancer, and thus responds to the therapy and e.g. may continue the treatment, or e.g. requires a therapy of low efficacy to be initiated.

Fourth Aspect of the Invention—a Method for Monitoring Therapeutic Treatment

The present invention relates in a fourth aspect, to a method for monitoring therapeutic treatment selected from the group consisting of chemotherapeutic agents, biological agents, radiotherapy, and combinations thereof, of an upper gastrointestinal cancer in a subject. The monitoring is performed by comparing a plasma YKL-40 level obtained from said subject with one or more reference levels of YKL-40. These reference levels may be YKL-40 levels as determined in healthy age-matched subjects or it may be one or more YKL-40 levels previously determined in the same subject. When the YKL-40 reference levels are previously determined in the same subject these may be levels e.g. determined prior to the gastrointestinal cancer in question, determined as a pre-treatment level, determined after a period of treatment, or determined after end of treatment period. Accordingly, it is an object of the present invention to use the YKL-40 level to monitor the development of the gastrointestinal cancer during or after a specific treatment regime, and thus also the specific therapeutic treatment administered to the subject.

A low YKL-40 level, i.e. an YKL-40 level below one or more reference levels, is indicative of responsiveness towards the treatment in question, such as e.g. chemotherapy, radiotherapy, biologics, or combinations thereof, and accordingly, whether the subject is benefiting from said treatment.

In addition to the herein above mentioned determination of an YKL-40 level prior to selection of a therapeutic regime, the YKL-40 level may furthermore advantageously be determined after a period of treatment. This period may depend on the treatment in question and hence factors like expected response time etc. Preferably the YKL-40 level may be determined after 2 or more weeks of treatment, such as e.g. 3 or more weeks of treatment, 4 or more weeks of treatment, or 5 or more weeks of treatment. More preferably the YKL-40 level may be determined after about 4 weeks treatment. This is for example preferred when the subjects are treated with biological agents and/or chemotherapeutics.

If for instance a treatment for gastrointestinal cancer is initiated when the determined level of YKL-40 is above one or more reference levels, then the treatment may be further evaluated after a period of treatment, such as e.g. about 1 week, about 2 weeks, about 3 weeks, about 4 weeks, or about 5 weeks, or every $4^{th}$ to $8^{th}$ weeks during the treatment period. If the YKL-40 level at that time is lower or the same than the previously determined level it can be established that the subject responds to the initiated treatment or has stable disease and the treatment may advantageously be continued. However, if the YKL-40 level is further increased compared to the previously determined level then the subject may be said to be non-responsive to the initiated treatment, and the treatment may be terminated or replaced by another treatment.

Furthermore, the present method of monitoring the treatment of a gastrointestinal disease may conveniently be utilised in connection with traditionally performed monitoring and/or follow-up procedures, such as e.g. CT scan, PET/CT scan, MRI scan or Ultra Sound, hereby contributing as a monitoring marker. The period of treatment could in this case be after end of treatment.

The fourth aspect of the present invention relates to a method for monitoring therapeutic treatment of a gastrointestinal cancer in a subject, said subject being treated for the specific disease, said method comprising
  i) determining the level of YKL-40 in a sample obtained from the subject;
  ii) comparing said level of YKL-40 with one or more reference levels of YKL-40; wherein the level of YKL-40 with respect to the one or more reference levels indicates the progress and/or state of said gastrointestinal cancer, and therefore the degree of efficacy of the ongoing therapeutic treatment; and
  iii) based thereon determining whether the therapeutic treatment of the gastrointestinal cancer is to be continued, terminated or replaced.

A preferred embodiment of the fourth aspect of the present invention relates to a method for monitoring therapeutic treatments selected from the group consisting of chemotherapeutic agents, biological agents, radiotherapy and combinations thereof, of an upper gastrointestinal cancer in a subject, said subject being treated for the specific disease, said method comprising
  i) determining the level of YKL-40 in a sample obtained from the subject;
  ii) comparing said level of YKL-40 with one or more reference levels of YKL-40; wherein the level of YKL-40 with respect to the one or more reference levels indicates the progress and/or state of said gastrointestinal cancer, and therefore the degree of efficacy of the ongoing therapeutic treatment; and
  iii) based thereon determining whether the therapeutic treatment of the gastrointestinal cancer is to be continued, terminated or replaced.

For the fourth aspect of the invention, the reference level may be one or more reference levels of YKL-40 obtained by measuring the YKL-40 levels in samples from healthy individuals. More detail in relation to these YKL-40 reference levels and the preferred reference levels, can be found herein in the section termed "reference levels". Preferably one of the one or more reference levels may be a previously determined YKL-40 level from the same subject. This level may be a pre-treatment level, as defined herein, or a level obtained from the same subject during the current therapeutic treatment.

Specifically an YKL-40 level obtained in step i) equal to or below the previously determined level from the same subject, it indicates a response to said therapeutic treatment, or an YKL-40 level obtained in step i) above the previously determined level from the same subject, indicates that the subject may be non-responsive to said therapeutic treatment. When there is a response to the treatment the treatment regime may be continued, whereas if the subject is non-responsive the treatment regime needs to be supplemented or replaced, i.e. a replacement may in it self be a continuation of the ongoing treatment with an additional further treatment added.

When the present method is used as a method of continued monitoring after end of treatment in order to discover recurrence or progression, then the YKL-40 level preferably is determined frequently, such as e.g. every 2 week, every 3 weeks, every 4 weeks, every 5 weeks, every 6 weeks, every 7 weeks, or every 8 weeks, for the first 1-2 years, after 1-2 years the YKL-40 level may be determined less frequent, such as e.g. every 2 months, every 3 months, every 4 months, every 5 months, or every 6 months, preferably every 3-6 months, more preferably every 4 months, and in connection with control visits and other follow-up procedures such as scans, see herein above.

A specific embodiment of this aspect relates to a method for monitoring therapeutic treatments selected from the group consisting of chemotherapeutic agents, biological agents, radiotherapy and combinations thereof, of an upper gastrointestinal cancer in a subject, said subject being treated for the specific disease, said method comprising
  i) determining the level of YKL-40 in a sample obtained from the subject;
  ii) comparing said level of YKL-40 with one or more reference levels of YKL-40; said reference levels being one or more previously determined levels of YKL-40 from the same subject wherein the level of YKL-40 with respect to the reference levels indicates the progress and/or state of said gastrointestinal cancer, and therefore the degree of efficacy of the ongoing therapeutic treatment; and
  iii) based thereon determining whether the therapeutic treatment of the gastrointestinal cancer is to be continued, terminated or replaced,
where a level of YKL-40 in the sample being increased to at least a factor 1.10 compared to the reference level of YKL-40 indicates that the gastrointestinal cancer has evolved to a more severe stage of the gastrointestinal cancer; and
where a level of YKL-40 in the sample being decreased to at least a factor 0.90 compared to the reference level of YKL-40 indicates that the gastrointestinal cancer has evolved to a less severe stage of the gastrointestinal cancer.

Example 3 herein relates to the correlation between the YKL-40 level as measured 4 weeks after start of treatment (chemotherapy) or as measured 4-6 weeks after end of chemoradiotherapy, and overall survival. The overall survival in this case being a measure for the severity of the gastrointestinal cancer.

A more specific embodiment of this aspect relates to a method for monitoring therapeutic treatments selected from the group consisting of chemotherapeutic agents, biological agents, radiotherapy and combinations thereof, of an upper gastrointestinal cancer in a subject, said subject being treated for the specific disease, said method comprising
  i) determining the level of YKL-40 in a sample obtained from the subject;
  ii) comparing said level of YKL-40 with one or more reference levels of YKL-40; said reference levels being one or more previously determined levels of YKL-40 from the same subject wherein the level of YKL-40 with respect to the reference levels indicates the progress and/or state of said gastrointestinal cancer, and therefore the degree of efficacy of the ongoing therapeutic treatment; and
  iii) based thereon determining whether the therapeutic treatment of the gastrointestinal cancer is to be continued, terminated or replaced,
wherein a level of YKL-40 in the sample being increased to at least a factor 1.10 compared to the reference level of YKL-40 indicates that the gastrointestinal cancer has evolved to a more severe stage of the gastrointestinal cancer, and e.g. requires a therapy of higher efficacy than the ongoing therapy to be initiated; and
wherein a level of YKL-40 in the sample being decreased to at least a factor 0.90 compared to the reference level of YKL-40 indicates that the gastrointestinal cancer has evolved to a less severe stage of the gastrointestinal cancer, and thus responds to the therapy and may continue the treatment, and e.g. requires a therapy of lower efficacy than the ongoing therapy to be initiated.

The GI cancer may be any upper GI cancer, such as e.g. local or metastatic upper GI cancer. The GI cancer may preferably be an upper gastrointestinal cancer selected from the group consisting of esophageal cancer, gastric/stomach cancer, pancreatic cancer and biliary cancer, even more preferably pancreatic cancer.

The treatment may be any treatment of the GI cancer (chemotherapeutics, radiotherapy, biologics or operation), such as e.g. 1. line, 2. line, 3. line etc. treatment of metastatic GI cancer, or adjuvant treatment of local GI cancer. The therapeutic treatment may preferably be treatments selected from the group consisting of chemotherapeutic agents, biological agents, radiotherapy and combinations thereof, more preferably chemotherapeutic agents and radiotherapy.

Specific embodiments of the third and fourth aspect of the present invention relates to monitoring of the gastrointestinal cancer during treatment with a chemotherapeutic agent, radiotherapy or biologics, i.e. biologic agents. More specific embodiments relates to the monitoring of the gastrointestinal cancer during treatment with a chemotherapeutic agent.

Another manner of monitoring a subject is by determining the prognosis during or after the specific treatment given. The present invention therefore in a further aspect relates to a method for determining a prognosis for a subject suffering from an upper gastrointestinal cancer and being treated with therapeutic treatments selected from the group consisting of chemotherapeutic agents, biological agents, radiotherapy and combinations thereof, said method comprising
i) determining the level of YKL-40 in a sample obtained from the subject;
ii) comparing said level of YKL-40 with one or more reference levels of YKL-40;
wherein the level of YKL-40 with respect to the reference levels indicates the development or progression of said gastrointestinal cancer during or after the specific treatment regime and therefore the prognosis. More specifically the prognosis of survival, such as e.g. the prognosis of survival expressed in months (e.g. more than 3 months, more than 6 months, more than 8 months, more than 10 months, more than 12 months, more than 14 months, or more than 16 months etc.).

In relation to this method the determination in step i) may preferably be performed after initiation of the treatment in question. Preferably, the determination in step i) is performed after at least 2 weeks of treatment, more preferably after at least 4 weeks of treatment, such as at least 6 weeks of treatment. The determination in step i) may furthermore be performed continuously during the treatment period, such as e.g. every 2 weeks, every 3 weeks, every 1 months, every 2 months etc. Alternatively or additionally, the determination in step i) is performed after end of treatment, such as at least 2 weeks after end treatment, preferably at least 4 weeks after end treatment, such as at least 6 weeks after end treatment.

The methods of the present invention may furthermore be used to monitor a subject after end of treatment. Depending on the specific gastrointestinal cancer, it may be relevant to continuously monitor the subject in a follow-up period, which may be e.g. 1 year or as long as 5 to 10 years after end of treatment. By determining the YKL-40 level in the follow-up period it is possible to diagnose a re-lapse, determine the prognosis, or initiate a new or repeat a treatment. Hereby enabling the best possible treatment of the subject.

An even more specific preferred embodiment of this method of the present invention relates to a method, wherein the one or more reference levels is one or more previously determined levels of YKL-40 from the same subject;
wherein the level of YKL-40 with respect to the one or more reference levels indicates the development or progression of said gastrointestinal cancer during or after the specific treatment regime and therefore the prognosis,
where a level of YKL-40 in the sample being increased to at least a factor 1.10 compared to the reference level of YKL-40 indicates that the gastrointestinal cancer has evolved to a more severe stage of the gastrointestinal cancer; and
where a level of YKL-40 in the sample being decreased to at least a factor 0.90 compared to the reference level of YKL-40 indicates that the gastrointestinal cancer has evolved to a less severe stage of the gastrointestinal cancer.

Details described herein for the fourth aspect of the invention applies mutatis mutandis for this aspect as well. The reference levels are further described in the section termed "reference levels".

Further Aspects of the Invention

The present invention further encompass a fifth aspect relating to a device for determining a therapy for and/or monitoring a therapeutic treatment of a gastrointestinal cancer in a subject, wherein the device comprises means for measuring the level of YKL-40 in a sample; and means for comparing the measured level of YKL-40 with one or more reference levels of YKL-40 from the following age dependent cut-off values defined as:

the $70^{th}$ percentile: ln(plasma YKL-40 µg/l)=3.1+0.02×age (years),
the $75^{th}$ percentile: ln(plasma YKL-40 µg/l)=3.2+0.02×age (years),
the $85^{th}$ percentile: ln(plasma YKL-40 µg/l)=3.4+0.02×age (years),
the $90^{th}$ percentile: ln(plasma YKL-40 µg/l)=3.5+0.02×age (years),
the $95^{th}$ percentile: ln(plasma YKL-40 µg/l)=3.6+0.02×age (years), and
the $97.5^{th}$ percentile: ln(plasma YKL-40 µg/l)=3.9+0.02×age (years).

Furthermore, the present invention encompass a sixth aspect relating to a kit of parts comprising i) means for measuring the level of YKL-40 in a sample; ii) means for comparing the measured level of YKL-40 with one or more reference level of YKL-40; and iii) instructions on how to age adjust the reference level of YKL-40, according to the age of the subject providing the sample.

A further aspect of the present invention relates to the use of YKL-40 as a biomarker for classifying the severity of a gastrointestinal cancer. Further details for this aspect of the present invention will be apparent from the text describing the above mentioned methods of the invention. Accordingly, any features mentioned in relation to the methods of the invention apply mutatis mutandis to the use of YKL-40 as a biomarker for classifying the severity of a gastrointestinal cancer.

An even further aspect of the present invention relates to the use of YKL-40 as a biomarker for determining whether to initiate a therapeutic treatment of a gastrointestinal cancer with biologic agents, such as e.g. EGFR inhibitors and/or VEGF inhibitors, as further described herein, and especially as described for the third aspect of the invention. Accordingly, any features mentioned in relation to the third aspect of the invention apply mutatis mutandis to the use of YKL-40 as a biomarker for determining whether to initiate a therapeutic treatment.

Gastrointestinal Cancer

The gastrointestinal tract runs from the mouth to the anus, and includes the esophagus (gullet), stomach, small bowel or intestine, and the large bowel (colon and rectum). Gastrointestinal cancer refers to malignant conditions of the gastrointestinal tract and can affect any part of the gastrointestinal tract, including the esophagus, stomach, liver, biliary system, pancreas, bowels, and anus.

Cancers of the gastrointestinal (GI) tract are one of the most common cancers in Europe and the US. Over half arise from the colon, with esophageal, gastric and pancreatic cancers the next most common. Gastric cancer is very common in Japan and Korea, presumably due to regional diets. The object of the present invention is to provide methods that by measuring the YKL-40 levels of the individual suffering from a gastrointestinal cancer and relating the measured levels to one or more reference levels, aids in the diagnosis of the disease, help classify the severity of the disease and ultimately assist in the best possible choice of initial and follow up treatment by monitoring of the YKL-40 levels of the individual.

Gastrointestinal cancers can arise in any part of the gastrointestinal (GI) tract. The GI tract has three main components: the tract itself, the accessory elements and the peritoneum. The tract component comprises the upper and lower GI tract and the accessory elements comprise the liver, gallbladder, bile duct and pancreas, and the peritoneum is the membrane lining the abdominal cavity.

It is an object of the present invention to diagnose and/or classify the severity, and/or determine a treatment for and/or monitoring a therapeutic treatment of a gastrointestinal cancer in a subject and/or monitor the progression of the disease before, during and after administering a treatment, wherein a predetermined level of YKL-40 above one or more reference levels indicates the need for administering a treatment and/or the severity of said GI cancer is deduced from said comparison.

In terms of cancer, the GI tract is divided into upper and lower GI cancers, with the upper GI tract cancers comprising cancers of the esophagus, stomach, pancreatic cancer and biliary cancer. The last three decades have seen significant changes in the demographics of upper GI cancer. The incidence of esophageal squamous cell carcinoma (usually affecting the middle third) and distal gastric carcinoma has been declining, while adenocarcinoma of the esophagus (usually affecting the lower third) and proximal stomach has been rising, particularly in males. Obesity and chronic gastroesophageal reflux have been implicated in this rise. Esophageal and gastric cancers together cause over 1,000,000 deaths each year. Because these upper gastrointestinal (UGI) cancers have very poor prognoses, discovering etiologic agents and improving methods of early detection for these cancers are of prime importance.

Operation is the only potentially curable treatment for upper GI cancers. A major problem is that 85% of patients with pancreatic cancer have already locally advanced or metastatic disease at time of diagnosis, and their median survival time is only 6 months and <10% are alive after 1 year.

For patients with gastric cancer and biliary cancers there is an ongoing tendency towards better survival, because more patients have a lower stage at time of diagnosis with equivalent better chance of successful surgery, however <50% are alive after 1 year (and 24% after 5 years, US). (Europe 137.9/171, EU 65/90 (30-32). The treatment options for patients that can not be radically operated are palliative radio- or chemotherapy, with only poor response rates (33-35). Although, there might in the future be more effective chemotherapy regimes or new biological treatments, the best way to improve survival for patients with upper GI cancers is to diagnose the patients at an earlier stage and determine the best possible treatment for the patient in question. Identification of new biomarkers is a step in this direction.

The lower GI tract cancers comprise any cancer of the bowel/intestines and thus include cancers of the small intestine, duodenum, appendix, the colon, rectum and anus. Bowel (colorectal) cancer is the second most common cause of cancer-related death (after lung cancer), affecting 6 percent of the population in industrialized countries and causing death in about 3 percent. About 25 percent of all deaths are caused by cancer in industrialized countries, and bowel cancer accounts for 12.5 percent of those deaths. The terms "bowel cancer" and "colorectal cancer" are used interchangeably herein.

The GI cancer, as mentioned herein, unless otherwise specified, may be any GI cancer, for example any GI cancer selected from the group consisting of local GI cancer (primary cancer) without local spread or metastases, locally advanced GI cancer, and mestastatic GI cancer.

Gastrointestinal stromal tumor (GIST) is a cancer form which can be found in both the upper and lower GI tract. Other types of GI cancers that fall out of the upper and lower GI classification system are the peritoneal cancers and liver/hepatic cancers. It is an object of the present invention to classify the severity, and/or select a treatment for a GI cancer, such as GIST, peritoneal and/or hepatic cancer, in a subject and/or monitor the progression of the disease before, during and after administering a treatment, wherein a predetermined level of YKL-40 above a reference level indicates the need for administering a treatment and/or the severity of said GI cancer is deduced from said comparison. In one embodiment of the invention it is preferred that the GI cancer is one or more of the following: GIST, peritoneal and/or hepatic cancer; more preferably the GI cancer is GIST.

Most GI cancers even in cancers in specific bodily compartments may be of one of several subtypes. The subtypes of the various GI cancers typically relate to which tissue, the cancer arises from. The most typical types of cancers of the GI system are squamous cell carcinomas and adenocarcinomas; thus it is an object of the present invention to diagnose and/or classify the severity, and/or determine a treatment for and/or monitoring a therapeutic treatment of a gastrointestinal cancer, such as, but not limited to, squamous cell carcinomas and/or adenocarcinomas, in a subject and/or monitor the progression of the disease before, during and after administering a treatment, wherein a predetermined level of YKL-40 above one or more reference level indicates the need for administering a treatment and/or the severity of said GI cancer is deduced from said comparison. Preferably, the GI cancer may be an adenocarcinoma.

One embodiment of the methods according to the present invention relates to gastrointestinal cancers that are one or more upper GI cancers; preferably the one or more upper GI cancers are selected from the group consisting of esophageal cancer, gastric/stomach cancer, pancreatic cancer and biliary cancer; more preferably the one or more upper GI cancer is pancreatic cancer. In some embodiments of the methods of the invention the upper GI cancer is preferably metastatic upper GI cancers, such as more preferably metastatic pancreatic cancer.

Another embodiment of the methods according to the present invention relates to gastrointestinal cancers that are one or more lower GI cancers; preferably the one or more lower GI cancers are selected from the group consisting of small intestine cancer, duodenum cancer, appendix cancer, colon cancer, rectal cancer, colorectal cancer, metastatic colorectal cancer, and anal cancer; more preferably the lower GI cancer may be colorectal cancer or metastatic colorectal cancer; even more preferably the lower GI cancer is metastatic colorectal cancer.

YKL-40

YKL-40 is named based on its three N-terminal amino acids Tyrosine (Y), Lysine (K) and Leucine (L) and its molecular mass of about 40 kDa. The complete amino acid (SEQ ID NO: 2) and coding sequence (SEQ ID NO: 1) of human YKL-40 is found in GenBank under Accession number: M80927. Human YKL-40 contains a single polypeptide chain of 383 amino acids and is a phylogenetically highly conserved heparin- and chitin-binding plasma glycoprotein. The sequence identity between human YKL-40 and homologs from several other mammals is: pig (84% sequence identity), cow (83%), goat (83%), sheep (83%), guinea pig, rat (80%), and mouse (73%). YKL-40 is a member of "mammalian chitinase-like proteins", but has no chitinase activity. YKL-40 expression in vitro is absent in normal human monocytes but strongly induced during late stages of macrophage differentiation by activated monocytes and neutrophils, by vascular smooth muscle cells, cancer cells and arthritic chondrocytes. In vivo YKL-40 mRNA and protein are expressed by a subpopulation of macrophages in tissues with inflammation such as atherosclerotic plaques, arthritic vessels of individuals with giant cell arthritis, inflamed synovial membranes, sarcoid lesions, and by peritumoral macrophages (36).

The molecular processes governing the induction of YKL-40 and its precise functions are unknown. YKL-40 is a secreted protein suggesting that its sites of actions are most likely to be extracellular; however, specific cell-surface or soluble receptors for YKL-40 have not yet been identified. YKL-40 is a growth factor for fibroblasts and chondrocytes, acts synergistically with IGF-1, is regulated by TNF and IL-6, and requires sustained activation of NF-kappaB. YKL-40 treatment of fibroblasts can counteract the inflammatory response to TNF and IL-1 by phosphorylation of AKT, thereby attenuating ASK1 mediated signaling pathways. This leads to decreased levels of metalloproteinase and IL-8 expression. Furthermore, YKL-40 binds to collagen types I, II and III and modulates the rate of type I collagen fibril formation. These observations suggest that YKL-40 may play a protective role in inflammatory environments, limiting degradation of the extracellular matrix and thereby controlling tissue remodeling. YKL-40 also acts as a chemo-attractant for endothelial cells, stimulates their migration and promotes migration and adhesion of vascular smooth muscle cells suggesting a role in angiogenesis. YKL-40 is also a growth factor for fibroblasts and has an anti-catabolic effect preserving extracellular matrix during tissue remodeling. In addition, macrophages in atherosclerotic plaques express YKL-40 mRNA, particularly macrophages that have infiltrated deeper in the lesion, and the highest YKL-40 expression is found in macrophages in the early lesion of atherosclerosis. Furthermore YKL-40 can be regarded as an acute phase protein, since its plasma or serum concentration is increased in several inflammatory diseases (36).

Cellular receptors mediating the biological effects of YKL-40 are not known, but the activation of cytoplasmic signal-transduction pathways suggests that YKL-40 interacts with signaling components on the cell membrane.

It is an object of the present invention to detect any transcriptional product of the YKL-40 gene. A transcriptional product of the gene may thus be hnRNA, mRNA, full length protein, fragmented protein, or peptides of the YKL-40 protein. It is understood that one or more proteins, RNA transcripts, fragments and/or peptides may be detected simultaneously. It is furthermore an aspect of the present invention to detect transcriptional products by any means available such as by immunoassays such as antibody detection of the YKL-40 protein, fragments or peptides hereof, as well as by detection by PCR based assays such as detection of RNA by RT-PCR.

Detection of YKL-40

Peptides and polynucleotides of the invention include functional derivatives of YKL-40, YKL-40 peptides and nucleotides encoding therefore. By "functional derivative" is meant the "fragments," "variants," "analogs," or "chemical derivatives" of a molecule. A "fragment" of a molecule, such as any of the DNA sequences of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical.

Further, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th Ed., Mack Publishing Co., Easton, Pa., 1980.

Minor modifications of the YKL-40 primary amino acid sequence may result in proteins and peptides that have substantially similar activity as compared to the YKL-40 peptides described herein. Such modifications may be deliberate, as by site-directed mutagenesis, or may be spontaneous. All of the peptides produced by these modifications are included herein as long as the biological activity of YKL-40 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which may not be required for the enzyme to exert the desired catalytic or antigenic activity.

Either polyclonal or monoclonal antibodies may be used in the immunoassays and therapeutic methods of the invention described below. Some anti-YKL-40 antibodies are available commercially or may alternatively be raised as herein described or known in the art. Polyclonal antibodies may be raised by multiple subcutaneous or intramuscular injections of substantially pure YKL-40 or antigenic YKL-40 peptides into a suitable non-human mammal. The antigenicity of YKL-40 peptides can be determined by conventional techniques to determine the magnitude of the antibody response of an animal which has been immunized with the peptide. Generally, the YKL-40 peptides which are used to raise the anti-YKL-40 antibodies should generally be those which induce production of high titers of antibody with relatively high affinity for YKL-40. In one embodiment of the invention the YKL-40 level is determined by use of a dipstick.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because YKL-40 may be conserved among mammalian species, use of a carrier protein to enhance the immunogenicity of YKL-40 proteins is preferred.

The antibodies are then obtained from blood samples taken from the mammal. The techniques used to develop polyclonal antibodies are known in the art see, e.g., Methods of Enzymology, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies, see, for example, Coligan, et al., Unit 9, Current Protocols in Immunology, Wiley Interscience, 1991).

Preferably, however, the YKL-40 antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and F(ab').sub.2, which are capable of binding an epitopic determinant. Also, in this context, the term "mAb's of the invention" refers to monoclonal antibodies with specificity for YKL-40.

The general method used for production of hybridomas secreting mAbs is well known (Kohler and Milstein, 1975). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines.

Confirmation of YKL-40 specificity among mAb's can be accomplished using relatively routine screening techniques (such as the enzyme-linked immunosorbent assay, or "ELISA") to determine the elementary reaction pattern of the mAb of interest. It is also possible to evaluate an mAb to determine whether it has the same specificity as a mAb of the invention without undue experimentation by determining whether the mAb being tested prevents a mAb of the invention from binding to YKL-40 isolated as described above, if the mAb being tested competes with the mAb of the invention, as shown by a decrease in binding by the mAb of the invention, then it is likely that the two monoclonal antibodies bind to the same or a closely related epitope. Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

Immunoassay Procedures

The immunoassay procedure used must be quantitative so that levels of YKL-40 in an individual with disease may be distinguished from normal levels which may be present in healthy humans and/or background levels measured in the individual. Competitive and sandwich assays on a solid phase using detectible labels (direct or indirect) are, therefore, preferred. The label will provide a detectible signal indicative of binding of antibody to the YKL-40 antigen. The antibody or antigen may be labeled with any label known in the art to provide a detectible signal, including radioisotopes, enzymes, fluorescent molecules, chemiluminescent molecules, bioluminescent molecules and colloidal gold. Of the known assay procedures, radioimmunoassay (RIA) or enzyme-linked immunoassay (ELISA) are most preferred for its sensitivity. A radioisotope will, therefore, be the preferred label. The most preferred immunoassay is ELISA.

Accordingly, in a specific embodiment of the method according to the present invention the YKL-40 level is determined using an immunoassay. In one version of this embodiment the immunoassay is a competitive immunoassay.

In one embodiment of the invention, the immunoassay uses a monoclonal antibody to measure YKL-40. In an alternative embodiment of the invention the immunoassay uses a polyclonal antibody to measure YKL-40.

When a method of the present invention utilizes an immunoassay, then a detectable label selected from the group consisting of radioisotopes, enzymes, fluorescent molecules, chemiluminescent molecules, bioluminescent molecules and colloidal metals, may be used to measure YKL-40.

Examples of metallic ions which can be directly bound to an antibody, or indirectly bound to the YKL-40 antigen are well-known to those of ordinary skill in the art and include $^{125}$I, $^{111}$In, $^{97}$Ru, $^{67}$Ga, $^{68}$Ga, $^{72}$As, $^{89}$Zr, $^{90}$Y and $^{201}$Tl. Preferred for its ease of attachment without compromise of antigen binding specificity is $^{125}$I (sodium salt, Amersham, United Kingdom). Labeling of YKL-40 with $^{125}$I may be performed according to the method described in Salacinski, et al. (1981). Iodogen for use to provide the $^{125}$I label (1,3,4,6-tetrachloro-3.alpha., 6.alpha.-diphenyl glycoluril) is commercially available from Pierce and Warriner, Chester, England.

In a specific preferred embodiment of the invention plasma levels of YKL-40 can be determined in duplicates by a two-site, sandwich-type enzyme-linked immunosorbent assay (ELISA) (such as e.g. the commercial Quidel, California, USA), using streptavidin-coated microplate wells, a biotinylated-Fab monoclonal capture antibody, and an alkaline phosphatase-labeled polyclonal detection antibody. When Quidel was used the recovery of the ELISA was 102% and the detection limit 10 μg/L. Sensitivity in this context is defined as the detectible mass equivalent to twice the standard deviation of the zero binding values. The standard curve will generally be linear between 20 and 300 μg/l. The intra-assay coefficients of variations were 5% (at 40 μg/L), 4% (at 104 μg/L), and 4% (at 155 μg/L). The inter-assay coefficient of variation was <6% (37).

In another embodiment of the invention a radioimmunoassay is used, wherein standards or samples are incubated with a substantially equal volume of YKL-40 antiserum and of YKL-40 tracer. Standards and samples are generally assayed in duplicate. The sensitivity (detection limit) of the assay of the invention is about 10 μg/l. Sensitivity in this context is defined as the detectible mass equivalent to twice the standard deviation of the zero binding values. The standard curve will generally be linear between 20 and 100 μg/l. The intra- and interassay coefficients of variance for the assay described in the following examples are <6.5% and <12%, respectively.

It will be appreciated by those skilled in the art that, although not necessarily as sensitive as an RIA, assay procedures using labels other than radioisotopes have certain advantages and may, therefore, be employed as alternatives to a RIA format. For example, an enzyme-linked immunosorbent assay (ELISA) may be readily automated using an ELISA microtiter plate reader and reagents which are readily available in many research and clinical laboratories. Fluorescent, chemiluminescent and bioluminescent labels have the advantage of being visually detectible, though they are not as useful as radioisotopes to quantify the amount of antigen bound by antibody in the assay.

PCR Based Assays

Further, it will be appreciated by those of skill in the art that means other than immunoassays may be employed to detect and quantify the presence of YKL-40 in a biological sample. For example, a polynucleotide encoding YKL-40 may be detected using quantitative polymerase chain reaction (PCR) protocols known in the art. Accordingly, in one embodiment of the method according to the present invention the YKL-40 level is determined in a PCR based assay. The preferred method for performance of quantitative PCR is a competitive PCR technique performed using a competitor template containing an induced mutation of one or more base pairs which results in the competitor differing in sequence or size from the target YKL-40 gene template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions.

Once the aminated or biotinylated strands of the PCR products are immobilized, the unbound complementary strands are separated in an alkaline denaturing wash and removed from the reaction environment. Sequence-specific oligonucleotides ("SSO's") corresponding to the target and competitor nucleic acids are labelled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates. This method is advantageous in that it is quantitative, does not depend upon the number of PCR cycles, and is not influenced by competition between the SSO probe and the complementary strand in the PCR product.

Alternatively, part of the polymerization step and the entire hybridization step can be performed on a solid phase support. In this method, it is a nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above.

A target to competitor nucleic acid ratio can be determined by detection of labeled oligonucleotide SSO probes using appropriate measurement means (preferably ELISA readers) and standard curve as described supra. The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

Molecules capable of providing different, detectible signals indicative of the formation of bound PCR products known to those skilled in the art (such as labeled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional noncompetitive PCR protocol.

Those of ordinary skill in the art will know, or may readily ascertain, how to select suitable primers for use in the above methods. For further details regarding the above-described techniques, reference may be made to the disclosures in Kohsaka, et al., Nuc. Acids Res., 21:3469-3472, 1993; Bunn, et al., U.S. Pat. No. 5,213,961; and to Innis, et al., PCR Protocols: A Guide to Methods and Applications, Acad. Press, 1990, the disclosures of which are incorporated herein solely for purposes of illustrating the state of the art regarding quantitative PCR protocols.

Reference Levels

Whether the YKL-40 level of a given subject is increased or not may be asserted by comparing a determined value with that of a reference level. The reference level may be one or more reference levels that for instance each reflects an increased severity of a gastrointestinal cancer, or for instance reflects an increasing probability that the subject have an GI cancer, or the reference level may for instance be one or more reference levels obtained by previous measurements of samples from the same subject.

Previously, YKL-40 levels have been reported for e.g. various diseases or from healthy individuals, hereby giving an indication of the normal level. However, such previously reported "normal" YKL-40 levels from healthy individuals where not supported by a follow-up over time investigating whether the "healthy individuals" remained healthy over time. Accordingly, previously reported YKL-40 levels therefore included individuals who at the time of sampling potentially had unidentified diseases, and the reported YKL-40 levels therefore did not represent a true "normal level". Such previously reported YKL-40 levels obtained from e.g. healthy individuals have also been reported as e.g. average levels without considering the effect of age.

As can be seen from the examples included in the present invention, the present inventors have identified a way to express a true "normal level". This normal level has been identified on the basis of a large population of healthy individuals, and the individuals have been followed over time to confirm whether they were true "healthy individuals". Individuals who did not continue to be healthy, e.g. who developed cancer, was removed from the normal data. The inventors have surprisingly found that the identified "normal level" can be used to diagnose the presence of diseases or disorders, determine a treatment to be initiated, or monitor an ongoing treatment in order to determine whether it is to be continued, terminated or replaced, in a subject in accordance with the methods of the present invention. The present inventors have furthermore found that age has a great influence on the YKL-40 level, and that this is to be considered when utilizing the methods of the present invention.

A reference level for YKL-40 can be expressed in various ways; traditionally reference levels may be from a group of healthy individuals of various ages. The present inventors have investigated the influence of age on the YKL-40 level and found that a measured YKL-40 level preferably is compared with age specific group.

An age specific group of individuals may comprise individuals that are all born within the same year or decade or any other groupings such as groups comprising individuals that are of 0 to 10 years of age, 10 to 20 years of age, 20 to 30 years of age, 30 to 40 years of age, 40 to 50 years of age, 50 to 60 years of age, 60 to 70 years of age, 70 to 80 years of age, 80 to 90 years of age, 90 to 100 years of age, and so on. The intervals may span 2 years of age difference, 3, 4, or 5 years of age difference, 6, 7, 8, 9, 10 years of age difference (as written), 12 15, 20 or more years of age difference. The intervals may furthermore be open ended e.g. the individuals are all above the age of 20, 30, 40, 50, 60 or other.

The present inventors have found that there is no statistically difference between the plasma YKL-40 level in men and in women (see example 1 herein). Accordingly, the group of individuals who form the basis for the calculation of the reference level may furthermore be a group of individuals of mixed sex or same sex. Reference levels may also be obtained from the same individual as the sample YKL-40 level that is to be compared with the reference level. When this is the case the one or more reference levels may for example be YKL-40 levels measured in one or more samples obtained prior to diagnosis of the gastrointestinal cancer (pre-illness), and/or prior to the establishment of symptoms of the gastrointestinal cancer (pre-symptom), or after a diagnosis of the gastrointestinal cancer has been established. Accordingly, the gastrointestinal cancer may be a cancer that is diagnosed prior to, during or after the measurement of the previously determined YKL-40 level(s). The gastrointestinal cancer to be treated, monitored, classified or diagnosed according to the methods of the present invention may be a previously diagnosed gastrointestinal cancer or a yet undiagnosed gastrointestinal cancer.

In a preferred embodiment of the invention, the one or more reference levels of YKL-40 is provided by measuring the YKL-40 levels in samples from healthy individuals; more preferably the reference level of YKL-40 is an average level obtained by measuring the YKL-40 levels in samples from healthy individuals. In an even more preferred embodiment the one or more reference levels of YKL-40 thereby obtained, or obtained from a previous measurement from the same subject, are one or more age adjusted reference levels. In an alternative embodiment the one or more reference levels is one or more previously determined levels of YKL-40 from the same subject.

Specifically, in one embodiment of the invention, the average level is an YKL-40 plasma level in a range from about 14 to about 168 µg/L (2.5%-97.5% percentile range), preferably a plasma level of less than about 124 µg/L (95% percentile), and more preferably a plasma level of less than 92 µg/L (90% percentile). Preferably, the average level is an YKL-40 plasma level in a range from about 35 to about 55 µg/l, such as preferably from about 40 to about 50 µg/l. In an even more specific embodiment of the invention the median level is an YKL-40 plasma level of about 42 µg/l. Plasma YKL-40 levels increase in both sexes with increasing age and there is no difference between plasma YKL-40 in women and men. These plasma YKL-40 levels have been found from samples of and by studying a large group of healthy subjects, hereby giving a well founded reference level for plasma YKL-40 levels that may be used in the method according to the present invention (see example 1 herein).

When the present invention utilizes one or more age-adjusted reference levels, then it may preferably be YKL-40 plasma levels that are age adjusted by adding 0.5 µg/l per year for women, and 0.8 µg/l per year for men. This age-adjustment is preferably performed for a previously measured YKL-40 level from the same subject, as may for example be relevant for the fourth aspect of the invention. Alternatively, the one or more reference levels may be a set of YKL-40 age dependent reference levels obtained by measuring the YKL-40 levels in samples from age distributed subpopulations of healthy individuals, i.e. age specific groups of individuals as described herein above, such as e.g. individuals that are all born within the same decade. For example a set of reference levels, each being the average YKL-40 plasma level for a group of healthy individuals within the following age groups: from 30 to 39 years, from 40 to 49 years, from 50 to 59 years, and from 60 to 69 years. Preferred sets of YKL-40 age dependent reference levels are given herein further below.

In one specific embodiment of the method according to the present invention one of the one or more reference levels of YKL-40 is an average or median level obtained by measuring the YKL-40 levels in samples from healthy individuals.

Another way of specifying a reference level is by the use of a cut-off value. A cut-off value is a value that typically divides a number of individuals into two groups: those that have an YKL-40 level above a specific cut-off value, and those that have an YKL-40 level below the specified cut-off value. The cut-off value may be any value that represents a physiological YKL-40 level as measured in any type of biological sample, or as chosen by a person skilled in the art.

The cut-off value may be used as a yes or no indicator of whether an individual is within a certain category, in relation to the present invention this may correspond to the presence of a GI cancer (as in relation to the first aspect of the invention), different stages of severity of a gastrointestinal cancer (as in relation to the second aspect of the present invention), or e.g. the advisability of initiating, continuing, terminating or replacing a specific therapy (as in relation to the third or fourth aspect of the invention).

In the same specific embodiment or in an alternative embodiment of the method(s), one of the one or more reference levels of YKL-40 is an age adjusted cut-off value corresponding to the $75^{th}$ percentile of YKL-40 as determined in healthy individuals.

In the same specific embodiment or in an alternative embodiment of the method(s), one of the one or more reference levels of YKL-40 is an age adjusted cut-off value corresponding to the $85^{th}$ percentile of YKL-40 as determined in healthy individuals.

In the same specific embodiment or in an alternative embodiment of the method(s), one of the one or more reference levels of YKL-40 is an age adjusted cut-off value corresponding to the $90^{th}$ percentile of YKL-40 as determined in healthy individuals.

In the same specific embodiment or in an alternative embodiment of the method(s), one of the one or more reference levels of YKL-40 is an age adjusted cut-off value corresponding to the $95^{th}$ percentile of YKL-40 as determined in healthy individuals.

In the same specific embodiment or in an alternative embodiment of the method(s), one of the one or more reference levels of YKL-40 is an age adjusted cut-off value corresponding to the $97.5^{th}$ percentile of YKL-40 as determined in healthy individuals.

Accordingly, in a preferred embodiment of the invention, the reference level of YKL-40 is an age adjusted cut-off value corresponding to the $90^{th}$ percentile of plasma YKL-40 in healthy individuals, such as for example a YKL-40 plasma value of 92 µg/l for a subject of about 50 years of age, or a YKL-40 plasma value of 111 µg/l for a subject of about 60 years of age; and more preferably it is an age adjusted cut-off value corresponding to the $95^{th}$ percentile of plasma YKL-40 in healthy individuals, such as for example a YKL-40 plasma value of 100 µg/l for a subject of about 50 years of age, or a YKL-40 plasma value of 124 µg/l for a subject of about 60 years of age. When the $95^{th}$ percentile plasma level is age adjusted and applied as a cut-off value, there is allowed for greater potential individual variations in the YKL-40 level. The use of the $95^{th}$ percentile, or even the $97.5^{th}$ percentile, may for instance be relevant when the methods of the invention are used with focus on one individual subject. However, in some instances of the methods of the present invention it is preferred that the $90^{th}$ percentile plasma YKL-40 level is applied. This is e.g. when the method according to the third aspect of the invention is used to determine whether a treatment is to be initiated or not, in this case when the YKL-40 level is below a certain value the treatment is to be initiated; by using the $90^{th}$ percentile instead of e.g. the $95^{th}$ percentile, less subjects with a high YKL-40 level is included. In the same manner, it may furthermore be relevant to utilize the $70^{th}$ percentile, the $75^{th}$ percentile, or the $85^{th}$ percentile of the plasma YKL-40 level in healthy individuals, which percentile is used will depend on which level of sensitivity is desired. The lower the percentile selected, as e.g. a cut-off value, the higher sensitivity is obtained. By using a low percentile subjects may be found that yet only are slightly affected by a disease or disorder, such as e.g. in an early stage of a disease or disorder.

The cut-off value may alternatively be defined as a plasma YKL-40 level corresponding to the following percentiles defined in 3610 healthy subjects:

the 70% percentile (defined as ln(plasma YKL-40)=3.1+0.02×age (years)), the 75% percentile (defined as ln(plasma YKL-40)=3.2+0.02×age (years)), the 90% percentile (defined as ln(plasma YKL-40)=3.5+0.02×age (years)); and the 95% percentile (defined as ln(plasma YKL-40)=3.6+0.02×age (years)) according to age.

The cut-off value may furthermore be defined as a plasma YKL-40 level corresponding to the following percentiles defined in 3610 healthy subjects:

the 70% percentile (defined as ln(plasma YKL-40)=3.1+ 0.02×age (years)),
the 75% percentile (defined as ln(plasma YKL-40)=3.2+ 0.02×age (years)),
the 85% percentile (defined as ln(plasma YKL-40)=3.4+ 0.02×age (years)),
the 90% percentile (defined as ln(plasma YKL-40)=3.5+ 0.02×age (years)),
the 95% percentile (defined as ln(plasma YKL-40)=3.6+ 0.02×age (years)), and
the 97.5% percentile (defined as ln(plasma YKL-40)=3.9+ 0.02×age (years)), according to age.

Figure 3A:
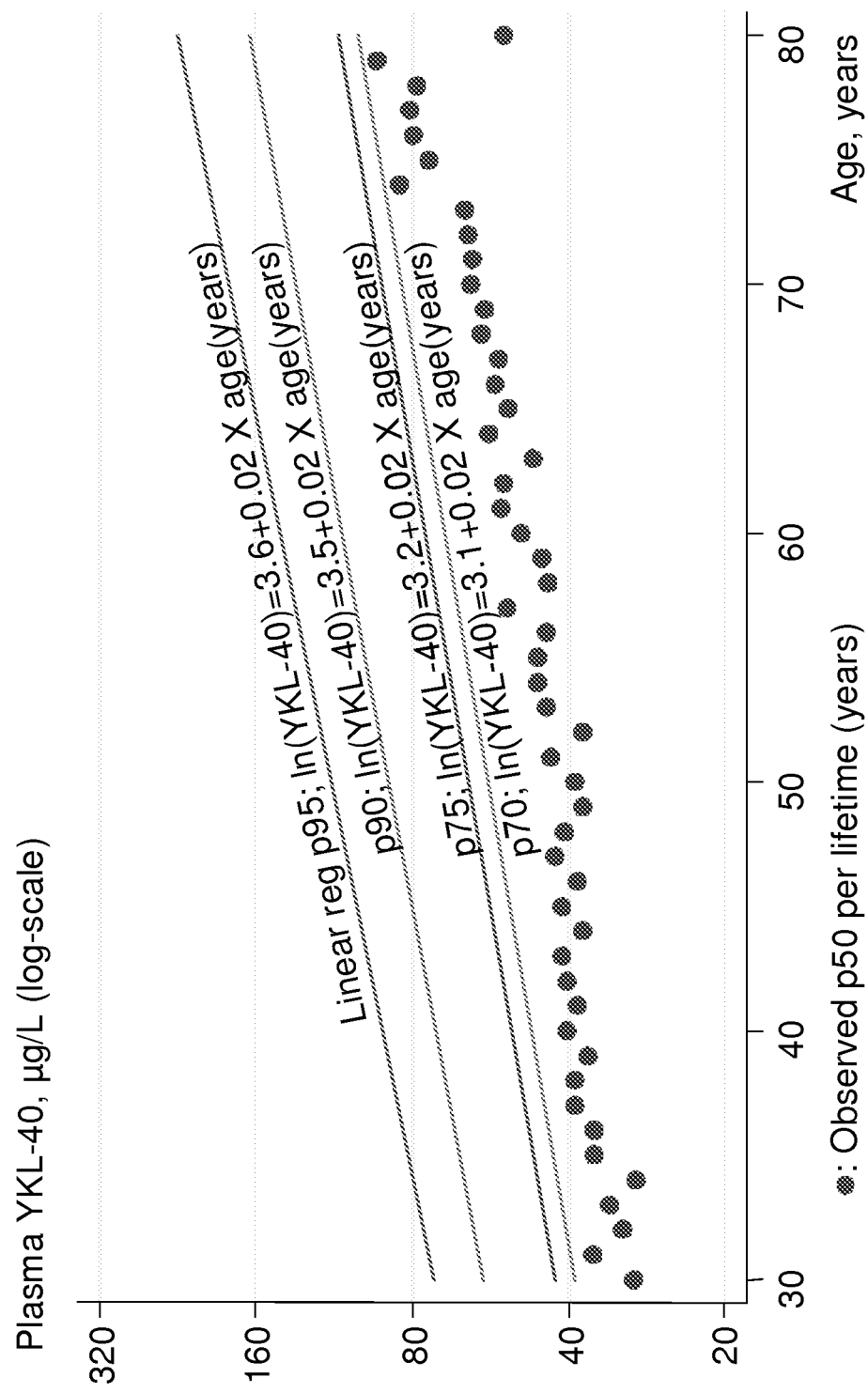
FIG. 3A. Plasma concentrations of YKL-40 were determined in 2116 healthy women and 1494 healthy men. The participants had no known disease at the time of blood sampling in 1991-1994 and remained healthy during the 16 years follow-up period (i.e. none were dead or had develop cancer, ischaemic cardiovascular disease, liver disease, diabetes, chronic obstructive pulmonary disease, asthma, rheumatoid arthritis, inflammatory bowel disease, and pneumonia). The figure illustrates the 50% percentile plasma YKL-40 in these healthy participants (circles), the 70% percentile (defined as ln(plasma YKL-40)=3.1+0.02×age (years)), the 75% percentile (defined as ln(plasma YKL-40)=3.2+0.02×age (years)), the 90 percentile (defined as ln(plasma YKL-40)=3.5+0.02×age (years)) and the 95% percentile (defined as ln(plasma YKL-40)=3.6+0.02×age (years)) according to age. Women and men were combined.
Figure 3B:
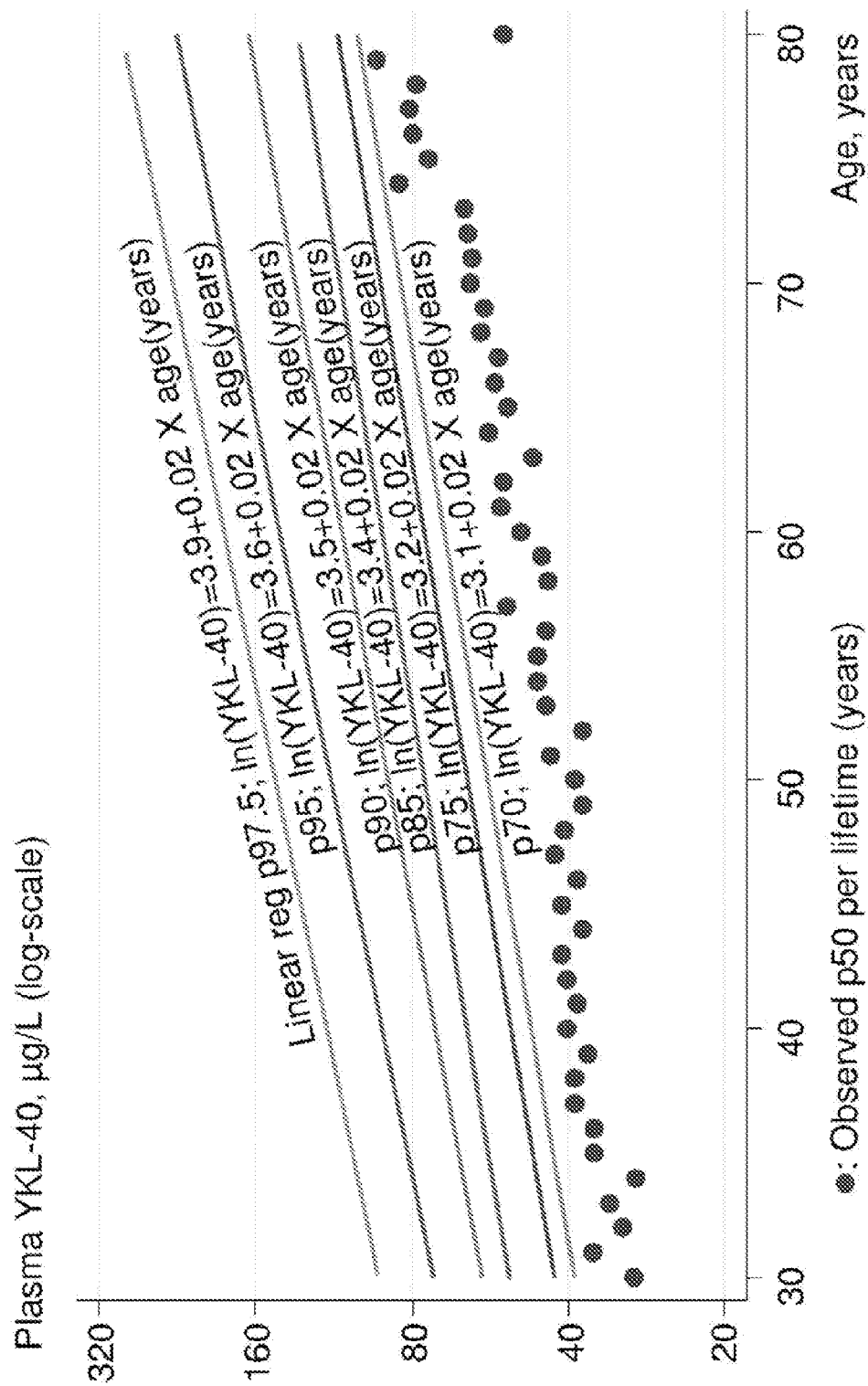
FIG. 3B. Corresponds to FIG. 3A, with additional percentiles for plasma YKL-40: the 85% percentile (defined as ln(plasma YKL-40)=3.4+0.02×age (years)), and the 97.5% percentile (defined as ln(plasma YKL-40)=3.9+0.02×age (years)).

In preferred embodiments of the methods according to the present invention the reference level of YKL-40 is calculated according to the immediately above mentioned formulas, by the use of the age of the subject. The formulas are furthermore depicted in FIG. 3A and FIG. 3B, which figures may be used in a more direct approach allowing for the determination of a cut-off value without the need for calculations. FIGS. 3A and 3B furthermore allows for an immediate comparison of a measured YKL-40 level and the subject age with e.g. both the $90^{th}$ percentile and the $95^{th}$ percentile. Hereby furthermore giving an immediate indication of the extend to which a measured YKL-40 level differs from the reference levels. By use of the above-mentioned formula for the $90^{th}$ percentile, the cut of value for subjects having an age of about 20 years, about 30 years, about 40 years, about 50 years, about 60 years, and about 70 years are: about 49 µg/l, about 60 µg/l, about 74 µg/l, about 90 µg/l, about 110 µg/l, and about 134 µg/l YKL-40, respectively. Correspondingly, the above mentioned formula for the $95^{th}$ percentile give the following cut-off values: about 55 µg/l, about 67 µg/l, about 81 µg/l, about 99 µg/l, about 122 µg/l, and about 148 µg/l YKL-40, respectively.

In one embodiment of the methods according to the invention the reference level of YKL-40 is an age adjusted cut-off value corresponding to the $70^{th}$ percentile of serum or plasma YKL-40 levels in healthy individuals. More preferably the age adjusted cut-off value is the $70^{th}$ percentile defined as: ln(plasma YKL-40)=3.1+0.02×age (years).

In another embodiment of the methods according to the invention the reference level of YKL-40 is an age adjusted cut-off value corresponding to the $75^{th}$ percentile of serum or plasma YKL-40 levels in healthy individuals. More preferably the age adjusted cut-off value is the $75^{th}$ percentile defined as: ln(plasma YKL-40)=3.2+0.02×age (years).

In another embodiment of the methods according to the invention the reference level of YKL-40 is an age adjusted cut-off value corresponding to the $85^{th}$ percentile of serum or plasma YKL-40 levels in healthy individuals. More preferably the age adjusted cut-off value is the $85^{th}$ percentile defined as: ln(plasma YKL-40)=3.4+0.02×age (years).

In another embodiment of the methods according to the invention the reference level of YKL-40 is an age adjusted cut-off value corresponding to the $90^{th}$ percentile of serum or plasma YKL-40 levels in healthy individuals. More preferably the age adjusted cut-off value is the $90^{th}$ percentile defined as: ln(plasma YKL-40)=3.5+0.02×age (years).

In another embodiment of the methods according to the invention the reference level of YKL-40 is an age adjusted cut-off value corresponding to the $95^{th}$ percentile of serum or plasma YKL-40 levels in healthy individuals. More preferably the age adjusted cut-off value is the $95^{th}$ percentile defined as: ln(plasma YKL-40)=3.6+0.02×age (years).

In another embodiment of the methods according to the invention the reference level of YKL-40 is an age adjusted cut-off value corresponding to the $97.5^{th}$ percentile of serum or plasma YKL-40 levels in healthy individuals. More preferably the age adjusted cut-off value is the $97.5^{th}$ percentile defined as: ln(plasma YKL-40)=3.9+0.02×age (years).

In a specific embodiment of the methods according to the invention the reference level of YKL-40 is a set of YKL-40 age dependent cut-off values defined as two or more of the herein immediately above mentioned age adjusted cut-off value corresponding to the $70^{th}$, $75^{th}$, $85^{th}$, $90^{th}$, $95^{th}$, or $97.5^{th}$ percentile, respectively.

In a preferred embodiment of the methods of the invention the one or more reference levels of YKL-40 is one or more of the following age dependent cut-off values defined as:

the $70^{th}$ percentile: ln(plasma YKL-40 µg/l)=3.1+0.02×age (years), the $75^{th}$ percentile: ln(plasma YKL-40 µg/l)=3.2+0.02×age (years), the $85^{th}$ percentile: ln(plasma YKL-40 µg/l)=3.4+0.02×age (years), the $90^{th}$ percentile: ln(plasma YKL-40 µg/l)=3.5+0.02×age (years), the $95^{th}$ percentile: ln(plasma YKL-40 µg/l)=3.6+0.02×age (years), and the $97.5^{th}$ percentile: ln(plasma YKL-40 µg/l)=3.9+0.02×age (years).

In a more preferred embodiment of the methods of the invention the one or more reference levels of YKL-40 is one or more of the following age dependent cut-off values defined as:

the $90^{th}$ percentile: ln(plasma YKL-40 µg/l)=3.5+0.02×age (years), and the $95^{th}$ percentile: ln(plasma YKL-40 µg/l)=3.6+0.02×age (years).

In another preferred embodiment of the methods of the inventions the reference level of YKL-40 is a set of YKL-40 age dependent cut-off values defined by two or more of the percentiles $70^{th}$, $75^{th}$, $85^{th}$, $90^{th}$, $95^{th}$, and $97.5^{th}$, as e.g. preferably calculated by the above mentioned formulas. A set of YKL-40 age dependent cut-off values may furthermore be calculated for a set of age groups, e.g. 20-29 years, 30-39 years, 40-49 years etc. where for instance the cut-off value is the highest value in the age group. In one preferred embodiment of the first or fourth aspect of the invention the set of cut-off values is as follows:

| Age intervals (years) | Age dependent cut-off values for healthy subjects | | | | |
|---|---|---|---|---|---|
| | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 40 | 44 | 54 | 59 | 65 |
| 30-39 | 48 | 54 | 65 | 72 | 80 |
| 40-49 | 59 | 65 | 80 | 88 | 98 |
| 50-59 | 72 | 80 | 98 | 108 | 119 |
| 60-69 | 88 | 98 | 119 | 132 | 145 |
| 70-79 | 108 | 119 | 154 | 161 | 178 |
| 80-89 | 132 | 145 | 178 | 196 | 217 |

Likewise obtained by the above mentioned formulas is a more detailed set of preferred age dependent cut-off values to be used in the methods according to the present invention:

| Age dependent cut-off values for healthy subjects | | | | | |
|---|---|---|---|---|---|
| Age intervals (years) | 70th percentile (µg/l YKL-40) | 75th percentile (µg/l YKL-40) | 85th percentile (µg/l YKL-40) | 90th percentile (µg/l YKL-40) | 95th percentile (µg/l YKL-40) |
| 20-24 | 36 | 40 | 48 | 54 | 59 |
| 25-29 | 40 | 44 | 54 | 59 | 65 |
| 30-34 | 44 | 48 | 59 | 65 | 72 |
| 35-39 | 48 | 54 | 65 | 72 | 80 |
| 40-44 | 54 | 59 | 72 | 80 | 88 |
| 45-49 | 59 | 65 | 80 | 88 | 98 |
| 50-54 | 65 | 72 | 88 | 98 | 108 |
| 54-59 | 72 | 80 | 98 | 108 | 119 |
| 60-64 | 80 | 88 | 108 | 119 | 132 |
| 65-69 | 88 | 98 | 119 | 132 | 145 |
| 70-74 | 98 | 108 | 132 | 145 | 161 |
| 75-79 | 108 | 119 | 145 | 161 | 178 |
| 80-84 | 119 | 132 | 161 | 178 | 196 |
| 85-89 | 132 | 145 | 178 | 196 | 217 |

As described above a set of YKL-40 age dependent reference levels can be used in the methods according to the present invention. A preferred set of age dependent reference levels for healthy subjects can be calculated by the above formulas. Accordingly, a set of preferred age dependent reference levels to be used in the methods according to the present invention are as follows:

| Age dependent reference levels for healthy subjects | | | | | |
|---|---|---|---|---|---|
| Age intervals (years) | 70th percentile (µg/l YKL-40) | 75th percentile (µg/l YKL-40) | 85th percentile (µg/l YKL-40) | 90th percentile (µg/l YKL-40) | 95th percentile (µg/l YKL-40) |
| 20-29 | 33-40 | 37-44 | 45-54 | 49-59 | 55-65 |
| 30-39 | 40-48 | 45-54 | 55-65 | 60-72 | 67-80 |
| 40-49 | 49-59 | 55-65 | 67-80 | 74-88 | 81-98 |
| 50-59 | 60-72 | 67-80 | 81-98 | 90-108 | 99-119 |
| 60-69 | 74-88 | 81-98 | 99-119 | 110-132 | 122-145 |
| 70-79 | 90-108 | 99-119 | 122-154 | 134-161 | 148-178 |
| 80-89 | 110-132 | 122-145 | 148-178 | 164-196 | 181-217 |

Likewise obtained by the above mentioned formulas is a more detailed set of preferred age dependent reference levels to be used in the methods according to the present:

| Age dependent reference levels for healthy subjects | | | | | |
|---|---|---|---|---|---|
| Age intervals (years) | 70th percentile (µg/l YKL-40) | 75th percentile (µg/l YKL-40) | 85th percentile (µg/l YKL-40) | 90th percentile (µg/l YKL-40) | 95th percentile (µg/l YKL-40) |
| 20-24 | 33-36 | 37-40 | 45-48 | 49-54 | 55-59 |
| 25-29 | 37-40 | 40-44 | 49-54 | 55-59 | 60-65 |
| 30-34 | 40-44 | 45-48 | 55-59 | 60-65 | 67-72 |
| 35-39 | 45-48 | 49-54 | 60-65 | 67-72 | 74-80 |
| 40-44 | 49-54 | 55-59 | 67-72 | 74-80 | 81-88 |
| 45-49 | 55-59 | 60-65 | 74-80 | 81-88 | 90-98 |
| 50-54 | 60-65 | 67-72 | 81-88 | 90-98 | 99-108 |
| 54-59 | 67-72 | 74-80 | 90-98 | 99-108 | 110-119 |
| 60-64 | 74-80 | 81-88 | 99-108 | 110-119 | 122-132 |
| 65-69 | 81-88 | 90-98 | 110-119 | 122-132 | 134-145 |
| 70-74 | 90-98 | 99-108 | 122-132 | 134-145 | 148-161 |
| 75-79 | 99-108 | 110-119 | 134-145 | 148-161 | 164-178 |
| 80-84 | 110-119 | 122-132 | 148-161 | 164-178 | 181-196 |
| 85-89 | 122-132 | 134-145 | 164-178 | 181-196 | 200-217 |

In a specific embodiment of the invention the following YKL-40 plasma levels may each independently be one of the one or more reference levels of YKL-40 to be used in a method according to the invention: a plasma level of from about 35 to about 55 µg/l, such as e.g. from about 40 to about 50 µg/l, preferably about 42 µg/l; a plasma level of from about 90 to about 100 µg/l, such as preferably about 97 µg/l; a plasma level of from about 120 to about 130 µg/l, such as preferably about 124 µg/l; and a plasma level of from about 160 to about 170 µg/l, such as preferably about 168 µg/l. These values may be used alone or in combinations of two or more of these values, such as for example as a set of reference values comprising three or more of these values. The specific values, as can be seen from the examples, have been determined from a large group of healthy individuals and correspond to the median value, the 90th percentile, the 95th percentile, and the 97.5th percentile, respectively.

In another preferred embodiment of the method according to the invention the one or more reference levels of YKL-40 comprises a set of reference levels of YKL-40 obtained by measuring the YKL-40 levels in samples from healthy individuals: a first reference level being the median value of YKL-40, a second reference level being the 75th percentile of YKL-40, a third reference level being the 85th percentile of YKL-40, a fourth reference level being the 90th percentile of YKL-40, a fifth reference level being the 95th percentile of YKL-40, a sixth reference level being the 97.5th percentile of YKL-40 in healthy individuals, a seventh reference level being a factor 4.5 of the median value of YKL-40, and a eighth reference level being a factor 5 of the median value of YKL-40 in healthy individuals.

Accordingly, by determining whether the determined level of YKL-40 in the sample is above one or more of the reference levels provides the classification of the severity of the gastrointestinal cancer and/or the prognosis for the subject suffering from the gastrointestinal cancer. In other words, the classification of the gastrointestinal cancer is provided by comparing the determined YKL-40 level from the sample with the one or more reference levels of YKL-40, wherein the higher the level of YKL-40 the more severe the gastrointestinal cancer is classified as or the worse the prognosis is. The more severe the gastrointestinal cancer, the higher is the efficacy required of the therapy to be initiated. And likewise if the subject is already undergoing treatment, the higher the YKL-40 level determined during monitoring of the subject the more severe the disease, the more must the ongoing treatment be altered as in administering more medicine, higher concentrations of same, or replacing the ongoing treatment for another, more efficient treatment. In other words: if the gastrointestinal cancer has evolved to a more severe stage of the gastrointestinal cancer and it requires a therapy of high efficacy to be initiated and/or requires a therapy with higher efficacy than the ongoing therapy to be initiated. There is furthermore the possibility that the increase in the YKL-40 level indicates that the subject is non-responsive to said treatment, and that the prognosis is so severe that the specific treatment can be terminated and in some cases no other treatment initiated.

In one embodiment of the methods of the invention where the one or more reference levels of YKL-40 is one or more previously determined levels of YKL-40 from the same subject that has been determined after diagnosis of the gastrointestinal cancer. This allows for a calculation of a ratio between the previous measurement and a new measurement or for example a calculation of factor of increase or decrease. In this case the method can be used to monitor the severity of the disease, i.e. whether the disease severity increases or decreases, and/or to determine the effect of a treatment, and/ or to determine the prognosis for the subject, by determining an increase or a decrease/no change in the YKL-40 level. Further details with regard to such increases or decreases will be evident from the below.

In a preferred embodiment of these methods of the invention, the one or more reference levels of YKL-40 are age adjusted. Preferably as described above, i.e. the one or more previously determined levels of YKL-40 from the same subject may be age adjusted by adding 0.5 µg/l per year for women, and 0.8 µg/l per year for men. This may for instance be relevant when the previously obtained reference level is more than 3 years old, such as e.g. more than 5 years old, more than 8 years old, or more than 10 years old. For example when the previously obtained reference level is more than 10 years old.

When the applied reference level is a previously determined level of YKL-40 from the same subject, the determined level of YKL-40 in the sample is said to be significantly above the reference level and thereby significantly indicating an increase in the determined YKL-40 level compared to the reference level, when the level of YKL-40 in the sample is increased by about 109% or more. Accordingly, in more preferred embodiments of the methods of the invention a level of YKL-40 in the sample being increased by 109% compared to the YKL-40 reference level indicates that the prognosis has worsened, such as the gastrointestinal cancer has evolved to a more severe stage of the gastrointestinal cancer. The following is a calculation example, where the previously measured YKL-40 level is 50 µg/l, and an YKL-40 level increased by 109% is calculated: 50 µg/l+(50×1.09) µg/l=50 µg/l+54.5 µg/l=104.5 µg/l. In an increase by about 109% or more is included any method variation, biological variation or other that may influence the YKL-40 level, see example 2 herein for details.

As mentioned herein above the present inventors have found the mean increase of the YKL-40 level to be 0.5 µg/l per year for women, and 0.8 µg/l per year for men. Accordingly, if a previously determined level of YKL-40 from the same subject increases by more than this, then there is a risk that a gastrointestinal cancer is present, or e.g. that an existing gastrointestinal cancer is getting more severe and/or the prognosis has worsened. Therefore an increase, but an increase by less than the above described 109%, may be indicative for the presence of a disease or disorder, or indicative for the worsening of a disease or disorder. Accordingly, if for instance a previously determined YKL-40 level was about 60 µg/l for a woman of about 25 years of age, and a new level was determined 5 years after, the increase due to age should be about 2.5 µg/l, i.e. a new age corrected value should be about 62.5 µg/l. If this value instead was measured to about 66 µg/l, it would give an indication that a gastrointestinal cancer may be present or may be getting more severe.

By determining the increase in the YKL-40 level of the sample compared to the one or more reference levels it can be determined whether a change in severity has taken place and/or a change in the prognosis. In a specially preferred embodiment of the methods according to the present invention, where the reference level is obtained as a previous measurement from the same individual, a level of YKL-40 in the sample being increased to at least a factor of 1.10 or more compared to the YKL-40 reference level indicates that the prognosis has worsened, such as e.g. that a gastrointestinal cancer has evolved to a more severe stage of the gastrointestinal cancer, more preferably increased to at least a factor of 1.25, such as e.g. a factor of 1.30, or a factor of 1.40; even more preferably increased to at least a factor of 1.50, such as e.g. a factor of 1.60, a factor of 1.70, or a factor of 1.75; yet even more preferably increased to at least a factor of 1.75, such as e.g. a factor of 1.80, or a factor of 1.90, or a factor of 2; most preferably increased to at least a factor of 2, such as e.g. a factor of 2.10, a factor of 2.20, a factor of 2.25, or a factor of 2.50 compared to the YKL-40 reference level indicates that the prognosis has worsened, such as e.g. that a gastrointestinal cancer has evolved to a more severe stage of the gastrointestinal cancer. That the severity of said cancer has evolved to a more severe stage of said cancer may optionally require a therapy of higher efficacy to be initiated and/or require a therapy with higher efficacy than the ongoing to be initiated. The following is a calculation example giving a level being increased to a factor of 1.10 compared to a reference level of 50 µg/l: 50 µg/l×1.10=55 µg/l (i.e. the new level is: 55 µg/l).

It follows from the above that the higher the increase the stronger is the indication that a gastrointestinal cancer is present or that a already existing gastrointestinal cancer is getting more severe. In preferred embodiments of the methods of the invention a level of YKL-40 in the sample increased to a factor of 2, such as at least a factor of 2, compared to the reference level of YKL-40 obtained as a previous measurement from the same individual, indicates a worsening, e.g. that a gastrointestinal cancer has evolved to a more severe stage of the gastrointestinal cancer. An increase to at least a factor of 2 corresponds to the above-mentioned significant increase by 109% or more.

If for instance a previously determined level of YKL-40 from the same subject already was at a level above one or more reference levels, such as above the 95$^{th}$ percentile for YKL-40 levels in healthy individuals, then an increase over time is not expected to be more than the age dependent increase of 0.5 µg/l per year for women or 0.8 µg/l per year for men; unless the GI cancer is worsening. In this case it is especially preferred that the factor describing an increase is low. Accordingly, preferably that a level of YKL-40 in the sample increased by at least a factor of 1.10 compared to the reference level of YKL-40 indicates that gastrointestinal cancer has evolved to a more severe stage of the gastrointestinal cancer. By a more severe stage is also meant a worsening of the prognosis.

Likewise the classification of the severity and/or monitoring a therapeutic treatment of a gastrointestinal cancer, as well as determining an effect of a therapy and/or determining a prognosis for a subject suffering from a gastrointestinal cancer according to methods of the present invention may be performed by determining a decrease in the YKL-40 level of the sample compared to the one or more reference levels.

Accordingly, in one embodiment of the methods of the present invention, where the reference level is obtained as a previous measurement from the same individual, a level of YKL-40 in the sample being decreased at least to a factor of 0.90 compared to the YKL-40 reference level indicates that the prognosis for the subject has become better, such as e.g. a gastrointestinal cancer has evolved to a less severe stage of the gastrointestinal cancer, more preferably decreased to least by a factor of 0.80, such as e.g. a factor of 0.70; even more preferably decreased at least to a factor of 0.60; yet even more preferably decreased at least to a factor of 0.50; most preferably decreased at least to a factor of 0.48, such as e.g. a factor of 0.45, a factor of 0.43, a factor of 0.40, or a factor of 0.38, compared to the YKL-40 reference level indicates that the prognosis has become better, such as a gastrointestinal cancer has evolved to a less severe stage of the gastrointestinal cancer. Thus in line with the above increase in severity, if a specific gastrointestinal cancer has evolved to a less severe stage of the gastrointestinal cancer and it may thus optionally require a therapy of low efficacy to be initiated and/or requires a therapy with lower efficacy than the ongoing therapy to be initiated. In relation to methods of the invention relating to monitoring a therapeutic treatment, a decrease in the YKL-40 level gives an indication that the subject responds to the said treatment and/or that the prognosis, e.g. the overall survival rate is increased.

The following is a calculation example giving a level being decreased to a factor of 0.90 compared to a reference level of 100 μg/l: 100 μg/l×0.90=90 μg/l, i.e. the new plasma YKL-40 level is 90 μg/l. When it is written that a level is decreased at least to a factor of e.g. 0.90, it is intended to mean that the level is decreased to a factor 0.90 or e.g. 0.80, 0.70 etc., i.e., that a level of 100 μg/l is decreased to at least 90 μg/l or a lower value.

In a more preferred embodiment of methods of the invention a level of YKL-40 in the sample being decreased by 52% compared to the YKL-40 reference level indicates that the prognosis has become better, such as a gastrointestinal cancer has evolved to a less severe stage of the gastrointestinal cancer and/or that the patient has responded to the treatment. This is especially relevant for embodiments of the methods of the invention where the applied reference level is a previously determined level of YKL-40 from the same subject. The following is a calculation example, where the previously measured YKL-40 level is 100 μg/l, and an YKL-40 level decreased by 52% is calculated: 100 μg/l−(100×0.52) μg/l=100 μg/l−52 μg/l=48 μg/l. In a decrease by about 52% is included any method variation, biological variation or other that may influence the YKL-40 level, see example 2 herein for details.

It follows from the above that the greater the decrease the stronger is the indication that the disease or disorder has evolved to a less severe stage and/or a better prognosis. In a preferred embodiment of the first aspect of the invention a level of YKL-40 in the sample decreased to a factor of 0.50, such as at least a factor of 0.50, compared to the reference level of YKL-40 obtained as a previous measurement from the same individual, significantly indicates that a change to the better has occurred, i.e. that the disease or disorder has evolved to a less severe stage. A decrease to at least a factor of 0.50 corresponds to the above-mentioned significant decrease by 52% or more.

In yet another embodiment of the invention, the determined level of YKL-40 in the sample is said to be above the reference level and thereby indicating the presence of a gastrointestinal cancer or indicating a increase in severity, when the level of YKL-40 in the sample is increased by about 25% or more, such as e.g. by about 50% or more, about 60% or more, about 70% or more, about 80% or more, about 90% or more, about 100% or more, about 110% or more, about 120% or more, about 130% or more, or about 150% or more.

Classification of Individuals

The best possible treatment is a treatment tailored to each individual, and to the stage/severity of a disease or a disorder in said individual. The present invention provides a method of classifying the severity of a gastrointestinal cancer, so as each individual may be classified according to e.g. a prognosis of survival or according to stages of the gastrointestinal cancer. The invention further provides a method of classifying the severity of a gastrointestinal cancer, where a gastrointestinal cancer may be followed by monitoring the development of the disease or the disorder to determine whether the diseases or disorder evolve towards a more or a less severe stage of the gastrointestinal cancer. The classification and monitoring are based on the measurement of YKL-40 levels in biological samples taken from the individuals to be classified/monitored and comparing the found YKL-40 levels with that of one or more reference levels of YKL-40.

By allowing the treatment for each individual to be tailored by the classification according to severity and/or survival prognosis, both the ameliorative and the curative effect of the administered treatment will improve, the survival rate of the patients as whole improve, the relapse risks will be lowered, and the quality of life will be heightened. Furthermore, there will be a financial benefit in that the amount of drugs administered may be adjusted acutely. Also, the ability to monitor this group of individuals and determined the development in disease severity will be of assistance in choosing the most effective immediate and follow-up treatment, and be of guidance when counseling on for example required lifestyle changes.

The classification of individuals based on their YKL-40 levels may be performed according to the results described in the Examples. As can be seen from these there is a relationship between increased YKL-40 levels and increased hazard ratio of death. High Hazard ratios indicate increased risk of death and are calculated as known to those skilled in the art. Accordingly, when classifying the severity of a gastrointestinal cancer according to the methods of the present invention, the severity of the disease or disorder may be deduced from cox analysis showing that patients with higher YKL-40 levels have a shorter time to disease progression and shorter time to death compared to patients/subjects with low YKL-40 levels (illustrated by the increased hazard ratio in patients with high YKL-40 levels). This was independent of other risk factors. Furthermore patients with metastatic gastrointestinal cancer had the highest YKL-40 levels and the poorest prognosis.

A statistically increased level of YKL-40 is indicative of an increased risk of death as can be seen in the Examples. YKL-40 is thus a biomarker that allows a prognosis of survival for the individual for which the YKL-40 level has been determined. The prognosis may be correlated with other signs of health status known to those skilled in the clinical arts. If the level of YKL-40 is increased to a statistically significant level a prognosis of death or reduced survival may be issued.

Based hereon, as an example, individuals may be grouped according to their YKL-40 levels in increments of 20 so that: group 0 individuals have serum YKL-40 levels of less than 90 μg/l (microgram/liter), group I individuals have serum YKL-40 levels of 100 μg/l+/−10 μg/l, group 2 individuals have serum YKL-40 levels of 120 μg/l+/−10 μg/l, group 3 individuals have serum YKL-40 levels of 140 μg/l+/−10 μg/l, group 4 individuals have serum YKL-40 levels of 160 μg/l+/−10 μg/l, group 5 individuals have serum YKL-40 levels of 180 μg/l+/−10 μg/l, group 6 individuals have serum YKL-40 levels of 200 μg/l+/−10 μg/l, group 7 individuals have serum YKL-40 levels of 220 μg/l+/−10 μg/l, group 8 individuals have serum YKL-40 levels of 240 μg/l+/−10 μg/l, group 9 individuals have serum YKL-40 levels of 260 μg/l+/−10 μg/l, group 10 individuals have serum YKL-40 levels of 280 μg/l+/−10 μg/l, group 11 individuals have serum YKL-40 levels of 300 μg/l+/−10 μg/l, group 12 individuals have serum YKL-40 levels of 320 μg/l+/−10 μg/l, group 13 individuals have serum YKL-40 levels of 340 μg/l+/−10 μg/l, group 14 individuals have serum YKL-40 levels of above 350 μg/l. In the given example serum YKL-40 levels have been used, however, YKL-40 levels obtained from other biological samples and measured as protein, RNA or other as herein mentioned also fall within the scope of the present invention. Furthermore, the increments between the groups may be of 2 μg/l, such as 4, 5, 6, 8, 10, 15, 20, 25, 30, 35, 40, 45, 50, 55, 60, 75, 80, 95, 90 or 100 μg/l YKL-40. Preferably, the increments are 20 or 30 µg/l YKL-40 as measured in serum. The increments of 20 or 30 µg/l YKL-40 may start at 50 µg/l serum YKL-40.

Alternatively to the example given above, the classification of individuals may be done in groups that commence at a lower serum YKL-40 level than indicated above such as a group 0 comprising individuals with serum YKL-40 levels of 40 µg/l+/−5 µg/l, and group 1 individuals have serum YKL-40 levels 50 µg/l+/−5 µg/l, group 2 individuals have serum YKL-40 levels of 60 µg/l+/−5 µg/l, group 3 individuals have serum YKL-40 levels of 70 µg/l+/−5 µg/l, group 4 individuals have serum YKL-40 levels of 80 µg/l+/−5 µg/l, group 5 individuals have serum YKL-40 levels of 90 µg/l+/−5 µg/l, and group 6 individuals have serum YKL-40 levels of 100 µg/l+/−5 µg/l and so on. The preferred groupings for the purpose of classification may be related to the age of the individuals to be classified as well disease state, future treatments and other.

A further example of a classification scheme is shown in the table below. In this example the groups are characterized by a concentration range of YKL-40 as measured in a biological sample. The ranges given in the example span increments of 25 µg/l, but may span smaller increments such as 5, 10, 15 or 20 µg/l, or alternatively span larger increments such as 30, 35, 40, 45 or 50, 60, 70 80 90 or 100 µg/l.

| Group | Serum YKL-40 µg/l |
|---|---|
| 1 | <85 |
| 2 | 85-110 |
| 3 | 110-135 |
| 4 | 135-160 |
| 5 | 160-185 |
| 6 | 185-210 |
| 7 | 210-235 |
| 8 | 235-260 |
| 9 | 260-285 |
| 10 | >285 |

For all the above and below mentioned classification groupings, it applies that the higher the YKL-40 level, the more severe/advanced is the gastrointestinal cancer, and the worse is the survival prognosis.

Due to the relationship between YKL-40 levels in serum and the associated hazard rations, the individuals to be classified may also be classified according to the calculated hazard ratios. A group of individuals may also be classified according to percentiles, such that the total group 100% and the 10% of the group with the lowest YKL-40 levels are group 1, the second lowest 10% percentile is group 2 and so forth. The percentiles may be 1%, 2%, 3%, 4%, 5%, 6%, 7%, 8%, 9%, 10%, 11%, 12%, 12.5%, 13%, 14%, 15%, 20%, 25%, 30%, 33% or 35% percentile groupings, or any percentile falling between or above the mentioned percentiles.

Classification of Severity

When classifying the severity of a gastrointestinal cancer, this may for example be in relation to predetermined stages of a given gastrointestinal cancer, it may for example be in relation to a prognosis of survival, or it may be as a general evaluation of whether the gastrointestinal cancer is evolving towards a more or a less severe stage. As the prognosis of a patient may be independent of a classical staging of the disease in question, the terms "a more severe stage" and "a less severe stage", as used herein, is also intended to mean a worsening or an improvement of the prognosis of the patient, respectively. For patients suffering from a gastrointestinal cancer disease the prognosis is typically a prognosis relating to expected time before progression, or time before death. Accordingly, a worsening of the prognosis typically corresponds to a shorter progression free interval and/or a shorter survival period.

For determining the extent of a cancer disease staging is performed. The stage of a cancer is a descriptor (usually numbers I to IV) of how much the cancer has spread. The stage often takes into account the size of a tumor, how deep it has penetrated, whether it has invaded adjacent organs, how many lymph nodes it has metastasized to (if any), and whether it has spread to distant organs. Staging of cancer is important because the stage at diagnosis is the most powerful predictor of survival, and treatments are often changed based on the stage.

Cancer staging can be divided into a clinical stage and a pathologic stage. In the TNM (Tumor, Node, Metastasis) system, clinical stage and pathologic stage are denoted by a small 'c' or 'p' before the stage (e.g., cT3N1 M0 or pT2N0). Clinical stage is based on all of the available information obtained before a surgery to remove the tumor. Thus, it may include information about the tumor obtained by physical examination, radiologic examination, and endoscopy. Pathologic stage adds additional information gained by examination of the tumor microscopically by a pathologist. Because they use different information, clinical stage and pathologic stage are often different. Pathologic staging is usually considered the "better" or "truer" stage because it allows direct examination of the tumor and its spread, contrasted with clinical staging which is limited by the fact that the information is obtained by making indirect observations at a tumor which is still in the body. However, clinical staging and pathologic staging should complement each other. Not every tumor is treated surgically, so sometimes pathologic staging is not available. Also, sometimes surgery is preceded by other treatments such as chemotherapy and radiation therapy which shrink the tumor, so the pathologic stage may underestimate the true stage.

Correct staging is critical because treatment is directly related to disease stage. Thus, incorrect staging would lead to improper treatment, and material diminution of patient survivability. Correct staging, however, can be difficult to achieve. Pathologic staging, where a pathologist examines sections of tissue, can be particularly problematic for two specific reasons: visual discretion and random sampling of tissue. "Visual discretion" means being able to identify single cancerous cells intermixed with healthy cells on a slide. Oversight of one cell can mean misstaging and lead to serious, unexpected spread of cancer. "Random sampling" refers to the fact that lymph nodes are cherry-picked from patients and random samples are examined. If cancerous cells present in the lymph node happen not to be present in the slices of tissue viewed, incorrect staging and improper treatment can result.

YKL-40 levels are herein demonstrated to be a new method of classification of severity (i.e. staging) of a GI cancer. The method of using YKL levels may be used alone or in combination with other staging methods to obtain the most accurate classification of the severity (staging) of a GI cancer. As demonstrated in the examples, the classification of the severity of the disease may also be calculated from the overall survival, hazard ratios and/or time to progression of the disease.

Thus it is an object of the present invention to classify the severity of a gastrointestinal cancer in a subject, said method comprising:
  i) determining the level of YKL-40 in a sample obtained from the subject;
  ii) comparing the level of YKL-40 with one or more reference levels of YKL-40;

wherein the severity of said non-specific disease or disorder is deduced from said comparison.

The YKL-40 sample may be taken prior to, during or after treatment of the disease has commenced.

Monitoring of Individuals

The present invention relates to the monitoring of individuals based on the prognosis of their survival as measured from their YKL-40 levels. Monitoring individuals according to the measured YKL-40 levels may be used as an indication of the general state of health of an individual and/or as an indication of the effectiveness of an administered treatment. The individuals or patients may be suffering from a specific, i.e. a diagnosed gastrointestinal cancer.

Monitoring YKL-40 levels as a prognosis of death in individuals suffering from a specific gastrointestinal cancer facilitates administration of the most optimal treatment for each individual. The administration of an effective treatment improves both the ameliorative and curative effect of the administered treatment as well as the survival chances of the individuals, and lessens relapse risks. Thus, YKL-40 can be used for monitoring the sufficiency of medical treatment of patients with any gastrointestinal cancer and thus improve the curative, ameliorate and general quality of life for an individual (subject) suffering from a gastrointestinal cancer. Furthermore, the administration of the most effective treatment is also an issue when assessing the cost/benefits of the given treatment.

Therefore it is an aspect of the present invention to provide a method for monitoring the health state of an individual in relation to a prognosis of their survival, said method comprising: measuring the level of YKL-40 in a biological sample from said individual; and comparing the measured level to a reference level of YKL-40; wherein an increase in the YKL-40 level, such as a statistically significant increase, is an indicator for shorter survival of the individual.

The method for monitoring therapeutic treatment of a gastrointestinal cancer in a subject, may be based on a general population marker such as in the following method which comprises:
  i) determining the level of YKL-40 in a sample obtained from the subject;
  ii) comparing said level of YKL-40 with one or more reference levels of YKL-40; wherein the level of YKL-40 with respect to the reference levels indicates the progress and/or state of said gastrointestinal cancer, and therefore the degree of efficacy of the ongoing therapeutic treatment; and
  iii) based thereon determining whether the therapeutic treatment of the gastrointestinal cancer is to be continued, terminated or replaced.

Alternatively the reference level may be a reference level based on previous determinations of YKL-40 levels in the individual such as the method comprising: monitoring therapeutic treatment of a gastrointestinal cancer in a subject, said subject being treated for the specific disease, said method comprising
  i) determining the level of YKL-40 in a sample obtained from the subject;
  ii) comparing said level of YKL-40 with one or more reference levels of YKL-40; said reference levels being one or more previously determined levels of YKL-40 from the same subject wherein the level of YKL-40 with respect to the reference levels indicates the progress and/or state of said gastrointestinal cancer, and therefore the degree of efficacy of the ongoing therapeutic treatment; and
  iii) based thereon determining whether the therapeutic treatment of the gastrointestinal cancer is to be continued, terminated or replaced, wherein a level of YKL-40 in the sample being increased to at least a factor 1.10 compared to the reference level of YKL-40 indicates that the gastrointestinal cancer has evolved to a more severe stage of the gastrointestinal cancer, and thus requires a therapy of higher efficacy than the ongoing therapy to be initiated; and wherein a level of YKL-40 in the sample being decreased to at least a factor 0.90 compared to the reference level of YKL-40 indicates that the gastrointestinal cancer has evolved to a less severe stage of the gastrointestinal cancer.

Monitoration in Combination with Treatment

GI cancers are commonly treated with one or more of surgery, chemotherapy, radiotherapy, biological therapy or combinations of these therapies. It is an important aspect of the present invention to monitor the status of an individual suffering from a gastrointestinal cancer during treatment of the disease.

Chemotherapeutic and biological agents which may be employed in the treatment of GI cancer include, but are not limited to: 5-Fluouracil (5-FU), Capecitabine (Xeloda®), Tegafur-uracil/Ufteral, S1, Irinotecan (Campto or Camtosar®), Oxaliplatin, Gemcitabin, Mitomycin, Taxoterre, Taxol, Carboplatin, Epirubicin, Doxorubicin, Docetaxel, Erlotinib (Tarceva®), Sunitinib (Sutent®) and Sorfenib (Nexavar®); VEGF-inhibitors: Bevacizumab (Avastin®), Kinase inhibitors of the VEGF receptor, PDGF-Receptor KIT (CD117) RET, CSF-1R, flt3, Sunitinib (Sutent®), monoclonal antibodies that inhibit the EGF receptor such as Cetuximab (Erbitux®), Panitumumab (Vectibix®) and Zalutumumab (HuMax-EGFr), Kinase inhibitors of the EGF-receptor: Gefitinib (Iressa) and Erlotinib (Tarceva), M-Tor inhibitors: Sirolimus, Everolimus (Cartisan®) and Temsirolimus (Torisel), Compounds that target the Raf/Mek/Erk signal pathway such as Sorafenib (Nexavar®).

Thus it as an object of the present invention to monitor the therapeutic treatment of a gastrointestinal cancer in a subject that has, will be or is being treated by surgery, the administration of a chemotherapeutic agent and/or a biological agent and/or radiotherapy, and/or combinations thereof. It is furthermore an object of the present invention to determining the effect of a therapy, as described herein in the section termed "Third aspect of the invention". Preferably, the therapeutic treatment is a chemotherapeutic treatment such as, but not limited to a treatment involving the administration of at least one of the following compounds: 5-Fluouracil, Capecitabine (Xeloda®), Tegafur-uracil/Ufteral, S1, Irinotecan, Oxaliplatin, Gemcitabin, Mitomycin, Taxoterre, Taxol, Carboplatin, Epirubicin, Docetaxel, Doxorubicin, Erlotinib (Tarceva®), Sunitinib (Sutent®) and Sorfenib (Nexavar®). Preferably the chemotherapeutic treatment comprises the administration of one or more of the compounds selected from the group consisting of fluorouracil, capecitabine, irinotecan, oxaliplatin, gemcitabin, docetaxel, erlotinib, and leucovorin. More preferably the treatment is the administration of at least one of docetaxel, irinotecan, 5-FU, leucovorin, Erlotinib (Tarceva®) and/or Gemcitabin.

These agents are used in discretionarily by persons skilled in the art depending on the cancer type the individual suffers from. Thus colorectal cancer is preferably treated with any one or more of the following: 5-Fluouracil, Capecitabine (Xeloda®), Tegafur-uracil/Ufteral, S1, Irinotecan, Oxaliplatin, Gemcitabin, Mitomycin; VEGF-inhibitors: Bevacizumab (Avastin®), Kinase inhibitors of the VEGF receptor, PDGF-Receptor KIT (CD117) RET, CSF-1R, flt3, Sunitinib (Sutent®), monoclonal antibodies that inhibit the EGF receptor such as Cetuximab (Erbitux®), Panitumumab (Vectibix®), and Zalutumumab (HuMax-EGFr), Kinase inhibitors of the EGF-receptor: Gefitinib (Iressa) and Erlotinib (Tarceva), M-Tor inhibitors: Sirolimus, Everolimus (Cartisan®) and Temsirolimus (Torisel), Compounds that target the Raf/Mek/Erk signal pathway such as Sorafenib (Nexavar®). Likewise, the preferred compounds for the treatment of gastric and esophageal cancer include, but are not limited to: Taxoterre, Taxol, Carboplatin, Epirubicin, Doxorubicin, Irinotecan, Oxaliplatin, and Mitomycin. Pancreatic cancer is preferably treated with any one or more of: irinotecan, docetaxel, 5-FU, leucovorin, Erlotinib (Tarceva®) and/or Gemcitabin; and primary liver cancer with: Sunitinib (Sutent®) and/or Sorfenib (Nexavar®).

Selected patients with upper GI cancer may in the future also be treated with VEGF-inhibitors: Bevacizumab (Avastin®), Kinase inhibitors of the VEGF receptor, PDGF-Receptor KIT (CD117) RET, CSF-1R, flt3, Sunitinib (Sutent®), monoclonal antibodies that inhibit the EGF receptor such as Cetuximab (Erbitux®), Panitumumab (Vectibix®), and Zalutumumab (HuMax-EGFr), Kinase inhibitors of the EGF-receptor: Gefitinib (Iressa) and Erlotinib (Tarceva), M-Tor inhibitors: Sirolimus, Everolimus (Cartisan®) and Temsirolimus (Torisel), Compounds that target the Raf/Mek/Erk signal pathway such as Sorafenib (Nexavar®). These compounds are of special relevance in relation to the methods of the present invention. More preferably Bevacizumab (Avastin®), Cetuximab (Erbitux®), Panitumumab (Vectibix®), and Zalutumumab (HuMax-EGFr); even more preferably Cetuximab (Erbitux®), Panitumumab (Vectibix®), and Zalutumumab (HuMax-EGFr); and even more preferably Cetuximab (Erbitux®).

Determination of Therapy and/or Treatment

Based upon the classification of the subject according to YKL-40 level as measured and compared to at least one reference level of YKL-40 a person skilled in the art is better equipped than ever before to determine the best possible treatment of the specific gastrointestinal cancer, together with determining the effect of a therapy. Thus it is possible for the person skilled in the art based on the methods herein disclosed to initiate, continue, terminate, alter or replace a therapy or therapeutic treatment in a subject suffering from the cancer. For example if a therapy may be envisaged to be ineffective or a subject is found to be non-responsive.

In relation to the methods of the invention, the therapy and/or treatment to be initiated, continued, terminated or replaced, which ever one or more is appropriate in the method in question, may be any treatment for a GI cancer, for example but not limited to a biologic agent, chemotherapeutic agent etc. In some embodiments of the invention the treatment comprises one or more agents selected from the group consisting of biologic agents and chemotherapeutic agents. In preferred embodiments the therapy and/or treatment comprises biologic agents; more preferably the therapy is a therapy comprising EGFR inhibitors or VEGF inhibitors; even more preferably the therapy is a therapy comprising EGFR inhibitors; and yet even more preferably the therapy comprises one or more selected from the group consisting of Cetuximab, Panitumumab, Zalutumumab, and Erlotinib. Most preferably the therapy comprises Cetuximab.

YKL-40 as a Marker of Gastrointestinal Cancer

YKL-40 levels are increased in subjects suffering from gastrointestinal cancers and thus the YKL-40 level of an individual can diagnose the presence of a gastrointestinal cancer in a subject.

Thus a first aspect of the present invention regards a method for the diagnosing of the presence of a gastrointestinal cancer in a subject, said method comprising
i) determining the level of YKL-40 in a sample obtained from the subject; and
ii) comparing said level of YKL-40 with a reference level of YKL-40;

wherein a level of YKL-40 in the sample above the reference level indicates the presence of a gastrointestinal cancer. The GI cancer may preferably be an upper GI cancer.

An following the above, a further embodiment regards a method for diagnosing the presence of a gastrointestinal cancer in a subject, said method comprising
i) determining the level of YKL-40 in a sample obtained from the subject; and
ii) comparing said level of YKL-40 with a reference level of YKL-40, said reference level being a previously determined level of YKL-40 from the same subject;

wherein a level of YKL-40 in the sample increased by at least a factor of 1.10 compared to the reference level of YKL-40 indicates the presence of a gastrointestinal cancer. Further details with regard to the reference levels may be found in the section termed "Reference levels".

Preferably, the reference level of YKL-40 is, if necessary, an age adjusted reference level, for example obtained by adding 0.5 µg/l per year for women, and 0.8 µg/l per year for men. This may for instance be relevant when the previously obtained reference level is more than 3 years old, such as e.g. more than 5 years old, more than 8 years old, or more than 10 years old. For example when the previously obtained reference level is more than 10 years old.

When the applied reference level is a previously determined level of YKL-40 from the same subject the determined level of YKL-40 in the sample is said to be significantly above the reference level and thereby indicating the presence of a gastrointestinal cancer when the level of YKL-40 in the sample is increased by about 109% or more. The following is a calculation example, where the previously measured YKL-40 level is 50 µg/l, and an YKL-40 level increased by 109% is calculated: 50 µg/l+(50×1.09) µg/l=50 µg/l+54.5 µg/l=104.5 µg/l.

In a specially preferred embodiment of the method according to the present invention, whether the reference level is obtained from a group of healthy individuals or obtained as a previous measurement from the same individual, a level of YKL-40 in the sample increased to a factor of 1.10 compared to the reference level of YKL-40 indicates the presence of a gastrointestinal cancer, more preferably at least a factor of 1.25, such as e.g. a factor of 1.30, or a factor of 1.40; even more preferably at least a factor of 1.50, such as e.g. a factor of 1.60, a factor of 1.70, or a factor of 1.75; yet even more preferably at least a factor of 1.75, such as e.g. a factor of 1.80, or a factor of 1.90, or a factor of 2; most preferably at least a factor of 2, such as e.g. a factor of 2.10, a factor of 2.20, a factor of 2.25, or a factor of 2.50 compared to the reference level of YKL-40 indicates the presence of a gastrointestinal cancer. The following is a calculation example giving a level being increased to a factor of 1.10 compared to a reference level of 50 µg/l: 50 µg/l×1.10=55 µg/l (i.e. The new level is: 55 µg/l).

Furthermore, in one embodiment of the method according to the present invention, whether the reference level is obtained from a group of healthy individuals or obtained as a previous measurement from the same individual, a level of YKL-40 in the sample decreased to a factor of 0.90 compared to a reference level indicates that a changes to the better has occurred. Accordingly, in one embodiment wherein a level of YKL-40 in the sample being decreased at least to a factor of 0.90 compared to the YKL-40 reference level indicates that a gastrointestinal cancer has evolved to a less severe stage of the disease or disorder, or even that the subject has been cured, more preferably decreased at least to a factor of 0.80, such as e.g. a factor of 0.70; even more preferably decreased at least to a factor of 0.60; yet even more preferably decreased at least to a factor of 0.50; most preferably decreased at least to a factor of 0.48, such as e.g. a factor of 0.45, a factor of 0.43, a factor of 0.40, or a factor of 0.38, compared to the YKL-40 reference level. The following is a calculation example giving a level being decreased to a factor of 0.90 compared to a reference level of 100 µg/l: 100 µg/l×0.90=90 µg/l, i.e. the new and lower plasma YKL-40 level is 90 µg/l. When it is written that a level is decreased at least to a factor of e.g. 0.90, it is intended to mean that the level is decreased to a factor 0.90 or e.g. 0.80, 0.70 etc., i.e., that a level of 100 µg/l is decreased to at least 90 µg/l or a lower value.

In a more preferred embodiment of the first aspect of the invention a level of YKL-40 in the sample being decreased by 52% compared to the YKL-40 reference level indicates that a gastrointestinal cancer has evolved to a less severe stage of the disease or disorder. The following is a calculation example, where the previously measured YKL-40 level is 100 µg/l, and an YKL-40 level decreased by 52% is calculated: 100 µg/l−(100×0.52) µg/l=100 µg/l−52 µg/l=48 µg/l.

Other Biomarkers

YKL-40 is an independent biomarker for classifying the severity of a gastrointestinal cancer and may be used accordingly. However, YKL-40 may also be used in combination with other known biomarkers such as C-reactive protein (CRP), ESR, carcinoembryonic antigen (CEA), CA-125, human epidermal growth factor receptor 2 (HER2), CA19-9, lactate dehydrogenase (LDH), brain natriuretic protein (BNP), interleukins (IL), tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases, pentraxin 3, secretory phospholipase A2 group IIA, intercellular adhesion molecule-1, Heart-type fatty acid-binding protein (H-FABP), Myosin light chain-1 (MLC-1), P-selectin and CKMB. Of the mentioned biomarkers, both the soluble and insoluble forms of the proteins are of relevance for the present invention, such as UPAR and soluble UPAR; intercellular adhesion molecule-1 and soluble intercellular adhesion molecule-1, and others. The levels of any of the abovementioned markers may be measured in a biological sample such as a blood, serum, plasma or tissue sample and by any means available such as by use of immunoassays or PCR based assays or several assay types in combination.

Recent data have demonstrated that patients with metastatic colorectal cancer and a mutation in the Kirsten ras (KRAS) gene, an oncogene downstream from the EGFR, have no effect of treatment with cetuximab and panitumumab. The KRAS encoded protein is a member of the small GTPAse superfamily, and a single amino acid substitution in the KRAS gene results in an activating mutation. Since summer 2008 only colorectal cancer patients with KRAS wild type are recommended to be treated with cetuximab and panitumumab. KRAS is mutated in approximately 30% to 45% of all colorectal tumors, resulting in a constitutively active EGF signalling pathway. The identification of KRAS as a predictive biomarker of response to anti-EGFR therapy has obvious benefits. First, close to half of patients with metastatic colorectal cancer will avoid unnecessary exposure to an ineffective therapy that has the potential to cause significant toxicities. Second, the potential cost savings to the health care system are profound, approximately $ 600 million each year in USA (8 weeks of treatment with cetuximab cost approximately $ 19,000).

However, KRAS mutations are not the only factor influencing response to anti-EGFR antibodies. Approximately 25% to 40% of patients with KRAS wild type do not respond to anti-EGFR antibody. Approximately 10% of these patients have mutations in the BRAF gene. This causes a change in the BRAF protein that can increase growth and spread of cancer cells. BRAF is an isoform of RAF. RAF proteins are intermediate to RAS and MAPK in the cellular proliferation pathway. RAF proteins are typically activated by RAS via phosphorylation, and activated RAF proteins in turn activate MAPK via phosphorylation. Furthermore some patients with KRAS wild type have a loss of protein expression of PTEN, a tumor supressor gene, and some have low expression of either amphiregulin (AREG) or epiregulin (EREG) and these patients have less response to cetuximab. These recent studies need to be validated and it is not yet recommended to test for BRAF mutations or expression of PTEN, AREG or EREG before treatment with cetuximab or panitumumab. Even if both KRAS and e.g. BRAF was used in order to predict the responsiveness to such treatment about 40% KRAS wildtype patients remain that are unresponsive towards the treatment.

Accordingly, the methods according to the present invention further relates to methods for diagnosing and/or classifying the severity and/or determining a therapy and/or monitoring a therapeutic treatment, as defined in the first, second, third and fourth aspects of the invention, where the methods further comprises a step of determining the level of one or more additional biomarkers. The one or more additional biomarker may be selected from the group consisting of KRAS mutation status, BRAF mutation status, PTEN expression, microsatelite instability (MSI), AREG expression, EREG expression, CRP, ESR, CEA, CA19-9, LDH, tissue inhibitor of metalloproteinase 1 (TIMP1), interleukins, IL-4, IL-6, IL-8, VEGF, metalloproteinases, soluble UPAR (sUPAR), tumor necrosis factor-alfa, the aminoterminal propeptide of type I and III procollagen (P-III-NP), monocyte chemoattractant protein-1, fibrin D-dimer and other gene-, microRNA and SNP biomarkers identified from array studies.

Preferably the one or more further biomarker is selected from the group consisting of KRAS mutation status, BRAF mutation status, PTEN expression, AREG expression, EREG expression, CRP, ESR, CEA, CA19-9, LDH, TIMP1, interleukins, IL-4, IL-6, IL-8, VEGF, metalloproteinases, sUPAR, tumor necrosis factor-alfa, the aminoterminal propeptide of type I and III procollagen, monocyte chemoattractant protein-1, fibrin D-dimer and other gene-, microRNA and SNP biomarkers identified from array studies. More preferably the one or more further biomarker is selected from the group consisting of KRAS mutation status, BRAF mutation status, CEA, CA19-9.

It is thus an aspect of the present invention to provide means for diagnosing subjects and/or means for determining a therapy for subjects according to their YKL-40 levels in combination with levels of other biomarkers these being selected from the non-limiting group consisting of KRAS mutation status, BRAF mutation status, PTEN expression, microsatelite instability (MSI), AREG expression, EREG expression, C-reactive protein (CRP), ESR, carcinoembryonic antigen (CEA), CA-125, human epidermal growth factor receptor 2 (HER2), CA19-9, lactate dehydrogenase (LDH), brain natriuretic protein (BNP), TIMP1, interleukins (IL), IL-6, IL-8, IL-4, VEGF, tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases and CKMB. Of these additional biomarkers C-reactive protein, brain natriuretic protein and homocysteine and other gene-, microRNA and SNP biomarkers identified from array studies are of particular interest. Even more preferably C-reactive protein, brain natriuretic protein and homocysteine.

The above mentioned embodiments may be comprised in a kit of parts together with any required medical and or sampling equipment and instructions for use of the equipment and how to perform the assay of choice.

Biological Sample

A biological sample is a sample obtained from a subject. As such a biological sample may be a sample selected from the group consisting of tissue, blood, serum, plasma samples, urine, cerebrospinal fluid, synovial fluid, ascites, and saliva. Of special relevance to the present invention are samples of blood, serum or plasma, more preferably the biological sample is serum or plasma. Those of ordinary skill in the art will be able to readily determine which assay sample source is the most appropriate for use in the diagnosis of a particular disease, or disorder or general state of health. As there is only a minor difference between the YKL-40 levels as measured in plasma and serum, the values as described herein can be applied for both plasma and serum samples.

Subjects

The subjects herein referred to are single members of a species, herein preferably a mammalian species. Any mammalian species is an object of the present invention, although any of the following species are of particular relevance: mouse, rat, guinea pig, hamster, rabbit, cat, dog, pig, cow, horse, sheep, monkey, and human. Most preferably the subject of the present invention is a human. The subjects may in the present text also be referred to as patients or individuals.

Device

A fifth aspect of the present invention relates to a device for classifying the severity of a gastrointestinal cancer, wherein the device comprises means for measuring the level of YKL-40 in a sample; and means for comparing the measured level of YKL-40 with at least one reference level of YKL-40, such as one or more reference levels of YKL-40. The means for measuring the level of YKL-40 in a sample may for example be a test system that applies any of the above mentioned assay systems, such as an immunoassay, a PCR based assay or an enzymatic assay. An immunoassay is preferred for the present device.

A device according to the present invention may for example comprise a rapid, qualitative and/or quantitative test system mounted on a solid support for the determination of YKL-40 levels in biological samples.

The solid support can be used in any phase in performing any of the above assays, particularly immunoassays, including dipsticks, membranes, absorptive pads, beads, microtiter wells, test tubes, and the like. Preferred are test devices which may be conveniently used by the testing personnel or the patient for self-testing, having minimal or no previous training. Such preferred test devices include dipsticks and membrane assay systems. The preparation and use of such conventional test systems is well described in the patent, medical, and scientific literature. If a stick is used, the anti-YKL-40 antibody is bound to one end of the stick such that the end with the antibody can be dipped into or onto the biological samples. Alternatively, the samples can be applied onto the antibody-coated dipstick or membrane by pipette, dropper, tweezers or the like, or be squirted directly from the body and onto the stick. Accordingly, in a preferred embodiment of this aspect of the invention, the device is a dipstick.

In the present aspect of the invention any biological sample that is or may be converted to a fluid is preferred. Particularly biological samples that are obtainable from a body as a fluid are preferred; examples hereof include, and are not limited to: blood, serum, plasma, urine, cerebrospinal fluid, synovial fluid, ascites, semen, and saliva. More preferably serum and plasma samples.

The antibody against YKL-40 can be of any isotype, such as IgA, IgG or IgM, Fab fragments, or the like. The antibody may be a monoclonal or polyclonal and produced by methods as generally described in Harlow and Lane, Antibodies, A Laboratory Manual, Cold Spring Harbor Laboratory, 1988, incorporated herein by reference. See also section on immunoassays. The antibody can be applied to the solid support by direct or indirect means. Indirect bonding allows maximum exposure of the YKL-40 binding sites to the assay solutions since the sites are not themselves used for binding to the support. Polyclonal antibodies may be used since polyclonal antibodies can recognize different epitopes of YKL-40 thereby enhancing the sensitivity of the assay. Alternatively, monoclonal antibodies against YKL-40 may be used.

The solid support is preferably non-specifically blocked after binding the YKL-40 antibodies to the solid support. Non-specific blocking of surrounding areas can be with whole or derivatized bovine serum albumin, or albumin from other animals, whole animal serum, casein, non-fat milk, and the like.

The sample is applied onto the solid support with bound YKL-40-specific antibody such that the YKL-40 will be bound to the solid support through said antibodies. Excess and unbound components of the sample are removed and the solid support is preferably washed so the antibody-antigen complexes are retained on the solid support. The solid support may be washed with a washing solution which may contain a detergent such as Tween-20, Tween-80 or sodium dodecyl sulphate.

After the YKL-40 has been allowed to bind to the solid support, a second antibody which reacts with YKL-40 is applied. The second antibody may be labelled, preferably with a visible label. The labels may be soluble or particulate and may include dyed immunoglobulin binding substances, simple dyes or dye polymers, dyed latex beads, dye-containing liposomes, dyed cells or organisms, or metallic, organic, inorganic, or dye solids. The labels may be bound to the YKL-40 antibodies by a variety of means that are well known in the art. In some embodiments of the present invention, the labels may be enzymes that can be coupled to a signal producing system. Examples of visible labels include alkaline phosphatase, beta-galactosidase, horseradish peroxidase, and biotin. Many enzyme-chromogen or enzyme-substrate-chromogen combinations are known and used for enzyme-linked assays.

Simultaneously with the sample, corresponding steps may be carried out with a known amount or amounts of YKL-40 and such a step can be the standard for the assay. In one embodiment of the method according to the present invention the one or more reference levels of YKL-40 are reference levels for one or more predetermined stages of the disease or the disorder.

The solid support is washed again to remove unbound labelled antibody and the labeled antibody is visualized and quantitated. The accumulation of label will generally be assessed visually. This visual detection may allow for detection of different colors, e.g., red color, yellow color, brown color, or green color, depending on label used. Accumulated label may also be detected by optical detection devices such as reflectance analyzers, video image analyzers and the like. The visible intensity of accumulated label could correlate with the concentration of YKL-40 in the sample. The correlation between the visible intensity of accumulated label and the amount of YKL-40 may be made by comparison of the visible intensity to a set of reference standards. Preferably, the standards have been assayed in the same way as the unknown sample, and more preferably alongside the sample, either on the same or on a different solid support. The concentration of standards to be used can range from about 1 µg of YKL-40 per liter of solution, up to about 1 mg of YKL-40 per liter of solution, preferably the range for testing serum samples will be from 40 µg/l to 400 µg/l YKL-40. Preferably, several different concentrations of YKL-40 standards are used so that quantitating the unknown by comparison of intensity of color is more accurate. An intensity of color similar to 110 µg/l of YKL-40 may for example be considered negative, as compared with an intensity of color similar to 200 µg/l.

The device, such as the herein described dipstick or other solid support based test system, may thus be used in aid of determining the approximate level of YKL-40 in a biological sample by comparison to one or more standards/control fields. Thus the concentration of YKL-40 can be ascertained to be within a range between two of the concentrations of YKL-40 applied to the standard/control fields of the device. Alternatively the concentration of YKL-40 can be judged to be above or below a cut-off value of YKL-40, the chosen concentration for the cut-off value being applied to the control field of the dipstick. There may be multiple reference levels/standards available within and/or on the device or single reference level/standard within and/or on the device. In the latter case, the device may be used as a yes no test, to compare a YKL-level in a sample with one reference level, i.e. to see whether the YKL-level of the sample is above or below the reference level. In a preferred embodiment of a device according to the invention, the device comprises a single reference level, representing a cut-off value. The reference level may be any of the reference levels described herein above in the section termed "reference levels".

For example, in one embodiment, the device may comprise means for comparing the measured level of YKL-40 with at a set of age adjusted reference levels of YKL-40. Preferably the reference levels is one or more reference levels selected from the following age dependent cut-off values defined as:
the $70^{th}$ percentile: ln(plasma YKL-40 µg/l)=3.1+0.02×age (years),
the $75^{th}$ percentile: ln(plasma YKL-40 µg/l)=3.2+0.02×age (years),
the $85^{th}$ percentile: ln(plasma YKL-40 µg/l)=3.4+0.02×age (years),
the $90^{th}$ percentile: ln(plasma YKL-40 µg/l)=3.5+0.02×age (years),
the $95^{th}$ percentile: ln(plasma YKL-40 µg/l)=3.6+0.02×age (years), and
the $97.5^{th}$ percentile: ln(plasma YKL-40 µg/l)=3.9+0.02×age (years).

Alternatively, in another embodiment, the device comprises means for comparing the measured level of YKL-40 with a set of age dependent cut-off values as defined in the following table:

| | Age dependent cut-off values for healthy subjects | | | | |
|---|---|---|---|---|---|
| Age intervals (years) | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 40 | 44 | 54 | 59 | 65 |
| 30-39 | 48 | 54 | 65 | 72 | 80 |
| 40-49 | 59 | 65 | 80 | 88 | 98 |
| 50-59 | 72 | 80 | 98 | 108 | 119 |
| 60-69 | 88 | 98 | 119 | 132 | 145 |
| 70-79 | 108 | 119 | 154 | 161 | 178 |
| 80-89 | 132 | 145 | 178 | 196 | 217 |

Alternatively, the device comprises means for comparing the measured level of YKL-40 with a set of age dependent as defined in the following table:

| | Age dependent reference levels for healthy subjects | | | | |
|---|---|---|---|---|---|
| Age intervals (years) | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 33-40 | 37-44 | 45-54 | 49-59 | 55-65 |
| 30-39 | 40-48 | 45-54 | 55-65 | 60-72 | 67-80 |
| 40-49 | 49-59 | 55-65 | 67-80 | 74-88 | 81-98 |
| 50-59 | 60-72 | 67-80 | 81-98 | 90-108 | 99-119 |
| 60-69 | 74-88 | 81-98 | 99-119 | 110-132 | 122-145 |
| 70-79 | 90-108 | 99-119 | 122-154 | 134-161 | 148-178 |
| 80-89 | 110-132 | 122-145 | 148-178 | 164-196 | 181-217 |

Although each of the steps can be carried out in the same vessel, such as a test tube, if it is cleaned and washed after each of the steps, a fast and convenient on-site assay is best performed according to the invention by using three separate vessels for each of the steps, one for the sample, one for washing, and one for developing the detectable label.

Figure 17:
FIGS. 17A and 17B Dipstick embodiments seen from above. Dipstick support material (1.) with assay field (2.) for use with the biological sample and one control or standard field (3.
Figure 17:
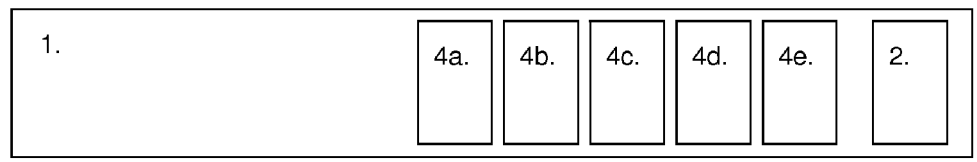

It is thus an object of the present invention that the YKL-40 level of a biological sample for use in the classification according to a reference level of YKL-40 of the individual from which the biological sample originated is measured by use of a dipstick. (see FIGS. 17A and 17B)

In an alternative embodiment of this aspect of the invention the device further comprises means for assaying additional biomarkers than YKL-40, such as any one or more of the biomarkers from the following non-limiting group: KRAS and BRAF mutation status, microsatelite instability (MSI), PTEN expression, other gene-, microRNA and SNP biomarkers identified from array studies C-reactive protein (CRP), ESR, carcinoembryonic antigen (CEA), CA-125, human epidermal growth factor receptor 2 (HER2), CA19-9, lactate dehydrogenase (LDH), TIMP1, Interleukins (IL), IL-6, IL-8, IL-4, VEGF, brain natriuretic protein (BNP), interleukins, tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases, pentraxin 3, secretory phospholipase A2 group IIA, intercellular adhesion molecule-1, Heart-type fatty acid-binding protein (H-FABP), Myosin light chain-1 (MLC-1), P-selectin and CKMB. Alternatively the device further comprises means for assaying further biomarkers as described herein in the section termed "other biomarkers". Preferably the device comprises means for assaying C-reactive protein and/or brain natriuretic protein and/or homocysteine; more preferably the device comprises means for assaying C-reactive protein, CA19-9, KRAS expression, BRAF expression, interleukins, IL-6, IL-8, IL-4, TIMP1, VEGF or sUPAR.

Kit of Parts

All the materials and reagents required for assaying YKL-40 according to the present invention can be assembled together in a kit, such kit includes at least elements in aid of assessing the level of YKL-40 in a biological sample obtained from an individual, and the instruction on how to do so.

Said elements may be a method of detecting the YKL-40 levels such as an immunoassay, or parts required to perform an immunoassay specific for YKL-40 detection. Optionally, a kit may further or alternatively comprise elements for performing PCR based assays for the detection of YKL-40 and determination of levels of the same from biological samples. The kit of parts may further comprise equipment for obtaining one or more biological samples, such equipment may for example be syringes, vials or other. The kit of parts may be packed for single use or for repeated usage, and the elements therein may be disposable such as to be disposed of after a single use or may be of a quality that allows repeated usage.

A sixth aspect of the present invention relates to a kit of parts comprising
i) means for measuring the level of YKL-40 in a sample;
ii) means for comparing the measured level of YKL-40 with at least one reference level of YKL-40; and
iii) instructions on how to age adjust the reference level of YKL-40, according to the age of the subject providing the sample.

Means for measuring the level of YKL-40 in a sample may include one or more solutions containing a known concentration of YKL-40, a washing solution, a solution of a chromogen which changes color or shade by the action of the enzyme directly or indirectly through action on a substrate, an anti-YKL-40 antibody conjugated to a label such that it could be detected, pipettes for the transfer of said solutions, test tubes for said solutions, and a solid support, in particular adapted to be inserted into the test tubes, carrying on the surface thereof a polyclonal antibody to YKL-40. The kit may also contain one or more solid support having an anti-YKL-40 antibody for use in assaying one or more samples simultaneously or individually, and the necessary reagent required to develop the label. Included in means for comparing the measured level of YKL-40 with at least one reference level of YKL-40 may be YKL-40 standards that can be assayed fresh along with the unknown sample. Such kits will comprise distinct containers for each individual reagent. The reference level may be any of the reference levels described herein above in the section termed "reference levels".

Preferably the reference level is one or more reference levels selected from the following age dependent cut-off values defined as:
the $70^{th}$ percentile: ln(plasma YKL-40 µg/l)=3.1+0.02×age (years),
the $75^{th}$ percentile: ln(plasma YKL-40 µg/l)=3.2+0.02×age (years),
the $85^{th}$ percentile: ln(plasma YKL-40 µg/l)=3.4+0.02×age (years),
the $90^{th}$ percentile: ln(plasma YKL-40 µg/l)=3.5+0.02×age (years),
the $95^{th}$ percentile: ln(plasma YKL-40 µg/l)=3.6+0.02×age (years), and
the $97.5^{th}$ percentile: ln(plasma YKL-40 µg/l)=3.9+0.02×age (years).

In the above test kit, the reagents may be supplied from storage bottles or one or more of the test tubes may be pre-filled with the reagents or controls.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the reagents such as vials or tubes in close confinement for commercial sale such as, e.g. injection or blow-molded plastic containers into which the desired vials are retained. The kits will also comprise a set of instructions on how to perform the assay.

In an alternative embodiment of this aspect of the invention the kit will comprise means for assaying additional biomarkers than YKL-40, such as any one or more of the biomarkers from the following non-limiting group: C-reactive protein (CRP), ESR, carcinoembryonic antigen (CEA), CA-125, human epidermal growth factor receptor 2 (HER2), CA19-9, lactate dehydrogenase (LDH), KRAS expression, BRAF expression, interleukins, IL-6, IL-8, IL-4, TIMP1, VEGF, sUPAR, brain natriuretic protein (BNP), interleukins, tumor necrosis factor-alfa, homocysteine, amyloid A protein, Pregnancy-Associated Plasma Protein-A, troponines, soluble intercellular adhesion molecule-1, soluble UPAR, the amino-terminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases, pentraxin 3, secretory phospholipase A2 group IIA, intercellular adhesion molecule-1, Heart-type fatty acid-binding protein (H-FABP), Myosin light chain-1 (MLC-1), P-selectin and CKMB. Alternatively the device further comprises means for assaying further biomarkers as described herein in the section termed "other biomarkers". Preferably the kit will comprise means for assaying C-reactive protein and/or brain natriuretic protein and/or homocysteine.

The kit according to the present invention may furthermore comprise a device according to the invention as described above here in the section termed "device".

All patent and non-patent references cited in the present application, are also hereby incorporated by reference in their entirety.

EXAMPLES

The following examples are for illustrative purposes only and should not be construed as limiting the scope of the invention, which is defined by the appended claims.

Example 1

Plasma YKL-40 Levels in Normal Subjects and Plasma YKL-40 as an Independent Risk Factor Methods
Participants We used a population-based prospective study of the Danish general population, the 1991-1994 examination of the Copenhagen City Heart Study (36,37). Participants aged 20 years and above were selected randomly after gender and age stratification into 5-year groups among residents of Copenhagen. Of the 17180 subjects invited, 10135 participated, and plasma was available for YKL-40 determination in 8899 participants. Participants were followed for 16 years using their unique Central Person Registry number from baseline at the 1991-1994 examination until July 2007. Follow-up was 100% complete. Roughly 99% were Caucasians of Danish descent. At time of blood sampling (1991-1994), 1763 participants had a disease known to be associated with increased levels of plasma YKL-40 (cancer, ischaemic cardiovascular disease, liver disease, diabetes, chronic obstructive pulmonary disease, asthma, rheumatoid arthritis, inflammatory bowel disease or pneumonia). During follow-up additional 3526 had developed at least one of these diseases. 3059 had died. Leaving 3610 healthy participants at the end of follow-up.

Plasma YKL-40 was measured a second time in blood samples of 929 participants of the 2001-2003 examination of the Copenhagen City Heart Study cohort. These participants were selected as having no known disease at the 1991-1994 and 2001-2003 examination, allowing correction for regression dilution bias (36).

The participants filled out a self-administered questionnaire, which was validated by the participant and an investigator on the day of attendance. Participants reported on smoking habits and subdivided into never, previous and current smoker.

Endpoints

Information on death and morbidity were collected from three different population registries using the participants' unique national Danish Central Person Registry number. Information on death was obtained from the national Danish Civil Registry System (36). Information on morbidity in ICD8 and ICD10 codes from 1976 until July 2007 was obtained from the national Danish Patient Registry (34) and subdivided into the following diagnoses associated with increased levels of plasma YKL-40: ischaemic cardiovascular disease, liver disease, diabetes, chronic obstructive pulmonary disease, asthma, rheumatoid arthritis, inflammatory bowel disease or pneumonia. Diagnoses of cancer were obtained from the national Danish Cancer Registry (from 1947 until 2004), which identifies 98% of all cancers in Denmark (35,36) and the national Danish Patient Registry (from 2004 until July 2007).

Ethics

All participants gave written informed consent. The study was approved by Herlev Hospital and a Danish ethical committee (No. 100.2039/91 and 01-144/01, Copenhagen and Frederiksberg committee) and conducted according to the Declaration of Helsinki.

YKL-40 Analysis

Plasma levels of YKL-40 were determined in duplicates in samples frozen for 12-15 years at −80° C. by a commercial two-site, sandwich-type enzyme-linked immunosorbent assay (ELISA) (Quidel Corporation, San Diego, Calif.) (36), using streptavidin-coated microplate wells, a biotinylated-Fab monoclonal capture antibody, and an alkaline phosphatase-labeled polyclonal detection antibody. The recovery of the ELISA was 102% and the detection limit 10 µg/L. The intra-assay coefficients of variations were 5% (at 40 µg/L), 4% (at 104 µg/L), and 4% (at 155 µg/L). The inter-assay coefficient of variation was <6%.

Statistical Analysis

We used STATA version 10.0 (Stata Corp LP, College Station, Tex.). Two-sided P<0.05 was considered significant. Mann-Whitney rank-sum test and Spearman's rho correlation were used. Plasma YKL-40 levels were stratified into categories according to plasma YKL-40 percentiles in gender and 10-year age-groups: the percentile categories were 0-33%, 34-66%, 67-90%, 91-95%, and 96-100%. In Table 3 only three percentile categories were used 0-33%, 34-90%, and 91-100%.

Kaplan-Meier curves plotted cumulative survival against left-truncated age and follow-up time in all participants. Kaplan-Meier curves also plotted cumulative survival in subgroups of participants with cancer, ischaemic cardiovascular disease, liver disease, diabetes, chronic obstructive pulmonary disease, and asthma against follow-up time. Differences between plasma YKL-40 percentile categories were examined using log-rank tests. Hazard ratios and 95% confidence intervals for death were calculated using Cox regression analysis. Hazard ratios were adjusted for other risk factors such as gender, age (deciles) and smoking habits (never/previous/current smokers) at the time of blood sampling. For trend-test, increasing plasma YKL-40 categories labelled 0, 1, 2, 3, and 4 or 0, 1, and 2 (only for the results in Table 3) were used as a continuous variable in the Cox regression. P-values for the trend-test were calculated using the Chi-square value (1 df) of the likelihood-ratio test of the model without YKL-40 categories nested in the model with YKL-40 categories. We tested for proportionality of hazards over time based on Schonefeld residuals and found no violation. Information on baseline covariates was more than 99% complete; individuals with incomplete information on covariates were excluded from multifactorial analysis. Hazard ratios were corrected for regression dilution bias using a non-parametric method (36). For this correction we used plasma YKL-40 values from 929 healthy individuals attending both the 1991-1994 baseline examination and the 2001-2003 follow-up examination; however, the main analysis were conducted on all 8899 participants. A regression dilution ratio of 0.8042 was computed.

Absolute 10-year mortality by plasma YKL-40 percentile categories was estimated by using the regression coefficients from a Poisson regression model including the following covariates: Gender, age (<50, 50-70, >70 years), and smoking habits (never, previous, current smokers) at time of blood sampling. Absolute mortality is presented as estimated incidence rates (events/10 years) in percentages.

Results

Plasma YKL-40 in Healthy Participants

Figure 1:
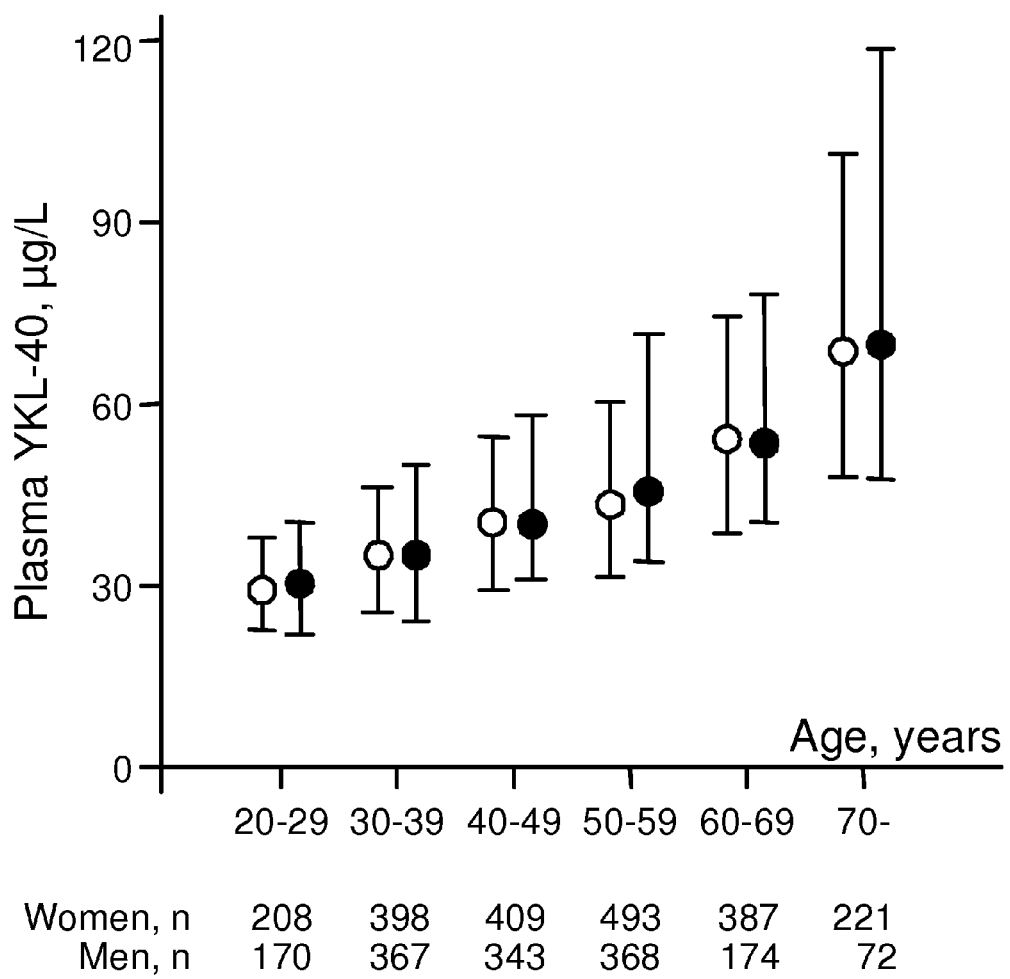
FIG. 1. Plasma concentrations of YKL-40 in 2116 healthy women and 1494 healthy men according to age and sex. The participants had no known disease at the time of blood sampling in 1991-1994 and remained healthy during the 16 years follow-up period (i.e. none were dead or had developed cancer, ischaemic cardiovascular disease, liver disease, diabetes, chronic obstructive pulmonary disease, asthma, rheumatoid arthritis, inflammatory bowel disease, and pneumonia). The median plasma YKL-40 in these healthy participants was 42 µg/L (2.5%-97.5% percentile range: 14-168 µg/L; 90% percentile 92 µg/L; 95% percentile 124 µg/L). Plasma YKL-40 levels increased in both sexes with increasing age (trend test $p<0.0001$). Spearman's rho correlation between plasma YKL-40 and age was 0.41 ($p<0.0001$). There was no difference between plasma YKL-40 in women and men (Mann-Whitney U; $p=0.27$).

The study population consisted of 8899 participants (56% women), aged from 20 to 95 years with a mean of 59 years. Baseline characteristics of all participants according to plasma YKL-40 percentile categories adjusted for age and sex are given in Table 4. 7136 (80%) participants had no known disease at the time of blood sampling in 1991-1994. During the 16 years follow-up period 3576 developed disease leaving 3610 healthy participants at the end of follow-up. The median plasma YKL-40 in these healthy participants was 42 µg/L (2.5%-97.5% percentile range: 14-168 µg/L; 90% percentile 92 µg/L; 95% percentile 124 µg/L). Plasma YKL-40 levels increased in both sexes with increasing age (trend test p<0.0001) (FIG. 1). Spearman's rho correlation between plasma YKL-40 and age was 0.41 (p<0.0001). There was no difference between plasma YKL-40 in women and men (Mann-Whitney U; p=0.27).

Figure 2:
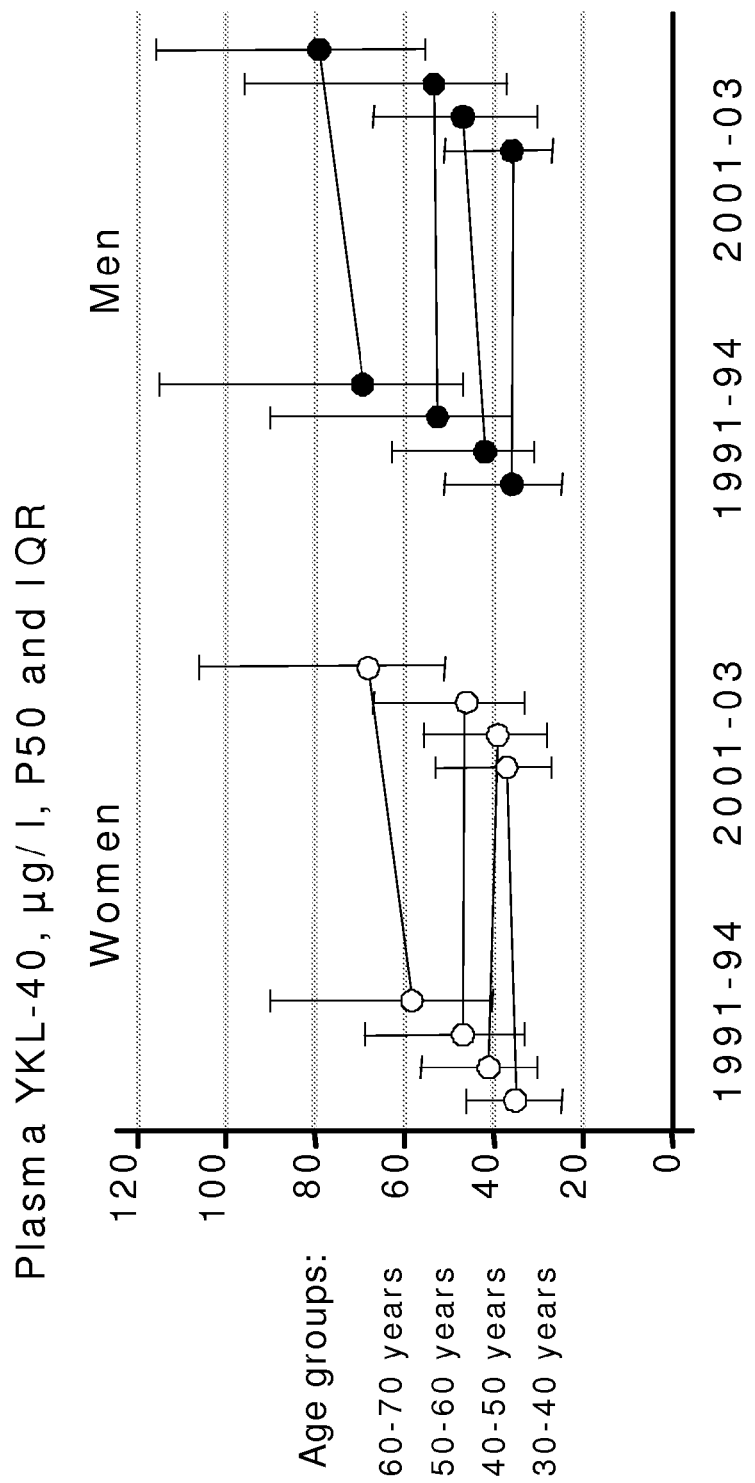
FIG. 2. Plasma concentrations of YKL-40 in a group of 929 healthy participants (463 women and 466 men), who had their first YKL-40 measurement in the blood from the 1991-1994 examination and the second YKL-40 measurement in the blood from the 2001-2003 examination. The mean increase was 0.5 µg/L/year (interquartile range −0.6-2.1 µg/L/year) in women and 0.8 µg/L/year (−0.3-2.9 µg/L/year) in men. This illustrates that plasma YKL-40 is very stable in subjects that remain healthy and a regression dilution ratio of 0.8042 was computed. There was no statistically difference between men and women.

Plasma concentrations of YKL-40 in a group of 929 healthy participants (463 women and 466 men), who had their first YKL-40 measurement in the blood from the 1991-1994 examination and the second YKL-40 measurement in the blood from the 2001-2003 examination can be seen from FIG. 2. The mean increase was 0.5 µg/L/year (interquartile range −0.6-2.1 µg/L/year) in women and 0.8 µg/L/year (−0.3-2.9 µg/L/year) in men. This illustrates that plasma YKL-40 is very stable in subjects that remain healthy and a regression dilution ratio of 0.8042 was computed. There was no statistically difference between men and women.

Plasma concentrations of YKL-40 in a group of 2116 healthy women and 1494 healthy men, which had no known disease at the time of blood sampling in 1991-1994 and remained healthy during the 16 years follow-up period (i.e. none were dead or had develop cancer, ischaemic cardiovascular disease, liver disease, diabetes, chronic obstructive pulmonary disease, asthma, rheumatoid arthritis, inflammatory bowel disease, and pneumonia) can be seen from FIG. 3. The figure illustrates the mean plasma YKL-40 in these healthy participants, the 70% percentile (defined as ln(plasma YKL-40)=3.1+0.02×age (years)), the 75% percentile (defined as ln(plasma YKL-40)=3.2+0.02×age (years)), the 90 percentile (defined as ln(plasma YKL-40)=3.5+0.02×age (years)) and the 95% percentile (defined as ln(plasma YKL-40)=3.6+0.02×age (years)) according to age. Women and men were combined.

In contrast to serum CRP (Kushner et al, 2006) we found no difference in plasma YKL-40 between sexes. Furthermore, we demonstrated in a large group of healthy participants that plasma YKL-40 remained stable over time.

The median increase of plasma YKL-40 in the group of 929 healthy participants (463 women and 466 men), who had their first YKL-40 measurement in the blood from the 1991-1994 examination and the second YKL-40 measurement in the blood from the 2001-2003 examination was 0.5 µg/L/year (interquartile range −0.6-2.1 µg/L/year) in women and 0.8 µg/L/year (−0.3-2.9 µg/L/year) in men. The difference between men and women was not significant.

The median plasma concentrations of YKL-40 are higher for the participants with incident events (cancer, ischaemic cardiovascular disease, liver disease, diabetes, chronic obstructive pulmonary disease, and asthma) than for the participants who stay healthy (Table 1).

Since minor elevations in serum C-reactive protein (CRP), a inflammatory biomarker, have been shown to predict death in both healthy and diseased individuals (Kushner et al, 2006) we also examined the predictive value of plasma YKL-40 in the participants with low plasma CRP (i.e. 1.75 mg/L). It was examined whether the predictive value of plasma YKL-40 concentration was independent of CRP. In the 4453 participants with low plasma CRP concentrations (i.e. 1.75 mg/L) the hazard ratios for death were 1.0 (95% Cl, 0.8-1.2) for plasma YKL-40 percentile category 34-66%, 1.4 (1.1-1.7) for plasma YKL-40 category 67-90%, 2.3 (1.6-3.3) for category 91-95%, and 3.4 (2.5-4.8) for category 96-100% versus plasma YKL-40 percentile category 0-33% ($\log_{10}$ p for trend 12.1). Similar results were found in the participants with plasma CRP>1.75 mg/L ($\log_{10}$ p for trend 18.3) (Table 2). Accordingly, in these subjects the hazard ratios for death increased highly significant with increasing plasma YKL-40 levels, confirming that plasma YKL-40 is independent of plasma CRP.

Elevated plasma YKL-40 and increased risk of death was not related to a specific type of disease, but was found in participants diagnosed with cancer, ischaemic cardiovascular disease, liver disease, diabetes, and chronic obstructive pulmonary disease either before the time of blood sampling in 1991-1994 or during the 16 years follow-up period.

The association between increasing plasma YKL-40 and increased risk of death was similar, or higher, than that of smoking status and risk of death. Furthermore, multivariate cox analysis including smoking status, age and sex demonstrated that plasma YKL-40 was an independent risk factor, i.e. it was shown that plasma YKL-40 percentile category was a risk factor for early death independent of age, gender, plasma CRP, smoking status or disease (cancer, ischemic cardiovascular disease, and other diseases associated with elevated plasma YKL-40). Increasing plasma YKL-40 was associated with smoking (trend, p=0.0005).

In this study of adults from the Danish general population we found that elevated plasma concentrations of YKL-40 predicted early death. The difference in the median survival age between participants with elevated plasma YKL-40 compared to low plasma YKL-40 was 14 years, and the difference in the percentage of participants alive at 15-years follow-up after the time of blood sampling between these two groups was 26%.

It is a strength of the study that the predictive value of plasma YKL-40 was evaluated in a large cohort of well characterized subjects, with a long follow-up period, and with no losses to follow-up.

Plasma YKL-40 as a Risk Factor of Death in the General Population

Figure 4A:
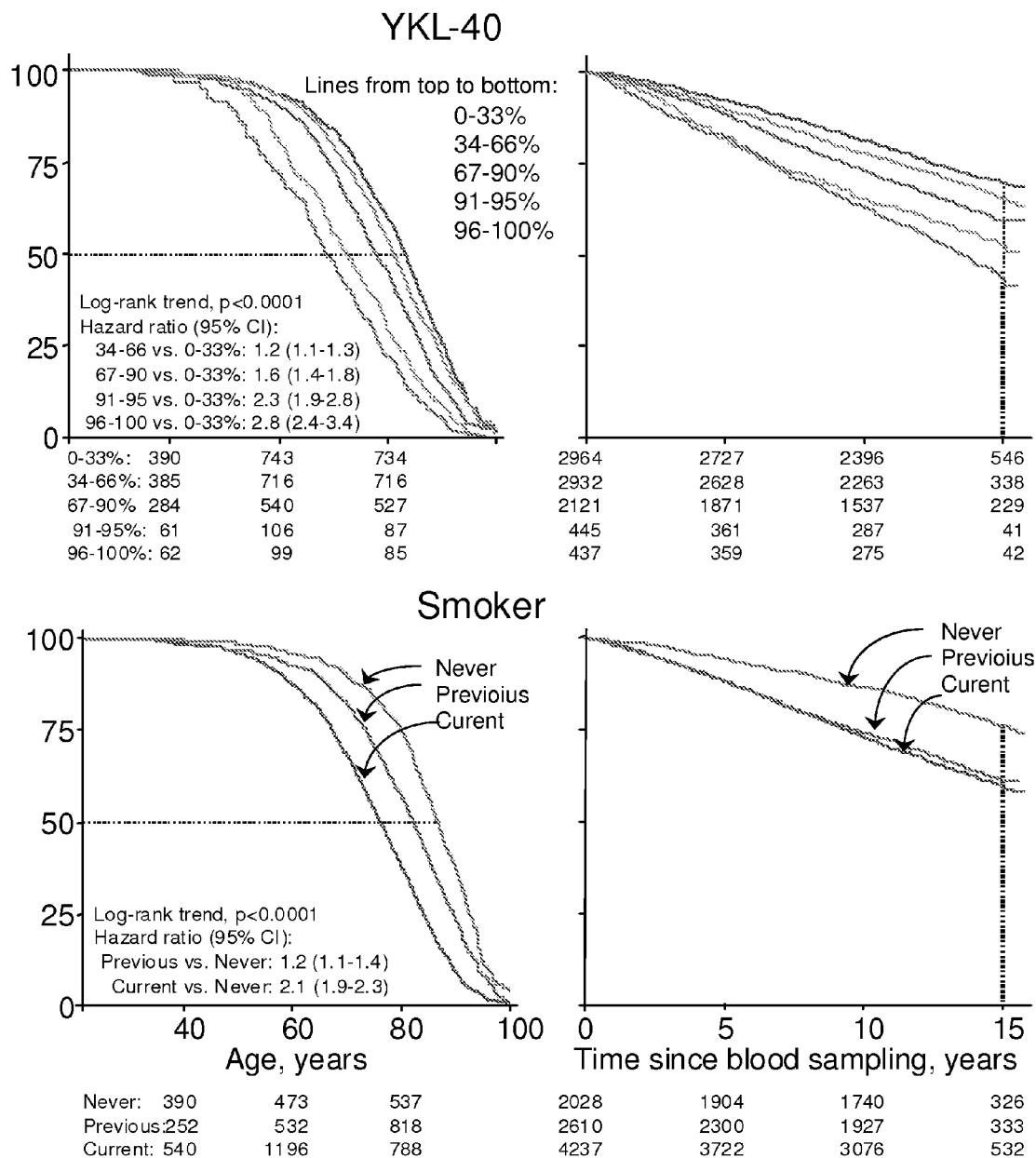
FIG. 4A. Longevity and survival of the general population according to increasing plasma concentrations of YKL-40 (divided into five gender and 10-year age percentile categories: 0-33% percentile, 34-66%, 67-90%, 91-95%, and 96-100%). Left-truncated age and follow-up time were the underlying time-scales, respectively. Follow-up started at time of blood sampling and ended at death or July 2007, whichever came first. Women and men are combined. For comparison the effect of smoking status in the same population is shown.

During 16 years follow-up, 3059 of the 8899 participants died. Increasing plasma YKL-40 (divided into five gender and 10-year age percentile categories) was associated with increasing risk of early death of all causes (log rank test, $p=3.8*10^{-46}$) (Table 3 and FIG. 4A). Participants with low plasma YKL-40 (percentile 0-33%) vs. participants with high plasma YKL-40 (percentile 96-100%) had a longer median survival age of 83 years vs. 69 years and a higher 15-year survival of 70% vs. 44%. Thus, the effect on median survival age and 15-year survival of increasing plasma YKL-40 was similar or even higher than that of smoking status (Table 3 and FIG. 4A).

Multifactorially adjusted (sex, age, and smoking status at time of blood sampling) hazard ratios for overall death were 1.2 (95% Cl, 1.1-1.3) for plasma YKL-40 percentile category 34-66%, 1.6 (1.4-1.8) for 67-90%, 2.3 (1.9-2.8) for 91-95%, and 2.8 (2.4-3.4) for plasma YKL-40 percentile category 96-100% versus plasma YKL-40 percentile category 0-33% (p-trend, $p=1.0*10^{-37}$). These estimates remained constant after adjusting for violent death (Table 2). Hazard ratios (HR) for death were calculated according to plasma YKL-40 in gender and 10-year age percentile categories.

In participants with cancer, in participants with ischaemic cardiovascular death and in participants with other diseases, highly significant associations were also found between increasing plasma YKL-40 percentile categories and increasing multifactorially adjusted hazard ratios for risk of death ($\log_{10}$ p for trend 11.4, 12.5, and 15.1, respectively) (Table 2).

Absolute 10-Year Mortality

Figure 4B:
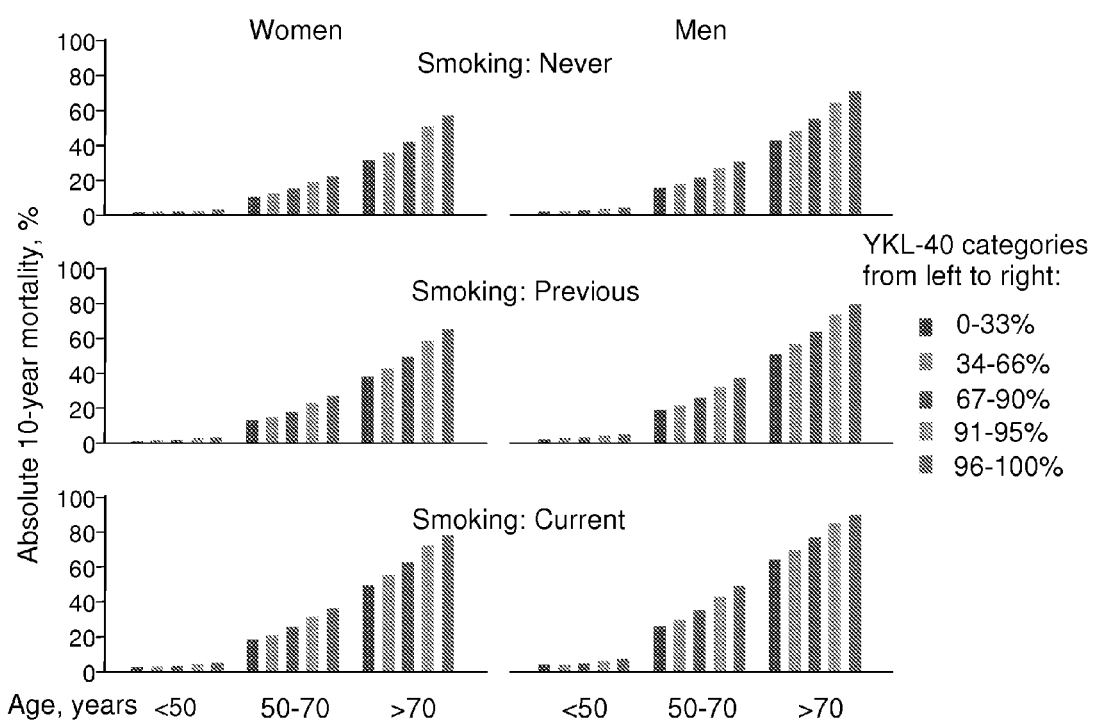
FIG. 4B. Absolute 10-year mortality according to plasma YKL-40 percentile categories, smoking status, gender and age. Based on 8899 participants from the Copenhagen City Hearth Study 1991-1994 examination followed for 16 years. P-values are test for log-rank trend. Plasma YKL-40 percentile categories 0-33%, 34-66%, 67-90%, 91-95%, and 96-100%, are given from left to right for each of the age groupings <50 years, 50-70 years, and >70 years.

The lowest absolute 10-year mortality was 1.2% in never smoking women aged <50 years in the plasma YKL-40 percentile category 0-33% (FIG. 4B). Absolute 10-year mortality was higher in men than in women and increased with increasing age and from never through previous to current smoking status. The highest absolute 10-year mortality was 78% and 90% in smoking women and men aged >70 years and in the 96-100% plasma YKL-40 percentile category (FIG. 4B).

In conclusion, in this large prospective study of subjects from the general population we found a strong association between elevated plasma concentrations of YKL-40 and early death, independent of smoking.

TABLE 1

Status of study participants from the general population and plasma YKL-40 concentration

| Status | At blood sampling, n | Median (IQR), µg/l | Participants with event during follow-up | | | | | During follow-up, n |
|---|---|---|---|---|---|---|---|---|
| | | | Sex and 10-year age-groups percentiles of plasma YKL-40, n (%) | | | | | |
| | | | 0-33% | 34-66% | 67-90% | 91-95% | 96-100% | |
| Healthy | 7136 | 42 (30-61) | 1364 (38) | 1247 (35) | 759 (21) | 138 (4) | 102 (3) | 3610 |
| Any disease* | 1763 | 67 (42-110) | 1121 (32) | 1117 (32) | 883 (25) | 207 (6) | 198 (6) | 3526 |
| Cancer | 704 | 65 (42-107) | 528 (34) | 509 (32) | 376 (24) | 83 (5) | 79 (5) | 1575 |
| Ischaemic cardiovasc. disease | 664 | 73 (46-116) | 455 (30) | 491 (33) | 397 (27) | 79 (6) | 76 (5) | 1498 |
| Liver disease | 81 | 96 (49-217) | 30 (20) | 37 (25) | 27 (18) | 20 (13) | 37 (25) | 151 |
| Diabetes | 156 | 71 (45-128) | 147 (28) | 159 (30) | 147 (28) | 36 (7) | 42 (8) | 531 |
| Chronic obstruct. pulm. disease | 155 | 71 (46-122) | 252 (29) | 251 (29) | 237 (28) | 51 (6) | 68 (8) | 859 |
| Asthma | 93 | 56 (39-96) | 98 (34) | 88 (31) | 67 (23) | 20 (7) | 15 (5) | 288 |

*Death (only incident), cancer, ischaemic cardiovascular disease, liver disease, diabetes, chronic obstructive pulmonary disease, asthma, rheumatoid arthritis, inflammatory bowel disease, pneumonia. Some participants had more than one disease.
IQR, interquartile range.

TABLE 2

Hazard ratios for death and plasma YKL-40 concentration

| Population/Event | Participants/ Events | Hazard ratio* by sex and 10-year age-groups percentiles of YKL-40 | | | | | $-\log_{10}$ (p-trend) |
|---|---|---|---|---|---|---|---|
| | | 0-33% | 34-66% | 67-90% | 91-95% | 96-100% | |
| All§/Death | 8875/3047 | 1.0 | 1.2 (1.1-1.3) | 1.6 (1.4-1.8) | 2.3 (1.9-2.8) | 2.8 (2.4-3.4) | 37.3 |
| All§/Non-violent death | 8804/2976 | 1.0 | 1.2 (1.1-1.3) | 1.6 (1.4-1.8) | 2.3 (1.9-2.8) | 2.8 (2.4-3.4) | 36.8 |
| All§/Violent death | 8875/71 | 1.0 | 1.6 (0.8-3.2) | 1.2 (0.5-2.8) | 1.9 (0.5-7.1) | 2.6 (0.8-8.8) | 0.7 |
| Never-smokers/Death | 2028/450 | 1.0 | 1.1 (0.8-1.4) | 1.6 (1.2-2.2) | 2.5 (1.5-4.2) | 3.6 (2.1-6.1) | 7.2 |
| Ever-smokers/Death | 6847/2597 | 1.0 | 1.2 (1.1-1.4) | 1.6 (1.4-1.8) | 2.2 (1.8-2.7) | 2.7 (2.2-3.3) | 30.4 |
| Plasma CRP-conc.¶ ≤1.75 mg/L/Death | 4453/1081 | 1.0 | 1.0 (0.8-1.2) | 1.4 (1.1-1.7) | 2.3 (1.6-3.3) | 3.4 (2.5-4.8) | 12.1 |
| Plasma CRP-conc.¶ >1.75 mg/L/Death | 4404/1958 | 1.0 | 1.3 (1.1-1.5) | 1.5 (1.3-1.8) | 2.1 (1.6-2.6) | 2.4 (1.9-3.0) | 18.3 |
| Participants with cancer§/Death | 2271/1400 | 1.0 | 1.1 (1.0-1.3) | 1.4 (1.2-1.6) | 2.1 (1.5-2.8) | 2.4 (1.8-3.1) | 11.4 |
| Participants with ischaemic cardiovascular disease§/Death | 2158/1327 | 1.0 | 1.2 (1.0-1.5) | 1.5 (1.2-1.8) | 2.4 (1.8-3.3) | 2.3 (1.7-3.1) | 12.5 |
| Participants with other diseases§**/Death | 2820/1599 | 1.0 | 1.2 (1.0-1.4) | 1.4 (1.2-1.7) | 2.0 (1.5-2.5) | 2.4 (1.9-3.0) | 15.1 |

§For 24 participants smoking status was unknown.
¶For additional 18 participants plasma concentration of CRP was unknown.
*Hazard ratios were adjusted for other risk factors such as gender, age (deciles) and smoking habits (never/previous/current smokers) at time of blood sampling, corrected for regression dilution bias.
CRP = C-reactive protein.
**Benign liver disease, diabetes, chronic obstructive pulmonary disease and asthma, rheumatoid arthritis, inflammatory bowel disease, pneumonia. Some participants had more than one disease.

TABLE 3

Median survival age and 15-year survival in participants from the general population according to plasma YKL-40 percentile category or smoking status#.

| Risk factor | Median survival age, years (95% confidence interval) | 15-year survival, % (95% CI) |
|---|---|---|
| YKL-40 | | |
| 96-100% | 69 (66-72) | 44 (39-49) |
| 91-95% | 73 (69-75) | 52 (47-58) |
| 67-90% | 78 (77-80) | 59 (57-62) |
| 34-66% | 81 (80-82) | 66 (64-67) |
| 0-33% | 83 (82-84) | 70 (68-71) |
| Smoking | | |
| Current | 76 (75-77) | 60 (58-61) |
| Previous | 82 (81-83) | 61 (59-63) |
| Never | 87 (86-88) | 76 (74-78) |

Based on 8899 participants from The Copenhagen City Heart Study 1991-1994 examination followed for 16 years.

TABLE 4

Baseline characteristics of study participants from the general population[a].

| Characteristics | Categories by sex and 10-year age plasma YKL-40 percentile | | | | | P Trend |
|---|---|---|---|---|---|---|
| | 0-33% | 34-66% | 67-90% | 91-95% | 96-100% | |
| Number (%) | 2964 (33) | 2932 (33) | 2121 (24) | 445 (5) | 437 (5) | — |
| Women, % | 57 | 56 | 56 | 56 | 57 | 0.96 |
| Age, years | 61 (48-71) | 61 (48-71) | 61 (48-71) | 60 (48-71) | 61 (48-71) | 0.12 |
| Current smokers, % | 43 | 48 | 51 | 56 | 58 | 0.0005 |

[a]Values were collected at the 1991 through 1994 examination of the Copenhagen City Heart Study, and expressed as number, percent, or median (inter-quartile range). Statistical comparisons between the five YKL-40 percentile categories were made using trend test (YKL-40 categories were coded 0, 1, 2, 3, and 4 for increasing percentile categories).

Example 2

Diurnal, Weekly and Long Time Variation in Serum Concentrations of YKL-40 in Healthy Subjects Materials and Methods
Reference Interval Serum was collected from 245 healthy subjects (women/men 134/111, median age 49 years, range 18-79).
Diurnal Variation Serum was collected seven times during a 24 hour period (day 1: 10 AM, 1 PM, 4 PM, 7 PM, 10 PM; day 2: 7 AM, 10 AM) from 16 healthy subjects (10/6, 48 years, range 32-66).
Day-to-Day Variation Over 3 Weeks Serum was collected at 8 AM five times during a 3 week period (day 1, 2, 8, 15, and 22) from 38 subjects recruited from the hospital staff (21/17, 41 years, range 22-66). At day 8 samples were also collected at 2 PM.
Week-to-Week Variation Over 2 Years Serum was collected from 23 subjects recruited from the hospital staff (14/9, 42 years, range 31-66) at 8 AM five times during a 3 week period (day 1, 2, 8, 15, and 22) and repeated 6, 12 and 24 months later.
Variation Over 3 Years Serum was collected between 8 AM and 10 AM five times during a 4 week period (day 1, 8, 15, 22 and 29) from 30 healthy women (48 years, range 24-62), and repeated 3 years later in 21 of the subjects.
Variation after Exercise Serum was collected before physical exercise, immediately after a biphasic 25 minutes exercise program using an ergometer bicycle, and 1 and 3 hours post-exercise from 14 healthy subjects (10/4, 50 years, range 35-64). The healthy subjects included in the present study had no previous medical history, did not experience any symptoms and had no signs of disease and were not taking any medicine.
Ethics The studies were approved by the regional scientific ethical committee and carried out in accordance with the Declaration of Helsinki. The subjects were informed about the studies verbally and in writing and all gave their written informed consent. All were informed that they could stop the study at any time.
YKL-40 ELISA Proper handling of blood samples are important to minimize changes in serum YKL-40 that are not related to disease processes but represent metodological variability (36). Blood samples were allowed to clot at room temperature, centrifuged within ½-2 hours at minimum 2500 g for 10 minutes and serum was stored at −80° C. until analysis. Serum YKL-40 was determined in duplicates by a commercial two-site, sandwich-type enzyme-linked immunoassay (ELISA) (Quidel Corporation, San Diego, Calif.) using streptavidin-coated microplate wells, a biotinylated-Fab monoclonal capture antibody, and an alkaline phosphatase-labeled polyclonal detection antibody (36). The recovery of the ELISA was 102% and detection limit 20 μg/L (36). The intra-assay coefficient of variation (CV) was ≤5.0% and inter-assay CVs ≤0.2% (personal observation). Samples from each subject were analyzed on the same ELISA plate (38).
Statistical Analysis Descriptive statistics for serum YKL-40 were presented by the median or the geometric mean, coefficient of variation and 95% confidence interval and range. The distribution of serum YKL-40 is skewed and therefore the log transform (natural) is used for statistical estimation. The reference interval was estimated using linear regression with YKL-40 on the log scale. The variations in serum YKL-40 analysed over time (variability during 24 hours, over 3 weeks, 6 months, 12 months, 24 months and 3 years) were given by the CV and compared to the intra- and inter-assay CV of the YKL-40 ELISA. The variance components for within subjects, between subjects and between rounds were estimated assuming a random effects model with YKL-40 log transformed (multiplicative model) and presented by the coefficient of variation of the geometric means (Kirkwood, 1979). The 95% confidence limits for the difference between 2 measurements of YKL-40 in an individual were calculated on the log scale and back transformed. The relative homogeneity between subjects compared to the total variation was estimated by the intraclass correlation coefficient. Serum YKL-40 in the analysis of diurnal long term variation and physical activity were analysed using a general linear model with repeated measures. P-values <5% were considered significant. P-values for multiple testing were corrected using the Boneferroni correction. All statistical calculations were done using SAS (9.1, SAS Institute, Cary, N.C., USA).
Results In healthy subjects the median serum YKL-40 was 43 μg/l (range: 20-184 μg/L; 5-95% interval: 20-124), and no difference between men and women (P=0.54). Serum YKL-40 increased with age (rho=0.45; P<0.0001). A normal reference interval for serum YKL-40 adjusted for age and gender was constructed by linear regression with serum YKL-40 as the dependent variable (log transformed) and age and gender as the explanatory variables. The upper limit was defined as the 95th percentile for given age and gender. The inter subject CV adjusted for age was 45%.

Figure 5:
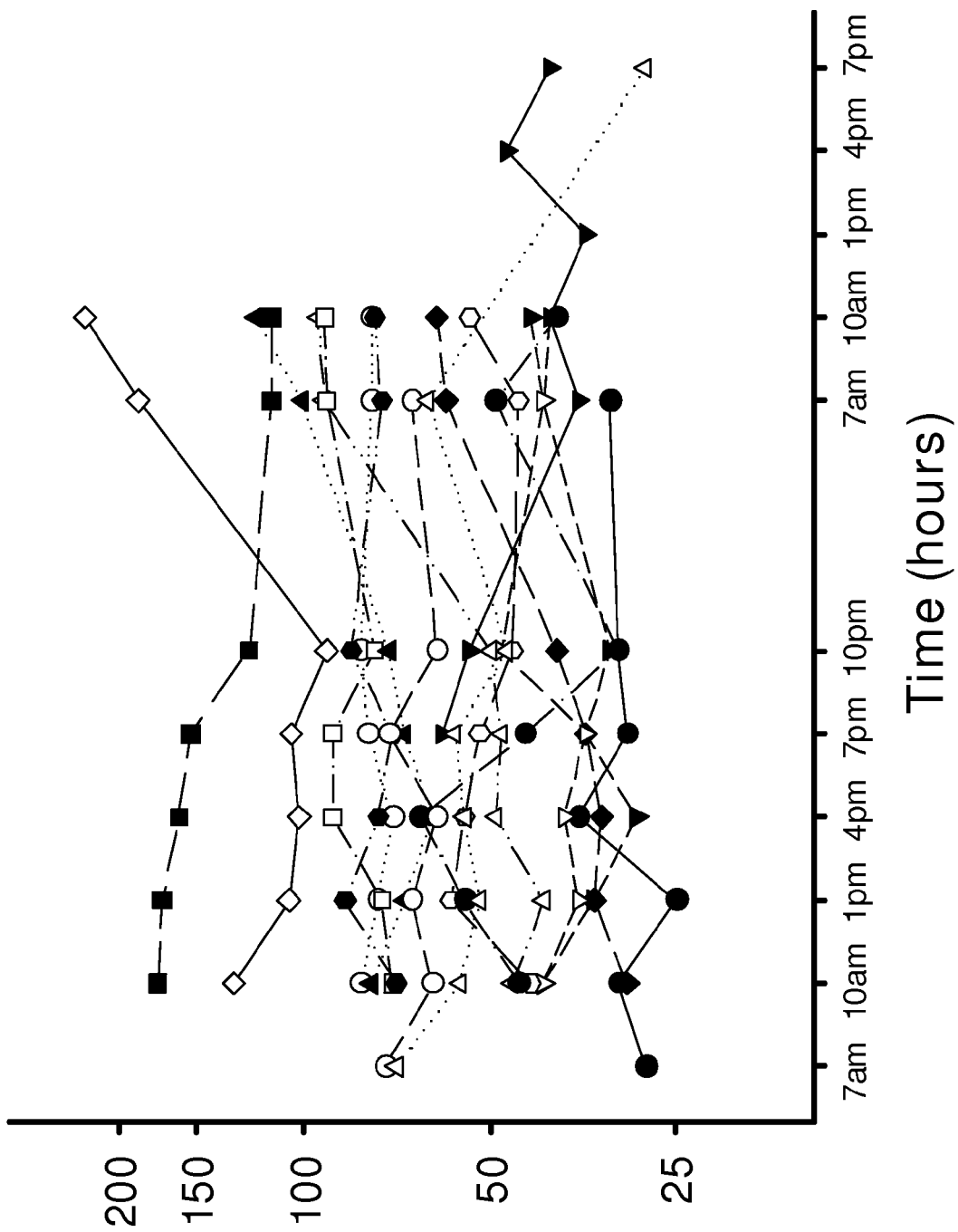
FIG. 5. Individual diurnal variation in serum concentrations of YKL-40 in 16 healthy subjects.

FIG. 5 illustrates the individual diurnal variation in serum YKL-40 at 7 time points during 24 hours. The mean serum YKL-40 increased 23% from 10 AM to 10 PM (P=0.01), however nonsignificant when corrected for multiple testing. No other significant differences were observed.

No changes in serum YKL-40 were found after 25 minutes of bicycling (P>0.08, linear model).

Figure 6:
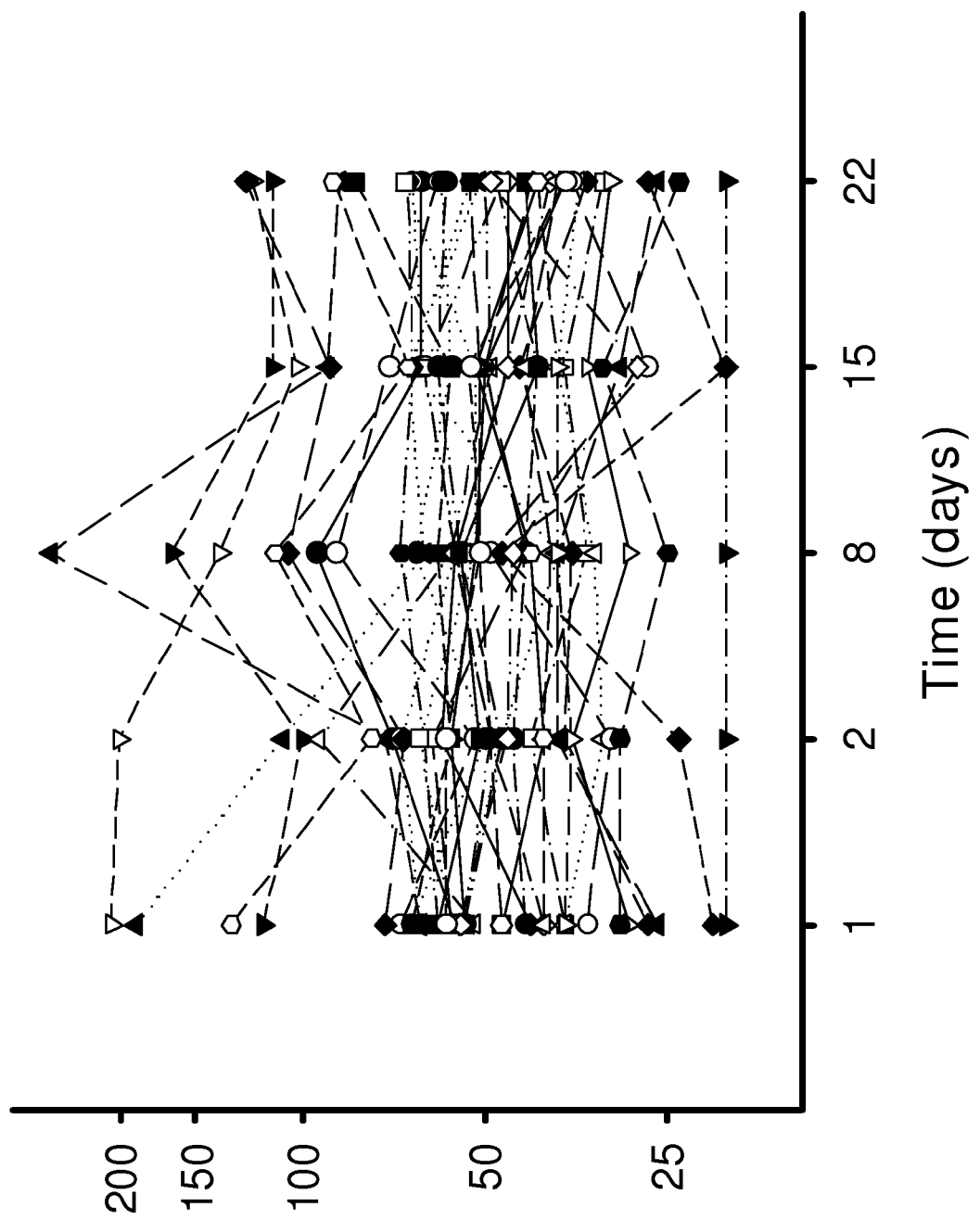
FIG. 6. Individual variation in serum YKL-40 levels of 38 healthy subjects over a period of 3 weeks.

FIG. 6 shows the individual weekly changes in serum YKL-40 at 6 time points during a 3 weeks period (at 8 AM on day 1, 2, 8, 15 and 22). The median day to day CV of serum YKL-40 for each subject was 16%. On day 8 samples were collected at 8 AM and 2 PM and serum YKL-40 increased slightly (47 µg/L vs. 52, 8% difference, P<0.0001).

Figure 7:
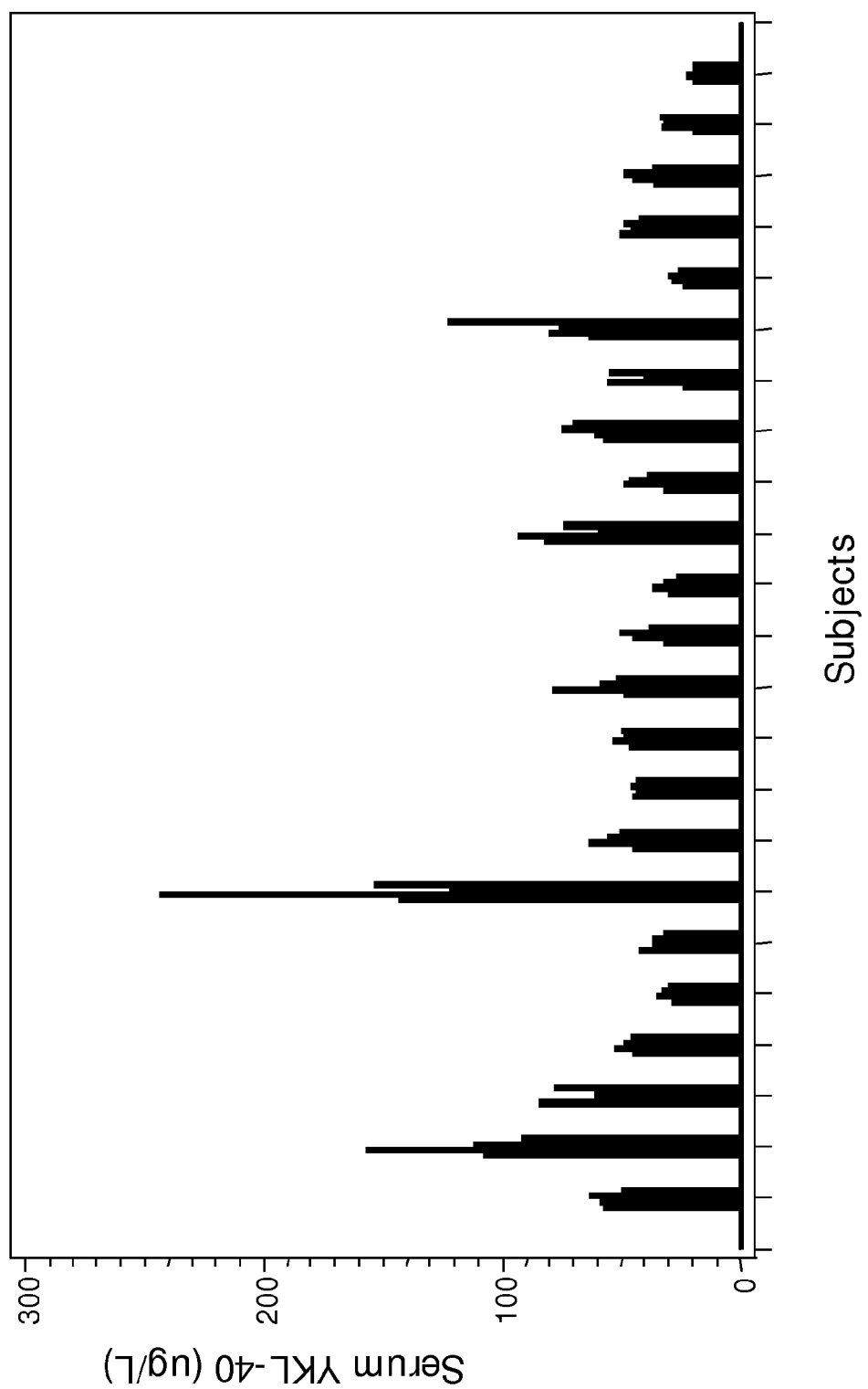
FIG. 7. The median serum YKL-40 level for 23 individuals over 3 weeks available in each of 4 rounds (each bar represents the median of one round for each subject).

FIG. 7 illustrates the individual variation in serum YKL-40 at five time points during a 3 week period (at 8 AM on day 1, 2, 8, 15 and 22, 1st round) and repeated after 6 months (2nd round), 12 months (3rd round) and 24 months (4th round). The median day to day CV of serum YKL-40 for each subject was overall 16% (range 0-92%), and 16% (0-63%, 1st round), 19% (5-92%, 2nd), 15% (0-64%, 3rd), and 21% (0-47%, 4th). No systematic increases or decreases were detected over the 4 rounds (P=0.09). The estimates of the variance components using a random effects model with serum YKL-40 log transformed results in a within subject CV of 27.3% and a CV over 24 months of 8.8%. The within subject CV including the variation over time and inter-assay variation was 30.2% over the 24 months period. The intraclass correlation coefficient over the 24 months was 72.4%. The estimated variation in serum YKL-40 within subjects including inter-assay variation results in 95% confidence limits for the difference between two measurements on the same subject if the second YKL-40 measurement is reduced by 52% or is increased by 109% and differences of this magnitude are significant and not only a reflection of pre-analytical conditions, methodological and normal biologic variability.

Figure 8:
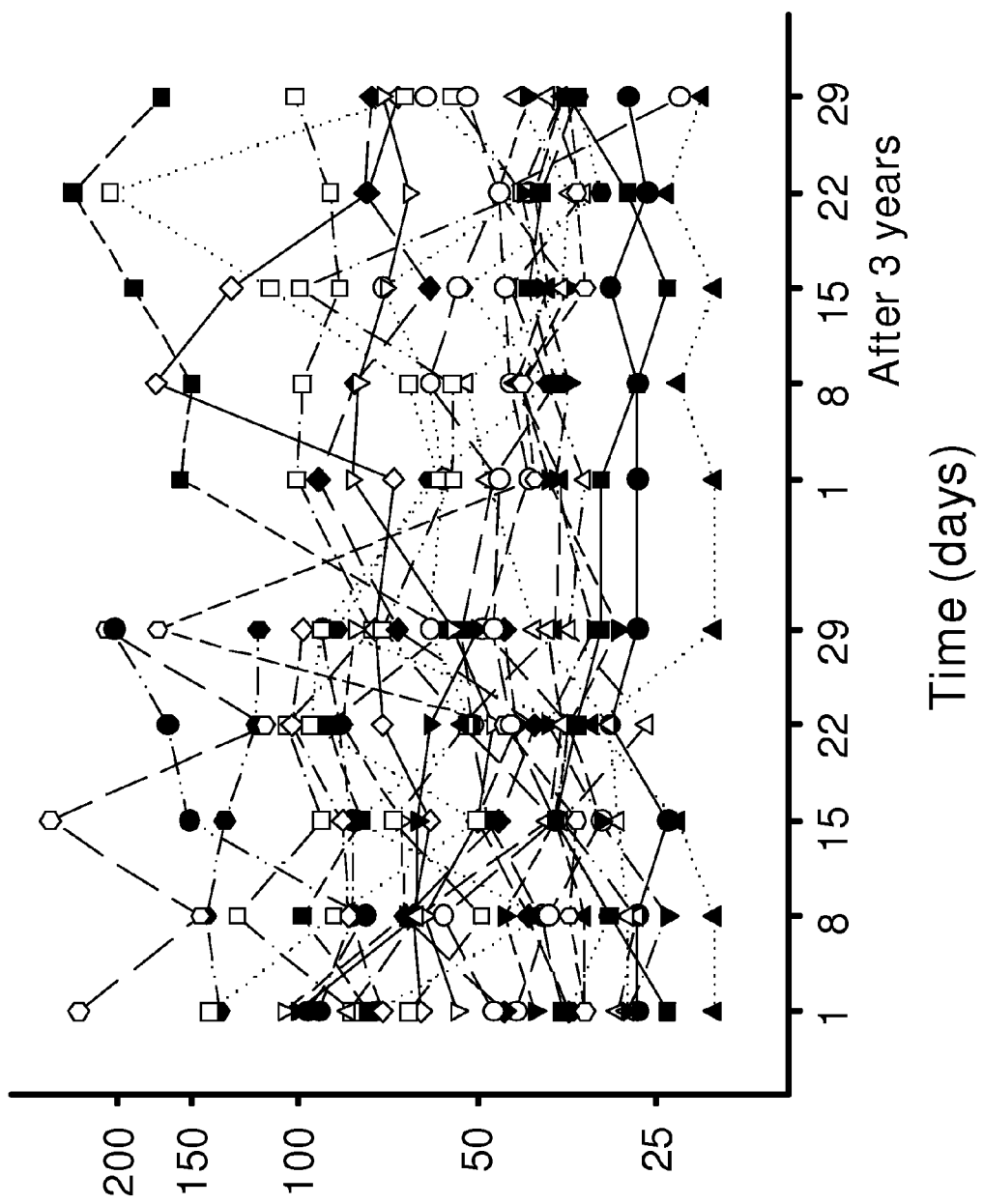
FIG. 8. Individual serum YKL-40 levels of 30 healthy women sampled over 4 weeks and repeated 3 years later for 21 of the women.

FIG. 8 shows the individual weekly changes in serum YKL-40 at five time points during a month and subsequently again after 3 years. The median CV in serum YKL-40 was 17% (1st round) and 13% (2nd round). In subjects analyzed in both rounds (n=21) no changes in serum YKL-40 were observed between the two periods (P=0.37, linear model). The estimates of the variance components using the random effects model with serum YKL-40 log transformed result in a within subject CV of 26.0% and CV over 3 years of 7.3%. The within subject CV including the variation over time and inter-assay variation was 28.8%. The between subject variation including within subject variation and variation over time was 54%. The intraclass correlation coefficient over 3 years was 72.2% suggesting a relatively low within subject variation compared to between subject variation.

Conclusions

The present study demonstrates that serum YKL-40 is stable in healthy subjects for short term as well as long term sampling periods of up to 3 years with a within subject CV of ~30% including inter-assay variation. The between subject variation in serum YKL-40 was 45% in the study determining a normal reference interval and similar to that found in the other studies of healthy subjects in the present study.

The intraclass correlations of serum YKL-40 were 72.4% and 72.2% over a period of 2 and 3 years, suggesting a relative low within subject variation compared to between subject variations. The intraclass correlations found in the present study are similar to those found for other serological markers, for example Ockene et al. reported an intraclass correlation of 66% for high sensitive C-reactive-protein (Ockene et al., 2001).

The present estimated variation in serum YKL-40 within healthy subjects including inter-assay variation determined that an increase of >109% or a decrease of >52% in serum YKL-40 is considered as significant and not only a reflection of pre-analytical conditions, methodological and normal biologic variability.

In conclusion, the present study showed that there are no significant diurnal variation in serum YKL-40 nor an effect of physical exercise. A relatively low within subject variation compared to between subject variation in serum YKL-40 was demonstrated confirming that that YKL-40 is a reliable biomarker.

Example 3

Upper GI Cancer—Prognostic and Predictive Value of YKL-40

The purpose of the present study was to investigate in patients with upper gastrointestinal cancer the prognostic and predictive value of plasma concentrations of YKL-40 and IL-6 treated with chemo/radiotherapy for localized disease or chemotherapy for metastatic disease.

Patients and Methods
Study Populations

CORGI Study: Forty patients with localized upper GI-cancers were included in a longitudinal study of the effect of chemo/radiotherapy. Plasma samples were collected before, after 2 cycles of Xelox (oxaliplatin 130 mg/m$^2$ iv on day 1 and capecitabine 1000 mg/m$^2$ twice daily po on days 1-14 and, every 3. week). The patients were then treated with radiotherapy (50.4 Gy in 1.8 Gy fractions) to gross tumour volume in combination with a reduced Xelox regimen (oxaliplatin 30-60 mg/m$^2$ iv on day 1 and capecitapin 675-750 mg/m$^2$ twice daily p.o. every day of radiotherapy). In patients with gastric and pancreatic cancer radiotherapy was also give to adjacent lymph nodes (41.4 Gy in 1.8 Gy fractions). Plasma samples were collected 4-6 weeks after the end of chemoradiotherapy.

GITAC Study: Seventy patients with metastatic upper GI-cancers were included in a longitudinal study of the effect of sequential treatment with docetaxel 45 mg/m$^2$ or irinotecan 180 mg/m$^2$ every second week together with 5-FU/leucovorin (500 mg/m$^2$+60 mg/m$^2$×2, Nordic schedule, except patients with gastric carcinomas, who were treated with de Gramont schedule). During treatment with chemotherapy plasma samples were collected after 2 weeks, 4 weeks, 6 weeks and 8 weeks.

YKL-40 Analysis

Plasma concentrations of YKL-40 were measured by a two-side, sandwich-type Elisa (Quidel, CA, USA) in accordance with the manufacturer's instructions. The sensitivity was 20 µg/l and the intra- and inter-assay coefficient of variations were 5.0% and 8.4%. To eliminate the inter-assay variation samples from each patient were analyzed in the same assay. ELISA kits with the same batch number were used for all patients.

Plasma YKL-40 in Healthy Subjects

The reference intervals for plasma YKL-40 were determined in 234 healthy subjects characterized by not being on medication and having no signs of pre-existing disorders such as joint, liver, metabolic or endocrine disease or malignancy (38).

Statistical Analysis I—Basis for FIGS. 9A, 9B, 10, 11, 12, 13 and Table 5

The clinical endpoints for this biomarker study were overall survival determined as the time from baseline blood sample before chemotherapy to time of death of all causes. All data on disease status and duration of survival were updated in 2008, where all patients were dead. Plasma concentrations of YKL-40 were considered both at baseline and after first, second, third and fourth treatment. Kruskal-Wallis test was used for comparison of three or more independent groups with nonparametric data distributions. Survival probabilities for overall survival were estimated by the Kaplan-Meier method and tests for differences between strata were done using the log-rank statistic. Graphical presentation of plasma YKL-40 levels using Kaplan-Meier estimates of survival were shown grouping patients by tertiles (normal, slightly/moderate elevated, highly elevated). Analyses of overall survival for continuous covariates as well as multivariate analyses were done using the Cox proportional hazards model. Plasma YKL-40 were entered by the actual value on the log scale (base 2). Model assessment was done using graphical methods. Analyses of updated levels of plasma YKL-40 during treatment were done using time-dependent a Results
Pretreatment YKL-40 of the Patients The baseline median plasma YKL-40 concentrations in the patients with localized upper GI-cancer plasma YKL-40 was higher (p<0.001) (median 64 µg/l, range 20-545) compared to healthy subjects (34 µg/l, 20-258) (Table 5.). The baseline median plasma YKL-40 concentrations of the patients with metastatic upper GI-cancer was higher (p<0.001) in the patients (median 127 µg/l, range 20-2869) compared to healthy subjects (34 µg/l, 20-258) (Table 5.). Plasma YKL-40 was higher than the upper normal level (i.e. defined as the age corrected upper 95% percentile in healthy subjects) in 33% of the patients with localized pancreatic cancer, in 50% of the patients with localized biliary or gastric cancer, in 81% of the patients with metastatic pancreatic cancer, in 85% with metastatic billiary cancer and in 77% with metastatic gastric cancer (Table 5.).

TABLE 5

Pre-treatment concentrations of plasma YKL-40 in 40 patients with localized upper GI cancer and in 70 patients with metastatic upper GI cancer

| Characteristic | Localized Cancer | | Metastatic Cancer | | |
|---|---|---|---|---|---|
| | Pancreatic | Gastric or Billiary | Pancreatic | Gastric | Biliary |
| Number | 30 | 10 | 27 | 22 | 21 |
| Plasma YKL-40 µg/l # | 54 (20-545) | 73 (20-396) | 124 (20-710) | 133 (20-1097) | 132 (25-2869) |
| Elevated YKL-40 ¤ | 10 (33%) | 5 (50%) | 22 (81%) | 17 (77%) | 17 (85%) |

\# Values are median (range)
¤ Number of patients with elevated YKL-40 (%) compared to age-matched healthy subjects (i.e. an YKL-40 value higher than the 95% percentile)

Cox proportional hazards model. P-values less than 5% were considered significant. All calculations were performed using SAS (version 9.1, SAS Institute, Cary, N.C., USA).

Figure 14:
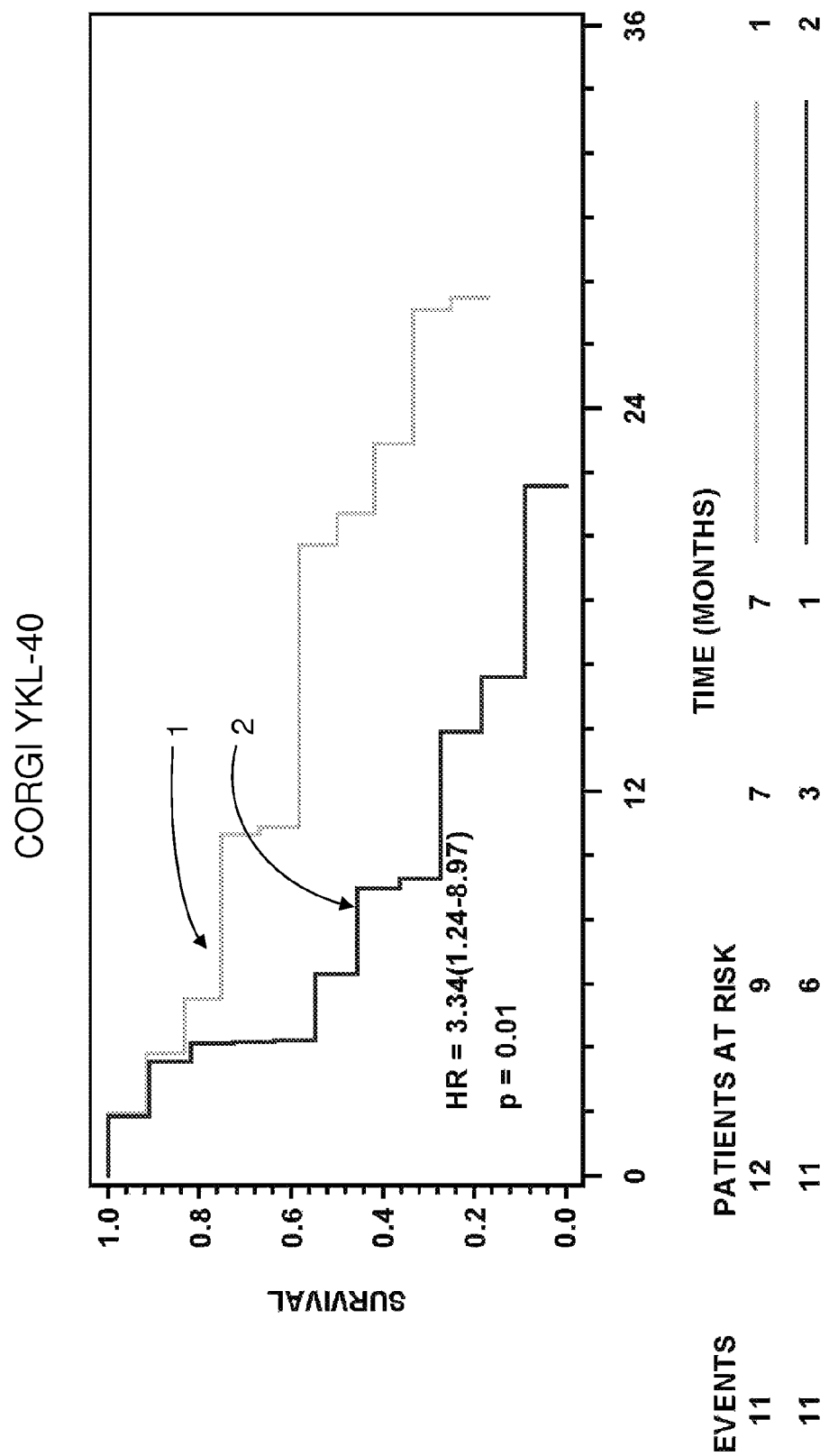
FIG. 14. Kaplan-Meier survival curves showing the association between the ratios of plasma YKL-40 in samples collected 4-6 weeks after end of chemoradiotherapy in patients with locally advanced pancreatic cancer (CORGI Study) and overall survival. The ratios are calculated as YKL-40 level after 4-6 weeks of treatment over YKL-40 baseline level, i.e. pretreatment level. The upper curve is the group with low ratios, and the lower curve the group with high ratios. The P-value refers to the log-rank test for equality of strata.
Figure 15:
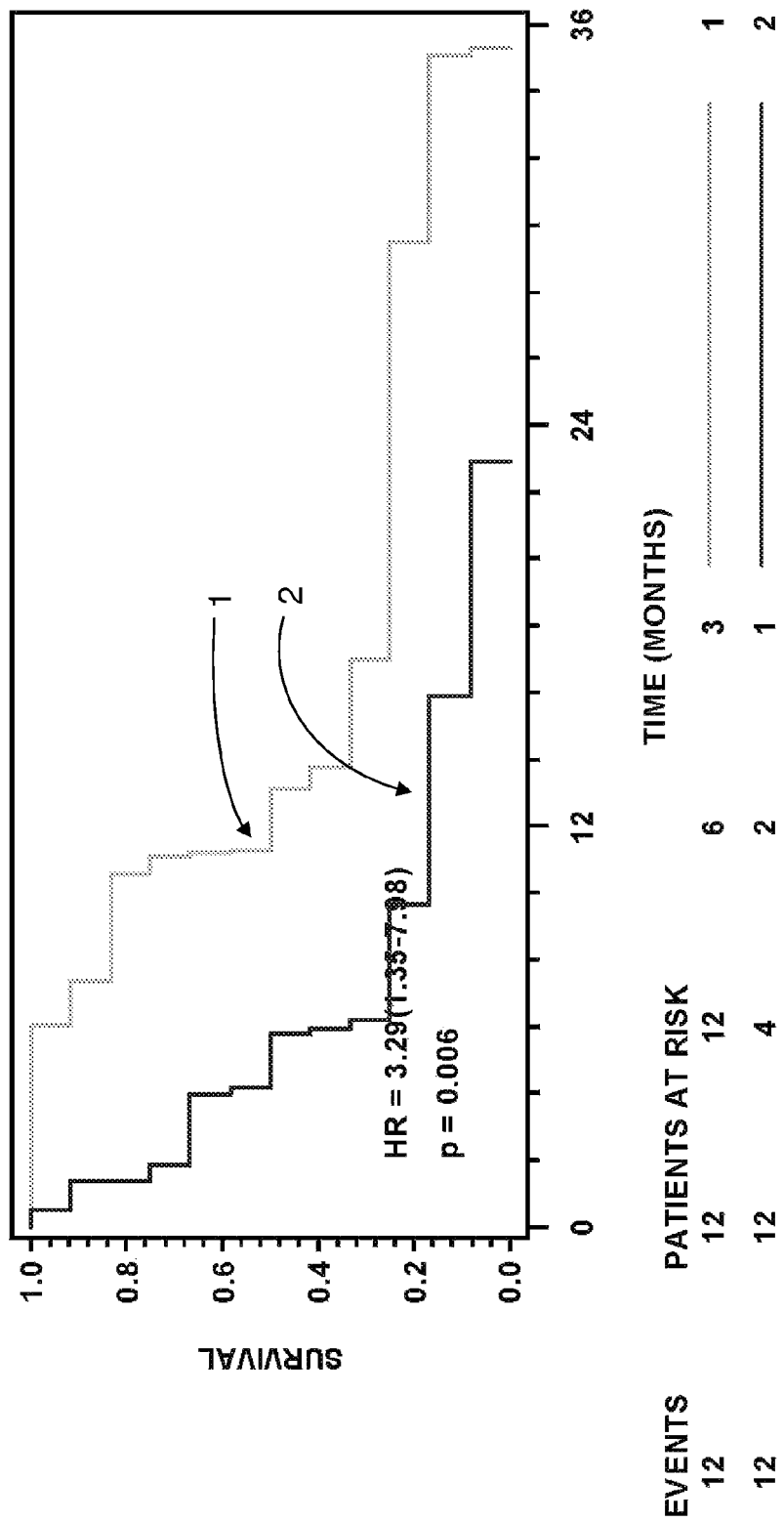
FIG. 15. Kaplan-Meier survival curves showing the association between the ratios of plasma YKL-40 in samples collected 4 weeks after start of chemotherapy in patients with metastatic pancreatic cancer (GITAC Study) and overall survival. The ratios are calculated as YKL-40 level after 4 weeks of treatment over YKL-40 baseline level, i.e. pretreatment level. The upper curve is the group with low ratios, and the lower curve the group with high ratios. The P-value refers to the log-rank test for equality of strata.

Statistical Analysis II—Basis for FIGS. 14 and 15

The clinical endpoint for this biomarker study were overall survival determined as the time from baseline blood sample before chemotherapy to time of death of all causes. All data on disease status and duration of survival were updated in September 2008 (CORGI Study) and in January 2008 (GITAC Study). Plasma YKL-40 and IL-6 were considered both at baseline and during treatment. Descriptive statistics for plasma YKL-40 and IL-6 are presented by their median levels and the range. Rank statistics were used for tests for location and performance status (Wilcoxon rank sum) and measures of association (Spearman rank correlation). Analyses of overall survival for continuous covariates as well as multivariate analyses were done using the Cox proportional hazards model. Plasma YKL-40 and IL-6 at baseline were entered by the actual value on the log scale (base 2). For analysis of survival at 4-6 weeks after end of radiochemotherapy were done using the landmark method for the CORGI Study, and for analysis of survival at 2, 4 and 6 weeks after start of chemotherapy were done using the landmark method for the GITAC Study. The ratios of the plasma YKL-40 and IL-6 levels to baseline levels were used for analysis of longitudinal data. Model assessment was done using graphical methods. Survival probabilities for overall survival were estimated by the Kaplan-Meier method and tests for differences between strata were done using the log-rank statistic. Patients were dichotomized by the median ratios of plasma YKL-40 and IL-6 compared to baseline levels. P-values less than 5% were considered significant All calculations were performed using SAS (version 9.1, SAS Institute, Cary, N.C., USA).

Figure 9A:
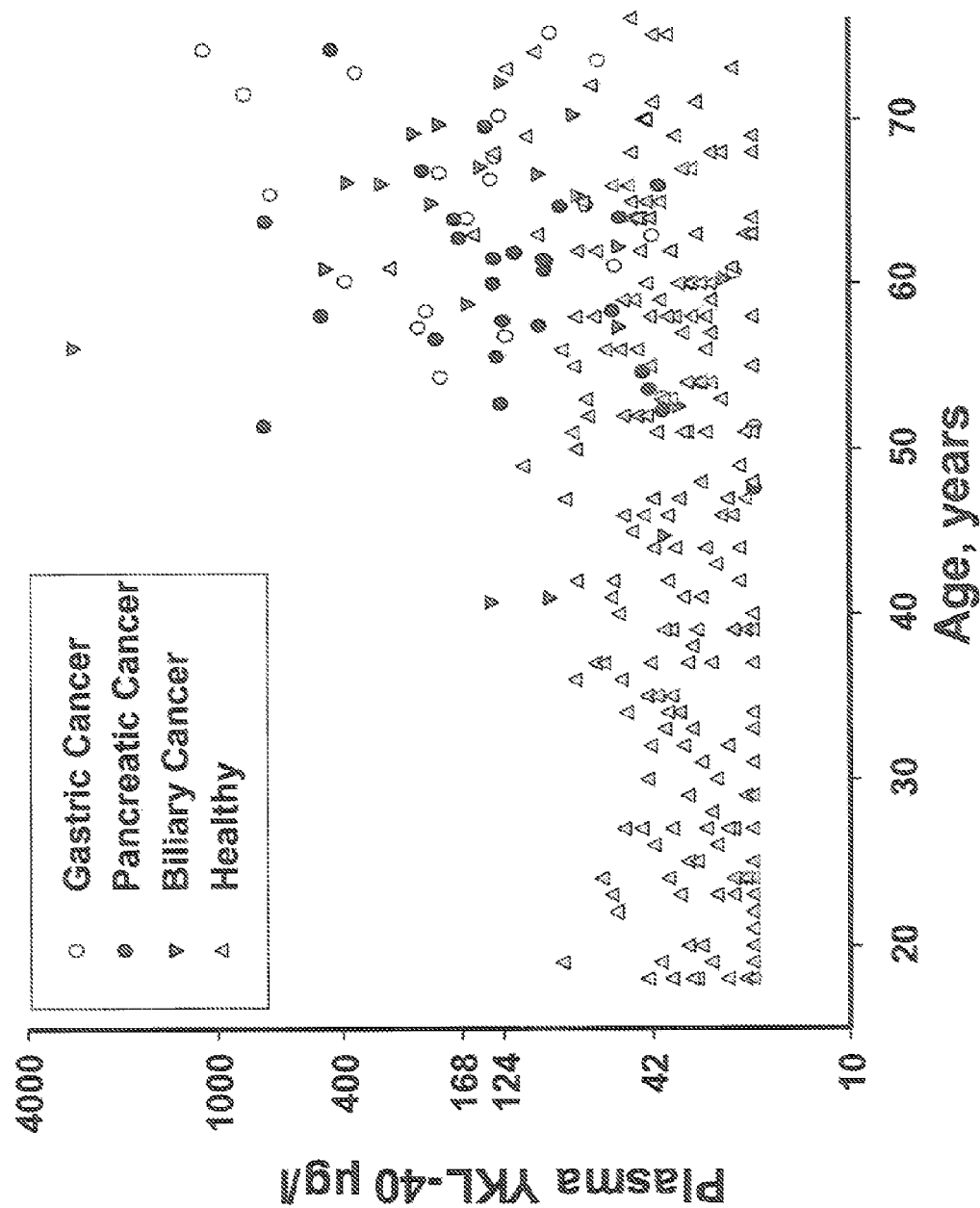
FIG. 9. A. Individual plasma YKL-40 levels in patients with metastatic upper GI cancer (n=70) and healthy subjects (n=234). B. Individual plasma YKL-40 levels in patients with localized upper GI cancer (n=40, triangles), metastatic upper GI cancer (n=70, white circles), chronic pancreatitis (n=65, upturned triangles), and healthy subjects (n=234, gray circles). The Y-axis is a logarithmic scale.

FIG. 9A illustrates the individual plasma YKL-40 levels according to age and type of cancer in patients with metastatic upper gastrointestinal cancer. For comparison plasma YKL-40 levels in healthy subjects are also included.

Figure 9B:
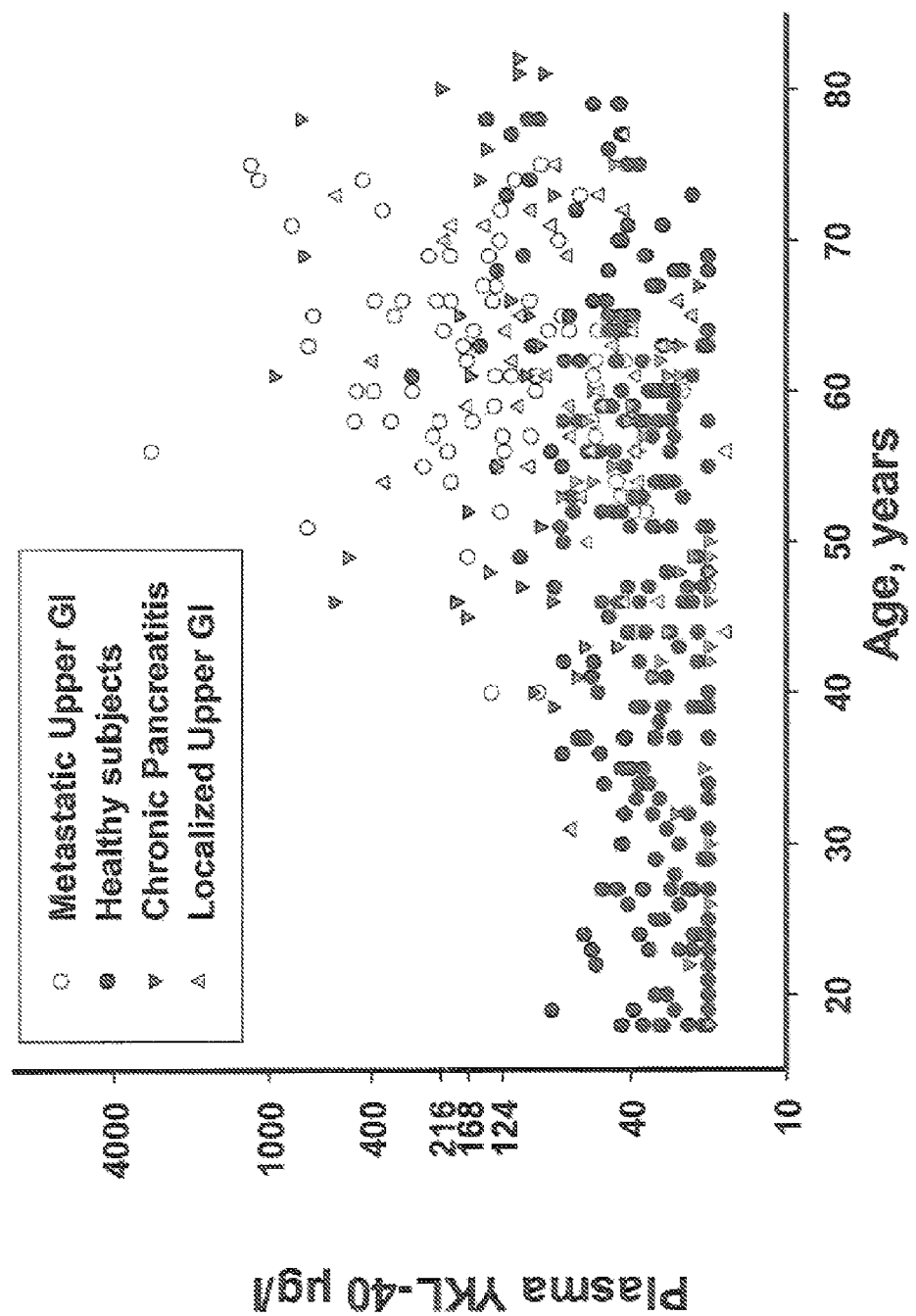

FIG. 9B illustrates the individual plasma YKL-40 levels in patients with localized upper gastrointestinal cancer, in patients with metastatic upper gastrointestinal cancer, and in patients with chronic pancreatitis. For comparison plasma YKL-40 levels in healthy subjects are also included.

Pretreatment plasma YKL-40 was not associated with performance status (p=0.08) and not correlated with serum CA 19-9 (p=0.39) and CEA (p=0.78) in patients with metastatic upper gastrointestinal cancer.

Pretreatment Plasma YKL-40 and Overall Survival—with Basis in Statistical Analysis I In patients with localized upper GI cancer pretreatment plasma YKL-40 levels (log transformed, treated as a continuous covariate) showed that YKL-40 was not associated to overall survival (HR=0.80, 95% CI 0.51-1.24, p=0.31)

Figure 10:
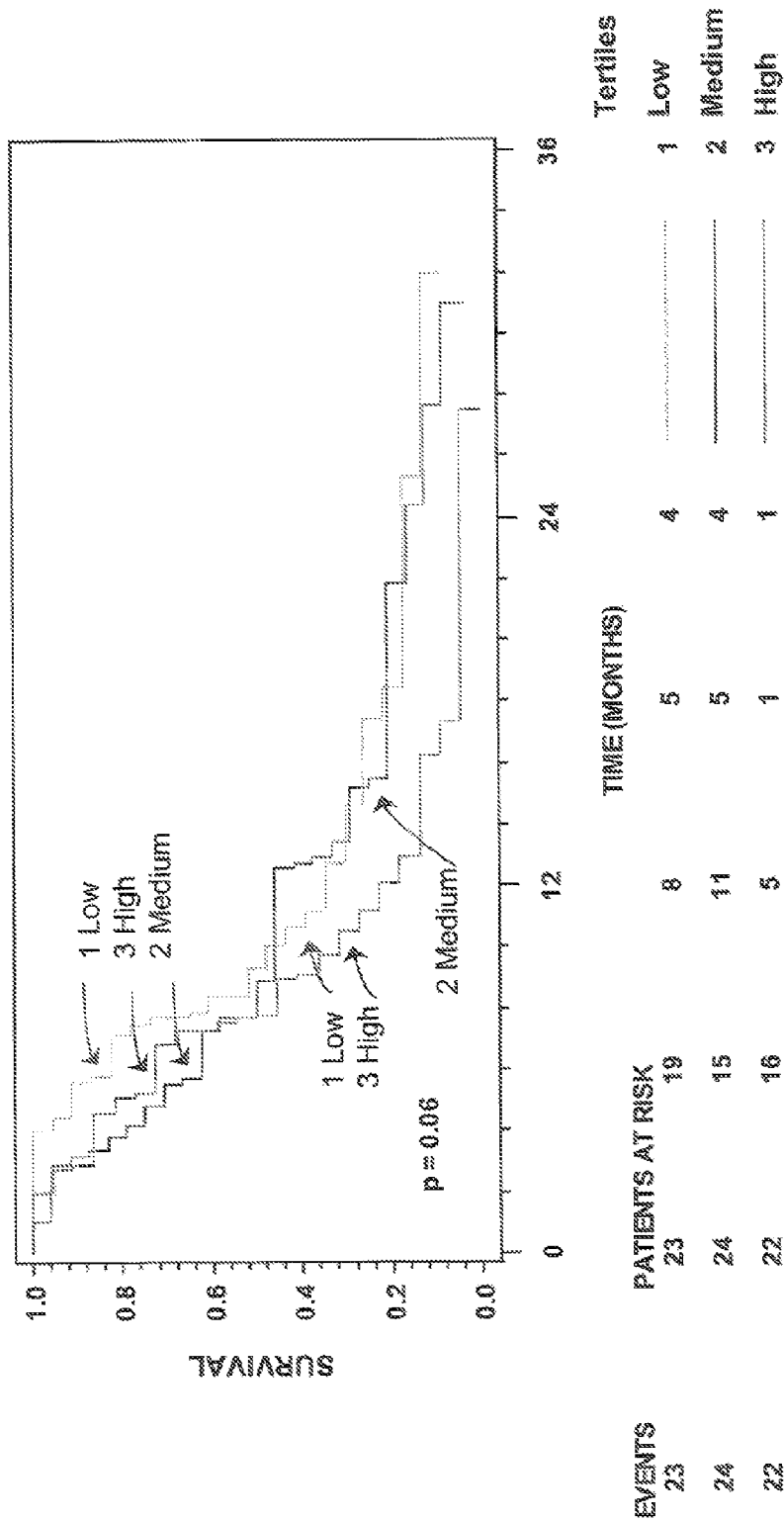
FIG. 10. Kaplan-Meier survival curves showing the association between baseline plasma YKL-40, i.e. pretreatment plasma YKL-40 levels, and overall survival in patients with metastatic upper gastrointestinal cancer. Plasma YKL-40 levels are divided in tertiles. The P-value refers to the log-rank test for equality of strata.

At time of follow-up all patients with metastatic upper GI had died. The median survival time was 8.6 months (range 1-38). The Kaplan-Meier estimates of survival stratified by pre-treatment plasma YKL-40 (dichotomized in tertiles) are shown in FIG. 10. Univariate analysis of pretreatment plasma YKL-40 (log transformed, treated as a continuous covariate), stratified by diagnostic group, showed that pretreatment YKL-40 was not associated to overall survival in patients with metastic upper GI (HR=1.21, 95% CI: 0.93-1.58, p=0.15) and progression free survival (HR=1.12, 95% CI: 0.87-1.46, p=0.35).

Figure 13:
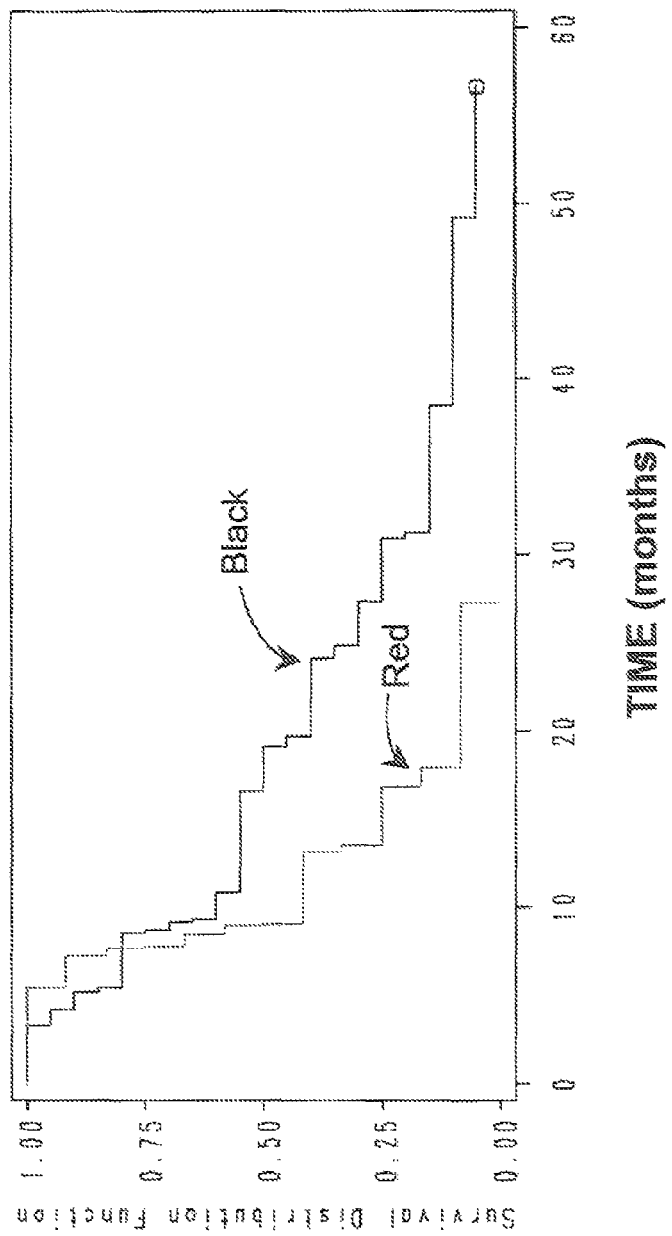
FIG. 13. Kaplan-Meier survival curves showing the association between plasma YKL-40 level 4-6 weeks after end of radiochemotherapy and overall survival in patients with localized pancreatic cancer. Plasma YKL-40 levels are dichotomized according to an increase or decrease/no change compared to the baseline level.

Plasma YKL-40 During Follow-Up and Prediction of Overall Survival—with Basis in Statistical Analysis I Samples were obtained from the patients with localized upper GI after radiotherapy. Univariate analysis of plasma YKL-40 levels after end of radiotherapy (defined as the ratio of plasma YKL-40=concentration at the end of radiotherapy compared to the baseline level) showed that an increase of plasma YKL-40 was associated to short overall survival in patients with localized upper GI (HR=2.42, 95% Cl: 1.16-5.04, p=0.019). The corresponding Kaplan-Meier estimates of survival are shown in FIG. 13. Only patients with localized pancreatic cancer are included in this analysis.

Figure 11:
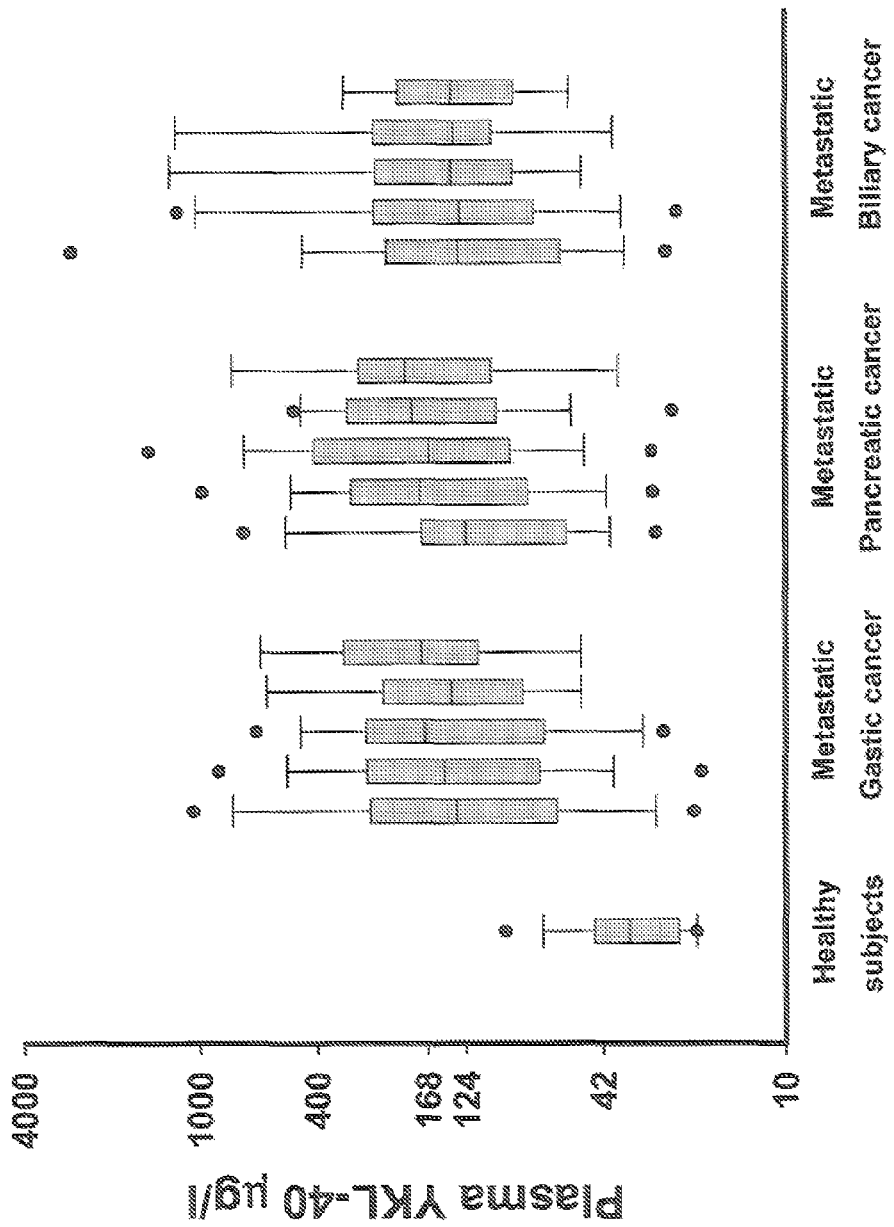
FIG. 11. Box-plots showing plasma YKL-40 at baseline and during treatment with chemotherapy in patients with metastatic upper gastrointestinal cancer. The Y-axis is a logarithmic scale.
Figure 12:
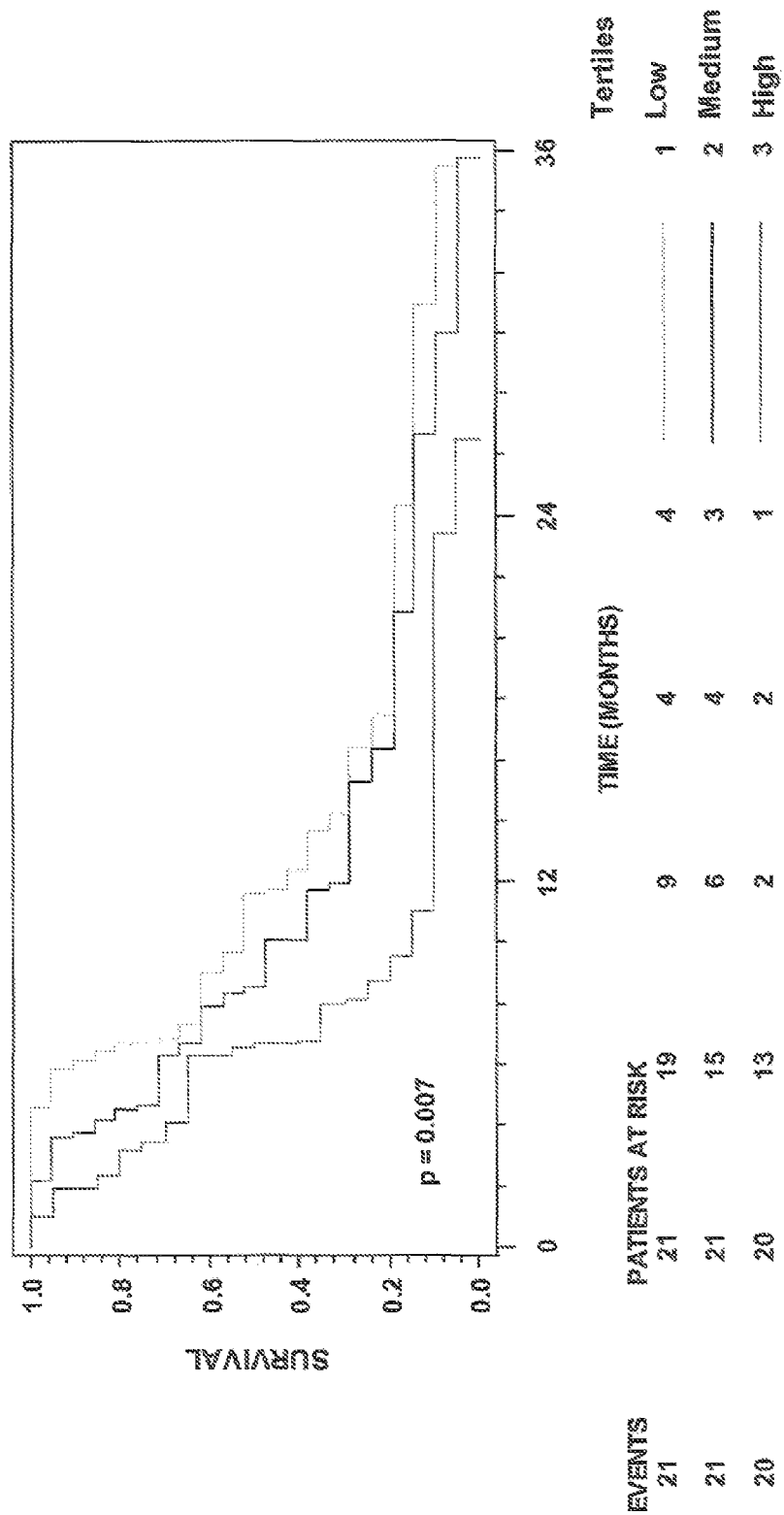
FIG. 12. Kaplan-Meier survival curves showing the association between plasma YKL-40 level after 4 weeks of chemotherapy and overall survival in patients with metastatic upper gastrointestinal cancer. Plasma YKL-40 levels are divided in tertiles. The P-value refers to the log-rank test for equality of strata.

Samples were obtained from the patients with metastatic upper GI after chemotherapy. During treatment plasma YKL-40 increased in patients with metastatic pancreatic cancer (p<0.01) and was unchanged in patients with gastric cancer and biliary cancer (FIG. 11). The Kaplan-Meier estimates of survival stratified by plasma YKL-40 after 4 weeks of radiotherapy treatment (dichotomized in tertiles, landmark test) are shown in FIG. 12. Patients with high plasma YKL-40 4 weeks after treatment had significantly shorter survival than patients with normal plasma YKL-40 (p=0.007, log-rank test).

Multivariate analysis including diagnostic group, age, performance status, and plasma YKL-40 after 4 weeks of treatment showed that YKL-40 was significant in predicting overall survival (HR=1.54, 1.08-2.19, p=0.017) and time to progression (HR=1.46, 1.01-2.02, p=0.04).

Pretreatment Plasma YKL-40 and Overall Survival—with Basis in Statistical Analysis II
CORGI Study.

At time of follow-up one patient was still alive. The median survival time was 12.0 months (95% Cl 9.0-16.8). Univariate analysis of pretreatment plasma YKL-40 (log transformed, continuous covariate) in patients with pancreatic cancer showed that pretreatment YKL-40 was not associated to overall survival (HR=0.86, 95% Cl 0.63-1.16, p=0.32).
GITAC Study.

At time of follow-up all patients had died. The median survival time was 8.4 months (range 1-38, 95% Cl 7.7-10.7). Univariate analysis of pretreatment plasma YKL-40 (log transformed, continuous covariate) showed that pretreatment YKL-40 was not associated to overall survival in patients with pancreatic cancer (HR=1.16, 95% Cl 0.84-1.62, p=0.36), gastric cancer (HR=1.12, 0.85-1.48, p=0.43) and biliary cancer (HR=1.07, 0.74-1.55, p=0.72).

Plasma YKL-40 During Treatment and Follow-Up and Prediction of Death—with Basis in Statistical Analysis II
CORGI Study.

After 2 cycles of Xelox and just before start of radiochemotherapy plasma YKL-40 increased in 23 (85%) of the patients with pancreatic cancer. 4-6 weeks after the end of radiochemotherapy 10 (42%) of the patients had lower plasma YKL-40 compared to pretreatment levels. Univariate analysis of plasma YKL-40 in pancreatic cancer patients 4-6 weeks after end of radiochemotherapy (ratio compared to baseline value, continuous variable) showed that high YKL-40 ratio was associated to short overall survival (HR=3.27, 1.40-7.63, p=0.006). The corresponding Kaplain-Meier estimates of survival 4-6 weeks after the end of radiochemotherapy are shown in FIG. 14. Multivariate analysis (PS, YKL-40 and IL-6, continuous variables) showed that the actual value of plasma YKL-40 4-6 weeks after end of treatment was an independent biomarker of short survival (HR=2.91, 1.09-7.75, p=0.032).
GITAC Study.

During treatment plasma YKL-40 increased compared to baseline in patients with pancreatic cancer (YKL-40: 2 weeks p=0.006, 4 weeks p=0.0002 and 6 weeks p=0.0002). In patients with pancreatic cancer univariate analysis of plasma YKL-40 ratios 2, 4 and 6 weeks after start of chemotherapy (ratio compared to baseline value, continuous variable) showed that high YKL-40 ratio after 4 weeks was associated with short overall survival (HR=1.35, 1.06-1.72, p=0.017). The corresponding Kaplain-Meier estimates of YKL-40 ratios 4 weeks after start of chemotherapy are shown in FIG. 15.

The actual plasma YKL-40 values (log transformed) were significant in univariate analysis in pancreatic cancer patients for week 4 (YKL-40: HR=1.50, 1.06-2.13, p=0.023).
Conclusion In the present study we found that 38% of patients with localized upper GI cancer and 81% with metastatic upper GI cancer had elevated plasma YKL-40 at time of diagnosis. These numbers are higher compared to other types of adenocarcinomas, and may reflect the very poor prognosis of patients with upper GI cancer. Interestingly, patients with localized pancreatic cancer and no change or a decrease, compared to baseline level, in plasma YKL-40 four to six weeks after the end of radiochemotherapy had a better survival compared to patients with an increase in plasma YKL-40. Similarly results were found in patients with metastatic pancreatic cancer for the ratio in plasma YKL-40 four weeks after start of chemotherapy. These are all novel observations and suggest that changes in plasma YKL-40 during or after treatment are useful biomarkers to monitor in patients with upper GI cancer.

Example 4

High Pretreatment Plasma YKL-40 Levels in Patients with Metastatic Colorectal Cancer Treated with Cetuximab are Associated with Short Survival Patients Prospective, longitudinal study of 140 patients (median age 63 years, range 36-87 years, performance status 0-2) with metastatic colorectal cancer resistant to 5-FU, oxaliplatin and irinotecan. The patients were then treated with irinotecan (130 mg/m$^2$) and cetuximab (500 mg/m$^2$) every second week independent of their KRAS status. Median follow-up time was 15 months (range 2.5-25 months). 86 patients died. Plasma YKL-40 was analyzed by ELISA (Quidel). KRAS was analyzed using DxS KRAS test kit (Roche).
Results The median overall survival was 9.6 months. KRAS status was analyzed in 86 (61%) patients (wild type n=47, mutated n=39). Overall survival in patients with KRAS wild type was 12.1 months compared to 7.0 months in patients with KRAS mutations (p=0.08).

Pretreatment plasma YKL-40 (median 131 µg/l, range 15-1766) was elevated (i.e. >95$^{th}$ percentile in healthy subjects, age-corrected level) in 66% of the patients. Plasma YKL-40 was not associated with KRAS status (p=0.39). YKL-40 correlated with CEA (r=0.32, p=0.0004).

Figure 16:
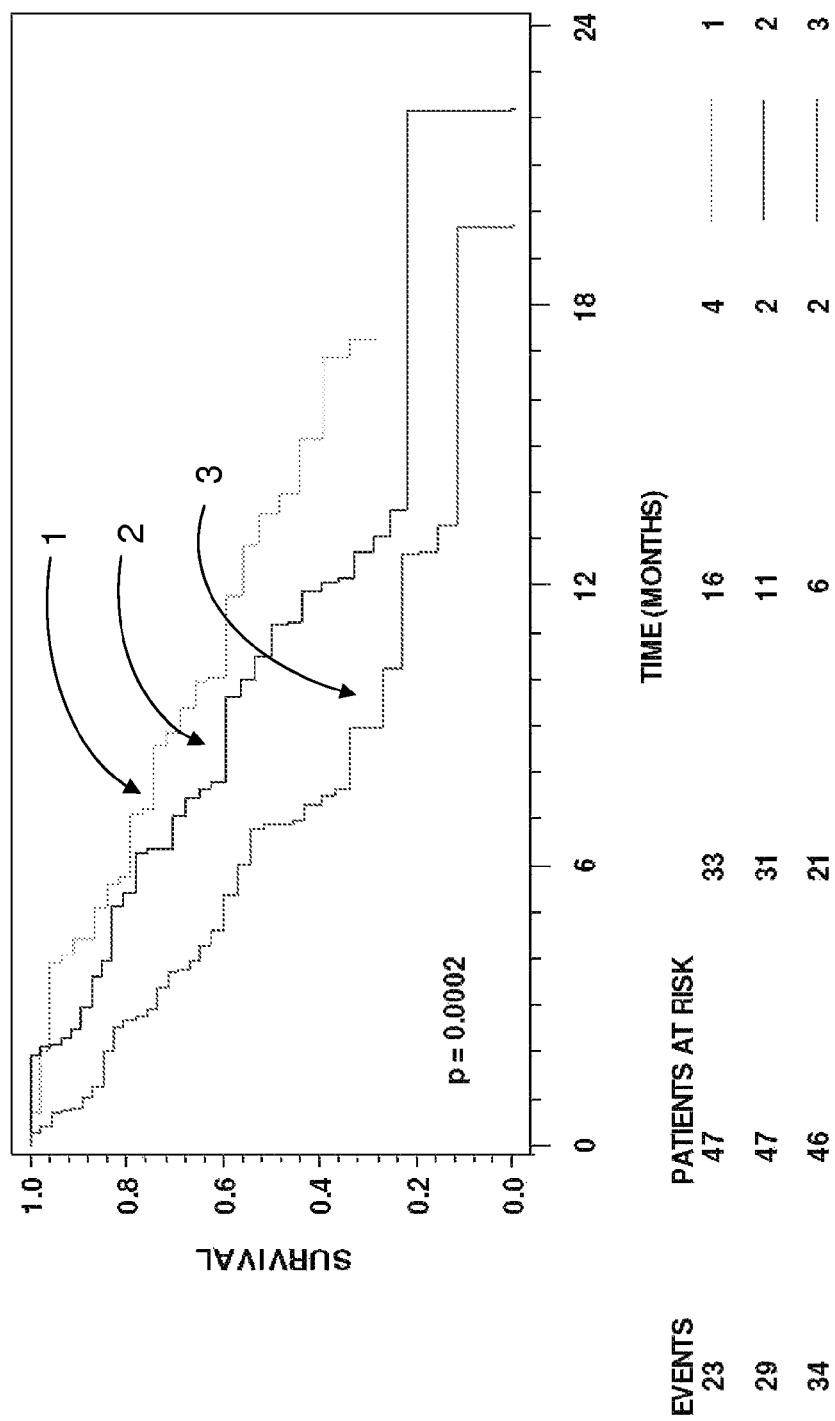
FIG. 16. Kaplan-Meier survival curves showing the association between pre-treatment plasma YKL-40 levels and overall survival in patients with metastatic colorectal cancer treated with irinotecan and Cetuximab every second week. Plasma YKL-40 levels are divided in tertiles. The upper curve is the tertile with the lowest YKL-40 levels, the curve in the middle is the tertile with the medium YKL-40 levels, and the bottom curve is the tertile with the highest YKL-40 levels. The P-value refers to the log-rank test for equality of strata.

Univariate analysis (log transformed continuous variable (base 2)), showed that high pretreatment plasma YKL-40 was associated with short overall survival (HR=1.29, 95% Cl: 1.12-1.49, p=0.0006). From this analysis patients with plasma YKL-40 levels 67 µg/l (first quartile), 131 µg/l (median) and 259 µg/l (third quartile) had 8 months survival of 62% (95% Cl: 52-72), 54% (95% Cl: 45-64) and 45% (95% Cl: 36-56), respectively. The Kaplan-Meier curves for these 3 groups for overall survival are illustrated in FIG. 16.

Multivariate Cox analysis (plasma YKL-40, age, sex, performance status, serum CEA) showed that pretreatment YKL-40 (HR=1.20, 95% Cl: 1.03-1.40, p=0.03) and performance status (0 vs. 1: 1.71, 0.99-2.94; 0 vs. 2: 3.62, 1.98-7.03, p=0.001) were independent factors of overall survival. Serum CEA (p=0.30) and KRAS status (p=0.13) were not significant in this model.

Conclusion

High pretreatment plasma YKL-40 was an independent prognostic biomarker of short overall survival in patients with metastatic colorectal cancer treated with cetuximab in combination with irinotecan. Thus plasma YKL-40 may be a new predictive biomarker of response to cetuximab.

Example 5

High Pretreatment Plasma and Serum Concentrations of YKL-40 in Patients with Metastatic Colorectal Cancer Treated with Irinotecan and Cetuximab are Associated with Short Overall Survival and Short Progression Free Survival and is Independent of KRAS Patients Study 1:

Prospective, longitudinal study of 196 patients with metastatic colorectal cancer resistant to 5-FU, oxaliplatin and irinotecan. The patients were treated with third-line irinotecan (130 mg/m$^2$ of body-surface area on day 1 of each 14-day period during the study) and cetuximab (first dose 400 mg/m$^2$ of body-surface area, then at a dose of 500 mg/m$^2$ of body-surface area every second week independent of their KRAS status). The patients were treated until disease progression. Median follow-up time was 19 months (range 6-31 months). 148 patients died. This study is a continuation of Example 4 herein, now including the entire group of patients.

Study 2:

Retrospective, longitudinal study of 134 patients with metastatic colorectal cancer resistant to 5-FU, oxaliplatin and irinotecan. The patients were treated with third-line irinotecan (130 mg/m$^2$ of body-surface area on day 1 of each 14-day period during the study) and cetuximab (first dose 400 mg/m$^2$ of body-surface area, then at a dose of 250 mg/m$^2$ of body-surface area once weekly independent of their KRAS status). The patients were treated until disease progression. Median follow-up time was 30 months (range 14-50 months). 98 patients died.

Methods

Pretreatment plasma was available for YKL-40 analysis from 185 of the patients included in Study 1. Pretreatment serum was available for YKL-40 analysis from 134 patients included in Study 2. Plasma concentrations of YKL-40 (Study 1) and serum concentrations of YKL-40 (Study 2) were analyzed by a commercial ELISA (Quidel, California, USA).

DNA from primary tumor was available for KRAS mutation status from 180 of the patients included in Study 1 and from 99 patients included in Study 2. KRAS was analyzed using DxS KRAS test PCR kit (Roche).

Statistical Analysis

The primary clinical endpoint for this study was overall survival determined as the time from baseline blood sample before start of treatment with cetuximab to time to death of all causes. All data on disease status and duration of survival were updated Jul. 2, 2009 (Study 1) and Mar. 9, 2009 (Study 2). Cases in which patients were alive by this date were censored. Secondary endpoint was time to disease progression (only Study 2).

Plasma or serum concentrations of YKL-40 were determined at baseline, prior to first treatment with cetuximab. Different cut-off levels of plasma YKL-40 (Study 1) and serum YKL-40 (Study 2) in healthy subjects (age-corrected) were chosen: The 90, 95, 97.5, 99, 99.5 and 99.9 percentile levels. Plasma and serum YKL-40 levels of the two patient groups were also divided into tertiles and used as cut-off levels. Descriptive statistics are presented by their median levels and range. Rank statistics were used for tests of association between plasma and serum YKL-40 with KRAS and performance status (Wilcoxon rank sum) and measures of association (Spearman rank correlation). Kruskal-Wallis test was used for comparison of three or more independent groups with nonparametric data distributions. Analysis of measurements for time to disease progression and death were done using the Cox proportional hazards model. Plasma and serum levels of YKL-40 were entered by their actual value (log transformed) on the log scale (base 2) or by high vs. normal level (the 95 percentile in healthy subjects was used as cut-off). Only cases with complete data were included in the multivariate analyses. Analysis of response to cetuximab was done using logistic regression and presenting the results using odds ratios (OR) with 95% confidence limits (Cl) as well as the area (AUC) under the receiver operating characteristic curve (ROC). Model assessment was done using graphical methods. Survival probabilities for overall survival were estimated by the Kaplan-Meier method and tests for differences between strata were done using the log-rank statistic. Graphical presentation using Kaplan-Meier estimates of survival was shown grouping patients by their tertiles of plasma and serum YKL-40 levels or the following cut-off levels of age-corrected YKL-40 levels in healthy subjects: 90%, 95%, 97.5%, 99%, 99.5%, and 99.9%. Model assessment was done using graphical methods, Schoenfeld and martingale residuals. P-values less than 5% were considered significant. All calculations were performed using SAS (version 9.1, SAS Institute, Cary, N.C., USA).

Results

Pretreatment Plasma and Serum YKL-40 Levels and Demographic Characteristics of the Patients The baseline demographic characteristics of the patients with metastatic colorectal cancer included in Study 1 and Study 2 are shown in Table 6. The two study populations are comparable. 38% had KRAS mutations in Study 1 and 45% in Study 2. The patients had significantly (p<0.001) higher pretreatment plasma and serum YKL-40 levels compared to healthy subjects. Plasma and serum YKL-40 levels were higher than the upper normal level (95 percentile used as cut-off) in 52% of the patients in Study 1 and in 68% of the patients in Study 2. YKL-40 was not associated with KRAS status (Study 1: p=0.34; Study 2: p=0.45).

TABLE 6

Clinical characteristics of the patients and pretreatment concentrations of plasma YKL-40 and serum YKL-40 in patients with metastatic colorectal cancer treated with irinotecan and cetuximab.

| Characteristic | Study 1 N = 196 | Study 2 N = 134 | P-value§ |
|---|---|---|---|
| Age, years | 64 (36-87) | 62 (38-82) | NS |
| Sex, male/female¤ % | 63%/37% | 54%/46% | NS |
| Metastatic sites, 1/2/3/4/ND | 104/53/17/1/21 | ND | ND |
| Number and percentages | 53%/27%/9%/0.5%/11% | ND | |
| Performance status, 0/1/2/ND | 93/60/33/10 | 51/40/8/35 | NS |
| Number and percentages | 47%/31%/17%/5% | 38%/30%/6%/26% | |
| KRAS mutations, MT/WT/ND | 69/111/16 | 45/54/35 | NS |
| Number and percentages# | 38%/62% | 45%/55% | |
| Plasma or serum YKL-40, µg/l Median (range) | 133 (15-1766) | 148 (16-1410) | NS |
| Patients with elevated YKL-40 Number (percentage)¤ | 97 (52%) | 91 (68%) | NS |

ND, not determined. NS, not significant. MT, KRAS mutations. WT, KRAS wild type.
Only the cohort with KRAS determinations.
¤Only the cohort with YKL-40 determinations. The 95 percentile of plasma and serum YKL-40 levels in healthy subjects are used as cut-off (age-corrected).
§Mann-Whitney's test or Kruskal Wallis tests are used.

Pretreatment Serum YKL-40 Levels and Response to Cetuximab Therapy
Data are Only Available from Study 2:

Twenty patients were classified as responders (all wild-type) and 76 as non-responders according to RECIST criteria (KRAS wild type: 33; KRAS mutated: 43). The corresponding serum YKL-40 levels in these 3 groups are shown in Table 7. Highest serum YKL-40 levels were found in patients with no response to treatment. Response is analyzed in the KRAS wild type group using logistic regression. The Odds ratio (OR) estimates are: serum YKL-40 entered by its actual value on the log scale (base 2): OR=1.34, 95% Cl: 0.89-2.01, p=0.16, AUC=0.61; and serum YKL-40 entered as its dichotomized level: OR=1.68, 95% Cl: 0.63-4.48, p=0.33. The fact that the 95% Cl's include 1 can likely be attributed to the small sample size.

Serum YKL-40 was independent of KRAS mutation status. High serum YKL-40 was associated with poor response to the Cetuximab treatment. Thus YKL-40 may be used to locate the group of true responders among the patients with KRAS wild type (20 out of 53, i.e. approximately 40% all KRAS wild type).

TABLE 7

Serum YKL-40 levels according to KRAS mutation status and response in patients from Study 2.

| KRAS Status | N | YKL-40, ug/l Median (range) |
|---|---|---|
| Wild type, response | 20 | 101 (44-639) |
| Wild type, no response | 33 | 159 (41-938) |
| Mutations, no response | 43 | 138 (16-1410) |

Pretreatment Serum YKL-40 Levels and Progression Free Survival
Data are Only Available from Study 2:

Progression free survival was determined as time from date of first treatment and time to disease progression. 105 had progression. Univariate Cox analysis showed that high pretreatment serum YKL-40 (log transformed continuous variable (base 2)) was associated with short progression free survival (HR=1.18, 95% Cl: 1.01-1.39, p=0.042). Multivariate Cox analysis (YKL-40 and KRAS) demonstrated that plasma YKL-40 was an independent biomarker of progression free survival (HR=1.20, 95% Cl: 1.02-1.41, p=0.026) and independent of KRAS status. The HR for YKL-40 is 1.20, i.e. the hazard increases by 20% for each doubling of YKL-40.

Figure 18:
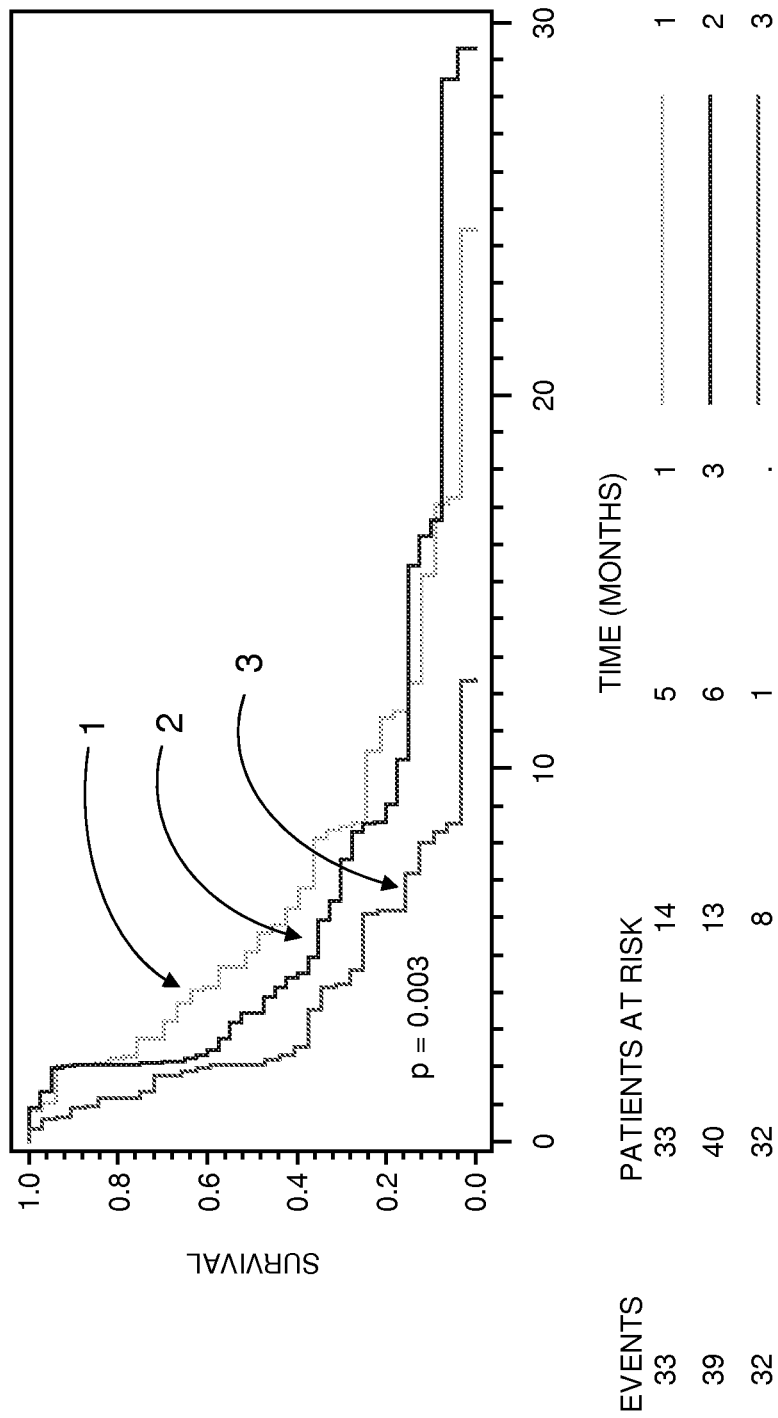
FIG. 18. Study 2. Kaplan-Meier curves showing the association between the pretreatment serum YKL-40 levels and progression free survival in patients with metastatic colorectal cancer treated with irinotecan and cetuximab. The P-value refers to the log-rank test for equality of strata. Patients are divided into tertiles according to their pretreatment serum YKL-40 levels. Patients in Group 3 have the highest serum YKL-40 levels. Serum YKL-40: Group 1: <94 µg/l; Group 2: ≥94 and ≤253 µg/l; and Group 3: >253 µg/l.

The Kaplan-Meier curves for increasing serum YKL-40 levels in the patients (tertiles are used as cut-off) and progression free survival are illustrated in FIG. 18. Significantly shorter survival was found according to increasing tertiles of pretreatment serum YKL-40.

Serum YKL-40 was independent of KRAS mutation status. High serum YKL-40 was associated with poor response to the Cetuximab treatment and short progression free survival. Thus YKL-40 may be used to locate the group of true responders among the patients with KRAS wild type (20 out of 53, i.e. approximately 40% all KRAS wild type).

Pretreatment Plasma and Serum YKL-40 Levels and Overall Survival
Study 1:

The median overall survival was 10.0 months. Overall survival in patients with KRAS wild type was 11.3 months compared to 7.5 months in patients with KRAS mutations (p=0.004).

Univariate Cox analysis showed that high pretreatment plasma YKL-40 (log transformed continuous variable (base 2)), was associated with short overall survival (HR=1.23, 95% Cl: 1.09-1.39, p=0.0006), Table 8. From this analysis the 6 months survival of patients with plasma YKL-40 levels <84 µg/l (first tertile), ≥84 and ≤218 µg/l (second tertile) and >218 µg/l (third quartile) was 68%, 72%, and 46%, respectively. The Kaplan-Meier curves for these 3 groups for overall survival are illustrated in FIG. 19A. Significantly shorter survival was found for the patients with the highest plasma YKL-40 levels.

Multivariate Cox analysis (plasma YKL-40 and KRAS status) showed that pretreatment plasma YKL-40 (log transformed continuous variable (base 2): HR=1.23, 95% Cl: 1.09-1.39, p=0.0007) and KRAS status (mutated vs. wildtype: HR=1.67, 1.17-2.39, p=0.0044) were independent biomarkers of overall survival. The corresponding results when plasma YKL-40 was dichotomized according to the plasma YKL-40 level in healthy subjects (age-corrected 95% level used as cut-off) are also given in Table 8, and plasma YKL-40 remained significant (HR=1.83, 95%: 1.28-2.60, p=0.0008)

and independent of KRAS. In another multivariate Cox analysis (including plasma YKL-40, KRAS, performance status, age and gender) plasma YKL-40 remained significant (HR=1.17, 95% Cl: 1.02-1.33, p=0.021).

Figure 20A:
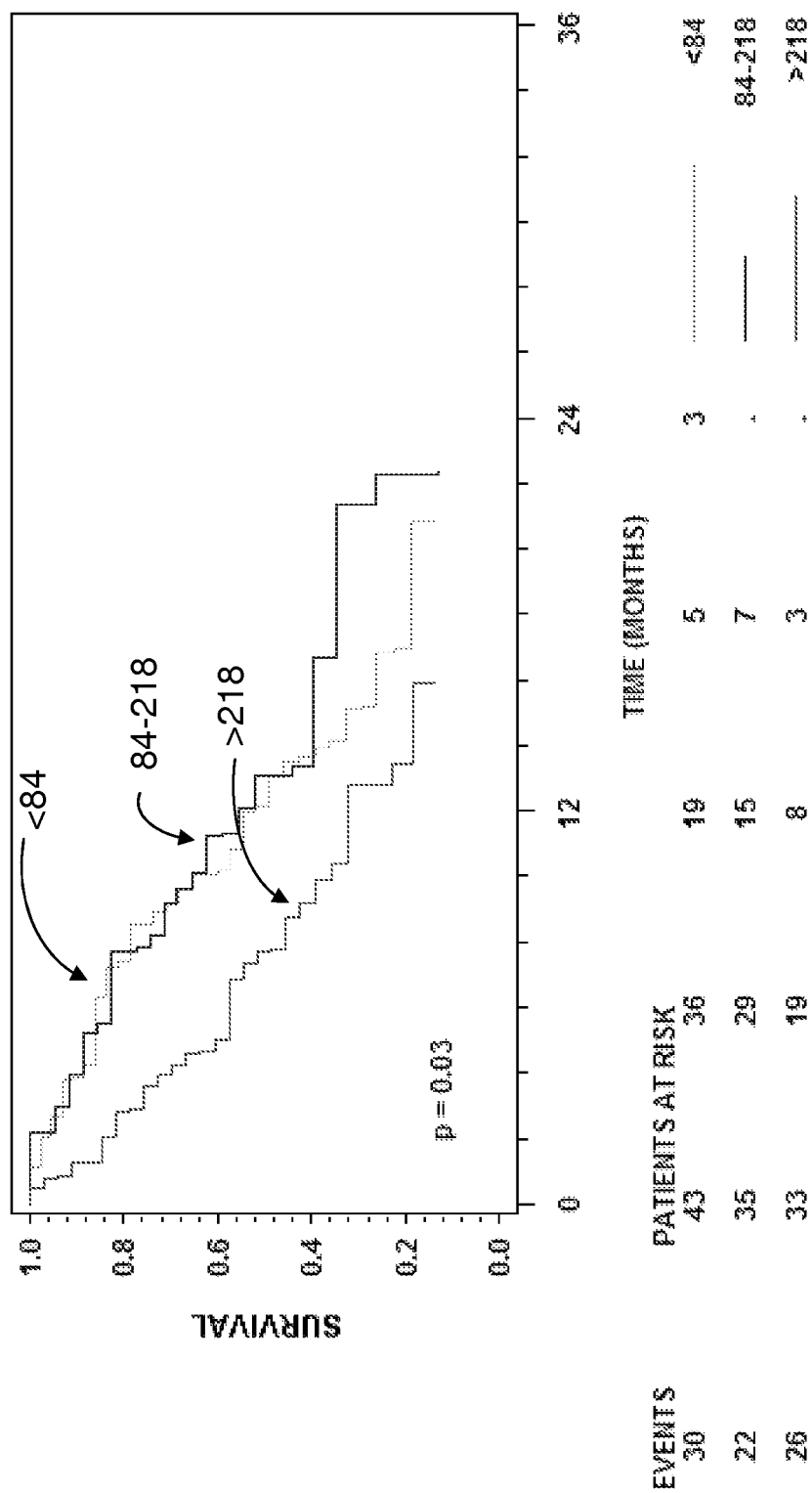
Figure 20B:
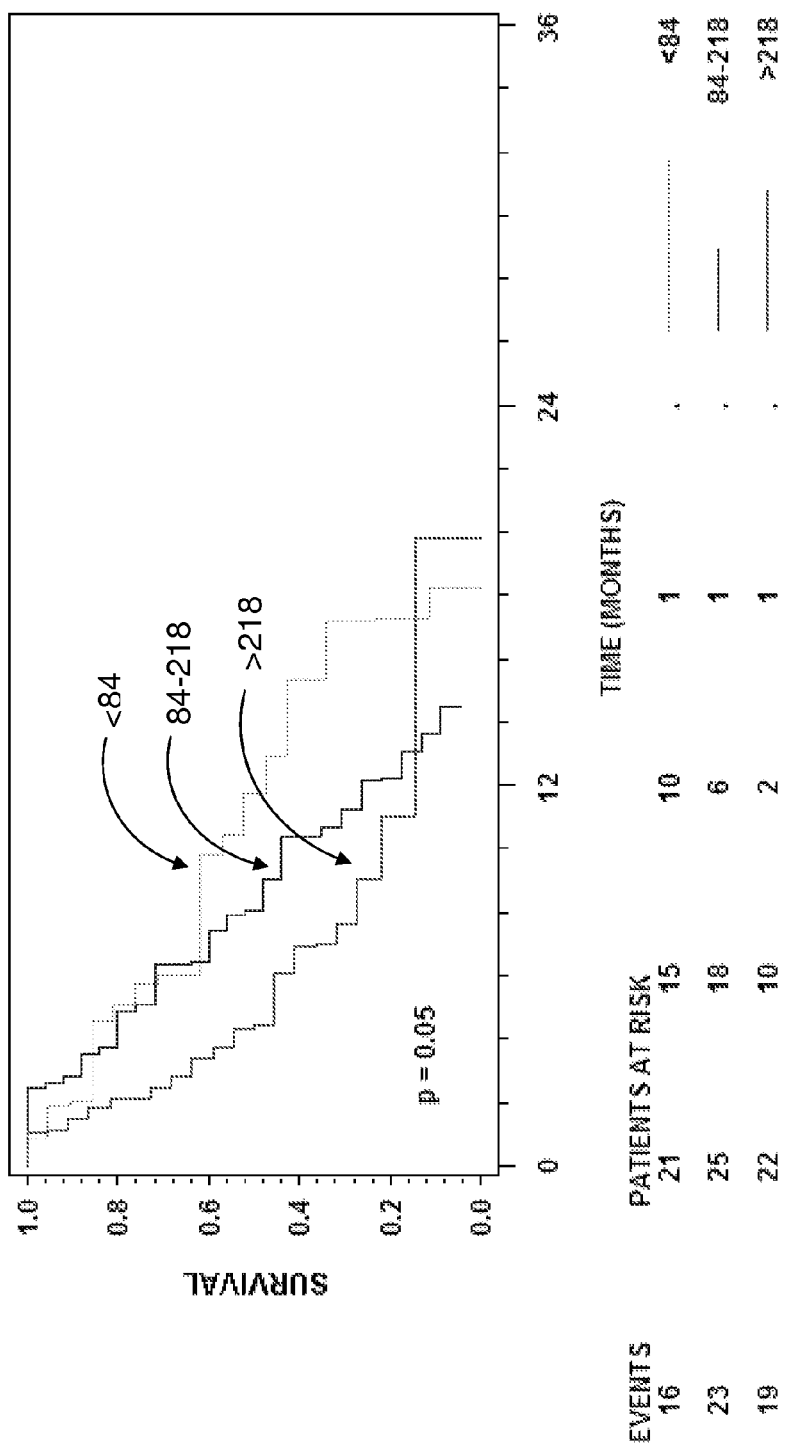

The Kaplan-Meier curves for plasma YKL-40 (the tertiles of the patients plasma YKL-40 levels are used as cut-off) and overall survival in patients with KRAS wild type are illustrated in FIG. 20A and in patients with KRAS mutations in FIG. 20B. In both patients groups significantly shorter survival were found for the patients with the highest plasma YKL-40 levels.

The Kaplan-Meier curves for plasma YKL-40 and overall survival in all patients included in Study 1 according to increasing cut-off levels of age-corrected plasma YKL-40 levels in healthy subjects: 90%, 95%, 97.5%, 99%, 99.5%, and 99.9% are given in FIG. 21A-F. Shorter survival was found with increasing cut-off, and the HRs increased with increasing cut-offs.

Study 2:

The median overall survival was 7.1 months. Overall survival in patients with KRAS wild type was 10.1 months compared to 6.0 months in patients with KRAS mutations (p=0.043).

Univariate Cox analysis showed that high pretreatment serum YKL-40 (log transformed continuous variable (base 2)), was associated with short overall survival (HR=1.30, 95% Cl: 1.09-1.56, p=0.003), Table 8. From this analysis the 6 months survival of patients with serum YKL-40 levels <94 µg/l (first tertile), Group 2: ≥4 and ≤253 µg/l (second tertile) and >253 µg/l (third tertile) was 67%, 53%, and 31%, respectively. The Kaplan-Meier curves for these 3 groups for overall survival are illustrated in FIG. 19B. Significantly shorter survival was found for the patients with the highest serum YKL-40 levels.

Multivariate Cox analysis (serum YKL-40 and KRAS status) showed that pretreatment serum YKL-40 (log transformed continuous variable (base 2): HR=1.41, 95% Cl: 1.18-1.69, p=0.0002) and KRAS status (mutated vs. wildtype: HR=1.57, 95% Cl: 1.02-2.42, p=0.042) were independent biomarkers of overall survival. The corresponding results when serum YKL-40 was dichotomized according to the serum YKL-40 level in healthy subjects (age-corrected 95% level used as cut-off) are also given in Table 8, and serum YKL-40 remained significant (HR=2.13, 95%: 1.40-3.33, p=0.0008) and independent of KRAS. In multivariate Cox analysis (including plasma YKL-40, KRAS, performance status) serum YKL-40 (HR=1.36, 95% Cl: 1.13-1.62, p=0.0009), KRAS (HR=1.58, 95% Cl: 1.03-2.44, p=0.037), and performance status (HR=1.69, 95%: 1.20-2.39, p=0.0028) were all significant biomarkers of survival.

Figure 20C:
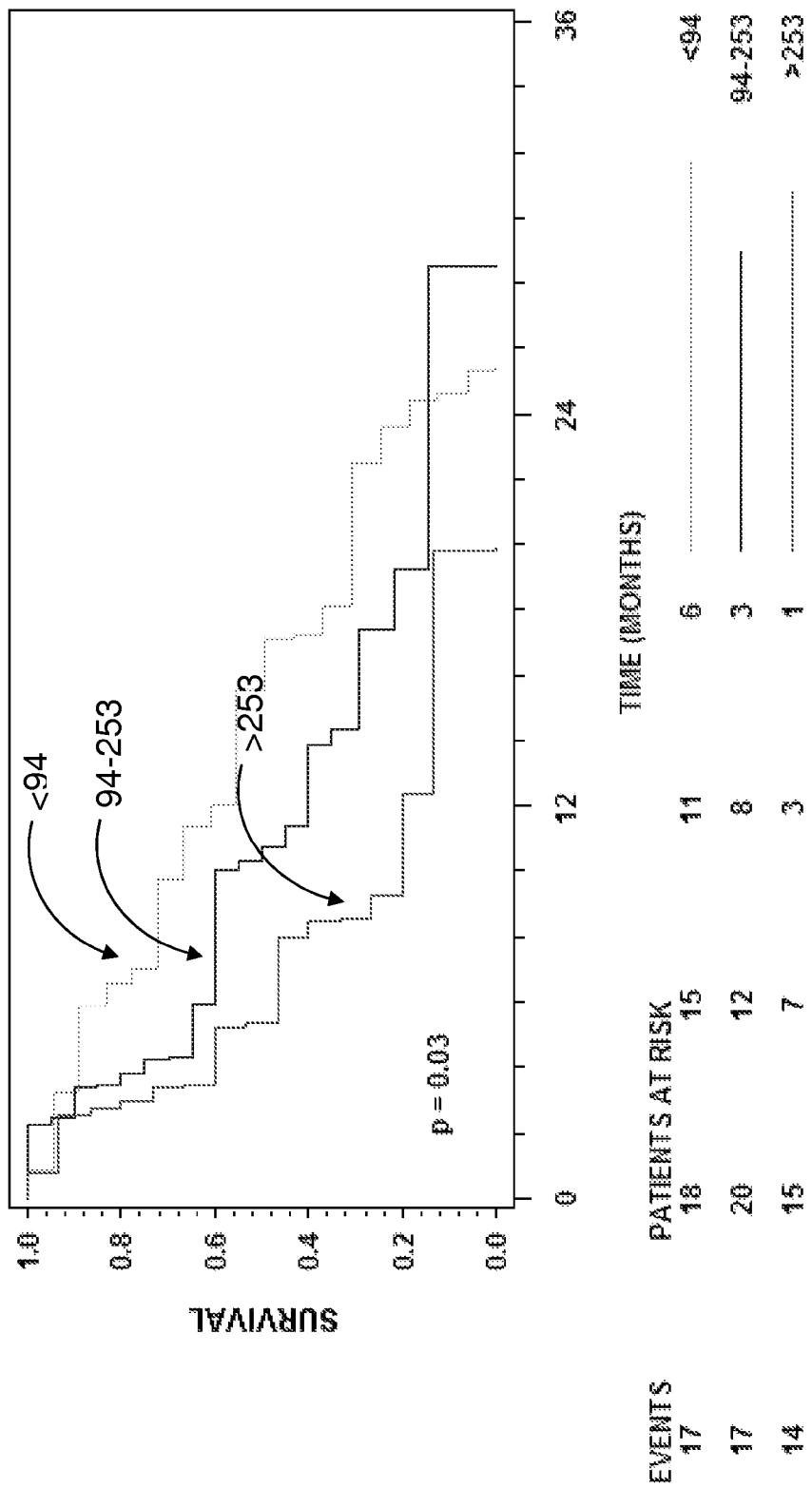
Figure 20D:
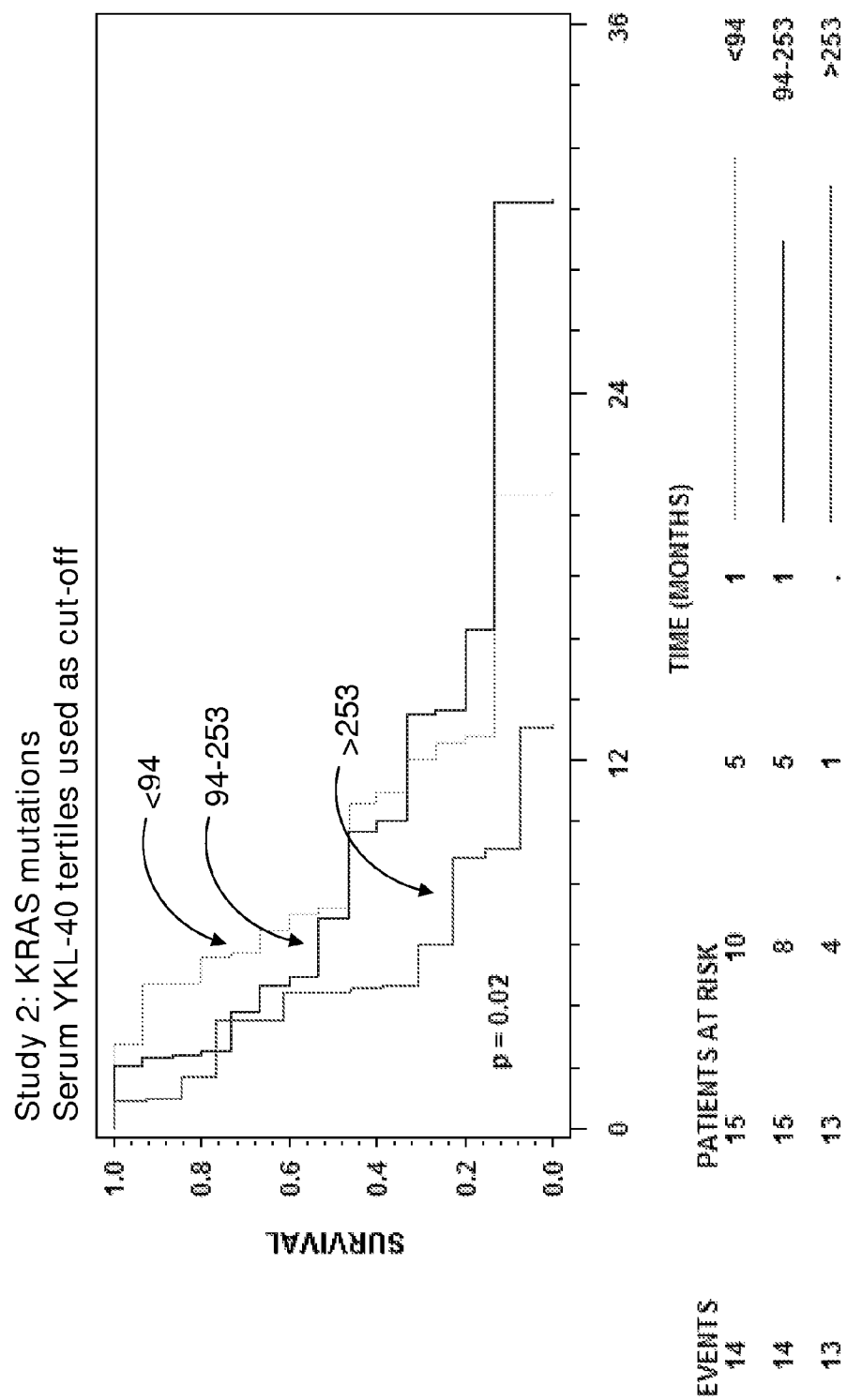
Figure 21A:
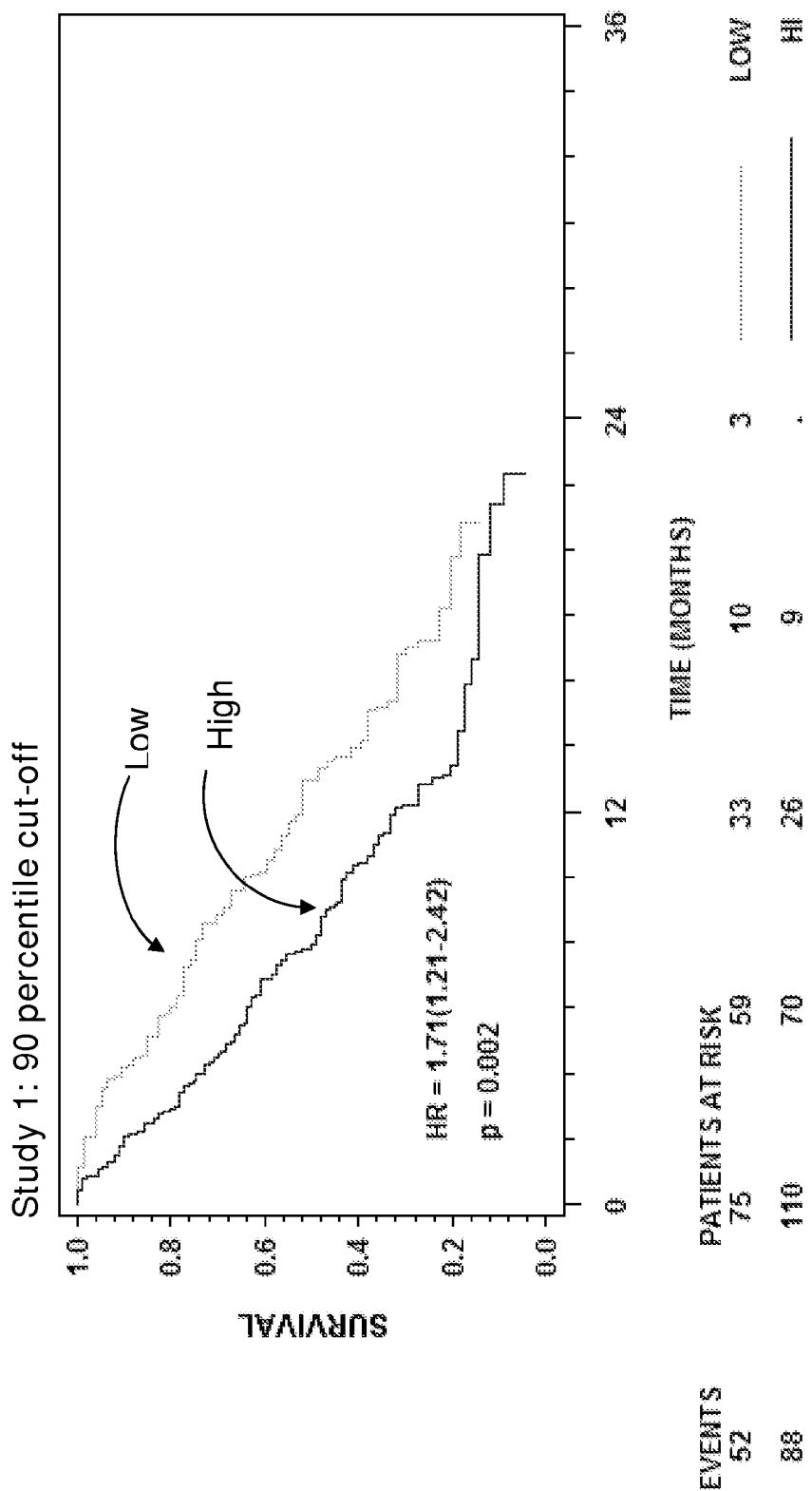
Figure 21B:
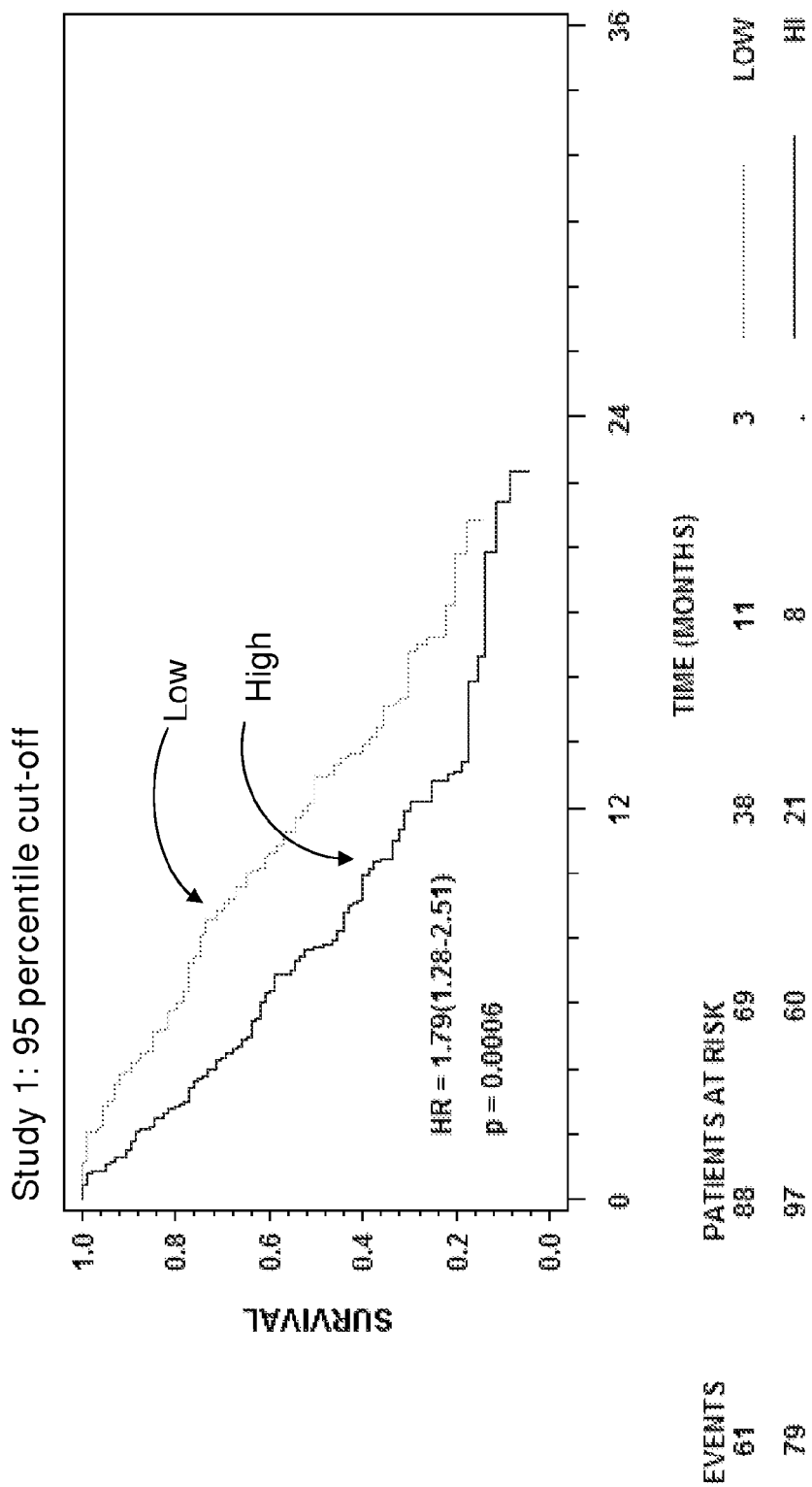
Figure 21C:
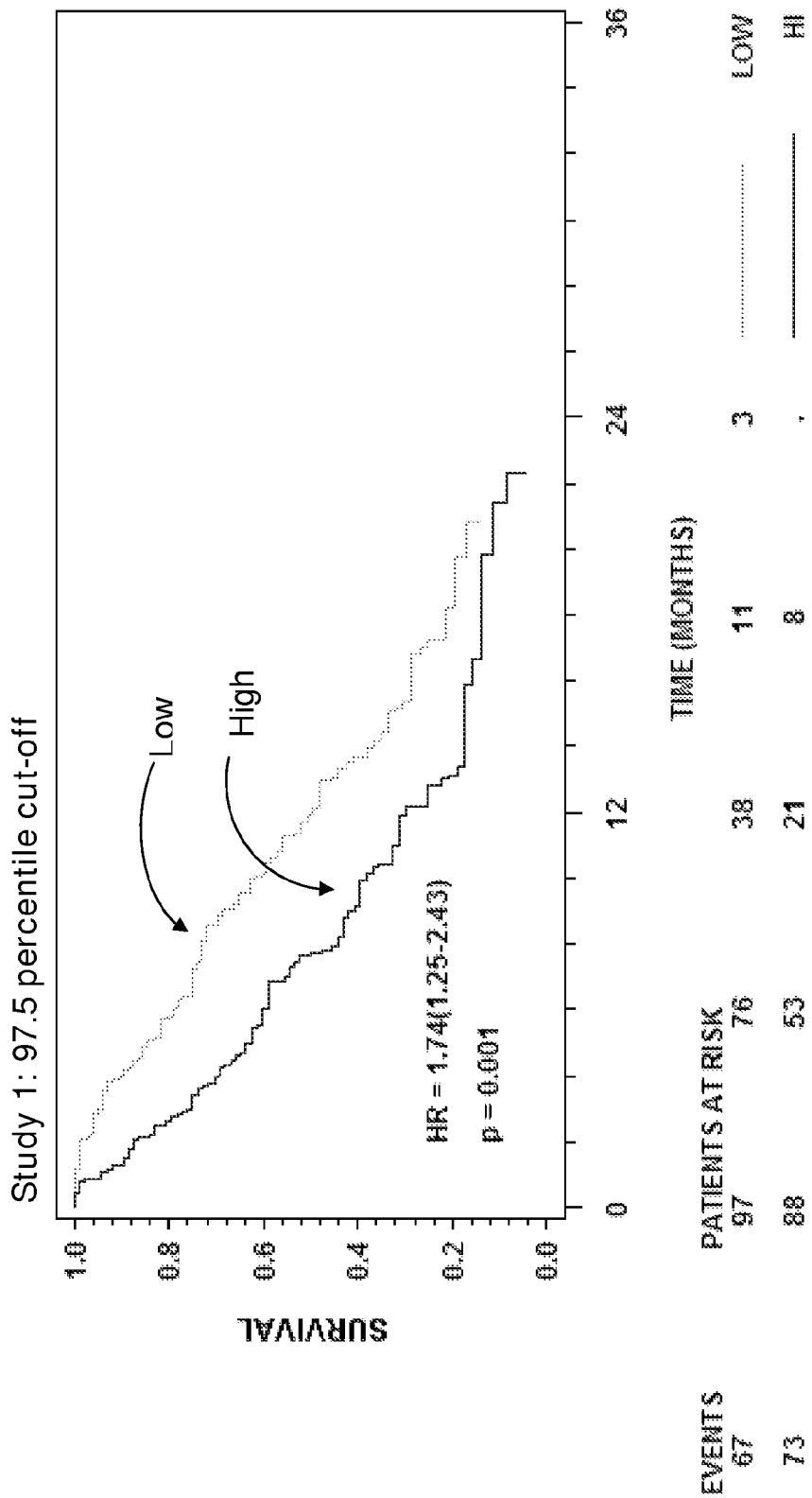
Figure 21D:
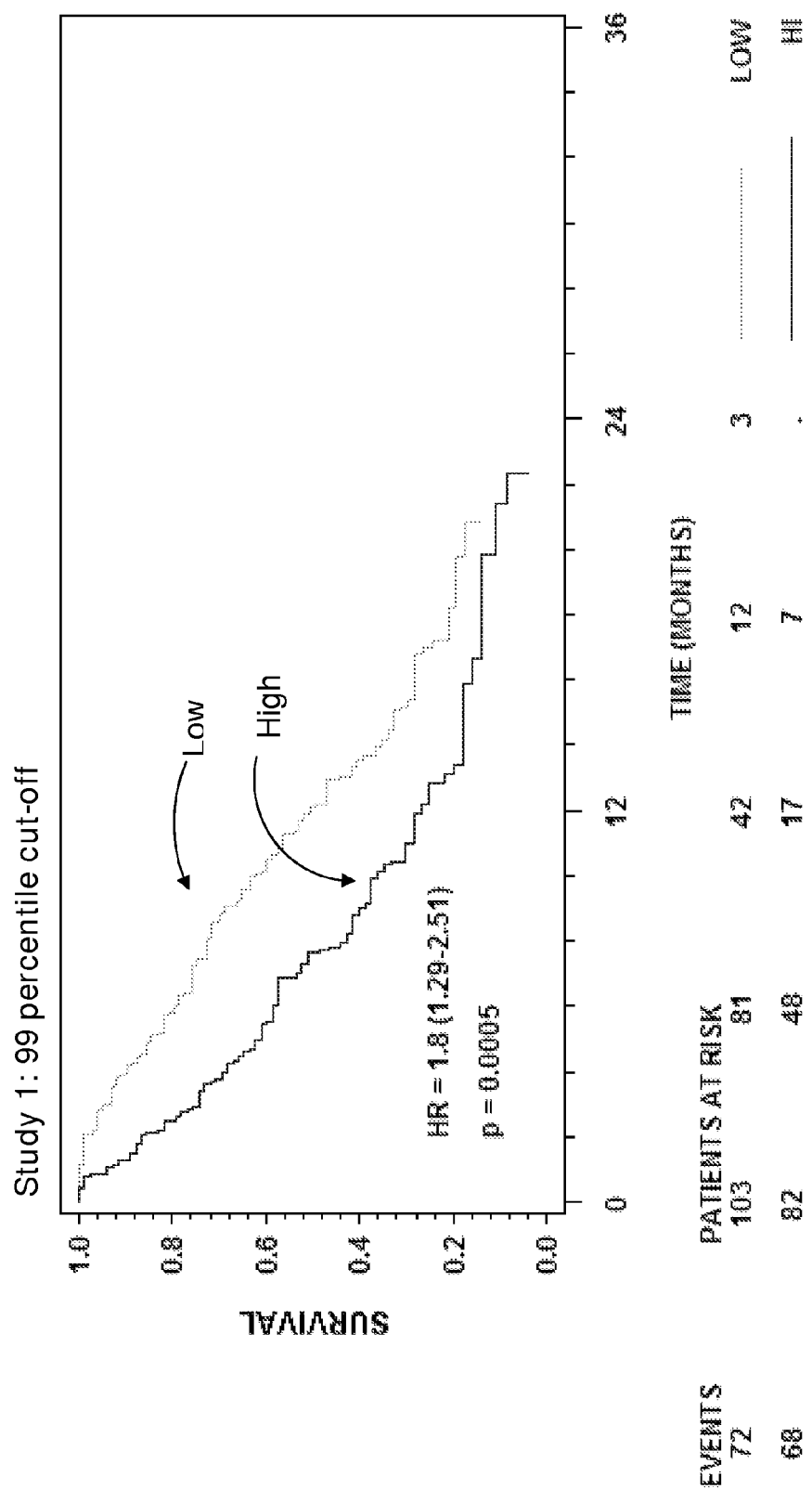
Figure 21E:
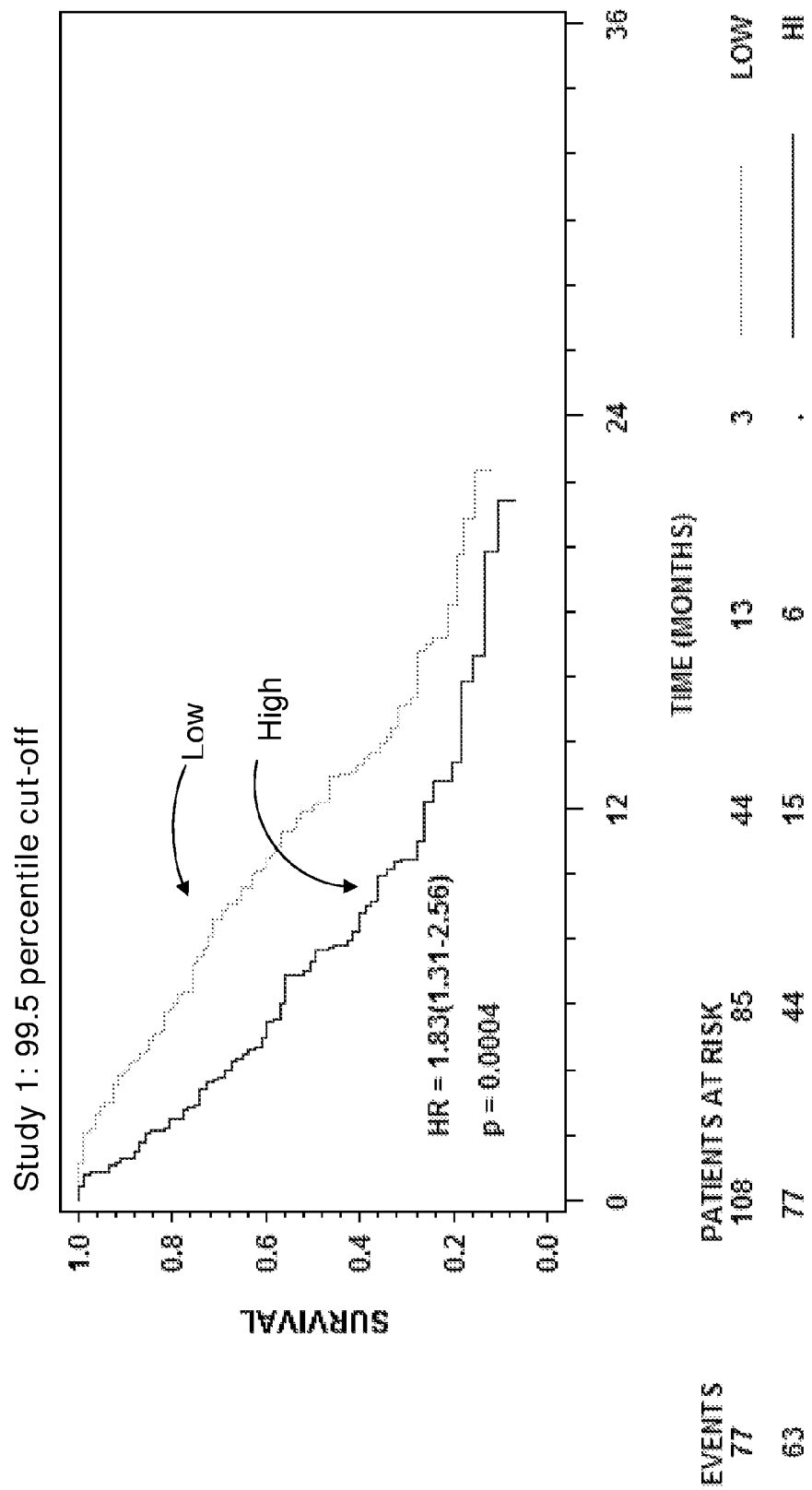
Figure 21F:
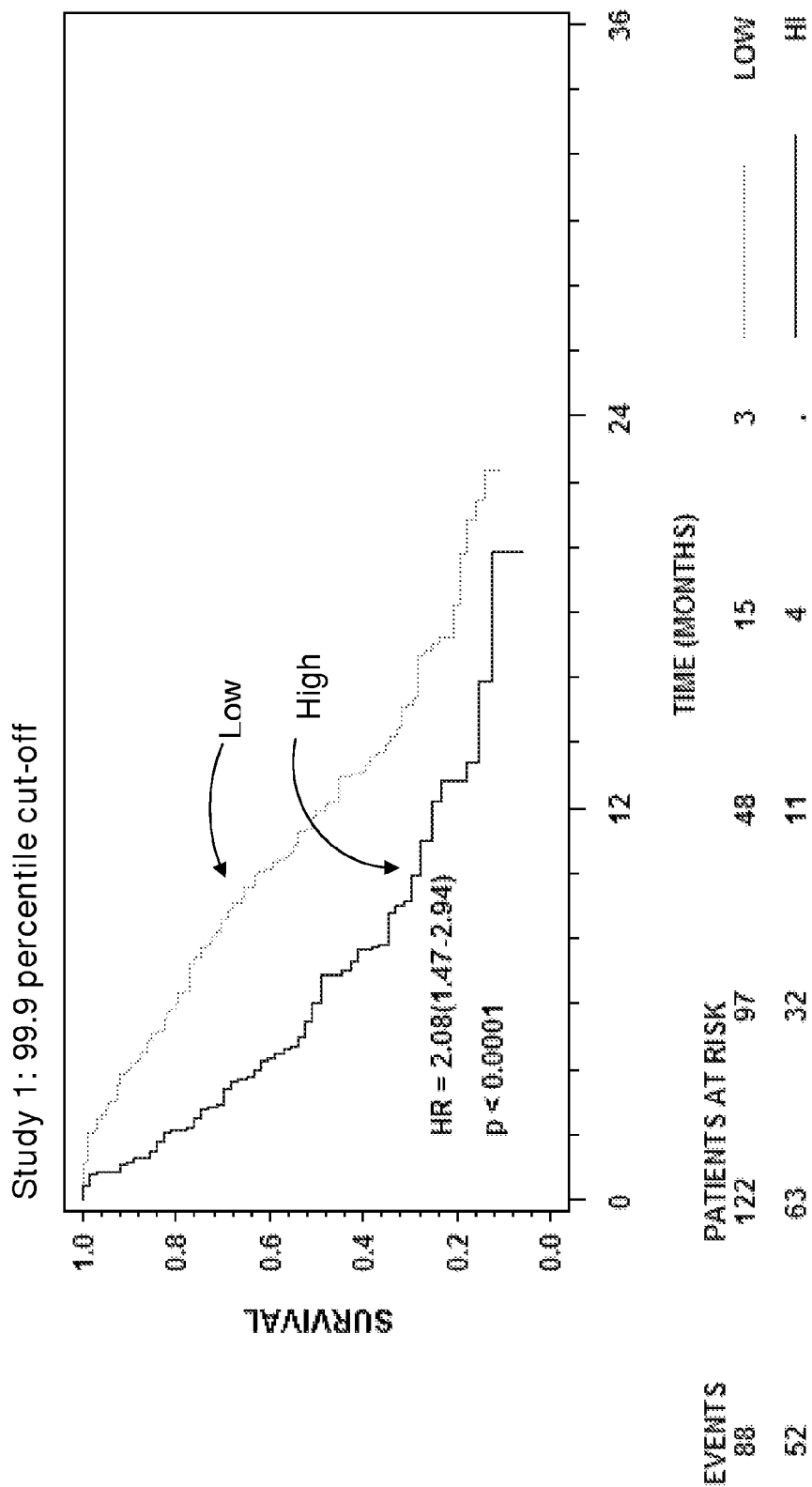
Figure 22A:
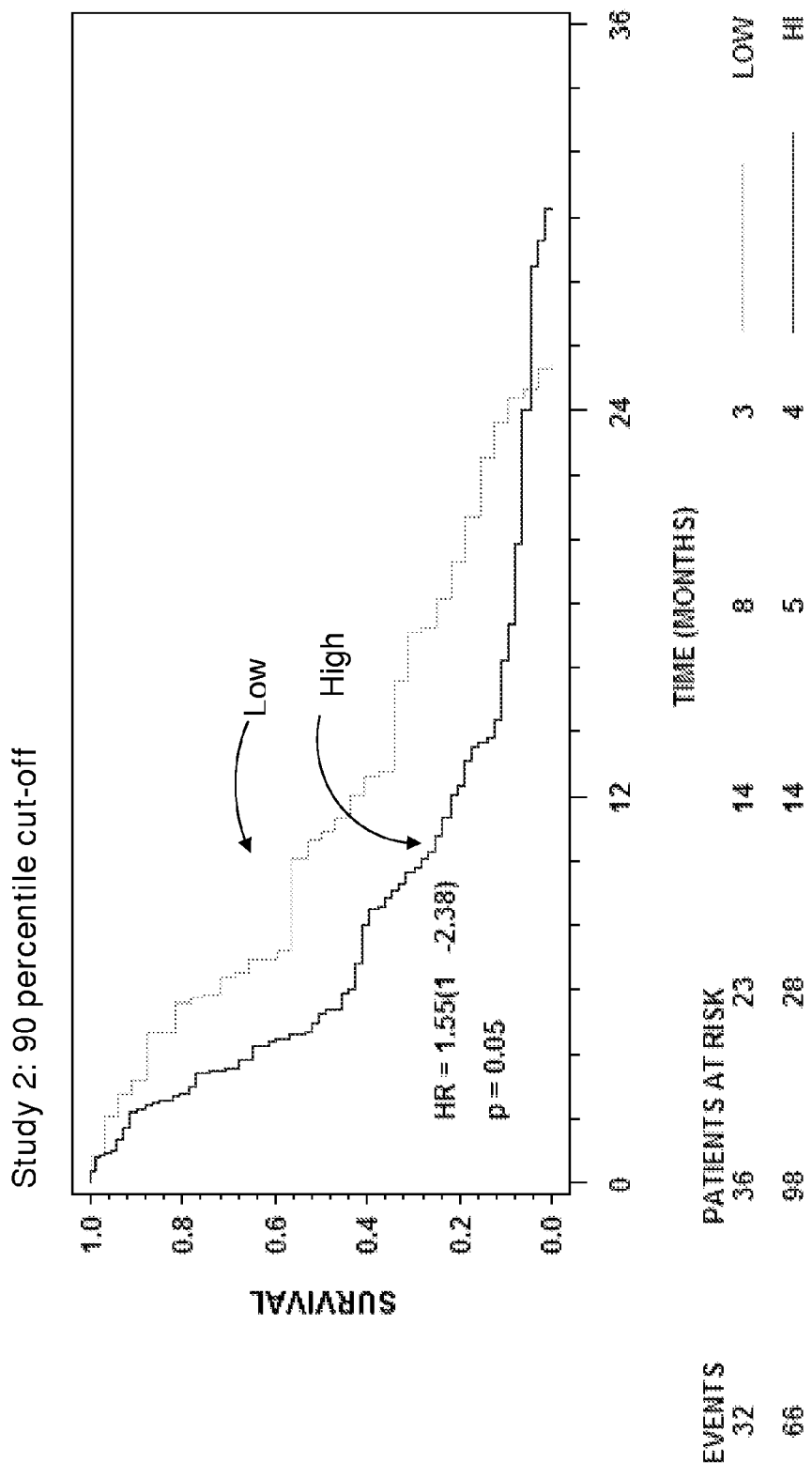
Figure 22B:
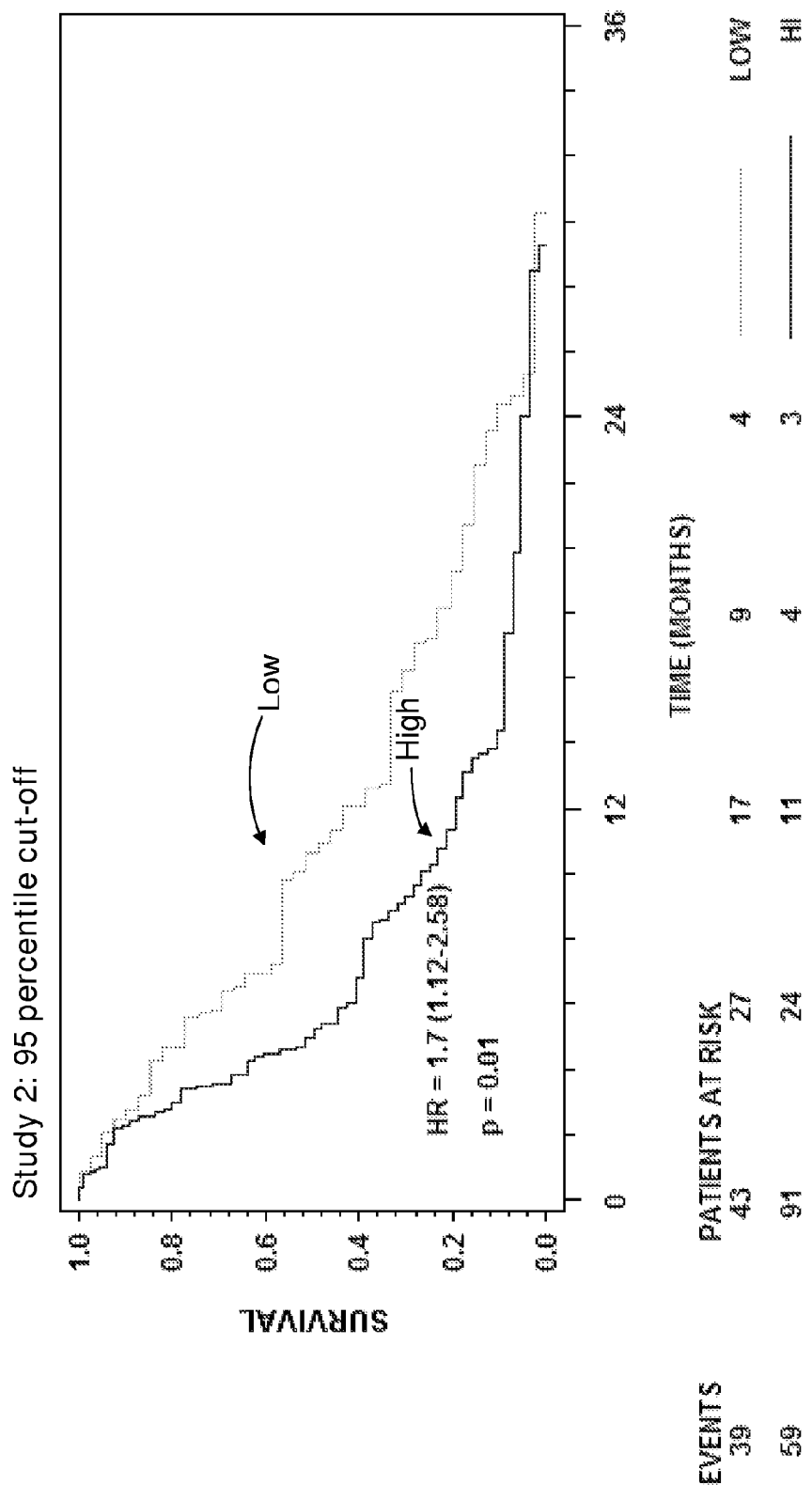
Figure 22C:
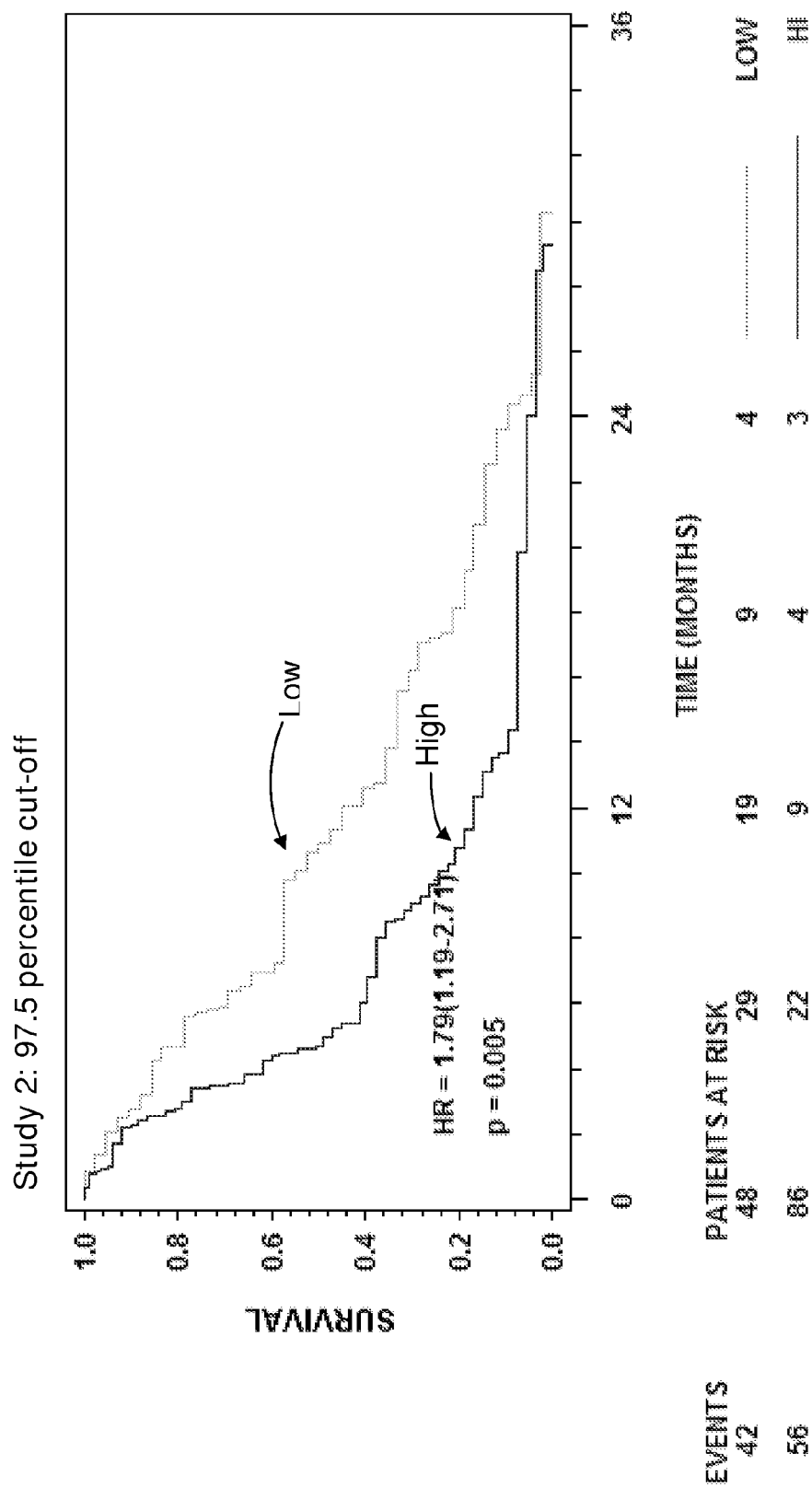
Figure 22D:
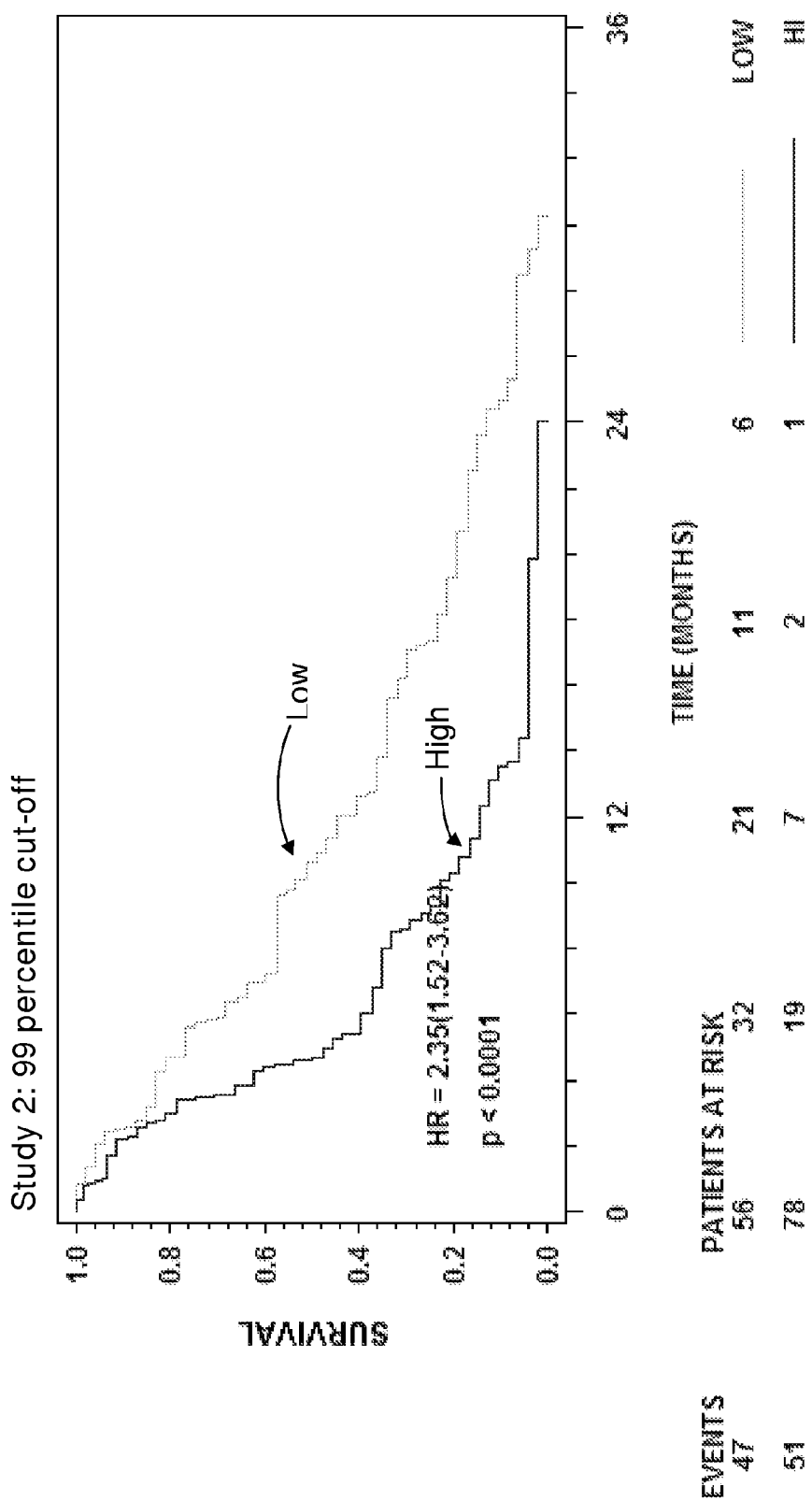
Figure 22E:
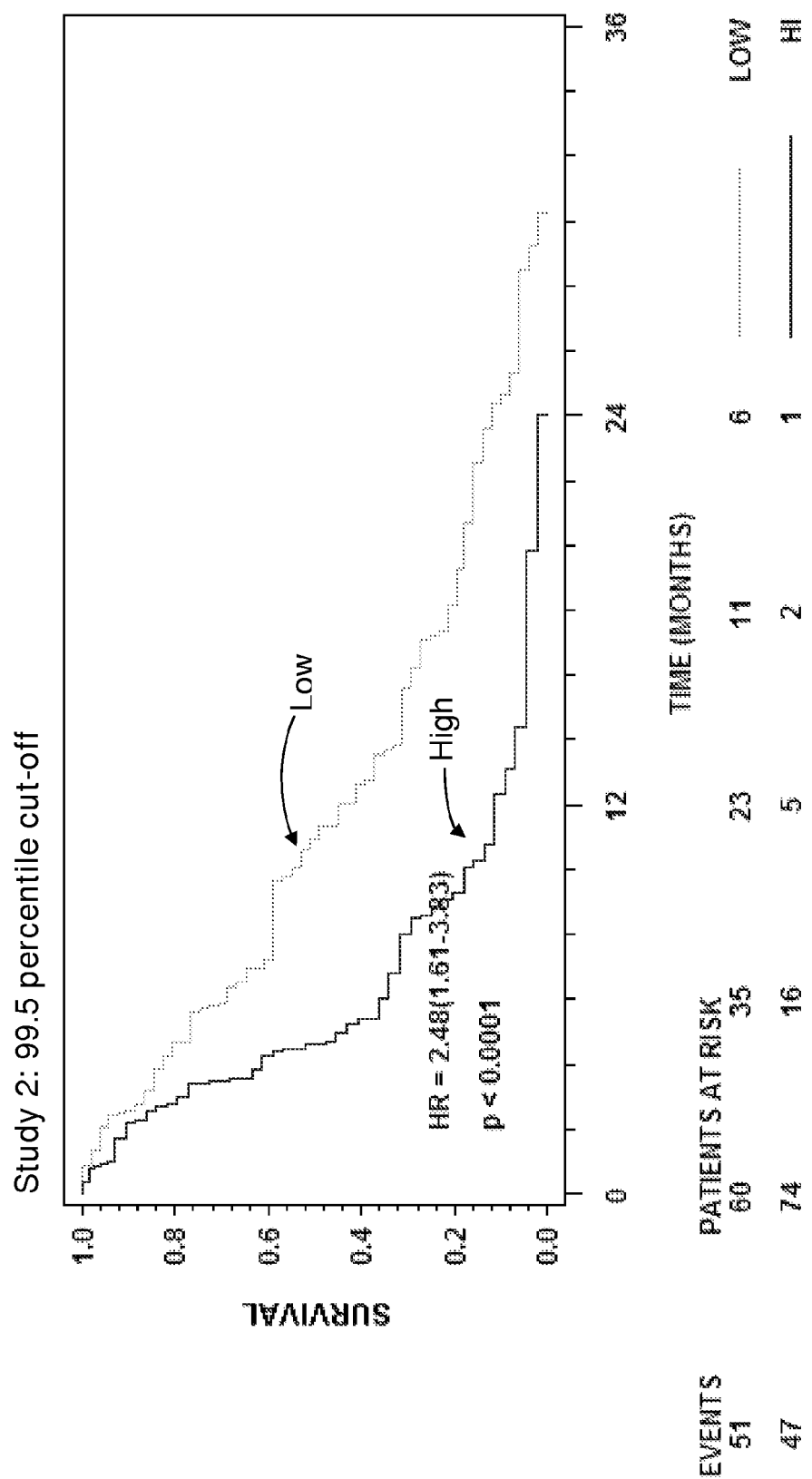
Figure 22F:
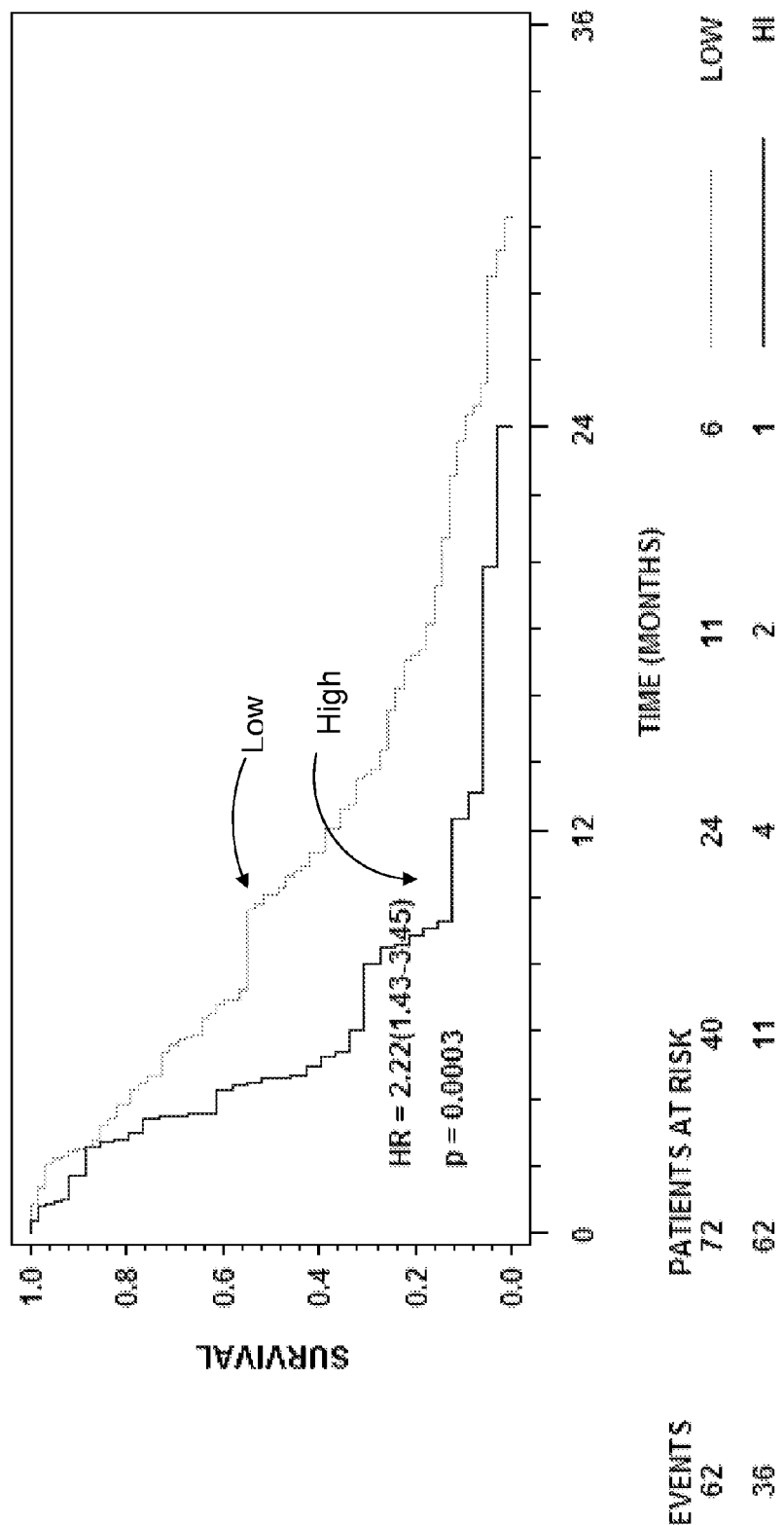

The Kaplan-Meier curves for serum YKL-40 (the tertiles of the patients serum YKL-40 levels are used as cut-off) and overall survival in patients with KRAS wild type are illustrated in FIG. 20C and in patients with KRAS mutations in FIG. 20D. In both patients groups significantly shorter survival were found for the patients with the highest serum YKL-40 levels.

The Kaplan-Meier curves for serum YKL-40 and overall survival in all patients included in Study 2 according to increasing cut-off levels of age-corrected serum YKL-40 levels in healthy subjects: 90%, 95%, 97.5%, 99%, 99.5%, and 99.9% are given in FIG. 22A-F. Shorter survival was found with increasing cut-off, and the HRs increased with increasing cut-offs.

TABLE 8

Univariate and multivariate analyses of overall survival for the pretreatment levels of plasma or serum YKL-40 and KRAS status in patients with metastatic colorectal cancer treated with cetuximab.

| Variables | Univariate analysis | | | Multivariate analysis | | |
|---|---|---|---|---|---|---|
| | HR | 95% CI | P | HR | 95% CI | P |
| Study 1 | | | | | | |
| Plasma YKL-40# | 1.23 | 1.09-1.39 | 0.0006 | 1.23 | 1.09-1.39 | 0.0007 |
| KRAS, mutations | 1.63 | 1.16-2.30 | 0.005 | 1.67 | 1.17-2.39 | 0.0044 |
| Plasma YKL-40§ | 1.78 | 1.26-2.53 | 0.001 | 1.83 | 1.28-2.60 | 0.0008 |
| KRAS, mutations | 1.63 | 1.16-2.30 | 0.005 | 1.72 | 1.21-2.46 | 0.0027 |
| Study 2 | | | | | | |
| Serum YKL-40# | 1.30 | 1.09-1.56 | 0.003 | 1.41 | 1.18-1.69 | 0.0002 |
| KRAS, mutations | 1.55 | 1.01-2.39 | 0.045 | 1.57 | 1.02-2.42 | 0.042 |
| Serum YKL-40§ | 1.59 | 1.04-2.45 | 0.03 | 2.13 | 1.40-3.33 | 0.0008 |
| KRAS, mutations | 1.55 | 1.01-2.39 | 0.045 | 1.61 | 1.04-2.49 | 0.034 |

HR = Hazard ratio.
CI = Confidence interval.
Plasma and serum YKL-40 levels are log transformed and used as a continuous variable (base 2). The HR is for one unit on the log scale, i.e. if the HR is 1.23, this means that the hazard increases by 23% for each doubling of YKL-40.
§Plasma and serum YKL-40 levels are dichotomized (high vs. normal according to the age-corrected upper 95% percentage limit of plasma and serum YKL-40 in healthy subjects).

Conclusions

High pretreatment plasma YKL-40 and serum YKL-40 levels were prognostic biomarkers of short overall survival in two independent studies of patients with metastatic colorectal cancer treated with third-line cetuximab in combination with irinotecan. In both studies plasma YKL-40 and serum YKL-40 were independent of KRAS mutation status. In one of the studies data were available regarding response to cetuximab and progression free survival and high serum YKL-40 was associated with poor response and short progression free survival. Thus YKL-40 may be used to locate the true responders among the patients with KRAS wild type (approximately 40% of all patients with KRAS wild type). Pretreatment plasma YKL-40 and serum YKL-40 may therefore be both a new predictive biomarker of response to cetuximab and a prognostic biomarker of short survival in patients treated with cetuximab. Furthermore, by monitoring the YKL-40 level during the treatment period the progression of the disease may be monitored and the treatment be adapted accordingly.

Example 6

Plasma and Serum YKL-40 Concentrations in Patients with Metastatic Colorectal Cancer During Treatment with Cetuximab and Irinotecan are Associated with Progression Free Survival and Overall Survival Patients and Methods
As described for Example 5 herein.
Statistical Analysis
The analysis of updated YKL-40 levels has been done using a Cox proportional hazard model with YKL-40 as a time dependent covariate. This model includes treatment (Study 1 and Study 2) and KRAS status. Kaplan-Meier estimates of survival probabilities using a landmark at approximately 2.5 months have been done for progression free survival and overall survival.

Results

Study 1 and 2 Combined:

FIG. 23A (Study 1) and 23B (Study 2) illustrate the individual changes in YKL-40 (µg/l) in patients with metastatic colorectal cancer during treatment with cetuximab and irinotecan. FIG. 24A (Study 1) and 24B (Study 2) show the changes in the ratios of YKL-40 (compared to pre-treatment levels).

During treatment with cetuximab and irinotecan YKL-40 increased compared to pretreatment (baseline) levels in some patients with metastatic colorectal cancer (2 weeks mean ratio 1.21 (95% CI: 0.81-1.60), 2 months mean ratio 1.17 (95% CI: 1.03-1.30), 4 months mean ratio 1.04 (0.91-1.17), 6 months mean ratio 1.11 (95% CI: 0.90-1.32), and 8 months mean ratio 1.12 (95% CI: 0.90-1.33).

Multivariate analysis of updated YKL-40 levels showed that high YKL-40 ratio was associated with short progression free survival (HR=1.30, 95% CI: 1.10-1.54, p=0.002) and short overall survival (HR=1.38, 95% CI: 1.17-1.63, p=0.0002). The updated YKL-40 values (log transformed) (adjusted for Study and KRAS mutation status) were also associated with progression free survival (HR=1.11, 95% CI: 1.04-1.20, p=0.002) and overall survival (HR=1.23, 95% CI 1.14-1.33, p<0.0001).

Kaplan-Meier estimates of progression free survival and overall survival and landmark time approximately 2-3 months after start of treatment with cetuximab and irinotecan are shown in FIGS. 25A and 25B. YKL-40 was dichotomized according to high or low YKL-40 ratio at this time point (defined as YKL-40 levels at 2-3 months compared to pre-treatment YKL-40 levels). The 104 patients from Study 1 and 53 patients from Study 2 are combined. A high ratio is a ratio of above 1, and a low ratio is a ratio equal to/below 1, i.e. corresponding to an increase or a no-change/decrease in the YKL-40 level.

Conclusion

During treatment with cetuximab and irinotecan in patients with metastatic colorectal cancer the updated YKL-40 levels as well as the ratio of updated YKL-40 levels to the pre-treatment level were associated to progression free survival and overall survival, with high values indicating poor prognosis. These results were independent of KRAS status. These are novel observations and suggest that changes in YKL-40 during treatment with cetuximab may be a useful biomarker to monitor in patients with colorectal cancer. Thus YKL-40 is a new biomarker for response to cetuximab treatment.

REFERENCES

1. Bokemeyer C, et al. Fluorouracil, leucovorin, and oxaliplatin with and without cetuximab in the first-line treatment of metastatic colorectal cancer. J Clin Oncol 2009; 27:663-70.
2. Bonner J A, et al. Radiotherapy plus cetuximab for squamous-cell carcinoma of the head and neck. N Engl J Med 2006; 354:567-78.
3. Cascinu S et al. Cetuximab plus gemcitabine and cisplatin compared with gemcitabine and cisplatin alone in patients with advanced pancreatic cancer: a randomised, multicentre, phase II trial. Lancet Oncology 2008; 9, 39-44.
4. Chung K Y, et al. Cetuximab shows activity in colorectal cancer patients with tumors that do not express the epidermal growth factor receptor by immunohistochemistry. J Clin Oncol 2005; 23:1803-10.
5. Cunningham D, et al. Cetuximab monotherapy and cetuximab plus irinotecan in irinotecan-refractory metastatic colorectal cancer. N Engl J Med 2004; 351:337-45.
6. De Reynies A, et al. KRAS mutation signature in colorectal tumors significantly overlaps with the cetuximab response signature. J Clin Oncol 2008; 26:2228-31.
7. De Roock W, et al. KRAS wild-type state predicts survival and is associated to early radiological response in metastatic colorectal cancer treated with cetuximab. Ann Oncol 2008; 19:508-15.
8. Di Fiore F, et al. Clinical relevance of KRAS mutation detection in metastatic colorectal cancer treated by cetuximab plus chemotherapy. Br J Cancer 2007; 96:1166-9.
9. Di Nicolantonia F, et al. Wild-type BRAF is required for response to panitumumab or cetuximab in metastatic colorectal cancer. J Clin Oncol 2008; 26:5705-12.
10. Jonker D J, et al. Cetuximab for the treatment of colorectal cancer. N Engl J Med 2007; 357:2040-8.
11. Karapetis C S, et al. K-ras mutations and benefit from cetuximab in advanced colorectal cancer. N Engl J Med 2008; 359:1757-65.
12. Khambata-Ford S, et al. Expression of epiregulin and amphiregulin and K-ras mutation status predict disease control in metastatic colorectal cancer patients treated with cetuximab. J Clin Oncol 2007; 25:3230-7.
13. Lievre A, et al. KRAS mutation status is predictive of response to cetuximab therapy in colorectal cancer. Cancer Res 2006; 66:3992-5.
14. Lievre A, et al. KRAS mutations as an independent prognostic factor in patients with advanced colorectal cancer treated with cetuximab. J Clin Oncol 2008; 26:374-9.
15. Pfeiffer P, et al. Cetuximab and irinotecan as third line therapy in patients with advanced colorectal cancer after failure of irinotecan, oxaliplatin and 5-fluorouracil. Acta Oncol 2007; 46:697-701.
16. Philip P A et al. Phase III study of gemcitabine (G) plus cetuximab (C) versus gemcitabine in patients (pts) with locally advanced or metastatic pancreatic adenocarcinoma (PC): SWOG S0205 study. Proc Am Soc Clin Oncol 2007; 25 (abstr 4509).
17. Saltz L B, et al. Phase II trial of cetuximab in patients with refractory colorectal cancer that expresses the epidermal growth factor receptor. J Clin Oncol 2004; 22:1201-8.
18. Tol J, et al. Chemotherapy, bevacizumab, and cetuximab in metastatic colorectal cancer. N Engl J Med 2009; 360: 563-72.
19. Vincenzi B, et al. Cetuximab and irinotecan as third-line therapy in advanced colorectal cancer patients: a single centre phase II trial. Br J Cancer 2006; 94:792-7.
20. Amado R G, et al. Wild-type KRAS is required for panitumumab efficacy in patients with metastatic colorectal cancer. J Clin Oncol 2008; 26:1626-34.
21. Freeman D J, et al. Association of K-ras mutational status and clinical outcomes in patients with metastatic colorectal cancer receiving panitumumab alone. Clin Colorectal Cancer 2008; 7:184-90.
22. Hecht J R, et al. A randomized phase IIIB trial of chemotherapy, bevacizumab, and panitumumab compared with chemotherapy and bevacizumab alone for metastatic colorectal cancer. J Clin Oncol 2009; 27:672-80.
23. Van Cutsem E, et al. Open-label phase III trial of panitumumab plus best supportive care compared with best supportive care alone in patients with chemotherapy-refractory metastatic colorectal cancer. J Clin Oncol 2007; 25:1658-64.

24. Andreyev H J, et al. K-ras mutations in patients with colorectal cancer: the multicenter "RASCAL" study. J Natl Cancer Inst 1998; 90:675-84.
25. Benvenuti S, et al. Oncogenic activation of the RAS/RAF signaling pathway impairs the response of metastatic colorectal cancers to anti-epidermal growth factor receptor antibody therapies. Cancer Res 2007; 67:2643-8.
26. Wong R, et al. Using predictive biomarkers to select patients with advanced colorectal cancer for treatment with epidermal growth factor receptor antibodies. Editorial. J Clin Oncol 2008; 26:5668-5670.
27. Frattini M, et al. PTEN loss of expression predicts cetuximab efficacy in metastatic colorectal cancer patients. Br J Cancer 2007; 97:1139-45.
28. Winer E, et al. Clinical cancer advances 2008: Major research advances in cancer treatment, prevention, and screening—a report from the American society of clinical oncology. J Clin Oncol 2008:27:812-26.
29. Messersmith W A, et al. Targeting EGFR in colorectal cancer. Editorial. N Engl J Cancer 2008; 359:1834-6.
30. Jemal A, et al. Cancer statistics, 2008. CA Cancer J Clin 2008; 58:71-96.
31. Bray F, et al. Estimates of cancer incidence and mortality in Europe in 1995. Eur J Cancer 2002; 38:99-166.
32. Ferlay J, et al. Estimates of the cancer incidence and mortality in Europe in 2006. Ann Oncol 2007; 18:581-92.
33. Lim J E, et al. Prognostic factors following curative resection for pancreatic adenocarcinoma: a population-based, linked database analysis of 396 patients. Ann Surg 2003; 237:74-85,
34. Li D, et al. Pancreatic cancer. Lancet 2004; 363:1049-57.
35. Burris H A, et al. Improvements in survival and clinical benefit with gemcitabin first-line therapy for patients with advanced pancreas cancer: a randomized trial. J Clin Oncol 1997; 15:2403-13.
36. Johansen J S. Studies on serum YKL-40 as a biomarker in diseases with inflammation, tissue remodelling, fibrosis and cancer. Dan Med Bull 2006; 53: 172-209.
37. Johansen J S, et al. Elevated plasma YKL-40 predicts increased risk of gastrointestinal cancer and decreased survival after any cancer diagnosis in the general population. J Clin Oncology 2009; 27:572-8.
38. Johansen J S, et al. Diurnal, weekly, and long-time variation in serum concentrations of YKL-40 in healthy subjects. Cancer Epidemiol Biomarkers Prev 2008; 17:2603-8.

The invention claimed is:

1. A method for determining a therapy for a gastrointestinal cancer expressing wild type KRAS in a subject, said method comprising:
   i) determining the level of YKL-40 in a blood, serum, or plasma sample obtained from the subject; and
   ii) comparing said level of YKL-40 with a reference level of YKL-40 obtained in healthy individuals selected from the following set of age dependent cut-off values defined as
      the $90^{th}$ percentile: natural log (ln)(plasma YKL-40 µg/l)= 3.5+0.02×age of the subject (years);
      the $95^{th}$ percentile: ln(plasma YKL-40 µg/l)=3.6+0.02× age of the subject (years); and
      the $97.5^{th}$ percentile: ln(plasma YKL-40 µg/l)=3.9+ 0.02×age of the subject (years); and
   iii) treating said subject with an EGFR inhibitor when the determined level of YKL-40 is below the reference level.

2. The method of claim 1, further comprising the following steps:
   iv) determining the level of YKL-40 in a sample obtained from said subject after a period of treatment; and
   v) comparing said YKL-40 level with the YKL-40 level obtained in step i),
   wherein the level of YKL-40 in the sample of step i) is age adjusted by adding 0.5 µg/l per year for women, and 0.8 µg/l per year for men, and wherein said treatment is continued if the level of YKL-40 in the sample of step iv) is below or equal to the age adjusted level obtained in step i).

3. The method according to claim 2, wherein a level of YKL-40 in the sample being increased to at least a factor of 1.60 or more compared to the level obtained in step i) indicates that the gastrointestinal cancer has evolved to a more severe stage of the cancer, therefore suggesting a therapy with higher efficacy than the treatment of step iii), or wherein a level of YKL-40 in the sample being decreased to at least a factor of 0.6 compared to the level obtained in step i) indicates that the gastrointestinal cancer has evolved to a less severe stage of the cancer, therefore suggesting a continuation of said treatment of step iii) or initiation of a therapy with lower efficacy than the treatment of step iii).

4. The method according to claim 2, wherein a level of YKL-40 in the sample being increased by at least 109% compared to the level obtained in step i) indicates that the gastrointestinal cancer has evolved to a more severe stage of the gastrointestinal cancer, therefore suggesting a therapy with higher efficacy than the treatment of step iii), or wherein a level of YKL-40 in the sample being decreased by 52% compared to the level obtained in step i) indicates that the gastrointestinal cancer has evolved to a less severe stage of the gastrointestinal cancer, therefore suggesting a continuation of said treatment of step iii) or initiation of a therapy with lower efficacy than the treatment of step iii).

5. The method according to claim 1, wherein the gastrointestinal cancer is an upper GI cancer and/or a lower GI cancer.

6. The method according to claim 1, wherein the gastrointestinal cancer is an upper GI cancer.

7. The method according to claim 1, wherein the gastrointestinal cancer is one or more upper GI cancers selected from the group consisting of esophageal cancer, gastric/stomach cancer, pancreatic cancer and biliary cancer.

8. The method according to claim 1, wherein the gastrointestinal cancer is pancreatic cancer.

9. The method according to claim 1, wherein the gastrointestinal cancer is one or more lower GI cancers selected from the group consisting of small intestine cancer, duodenum cancer, appendix cancer, colon cancer, rectal cancer, colorectal cancer and anal cancer.

10. The method according to claim 1, wherein the gastrointestinal cancer is colorectal cancer or metastatic colorectal cancer.

11. The method according to claim 1, wherein the gastrointestinal cancer is metastatic colorectal cancer.

12. The method according to claim 1, wherein the EGFR inhibitor is selected from the group consisting of Cetuximab, Panitumumab, Zalutumumab, and Erlotinib.

13. The method according to claim 1, further comprising determining wherein the level of one or more additional biomarkers in the same sample as the YKL-40 level.

14. The method according to claim 13, wherein the one or more additional biomarkers is selected from the group consisting of BRAF mutation status, PTEN expression, microsatellite instability (MSI), AREG expression, EREG expression, CRP, ESR, CEA, CA19-9, LDH, tissue inhibitor of metalloproteinase 1 (TIMP1), interleukins, IL-4, IL-6, IL-8, VEGF, metalloproteinases, soluble UPAR (sUPAR), tumor necrosis factor-alpha, the aminoterminal propeptide of type I and III procollagen (P-III-NP), monocyte chemoattractant protein-1, fibrin D-dimer and other gene-, microRNA and SNP biomarkers identified from array studies.

* * * * *

UNITED STATES PATENT AND TRADEMARK OFFICE
CERTIFICATE OF CORRECTION

| | |
|---|---|
| PATENT NO. | : 8,580,520 B2 |
| APPLICATION NO. | : 13/063402 |
| DATED | : November 12, 2013 |
| INVENTOR(S) | : Julia Sidenius Johansen et al. |

It is certified that error appears in the above-identified patent and that said Letters Patent is hereby corrected as shown below:

Title Page, item [75] under Inventors, in Borge Gronne Nordestgaard, replace "Genrofte" with --Gentofte--.

Title Page 3, References Cited under OTHER PUBLICATIONS, in Jonker et al., replace "Medecine" with --Medicine--.

in Nøjgaard, C et al., replace "PIINP" with --PIIINP--.

In the Specification

Column 1, Line 50, replace "gastic" with --gastric--;

Line 65, replace "can not" with --cannot--.

Column 3, Line 7, replace "signalling" with --signaling--;

Line 28, replace "supressor" with --suppressor--;

Line 36, replace "wildtype" with --wild type--.

Column 4, Line 2, replace "chances" with --changes--.

Column 6, Line 1, replace "relastes" with --relates--.

Column 9, Line 41, replace "timepoints" with --time points--.

Column 15, Line 12, replace "values" with --value--;

Line 16, replace "(years))." with --(years).--;

Line 17, replace "a even" with --an even--.

Signed and Sealed this
Fourteenth Day of October, 2014

Michelle K. Lee
*Deputy Director of the United States Patent and Trademark Office*

CERTIFICATE OF CORRECTION (continued)

U.S. Pat. No. 8,580,520 B2

Column 16, Line 25, replace "Alternatively the one" with --Alternatively, the one--.

Column 17, Line 12-13, replace "This may for instance be relevant" with --For instance, this may be relevant--;

Line 15, replace "For example when" with --For example, when--.

Column 18, Line 10-11, replace "Likewise has the BRAF mutation status been found" with --Likewise, the BRAF mutation status has been found--;

Line 44, replace "a EGFR" with --an EGFR--.

Column 22, Line 33, replace "about 4 weeks treatment" with --about 4 weeks of treatment--;

Line 49, replace "chemotreated" with --chemo treated--.

Column 23, Line 26, replace "1 months" with --1 month--;

Line 30, replace "1 months" with --1 month--;

Line 33, replace "of 1" with --of $\leq 1$--.

Column 25, Line 62, replace "about 4 weeks treatment" with --about 4 weeks of treatment--.

Column 26, Line 14-15, replace "utilised" with --utilized--.

Column 27, Line 5, replace "it self" with --itself--;

Line 10, replace "2 week" with --2 weeks--.

Column 28, Line 65, replace "1 months" with --1 month--.

Column 30, Line 65-66, replace "or metastatic disease" with --or have a metastatic disease--.

Column 31, Line 6, replace "(30-32)." with --(30-32)).--;

Line 29, replace "mestastatic" with --metastatic--.

Column 32, Line 24, replace "homologs" with --homologues--.

Column 33, Line 61, replace "carboxy" with --carboxyl--.

Column 35, Line 41, replace ".sup.125 I" with --$^{125}$I--;

replace "sup.111 In" with --$^{111}$In--;

replace ".sup.97 Ru" with --$^{97}$Ru--;

replace ".sup.67 Ga" with --$^{67}$Ga--;

replace ".sup.68 Ga" with --$^{68}$Ga--;

Line 42, replace ".sup.72 As" with --$^{72}$As--;

replace ".sup.89 Zr" with --$^{89}$Zr--;

replace ".sup.90 Y" with --$^{90}$Y--;

replace ".sup.201 Tl" with --$^{201}$Tl--;

Line 44, replace ".sup.125 I" with --$^{125}$I--;

Line 45, replace ".sup.125 I" with --$^{125}$I--;

Line 47, replace ".sup.125 I" with --$^{125}$I--;

Line 48, replace "3.alpha., 6.alpha." with --3α, 6α--.

Column 36, Line 8, replace "interassay" with --inter-assay--;

Line 50, replace "labelled" with --labeled--.

Column 37, Line 51, replace "an GI" with --a GI--.

Column 41, Line 23, replace "extend" with --extent--.

Column 46, Line 18, replace "a already" with --an already--;

Line 56, replace "decreased to least by" with --decreased at least by--.

Column 47, Line 47, replace "a increase" with --an increase--.

Column 48, Line 26, replace "cox" with --Cox--;

Line 41, replace "hereon" with --here on--.

Column 50, Line 46, replace "misstaging" with --incorrectly staging--.

Column 52, Line 24, replace "Ufteral" with --Uftoral--;

Line 24-25, replace "Camtosar" with --Camptosar--;

Line 25, replace "Gemcitabin" with --Gemcitabine--;

replace "Taxoterre" with --Taxotere--;

Line 27, replace "Sorfenib" with --Sorafenib--;

Line 49, replace "Ufteral" with --Uftoral--;

Line 50, replace "Gemcitabin" with --Gemcitabine--;

replace "Taxoterre" with --Taxotere--;

Line 53, replace "Sorfenib" with --Sorafenib--;

Line 64, replace "Ufteral" with --Uftoral--;

Line 65, replace "Gemcitabin" with --Gemcitabine--.

Column 53, Line 10, replace "Taxoterre" with --Taxotere--;

Line 13, replace "Gemcitabin" with --Gemcitabine--;

Line 15, replace "Sorfenib" with --Sorafenib--;

Line 49, replace "whichever" with --which ever--.

Column 54, Line 66, replace "a changes" with --a change--.

Column 55, Line 37, replace "troponines" with --troponins--;

Line 42, replace "pentraxin" with --pentraxins--;

Line 66, replace "signalling" with --signaling--.

Column 56, Line 20, replace "supressor" with --suppressor--;

Line 27, replace "wildtype" with --wild type--;

Line 38, replace "microsatelite" with --microsatellite--;

Line 65, replace "microsatelite" with --microsatellite--.

Column 57, Line 5, replace "troponines" with --troponins--.

Column 58, Line 44, replace "sulphate" with --sulfate--;

Line 47, replace "labelled" with --labeled--.

Column 59, Line 2, replace "labelled" with --labeled--.

Column 60, Line 49, replace "microsatelite" with --microsatellite--;

Line 57, replace "troponines" with --troponins--;

Line 63, replace "pentraxin" with --pentraxins--.

Column 61, Line 10, replace "in a kit such kit" with --in a kit; such kit--.

Column 62, Line 25, replace "troponines" with --troponins--;

Line 31, replace "pentraxin" with --pentraxins--.

Column 64, Line 13, replace "labelled" with --labeled--.

CERTIFICATE OF CORRECTION (continued)
U.S. Pat. No. 8,580,520 B2

Column 65, Line 39, replace "(i.e. 1.75 mg/L)" with --(i.e. $\leq$ 1.75 mg/L)--;

Line 42, replace "(i.e. 1.75 mg/L)" with --(i.e. $\leq$ 1.75 mg/L)--;

Line 65, replace "cox" with --Cox--.

Column 66, Line 24, replace "During 16 years follow-up" with --During the 16 year follow-up--.

Column 69, Line 61, replace "are" with --is--;

Line 63, replace "metodological" with --methodological--.

Column 70, Line 24, replace "$\leq 0.2\%$" with --$\leq 10.2\%$--;

Line 33, replace "analysed" with --analyzed--;

Line 59, replace "analysed" with --analyzed--.

Column 71, Line 6, replace "3 weeks" with --3 week--;

Line 47, replace "72.2% suggesting" with --72.2%, suggesting--;

Line 48, replace "variation" with --variations--.

Column 72, Line 4-5, replace "there are no significant diurnal variations" with --there is no significant diurnal variation--;

Line 5, replace "nor" with --or--;

Line 7, replace "variation" with --variations--;

Line 8, replace "confirming that that YKL-40" with --confirming that YKL-40--;

Line 27, replace "po" with --p.o.--;

Line 28, replace "every 3. week" with --every 3 weeks--;

Line 29, replace "tumour" with --tumor--;

Line 31, replace "capecitapin" with --capecitabine--;

Line 50-51, replace "coefficient of variations were" with --coefficients of variations were--;

Line 51, replace "were 5.0% and 8.4%" with --were $\leq$ 5.0% and $\leq$ 8.4%--.

Column 73, Line 66, replace "significant All" with --significant. All--.

Column 74, Line 61, replace "metastic" with --metastatic--.

CERTIFICATE OF CORRECTION (continued)
U.S. Pat. No. 8,580,520 B2

Column 81, Line 30, replace "Group 2: ≥4" with --Group 2: ≥94--;

Line 40, replace "wildtype" with --wild type--.

SEQUENCE LISTING

<160> NUMBER OF SEQ ID NOS: 2

<210> SEQ ID NO 1
<211> LENGTH: 1741
<212> TYPE: DNA
<213> ORGANISM: Homo sapiens

<400> SEQUENCE: 1

```
ctaggtagct ggcaccagga gccgtgggca agggaagagg ccacaccctg ccctgctctg      60
ctgcagccag aatgggtgtg aaggcgtctc aaacaggctt tgtggtcctg gtgctgctcc     120
agtgctgctc tgcatacaaa ctggtctgct actacaccag ctggtcccag taccgggaag     180
gcgatgggag ctgcttccca gatgcccttg accgcttcct ctgtacccac atcatctaca     240
gctttgccaa tataagcaac gatcacatcg acacctggga gtggaatgat gtgacgctct     300
acggcatgct caacacactc aagaacagga ccccaacct gaagactctc ttgtctgtcg     360 gaggatgaa ctttgggtct caaagatttt ccaagatagc ctccaacacc cagagtcgcc     420
ggactttcat caagtcagta ccgccattcc tgcgcaccca tggctttgat gggctggacc     480
ttgcctggct ctaccctgga cggagagaca aacagcattt taccaccta atcaaggaaa     540 tgaaggccga atttataaag gaagcccagc cagggaaaaa gcagctcctg ctcagcgcag     600
cactgtctgc ggggaaggtc accattgaca gcagctatga cattgccaag atatcccaac     660
acctggattt cattagcatc atgacctacg attttcatgg agcctggcgt gggaccacag     720
gccatcacag tccctgttc cgaggtcagg aggatgcaag tcctgacaga ttcagcaaca     780
ctgactatgc tgtggggtac atgttgaggc tgggggctcc tgccagtaag ctggtgatgg     840 gcatcccac cttcgggagg agcttcactc tggcttcttc tgagactggt gttggagccc     900
caatctcagg accgggaatt ccaggccggt tcaccaagga ggcagggacc cttgcctact     960
atgagatctg tgacttcctc cgcggagcca cagtccatag aaccctcggc cagcaggtcc    1020
cctatgccaa caagggcaac cagtgggtag gatacgacga ccaggaaagc gtcaaaagca    1080
aggtgcagta cctgaaggat aggcagctgg caggcgccat ggtatgggcc ctggacctgg    1140
```

```
atgacttcca gggctccttc tgcggccagg atctgcgctt ccctctcacc aatgccatca   1200
aggatgcact cgctgcaacg tagccctctg ttctgcacac agcacggggg ccaaggatgc   1260
cccgtccccc tctggctcca gctggccggg agcctgatca cctgccctgc tgagtcccag   1320
gctgagcctc agtctcccctc ccttggggcc tatgcagagg tccacaacac acagatttga   1380
gctcagccct ggtgggcaga gaggtaggga tggggctgtg gggatagtga ggcatcgcaa   1440
tgtaagactc gggattagta cacttgtt gatgattaat ggaaatgttt acagatcccc   1500
aagcctggca agggaatttc ttcaactccc tgcccctag ccctccttat caaaggacac   1560
cattttggca agctctatca ccaaggagcc aaacatccta caagacacag tgaccatact   1620
aattataccc cctgcaaagc cagcttgaaa ccttcactta ggaacgtaat cgtgtcccct   1680
atcctacttc cccttcctaa ttccacagct gctcaataaa gtacaagagt ttaacagtgt   1740
g                                                                   1741
```

```
<210> SEQ ID NO 2
<211> LENGTH: 383
<212> TYPE: PRT
<213> ORGANISM: Homo sapiens

<400> SEQUENCE: 2

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270
```

```
Gly Val Gly Ala Pro Ile Ser Gly Pro Gly Ile Pro Gly Arg Phe Thr
    275                 280                 285

Lys Glu Ala Gly Thr Leu Ala Tyr Tyr Glu Ile Cys Asp Phe Leu Arg
    290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
                340                 345                 350

Ala Leu Asp Leu Asp Asp Phe Gln Gly Ser Phe Cys Gly Gln Asp Leu
            355                 360                 365

Arg Phe Pro Leu Thr Asn Ala Ile Lys Asp Ala Leu Ala Ala Thr
    370                 375                 380
```